US009000259B2

(12) United States Patent
Puthigae et al.

(10) Patent No.: US 9,000,259 B2
(45) Date of Patent: Apr. 7, 2015

(54) POLYNUCLEOTIDES AND METHODS FOR THE IMPROVEMENT OF PLANTS

(75) Inventors: Sathish Puthigae, Auckland (NZ); Jonathan Robert Phillips, Chesterfield, MO (US); Claudia Jeannette Smith-Espinoza, Chesterfield, MO (US); Catherine Jane Bryant, Auckland (NZ); Kieran Michael Elborough, Franklin (NZ); Margaret Biswas, Auckland (NZ)

(73) Assignee: Vialactia Biosciences (NZ) Limited (NZ)

( * ) Notice: Subject to any disclaimer, the term of this patent is extended or adjusted under 35 U.S.C. 154(b) by 1344 days.

(21) Appl. No.: 12/288,930

(22) Filed: Oct. 24, 2008

(65) Prior Publication Data

US 2010/0095397 A1 Apr. 15, 2010

Related U.S. Application Data

(60) Provisional application No. 60/982,862, filed on Oct. 26, 2007.

(51) Int. Cl.

| | |
|---|---|
| ***A01H 1/00*** | (2006.01) |
| ***A01H 5/00*** | (2006.01) |
| ***A01H 5/10*** | (2006.01) |
| ***C07H 21/04*** | (2006.01) |
| ***C12N 15/29*** | (2006.01) |
| ***C12N 15/82*** | (2006.01) |
| ***C07K 14/415*** | (2006.01) |
| ***C12N 9/88*** | (2006.01) |

(52) U.S. Cl.
CPC .......... *C12N 15/8261* (2013.01); *C07K 14/415* (2013.01); *C12N 9/88* (2013.01)

(58) Field of Classification Search
None
See application file for complete search history.

(56) References Cited

U.S. PATENT DOCUMENTS

| | | | | |
|---|---|---|---|---|
| 7,214,786 | B2 * | 5/2007 | Kovalic et al. ............... | 536/23.6 |
| 2003/0046732 | A1 | 3/2003 | Kinnersley et al. | |
| 2004/0031072 | A1 | 2/2004 | La Rosa et al. | |
| 2004/0034888 | A1 | 2/2004 | Liu et al. | |
| 2004/0123343 | A1 | 6/2004 | La Rosa et al. | |
| 2004/0216190 | A1 | 10/2004 | Kovalic | |
| 2005/0108791 | A1 | 5/2005 | Edgerton | |
| 2006/0236419 | A1 | 10/2006 | La Rosa et al. | |
| 2007/0044171 | A1 | 2/2007 | Kovalic et al. | |

FOREIGN PATENT DOCUMENTS

| | | |
|---|---|---|
| WO | WO 2007/027866 | 3/2007 |
| WO | WO 2007/044043 | 4/2007 |

OTHER PUBLICATIONS

Adams et al., Complementary DNA Sequencing: Expressed Sequence Tags and Human Genome Project, Academic Research Library, Jun. 21, 1991, vol. 252, Issue 5013, pp. 1651-1656.
Akama et al., C-terminal extension of rice glutamate decarboxylase (OsGAD2) functions as an autoinhibitory domain and overexpression of a truncated mutant results in the accumulation of extremely high levels of GABA in plant cells, Journal of Experimental Botany, 2007, vol. 58, Issue 10, pp. 2699-2707.
Baum et al., Calmodulin binding to glutamate decarboxylase is required for regulation of glutamate and GABA metabolism and normal development in plants, The EMBO Journal, 1996, vol. 15, Issue 12, pp. 2988-2996.
Bouche et al., The root-specific glutamate decarboxylase (GAD1) is essential for sustaining GABA levels in Arabidopsis, Plant Molecular Biology, 2004, vol. 55, pp. 315-325.
Chen et al., Enhanced recovery of transformants of Agrobacterium tumefaciens after freeze-thaw transformation and drug selection, BioTechniques, 1994, vol. 16, Issue 4, pp. 664-668, 670.
Chen et al., Identifying novel transcripts and novel genes in the human genome by using novel SAGE tags, PNAS, Sep. 17, 2002, vol. 99, Issue 19, pp. 12257-12262.
Den Dulk-Ras et al., Electroporation of *Agrobacterium tumefaciens,* Methods in Molecular Biology, 1995, vol. 55, pp. 63-72.
Inatomi et al., Glutamate Decarboxylase from Barley Embryos and Roots, Biochem. J., 1975, vol. 147, pp. 479-484.
Kathiresan et al., y-Aminobutyric Acid Stimulates Ethylene Biosynthesis in Sunflower, Plant Physiol., 1997, vol. 115, pp. 129-135.
Lee et al., Use of Serial Analysis of Gene Expression Technology to Reveal Changes in Gene Expression in Arabidopsis Pollen Undergoing Cold Stress, Plant Physiology, Jun. 2003, vol. 132, pp. 517-529.
Mayer et al., Effects of Heat Shock on Amino Acid Metabolism of Cowpea Cells, Plant Physiol., 1990, vol. 94, pp. 796-810.
Murashige et al., A Revised Medium for Rapid Growth and Bio Assays with Tobacco Tissue Cultures, Physiologia Plantarum, 1962, vol. 15, Issue 3, pp. 473-497.
Patterson et al., Temperature and Metabolism, The Biochemistry of Plants, 1987, vol. 12, pp. 153-199.
Richmond et al., Chasing the dream: plant EST microarrays, Current Opinion in Plant Biology, 2000, vol. 3, pp. 108-116.
Ruan et al., Interrogating the transcriptome, TRENDS in Biotechnology, Jan. 2004, vol. 22, Issue 1, pp. 23-30.
Schmidt-Eisenlohr et al., Vir Proteins Stabilize VirB5 and Mediate Its Association with the T Pilus of *Agrobacterium tumefaciens,* Journal of Bacteriology, Dec. 1999, vol. 181, Issue 24, pp. 7485-7492.

(Continued)

*Primary Examiner* — Eileen B O Hara
(74) *Attorney, Agent, or Firm* — Knobbe, Martens, Olson & Bear, LLP

(57) ABSTRACT

Methods are described for producing a plant with altered seed yield comprising transformation of a plant with a genetic construct including a polynucleotide encoding of a polypeptide with the amino acid sequence of SEQ ID NO: 1 or a variant or fragment thereof. Also provided by the disclosed methods are isolated polypeptides, polynucleotides, constructs and vectors useful for producing a plant with altered seed yield. The methods also provide plant cells and plants transformed to contain and express the polypeptides, polynucleotides and constructs. Plants produced by the disclosed methods are further provided.

27 Claims, 38 Drawing Sheets
(6 of 38 Drawing Sheet(s) Filed in Color)

(56) References Cited

OTHER PUBLICATIONS

Sun et al., Sage is far more sensitive than EST for detecting low-abundance transcripts, BMC Genomics, 2004, vol. 5, Issue 1, pp. 1-4.

Thompson et al., Improved sensitivity of profile searches through the use of sequence weights and gap excision, CABIOS, 1994, vol. 10, Issue 1, pp. 19-29.

Updegraff et al., Investigating the role of GABA in pollen tube growth and guidance in Arabidopsis, International Arabidopsis Conference, 2004.

Velculescu et al., Serial Analysis of Gene Expression, Science, Oct. 20, 1995, vol. 270, pp. 484-487.

Wallace et al., Rapid Accumulation of y-Aminobutyric Acid and Alanine in Soybean Leaves in Response to an Abrupt Transfer to Lower Temperature, Darkness, or Mechanical Manipulation, Plant Physiol., 1984, vol. 75, pp. 170-175.

Yuan et al., Calcium-Calmodulin-induced Dimerization of the Carboxyl-terminal Domain from Petunia Glutamate Decarboxylase, The Journal of Biological Chemistry, Nov. 13, 1998, vol. 273, Issue 46, pp. 30328-30335.

* cited by examiner

FIG. 1

| Sequences producing High-scoring Segment Pairs: | High Score | Smallest Sum Probability P(N) | N |
|---|---|---|---|
| UR100:UniRef100_Q7XZU7 Cluster: GAD1; n=1; Hordeum vulgar... | 2161 | 1.0e-222 | 1 |
| UR100:UniRef100_Q9AQU4 Cluster: Glutamate decarboxylase; ... | 2125 | 6.8e-219 | 1 |
| UR100:UniRef100_Q6YSB2 Cluster: Putative glutamate decarb... | 2090 | 3.5e-215 | 1 |
| UR100:UniRef100_A7P433 Cluster: Chromosome chr1 scaffold_... | 1931 | 2.4e-198 | 1 |
| UR100:UniRef100_Q07346 Cluster: Glutamate decarboxylase; ... | 1916 | 9.5e-197 | 1 |
| UR100:UniRef100_O81102 Cluster: Glutamate decarboxylase i... | 1914 | 1.5e-196 | 1 |
| UR100:UniRef100_Q8LKR4 Cluster: Glutamate decarboxylase; ... | 1912 | 2.5e-196 | 1 |
| UR100:UniRef100_Q9AT17 Cluster: Glutamate decarboxylase i... | 1911 | 3.2e-196 | 1 |
| UR100:UniRef100_P93369 Cluster: Glutamate decarboxylase; ... | 1906 | 1.1e-195 | 1 |
| UR100:UniRef100_Q1I1D8 Cluster: Glutamate decarboxylase; ... | 1900 | 4.7e-195 | 1 |
| UR100:UniRef100_Q42521 Cluster: Glutamate decarboxylase 1... | 1898 | 7.7e-195 | 1 |
| UR100:UniRef100_Q94KK8 Cluster: Glutamate decarboxylase i... | 1892 | 3.3e-194 | 1 |
| UR100:UniRef100_Q9ZPS3 Cluster: Putative glutamate decarb... | 1890 | 5.4e-194 | 1 |
| UR100:UniRef100_Q6Q4I2 Cluster: Glutamate decarboxylase 4... | 1888 | 8.8e-194 | 1 |
| UR100:UniRef100_A0EJ88 Cluster: Glutamate decarboxylase; ... | 1883 | 3.0e-193 | 1 |
| UR100:UniRef100_A5BI27 Cluster: Putative uncharacterized ... | 1879 | 7.9e-193 | 1 |
| UR100:UniRef100_Q6Q4I1 Cluster: Glutamate decarboxylase 4... | 1877 | 1.3e-192 | 1 |
| UR100:UniRef100_O81101 Cluster: Glutamate decarboxylase i... | 1876 | 1.6e-192 | 1 |
| UR100:UniRef100_Q6ASV4 Cluster: Putative glutamate decarb... | 1869 | 9.1e-192 | 1 |
| UR100:UniRef100_Q42472 Cluster: Glutamate decarboxylase 2... | 1867 | 1.5e-191 | 1 |
| UR100:UniRef100_P54767 Cluster: Glutamate decarboxylase; ... | 1867 | 1.5e-191 | 1 |
| UR100:UniRef100_A2XEB3 Cluster: Putative uncharacterized ... | 1863 | 3.9e-191 | 1 |
| UR100:UniRef100_Q84U04 Cluster: Glutamate decarboxylase; ... | 1863 | 3.9e-191 | 1 |
| UR100:UniRef100_Q944L6 Cluster: At1g65960/F12P19_12; n=1;... | 1863 | 3.9e-191 | 1 |
| UR100:UniRef100_Q6Q4I3 Cluster: Glutamate decarboxylase 2... | 1855 | 2.8e-190 | 1 |
| UR100:UniRef100_Q9LSH2 Cluster: Glutamate decarboxylase; ... | 1846 | 2.5e-189 | 1 |
| UR100:UniRef100_Q8LFR4 Cluster: Glutamate decarboxylase, ... | 1842 | 6.6e-189 | 1 |
| UR100:UniRef100_Q9ZPS4 Cluster: Putative glutamate decarb... | 1819 | 1.8e-186 | 1 |
| UR100:UniRef100_A3AM59 Cluster: Putative uncharacterized ... | 1806 | 4.3e-185 | 1 |
| UR100:UniRef100_Q01J81 Cluster: OSIGBa0152K17.6 protein; ... | 1755 | 1.1e-179 | 1 |
| UR100:UniRef100_Q9AR41 Cluster: Glutamate decarboxylase; ... | 1752 | 2.3e-179 | 1 |
| UR100:UniRef100_A7P434 Cluster: Chromosome chr1 scaffold_... | 1654 | 5.5e-169 | 1 |

FIG. 2A

```
Multiple Sequence Alignment

CLUSTAL (1.0) multiple sequence alignment

LP ORF56 PROTEIN      MVLTVA-ATAADTAEPLN-STFFATRYVRDQLPRYRMPENSIPKEAAYQIISDELMLDGN 58 Seq ID #   1
UNIREF100_Q7XZU7      MVVTVA-ATGPDTAETLH-STTFASRYVRDQLPRYRMPENSIPKEAAYQIISDELMLDGN 58 Seq ID #  22
UNIREF100_Q9AQU4      MVVSVA-ATDSDTAQPVQYSTFFASRYVRDPLPRERMPEQSIPKEAAYQIINDELMLDGN 59 Seq ID # 128
UNIREF100_Q6YSB2      MVLSHA-SSGRDDAVRCT----FATRYACETLPRERMPEQSIPKEAAYQIINDELMLDGN 55 Seq ID #  21
UNIREF100_A7P433      MVLSKT-ASESDVSVHST----FASRYVKASLPREKLPENSIPKEAAYQIINDELMLDGN 55 Seq ID #  10
UNIREF100_Q07346      MVLSKT-VSQSDVSIHST----FASRYVRTSLPREKMPDNSIPKEAAYQIINDELMLDGN 55 Seq ID #   4
UNIREF100_O81102      MVLSKT-ASESDVSIHST----FASRYVRTSLPREKMPENSIPKEAAYQIINDELMLDGN 55 Seq ID #  13
UNIREF100_Q8LKR4      MVLSKT-ASESDVSIHST----FASRYVRTSLPREKMPENSIPKEAAYQIINDELMLDGN 55 Seq ID #  25
UNIREF100_Q9AT17      MVLSKT-ASESDVSIHST----FASRYVRTSLPREKMPENSIPKEAAYQIINDELMLDGN 55 Seq ID #  30
UNIREF100_P93369      MVLSKT-ASESDVSIHST----FASRYVRTSLPREKMPENSIPKEAAYQIINDELMLDGN 55 Seq ID #  14
UNIREF100_Q1I1D8      MVLSKT-FSESDESIHST----FASRYVRNSLPREIMPENSIPKEAAYQIINDELMLDGN 55 Seq ID #  16
UNIREF100_Q42521      MVLSHA-VSESDVSVHST----FASRYVRTSLPREKMPENSIPKEAAYQIINDELMLDGN 55 Seq ID #   2
UNIREF100_Q94KK8      MVLSKT-SSESDVSVHST----FASRYVRTSLPREEMAENSIPKEAAFQIINDELMLDGN 55 Seq ID #  27
UNIREF100_Q9ZPS3      MVLSKT-VSESDVSIHST----FASRYVRNSLPREEMPENSIPKEAAYQIINDELMLDGN 55 Seq ID # 129
UNIREF100_Q6Q4I2      MVLSKT-ASESDVSIHST----FASRYVRTSLPREEMPENSIPKEAAYQIINDELMLDGN 55 Seq ID #  19
UNIREF100_A0EJ88      MVLSKT-ASESDVSVHST----FASRYVRASLPREKMPENSIPKEAAFQIINDELMLDGN 55 Seq ID #   6
UNIREF100_A5BI27      MVLSKT-ASESDVSVHST----FASRYVKASLPREKLPENSIPKEAAYQIINDELMLDGN 55 Seq ID #   9
UNIREF100_Q6Q4I1      MVLSKT-ASGTDVSVHST----FASRYVRNSLPREEMPENSIPKEAAYQIINDELMLDGN 55 Seq ID #  18
UNIREF100_O81101      MVLSKT-ASESDVSVHST----FASRYVRTSLPREKMPENSIPKEAAYQIINDELMLDGN 55 Seq ID #  12
UNIREF100_Q6ASV4      MVLSHG-VSGSDESVHST----FASRYVRTSLPRERMPEQSIPKEAAYQIINDELMLDGN 55 Seq ID #  17
UNIREF100_Q42472      MVLTKT-ATND-ESVCEM----FGSRYVRTTLPKYEIGENSIPKDAAYQIIKDELMLDGN 54 Seq ID #   3
UNIREF100_P54767      MVLTTISIRDSEESLHCT----FASRYVQEPLPKFKMPKKSMPKEAAYQIVNDELMLDGN 56 Seq ID # 130
UNIREF100_A2XEB3      MVLSKA-VSESDMSVHST----FASRYVRASLPRYRMPENSIPKEAAYQIINDELMLDGN 55 Seq ID #   7
UNIREF100_Q84U04      MVLSKA-VSESDMSVHST----FASRYVRASLPRYRMPENSIPKEAAYQIINDELMLDGN 55 Seq ID #  23
UNIREF100_Q944L6      MVLTKT-ATND-ESVCEM----FGSRYVRTTLPKYEIGENSIPKDAAYQIIKDELMLDGN 54 Seq ID #  26
UNIREF100_Q6Q413      MVLSKA-ATESGENVCST----FGSRYVRTALPKHKLGESSIPKEAAYQIIKDELMLDGN 55 Seq ID #  20
UNIREF100_Q9LSH2      ---MVL-ATNSDSDEHLH--STFASRYVRAVVPREKMPDHCMPKDAAYQVINDELMLDGN 54 Seq ID #  31
UNIREF100_Q8LFR4      ---MVL-ATNSDSDEHLH--STFASRYVRAVVPREKMPDHCMPKDAAYQVINDELMLDGN 54 Seq ID #  24
UNIREF100_Q9ZPS4      MVLSKT-ASKSDDSIHST----FASRYVRNSLSREELPKNSIPKEAAYQIINDELKFDGN 55 Seq ID # 131
UNIREF100_A3AM59      ------------------------------------MPEQSIPKEAAYQIINDELMLDGN 24 Seq ID #   8
UNIREF100_Q01J81      MVLTHVEAVEEGSEAAAA---VFASRYVQDPVPRYELGERSLSKDAAYQIVHDELLLDSS 57 Seq ID #  15
UNIREF100_Q9AR41      MVLTHVEAVEEGSEAAAA---VFASRYVQDPVPRYELGERSISKDAAYQIVHDELLLDSS 57 Seq ID #  29
UNIREF100_A7P434      ------------------------------------MPEKSIPKEAAYQIVHDELLLDGL 24 Seq ID #  11
                                                          :  .  .:.::**:*::  *** :*.
```

FIG. 2B

```
LP ORF56 PROTEIN    PRLNLASFVTTRMEPEVGKLLMDSVNKNYVDMDEYPVLTELQNRCVNMIAHLFNAPIKEE 118 Seq ID #   1
UNIREF100_Q7XZJ7    PRLNLASFVTTWMEPECGKLIMDSVNKNYVDMDEYPVTTELQDRCVNMIAHLFNAPIGED 118 Seq ID #  22
UNIREF100_Q9AQJ4    PRLNLASFVTTWMEPECDKLIMDSVNKNYVDMDEYPVTTELQNRCVNMIAHLFNAPIKED 119 Seq ID # 128
UNIREF100_Q8YSB2    PRLNLASFVTTWMEPECDKLIMDSVNKNYVDMDEYPVTTELQNRCVNMIAHLFNAPIKED 115 Seq ID #  21
UNIREF100_A7P433    PRLNLASFVTTWMEPECDKLMMAAINKNYVDMDEYPVTTELQNRCVNIIAHLFNAPLEDS 115 Seq ID #  10
UNIREF100_Q07346    PRLNLASFVTTWMEPECDKLMMDSINKNYVDMDEYPVTTELQNRCVNMIAHLFNAPLEDG 115 Seq ID #   4
UNIREF100_Q811C2    PRLNLASFVTTWMEPECNKLMMDSINKNYVDMDEYPVTTELQNRCVNMIAHLFNAPLEDG 115 Seq ID #  13
UNIREF100_Q8LKR4    PRLNLASFVTTWMEPECNTLMMDSINKNYVDMDEYPVTTELQNRCVNMIAHLFNAPLCDG 115 Seq ID #  25
UNIREF100_Q9AT17    PRLNLASFVTTWMEPECNKLMMDSTNKNYVDMGEYPVTTELQNRCVNMTAHLFNAPLGDG 115 Seq ID #  30
UNIREF100_P93369    PRLNLASFVTTWMEPECNKLMMDSINKNYVDMDEYPVTTELQNRCVNMIAHLFNAPLGDG 115 Seq ID #  14
UNIREF100_Q1T1D8    PRLNLASFVTTWMEPECDKLMMAAINKNYVDMDEYPVTTELQNRCVNIIARLFNAPLEDS 115 Seq ID #  16
UNIREF100_Q42521    PRLNLASFVTTWMEPECDKLIMSSINKNYVDMDEYPVTTELQNRCVNMIAHLFNAPLEEA 115 Seq ID #   2
UNIREF100_Q94KK8    PRLNLASFVTTWMEPECDKLMMDSINKNYVDMDEYPVTTELQNRCVNMIARLFNAPLEEK 115 Seq ID #  27
UNIREF100_Q9ZPS3    PRLNLASFVTTWMEPECDKLMMESTNKNYVDMDEYPVTTELQNRCVNMIARLFNAPLGDG 115 Seq ID # 129
UNIREF100_Q6Q4I2    PRLNLASFVTTWMEPECDKLMMESINKNYVDMDEYPVTTELQNRCVNMIARLFNAPLGDG 115 Seq ID #  19
UNIREF100_A0DJ88    PRLNLASFVTTWMEPECDKLIIASINKNYVDMDEYPVTTELQNRCVNMIAHLFNAPLGDG 115 Seq ID #   6
UNIREF100_A5BI27    PRLNLASFVTTWMEPECDKLMMAAINKNYVDMDEYP------NRCVNIIAHLFNAPLEDS 109 Seq ID #   9
UNIREF100_Q6Q4I1    PRLNLASFVTTWMEPECDKLMMESTNKNYVDMDEYPVTTELQNRCVNMIARLFNAPLGDG 115 Seq ID #  18
UNIREF100_Q811C1    PRLNLASFVTTWMEPECNTLMMDSINKNYVDMDEYPVTTELQNRCVNMIAHLFNAPLGDG 115 Seq ID #  12
UNIREF100_Q6ASV4    PRLNLASFVTTWMEPECDKLIQASVNKNYVDMDEYPVTTELQNRCVNMIAHLFNAPLGDS 115 Seq ID #  17
UNIREF100_Q42472    PRLNLASFVTTWMEPECDKLIMDSINKNYVDMDEYPVTTELQNRCVNIIARLFNAPLEES 114 Seq ID #   3
UNIREF100_P54767    PRLNLASFVSTWMEPECDKLIMSSINKNYVDMDEYPVTTELQNRCVNMLAHLHAPVCDD  116 Seq ID # 130
UNIREF100_A2XEB3    PRLNLASFVTTWMEPECDKLIMAAINKNYVDMDEYPVTTELQNRCVNMIAHLFHAPLGED 115 Seq ID #   7
UNIREF100_Q84JC4    PRLNLASFVTTWMEPECDKLIMAAINKNYVDMDEYPVTTELQNRCVNMIAHLFHAPLGED 115 Seq ID #  23
UNIREF100_Q944L6    PRLNLASFVTTWMEPECDKLIMDSINKNYVDMDEYPVTTELQNRCVNIIARLFNAPLEES 114 Seq ID #  26
UNIREF100_Q6Q4I3    PRLNLASFVTTWMEPECDKLIMESINKNYVDMDEYPVTTELQNRCVNMIARLFNAPLEET 115 Seq ID #  20
UNIREF100_Q9LSH2    PRLNLASFVTTWMEPECDKLIMDSINKNYVDMDEYPVTTELQNRCVNMIAHLFHAPVGED 114 Seq ID #  31
UNIREF100_Q8LFR4    PRLNLASFVTTWMEPECDKLIMDSVNKNYVDMDEYPVTTELQNRCVNMIANLFHAPVGED 114 Seq ID #  24
UNIREF100_Q9ZPS4    PRLNLASFVTTWMEPECDKLMMESINKNVVEMDQYPVTTELQNRCVNMIARLFNAPLGDG 115 Seq ID # 131
UNIREF100_A3AM59    PRLNLASFVTTWMEPECDKLIQASVNKNYVDMDEYPVTTELQNRCVNMIAHLFNAPLGDS 84  Seq ID #   8
UNIREF100_Q01J81    PRLNLASFVTTWMEPECDRLILEAINKNYADMDEYPVTTELQNRCVNIIARLFNAPVCDG 117 Seq ID #  15
UNIREF100_Q9AR41    PRLNLASFVTTWMEPECDRLILEAINKNYADMDEYPVTTELQNRCVNIIARLFNAPVGDG 117 Seq ID #  29
UNIREF100_A7P434    PRLNLATFVTTWMEPECDKLMAEAINKNYVDMDEYPVTTELQNRCVNMIARLFNAPSADQ 84  Seq ID #  11
                    ******:**:* ****  .*:  ::***  .:*.:**    :****::*.:*:**  :
```

FIG. 2C

```
LP ORF56 PROTEIN        ET-AIGVATVGSSEAIMLAGLAFKRKWANKRKEEGKPYDKPNIVTGANVQVCWEKFARYF 177 Seq ID #   1
UNIREF100_Q7XZU7        ET-AIGVSTVGSSEAIMLAGLAFKRKWANKMKEQGKPCDKPNIVTGANVQVCWEKFARYF 177 Seq ID #  22
UNIREF100_Q9AQU4        ET-AIGVGTVGSSEAIMLAGLAFKRKWQNKRKEQGKPCDKPNIVTGANVQVCWEKFARYF 178 Seq ID # 128
UNIREF100_Q6YSB2        ET-AIGVGTVGSSEAIMLAGLAFKRKWQNKRKEQGKPCDKPNIVTGANVQVCWEKFARYF 174 Seq ID #  21
UNIREF100_A7P433        EA-AVGVGTVGSSEAIMLAGLAFKRKWQNKRKAEGKPYDKPNIVTGANVQVCWEKFARYF 174 Seq ID #  10
UNIREF100_Q07346        ET-AVGVGTVGSSEAIMLAGLAFKRKWQNKMKAQGKPCDKPNIVTGANVQVCWEKFARYF 174 Seq ID #   4
UNIREF100_O81102        ET-AVGVGTVGSSEAIMLAGLAFKRKWQNKMKAQGKPCDKPNIVTGANVQVCWEKFARYF 174 Seq ID #  13
UNIREF100_Q8LKR4        ET-AVGVGTVGSSEAIMLAGLAFKRKWQNKMKAQGKPFDKPNIVTGANVQVCWEKFARYF 174 Seq ID #  25
UNIREF100_Q9AT17        ET-AVGVGTVGSSEAIMLAGLAFKRKWQNKMKAQGKPCDKPNIVTGANVQVCWEKFARYF 174 Seq ID #  30
UNIREF100_P93369        ET-AVGVGTVGSSEAIMLAGLAFKRKWQNKMKAQGKPCDKPNIVTGANVQVCWEKFARYF 174 Seq ID #  14
UNIREF100_Q1I1D8        ET-AVGVGTVGSSEAIMLAGLAFKRKWQNKRKAEGKPFDKPNIVTGANVQVCWEKFARYF 174 Seq ID #  16
UNIREF100_Q42521        ET-AVGVGTVGSSEAIMLAGLAFKRKWQNKRKAEGKPVDKPNIVTGANVQVCWEKFARYF 174 Seq ID #   2
UNIREF100_Q94KK8        ET-AVGVGTVGSSEAIMLAGLAFKRNWQNKRKAEGKPYNKPNIVTGANVQVCWEKFANYF 174 Seq ID #  27
UNIREF100_Q9ZPS3        EA-AVGVGTVGSSEAIMLAGLAFKRQWQNKRKAQGLPYDKPNIVTGANVQVCWEKFARYF 174 Seq ID # 129
UNIREF100_Q6Q412        EA-AVGVGTVGSSEAIMLAGLAFKRQWQNKRKAQGLPYDKPNIVTGANVQVCWEKFARYF 174 Seq ID #  19
UNIREF100_A0EJ88        ET-AVGVGTVGSSEAIMLAGLAFKRKWQNKRKAEGKPYDKPNIVTGANVQVCWEKFARYF 174 Seq ID #   6
UNIREF100_A5BI27        EA-AVGVGTVGSSEAIMLAGLAFKRKWQNKRKAEGKPYDKPNIVTGANVQVCWEKFARYF 168 Seq ID #   9
UNIREF100_Q6Q4I1        EA-AVGVGTVGSSEAIMLAGLAFKRQWQNKRKAQGLPYDKPNIVTGANVQVCWEKFARYF 174 Seq ID #  18
UNIREF100_O81101        ET-AVGVGTVGSSEAIMLAGLAFKRKWQNKMKAQGKPFDKPNIVTGANVQVCWEKFARYF 174 Seq ID #  12
UNIREF100_Q6ASV4        ET-AVGVGTVGSSEAIMLAGLAFKRRWQNKMKAAGKPCDKPNIVTGANVQVCWEKFARYF 174 Seq ID #  17
UNIREF100_Q42472        ET-AVGVGTVGSSEAIMLAGLAFKRKWQNKRKAEGKPYDKPNIVTGANVQVCWEKFARYF 173 Seq ID #   3
UNIREF100_P54767        ET-AVGVGTVGSSEAIMLAGLAFKRKWQSKRKAEGKPFDKPNIVTGANVQVCWEKFARYF 175 Seq ID # 130
UNIREF100_A2XEB3        ET-AVGVGTVGSSEAIMLAGLAFKRRWQNKRKAEGKPFDKPNIITGANVQVCWEKFARYF 174 Seq ID #   7
UNIREF100_Q84U04        ET-AVGVGTVGSSEAIMLAGLAFKRRWQNKRKAEGKPFDKPNIITGANVQVCWEKFARYF 174 Seq ID #  23
UNIREF100_Q944L6        ET-AVGVGTVGSSEAIMLAGLAFKRKWQNKRKAEGKPYDKPNIVTGANVQVCWEKFARYF 173 Seq ID #  26
UNIREF100_Q6Q4I3        ET-AMGVGTVGSSEAIMLAGLAFKRNWQNKRKAEGKPYDKPNIVTGANVQVCWEKFARYF 174 Seq ID #  20
UNIREF100_Q9LSH2        EA-AIGCGTVGSSEAIMLAGLAFKRKWQHRRKAQGLPIDKPNIVTGANVQVCWEKFARYF 173 Seq ID #  31
UNIREF100_Q8LFR4        EA-AIGCGTVGSSEAIMLAGLAFKRKWQHRRKAQGLPIDKPNIVTGANVQVCWEKFARYF 173 Seq ID #  24
UNIREF100_Q9ZPS4        EA-AIGVGTVGSSEAVMLAGLAFKRQWQNKRKALGLPYDRPNIVTGANTQVCLEKFARYF 174 Seq ID # 131
UNIREF100_A3AM59        ET-AVGVGTVGSSEAIMLAGLAFKRRWQNKMKAAGKPCDKPNIVTGANVQVCWEKFARYF 143 Seq ID #   8
UNIREF100_Q01J81        EK-AVGVGTVGSSEAIMLAGLAFKRRWQNRRKAAGKPHDKPNIVTGANVQVCWEKFARYF 176 Seq ID #  15
UNIREF100_Q9AR41        EK-AVGVGTVGSSEAIMLAGLAFKRRWQNRRKAAGKPHDKPNIVTGANVQVCWEKFARYF 176 Seq ID #  29
UNIREF100_A7P434        TKQAVGVGTVGSSEAMMLAGLAFKKKWQNKRKAQKKPFDKPNIVTGANVQVCWEKFARYF 144 Seq ID #  11
                           *:* .*******:********:.*  : *    * ::***:****:*** ****.**
```

FIG. 2D

```
LP ORF56 PROTEIN        EVEIKEVKLTEGYYVMDPLKAVEMVDENTICVAAILGSTLTGEYEDVKLLNDLLVEKNKK 237 Seq ID #   1
UNIREF100_Q7XZU7        EVEIKEVKLTEGYYVMDPKKAVEMVDENTICVAAILGSTLTGEYEDVKLLNDLLVEKNKE 237 Seq ID #  22
UNIREF100_Q9AQU4        EVEIKEVKLSEGYYVMDPVKAVEMVDENTICVAAILGSSLTGEFEDVKLLNNLLTEKNKE 238 Seq ID # 128
UNIREF100_Q6YSB2        EVEIKEVKLSEGYYVMDPVKAVEMVDENTICVAAILGSSLTGEFEDVKLLNNLLTEKNKE 234 Seq ID #  21
UNIREF100_A7P433        EVEIKEVKLRDGYYVMDPEKAVEMVDENTICVAAILGSSLNGEFEDVKLLNDLLVEKNKQ 234 Seq ID #  10
UNIREF100_Q07346        EVEIKEVKLSEGYYVMDPEKAVEMVDENTICVAAILGSSLNGEFEDVKRLNDLLVEKNKE 234 Seq ID #   4
UNIREF100_O81102        EVEIKEVKLSDGYYVMDPEKAVEMVDENTICVAAILGSSLNGEFEDVKRLNDLLIEKNKE 234 Seq ID #  13
UNIREF100_Q8LKR4        EVEIKEVKLSDGYYVMDPEKAVEMVDENTICVAAILGSSLNGEFEDVKRLNDLLIEKNKE 234 Seq ID #  25
UNIREF100_Q9AT17        EVEIKEVKLSDGYYVMDPEKAVEMVDENTICVAAILGSSLNGEFEDVKRLNDLLIEKNKE 234 Seq ID #  30
UNIREF100_P93369        EVEIKEVKLSDGYYVMDPEKAVEMVDENTICVAAILGSSLNGEFEDVKRLNDLLIEKNKE 234 Seq ID #  14
UNIREF100_Q1I1D8        EVEIKEVKLSEGYYVMDPAKAVEMVDENTICVAAILGSSLNGEFEDVKLLNDLLTEKNKE 234 Seq ID #  16
UNIREF100_Q42521        EVEIKEVKLSEGYYVMDPQQAVDMVDENTICVAAILGSSLNGEFEDVKLLNDLLVEKNKE 234 Seq ID #   2
UNIREF100_Q94KK8        EVEIKEVKLREGYYVMDPVQAVEMVDENTICVAAILGSSLNGEFEDVKLLNDLLIEKNKQ 234 Seq ID #  27
UNIREF100_Q9ZPS3        EVEIKEVNLREDYYVMDPVKAVEMVDENTICVAAILGSSLTGEFEDVKLLNDLLVEKNKQ 234 Seq ID # 129
UNIREF100_Q6Q4T2        EVEIKEVKLREGYYVMDPEKAVEMVDENTICVAAILGSSLTGEFEDVKLLNDLLVEKNKQ 234 Seq ID #  19
UNIREF100_A0EJ88        EVEIKEVKLSDGYYVMDPEKAVQMVDENTICVAAILGSSLNGEFEDVKLLNDLLVEKNKS 234 Seq ID #   6
UNIREF100_A5BI27        EVEIKEVKLRDGYYVMDPEKAVEMVDENTICVAAILGSSLNGEFEDVKLLNDLLVEKNKQ 228 Seq ID #   9
UNIREF100_Q6Q4T1        EVEIKEVKLREGYYVMDPEKAVEMVDENTICVAAILGSSLTGEFEDVKLLNDLLVEKNKQ 234 Seq ID #  18
UNIREF100_O81101        EVEIKEVKLSDGYYVMDPEKAVEMVDENTICVAAILGSSLNGEFEDVKRLNDLLIEKNKE 234 Seq ID #  12
UNIREF100_Q6ASV4        EVEIKEVKLSDGYYVMDPAKAVDMVDENTICVAAILGSSLNGEFEDVKLLNDLLTKKNAE 234 Seq ID #  17
UNIREF100_Q42472        EVEIKEVNLSEGYYVMDPDKAAEMVDENTICVAAILGSSLNGEFEDVKRLNDLLVKKNEE 233 Seq ID #   3
UNIREF100_P54767        EVEIKEVKLKEGYYVMDPAKAVEIVDENTICVAAILGSSLTGEFEDVKLLNELLTKKNKE 235 Seq ID # 130
UNIREF100_A2XEB3        EVEIKEVKLRDGYYVMDPEKAVDMVDENTICVAAILGSSLNGEFEDVKLLNDLLDKKNKE 234 Seq ID #   7
UNIREF100_Q84U04        EVEIKEVKLRDGYYVMDPEKAVDMVNENTICVAAILGSSLNGEFEDVKLLNDLLDKKNKE 234 Seq ID #  23
UNIREF100_Q944L6        EVEIKEVNLSEGYYVMDPDKAAEMVDENTICVAAILGSSLNGEFEDVKRLNDLLVKKNEE 233 Seq ID #  26
UNIREF100_Q6Q4T3        EVEIKEVKLSEGYYVMDPDKAAEMVDENTICVAAILGSSLNGEFEDVKRLNDLLVKKNEE 234 Seq ID #  20
UNIREF100_Q9LSH2        EVEIKEVKLSEDYYVMDPAKAVEMVDENTICVAAILGSSLTGEFEDVKQLNDLLAEKNAE 233 Seq ID #  31
UNIREF100_Q8LFR4        EVEIKEVKLSEDYYVMDPAKAVEMVDENTICVAAILGSSLTGEFEDVKQLNDLLAEKNAE 233 Seq ID #  24
UNIREF100_Q9ZPS4        EVEIKEVKLREGYYVMDPDKAVEMVDENTICVVAILGSSLTGEFEDVKLLNDLLVEKNKK 234 Seq ID # 131
UNIREF100_A3AM59        EVEIKEVKLSDGYYVMDPAKAVDMVDENTICVAAILGSSLNGEFEDVKLLNDLLTKKNAE 203 Seq ID #   8
UNIREF100_Q01J81        EVEIKEVKLTEGCYVMDPVKAVDMVDENTICVAAILGSSLTGEFEDVRRLNDLLAAKNKR 236 Seq ID #  15
UNIREF100_Q9AR41        EVEIKEVKLTEGCYVMDPVKAVDMVDENTICVAAILGSSLTGEFEDVRRLNDLLAAKNKR 236 Seq ID #  29
UNIREF100_A7P434        EVEIKEVKLREGYYVMDPVKAVEMVDENTICVAAILGSTFNCEFEDVKLLNTLLTQKNKR 204 Seq ID #  11
                        *******:* :. ***** :*.::*:******.******:.**:***: ** **  **
```

FIG. 2E

```
LP ORF56 PROTEIN      TGFNVPIHVDAASGGFIAPFLHPELEWDTRLPLVKSINVSGHKYGLVYPGVGWVIWRSKD 297 Seq ID #   1
UNIREF100_Q7XZU7      TGWNVPIHVDAASGGFIAPFLQPELEWDFRLPLVKSINVSGHKYGLVYPGVGWVIWRSKD 297 Seq ID #  22
UNIREF100_Q9AQU4      TGWDVPIHVDAASGGFIAPFLYPELEWDFRLPLVKSINVSGHKYGLVYPGVGWVIWRSKE 298 Seq ID # 128
UNIREF100_Q6YSB2      TGWDVPIHVDAASGGFIAPFLYPELEWDFRLPLVKSINVSGHKYGLVYPGVGWVIWRSKE 294 Seq ID #  21
UNIREF100_A7P433      TGWDTPIHVDAASGGFIAPFLYPELEWDFRLPLVKSINVSGHKYGLVYAGIGWVVWRSKE 294 Seq ID #  10
UNIREF100_Q07346      TGWDTPIHVDAASGGFIAPFIYPELEWDFRLPLVKSINVSGHKYGLVYAGIGWVVWRNKD 294 Seq ID #   4
UNIREF100_O81102      TGWDTPIHVDAASGGFIAPFLYPELEWDFRLPLVKSINVSGHKYGLVYAGIGWAIWRNKE 294 Seq ID #  13
UNIREF100_Q8LKR4      TGWDTPIHVDAASGGFIAPFLYPELEWDFRLPLVKSINVSGHKYGLVYAGIGWAIWRNKE 294 Seq ID #  25
UNIREF100_Q9AT17      TGWDTPIHVDAASGGFIAPFLYPELEWDFRLPLVKSINVSGHKYGLVYAGIGWAIWRNKE 294 Seq ID #  30
UNIREF100_P93369      TGWDTPIHVDAASGEFIAPFLYPELEWDFRLPLVKSINVSGHKYGLVYAGIGWAIWRNKE 294 Seq ID #  14
UNIREF100_Q1I1D8      TGWDTPIHVDAASGGFIAPFLYPELEWDFRLPLVKSINVSGHKYGLVYAGIGWVVWRNKE 294 Seq ID #  16
UNIREF100_Q42521      TGWDTPIHVDAASGGFIAPFLYPELEWDFRLPLVKSINVSGHKYGLVYAGIGWVIWRNKE 294 Seq ID #   2
UNIREF100_Q94KK8      TGWNTPIHVDAASGGFIAPFLYPELEWDFRLPLVKSINVSGHKYGLVYAGIGWVIWRTKQ 294 Seq ID #  27
UNIREF100_Q9ZPS3      TGWDTPIHVDAASGGFIAPFLYPELEWDFRLPLVKSINVSGHKYGLVYAGIGWVVWRTKT 294 Seq ID # 129
UNIREF100_Q6Q4I2      TGWDTGIHVDAASGGFIAPFLYPELEWDFRLPLVKSINVSGHKYGLVYAGIGWVVWRTKS 294 Seq ID #  19
UNIREF100_A0EJ88      TGWDTPIHVDAASGGFIAPFIYPELEWDFRLPLVKSINVSGHKYGLVYAGIGWVIWRNKE 294 Seq ID #   6
UNIREF100_A5BI27      XGWDTPIHVDAASGGFIAPFLYPELEWDFRLPLVKSINVSGHKYGLVYAGIGWVVWRSKE 288 Seq ID #   9
UNIREF100_Q6Q4T1      TGWDTGNHVDAASGGFIAPFLYPELEWDFRLPLVKSINVSGHKYGLVYAGIGWVVWRTKS 294 Seq ID #  18
UNIREF100_O81101      TGWDTPIHVDAASGGFIAPFLYPELEWDFRLPLEKSINVSGHKYGLVYAGIGWAIWRNKE 294 Seq ID #  12
UNIREF100_Q6ASV4      TGWDTPIHVDAASGGFIAPFLYPELEWDFRLPLVKSINVSGHKYGLVYAGIGWCIWRSKE 294 Seq ID #  17
UNIREF100_Q42472      TGWNTPIHVDAASGGFIAPFIYPELEWDFRLPLVKSINVSGHKYGLVYAGIGWVVWRAAE 293 Seq ID #   3
UNIREF100_P54767      TGWETPIHVDAASGGFIAPFLNPDLEWDFRLPLVKSINVSGHKYGLVYAGVGWVIWRSKE 295 Seq ID # 130
UNIREF100_A2XEB3      TGWETPIHVDAASGGFIAPFLYPELEWDFRLPWVKSINVSGHKYGLVYAGIGWCIWRNKE 294 Seq ID #   7
UNIREF100_Q84U04      TGWETPIHVDAASGGFIAPFLYPELEWDFRLPWVKSINVSGHKYGLVYAGIGWCIWRNKE 294 Seq ID #  23
UNIREF100_Q944L6      TGWNTPIHVDAASGGFIAPFIYPELEWDFRLPLVKSINVSGHKYGLVYAGIGWVVWRAAE 293 Seq ID #  26
UNIREF100_Q6Q4T3      TGWNTPIHVDAASGGFIAPFIYPELEWDFRLPLVKSINVSGHKYGLVYAGIGWVVWRTQQ 294 Seq ID #  20
UNIREF100_Q9LSH2      TGWETPIHVDAASGGFIAPFLYPDLEWDFRLPWVKSINVSGHKYGLVYAGVGWVVWRTKD 293 Seq ID #  31
UNIREF100_Q8LFR4      TGWETPIHVDAASGGFIAPFLYPDLEWDFRLPWVKSINVSGHKYGLVYAGVGWVVWRTKD 293 Seq ID #  24
UNIREF100_Q9ZPS4      TGWDTPIHVDAASGGFIAPFLYPDLEWDFRLPLVKSINVSGHKYGLVYAGIGWVVWRTKT 294 Seq ID # 131
UNIREF100_A3AM59      TGWDTPIHVDAASGGFIAPFLYPELEWDFRLPLVKSINVSGHKYGLVYAGIGWCIWRSKE 263 Seq ID #   8
UNIREF100_Q01J81      TGWDTPIHVDAASGGFIAPFIYPELEWDFRLPLVKSINVSGHKYGLVYAGVGWVIWRNKE 296 Seq ID #  15
UNIREF100_Q9AR41      TGWDTPIHVDAASGGFIAPFIYPELEWDFRLPLVKSINVSGHKYGLVYAGVGWVIWRNKE 296 Seq ID #  29
UNIREF100_A7P434      TGWDTPIHVDAASGGFVAPFLYPELEWDFRLPLVKSINVSGHKYGLVYAGVGWAIWRSKE 264 Seq ID #  11
                       *::.  ******* *:***: *:********  *************.*:** :**
```

FIG. 2F

```
LP ORF56 PROTEIN       DLPGELIFHINYLGTDQPTFTLNFSKGASQIIAQYYQLIRLGFEGYKHIMENCQANATAL 357 Seq ID #   1
UNIREF100_Q7XZU7       DLPEELIFHINYLGADQPTFTLNFSKGQ-QIIAQYYQLIRLGFEGYKHIMENCKLNAAVL 356 Seq ID #  22
UNIREF100_Q9AQU4       DLPEELIFHINYLGTDQPTFTLNFSKGSSQIIAQYYQLIRLGFEGYKNIMQNCMENTAIL 358 Seq ID # 128
UNIREF100_Q6YSB2       DLPEELIFHINYLGTDQPTFTLNFSKGSSQIIAQYYQLIRLGFEGYKNIMQNCMENTAIL 354 Seq ID #  21
UNIREF100_A7P433       DLPEELIFHINYLGADQPTFTLNFSKGSSQVIAQYYQLIRLGFEGYRNVMENCQENAMAL 354 Seq ID #  10
UNIREF100_Q07346       DLPDELIFHINYLGADQPTFTLNFSKGSSQVIAQYYQLIRLGYEGYKNVMENCQENASVL 354 Seq ID #   4
UNIREF100_O81102       DLPDELIFHINYLGADQPTFTLNFSKGSSQVIAQYYQLIRLGFEGYKNVMENCQENARVL 354 Seq ID #  13
UNIREF100_Q8LKR4       DLPDELIFHINYLGADQPTFTLNFSKGSSQVIAQYYQLIRLGFEGYKNVMENCQENARVL 354 Seq ID #  25
UNIREF100_Q9AT17       DLPDELIFHINYLGADQPTFTLNFSKGSSQVIAQYYQLIRLGFEGYKNVMENCQENARVL 354 Seq ID #  30
UNIREF100_P93369       DLPDELIFHINYLGADQPTFTLNFSKGSSQVIAQYYQLIRLGFEGYKNVMENCQENARVL 354 Seq ID #  14
UNIREF100_Q1I1D8       DLPEELIFHINYLGADQPTFTLNFSKGSSQVIAQYYQLIRLGFEGYRNVMENCHENAMVL 354 Seq ID #  16
UNIREF100_Q42521       DLPEELIFHINYLGADQPTFTLNFSKGSSQVIAQYYQLIRLGHEGYRNVMENCRENMIVL 354 Seq ID #   2
UNIREF100_Q94KK8       DLPEELIFHINYLGADQPTFTLNFSKGSSQVIAQYYQLIRLGYEGYRNVMENCRENAIVL 354 Seq ID #  27
UNIREF100_Q9ZPS3       DLPDELIFHINYLGADQPTFTLNFSKGSSQVIAQYYQLIRLGFEGYRNVMDNCRENMMVL 354 Seq ID # 129
UNIREF100_Q6Q412       DLPDELIFHINYLGADQPTFTLNFSKGSSQVIAQYYQLIRLGFEGYRNVMDNCRENMMVL 354 Seq ID #  19
UNIREF100_A0EJ88       DLPEELIFHINYLGADQPTFTLNFSKGSSQVIAQYYQLIRLGYEGYKNVMENCRDNMIVL 354 Seq ID #   6
UNIREF100_A5B127       DLPEELIFHINYLGADQPTFTLNFSKGSSQVIAQYYQLIRLGFEGYRNVMENCQENAMAL 348 Seq ID #   9
UNIREF100_Q6Q4T1       DLPDELIFHINYLGADQPTFTLNFSKGSSQVIAQYYQLIRLGFEGYRNVMDNCRENMMVL 354 Seq ID #  18
UNIREF100_O81101       DLPDELIFHINYLGADQPTFTLNFSKGSSQVIAQYYQLIRLGFEGYKNVMENCQENARVL 354 Seq ID #  12
UNIREF100_Q6ASV4       DLPEELIFHINYLGADQPTFTLNFSKGSSQVIAQYYQLIRLGFEGYKNIMENCQENAMVL 354 Seq ID #  17
UNIREF100_Q42472       DLPEELIFHINYLGADQPTFTLNFSKGSSQIIAQYYQLIRLGFEGYKNVMENCIENMVVL 353 Seq ID #   3
UNIREF100_P54767       DLPDELVFHINYLGSDQPTFTLNFSKGSYQIIAQYYQLIRLGFEGYKNVMKNCLSNAKVL 355 Seq ID # 130
UNIREF100_A2XEB3       DLPEELIFHINYLGADQPTFTLNFSKGSSQVIAQYYQLIRHGFEGYRNIMENCHENAMVL 354 Seq ID #   7
UNIREF100_Q84U04       DLPEELIFHINYLGTDQPTFTLNFSKGSSQVIAQYYQLIRHGFEGYRNIMENCHENAMVL 354 Seq ID #  23
UNIREF100_Q944L6       DLPEELIFHINYLGADQPTFTLNFSKGSSQIIAQYYQLIRLGFEGYKNVMENCIENMVVL 353 Seq ID #  26
UNIREF100_Q6Q4I3       DLPDELIFHINYLGADQPTFTLNFSKGSSQIIAQYYQLIRLGFEGYKNVMENCRENMVVL 354 Seq ID #  20
UNIREF100_Q9LSE2       DLPEELVFHINYLGADQPTFTLNFSKGSSQIIAQYYQFIRLGFEGYKNIMENCMDNARRL 353 Seq ID #  31
UNIREF100_Q8LFR4       DLPEELVFHINYLGADQPTFTLNFSKGSSQIIAQYYQFIRLGFEGYKNIMENCMDNARRL 353 Seq ID #  24
UNIREF100_Q9ZPS4       DLPDELIFHINYLGADQPTFTLNFSKGSSQVIAQYYQLIRLGFEGYRNVMDNCRENMMVL 354 Seq ID # 131
UNIREF100_A3AM59       DLPEELIFHINYLGADQPTFTLNFSKGSSQVIAQYYQLIRLGFEGYKNIMENCQENAMVL 323 Seq ID #   8
UNIREF100_Q01J81       DLPEELIFHINYLGADQPTFTLNFSKGSSQIIAQYYQFIRLGFEGYKSVMKNCMESARIL 356 Seq ID #  15
UNIREF100_Q9AR41       DLPEELIFHINYLGADQPTFTLNFSKGSSQIIAQYYQFLRLGFEGYKSVMKNCMESARIL 356 Seq ID #  29
UNIREF100_A7P434       ELPEELIFHINYLGGDEPTFTLNFSKGN-QVIAQYYQFLRMGFEGYKKVMGNCMESARIL 323 Seq ID #  11
                       :** **:******* *:**********  *:******::* *.***: :*.**  .   *
```

FIG. 2G

```
LP ORF56 PROTEIN      REGLEATGRFDILSKIDGVPLVAIRLKDSSK-FSVFDISENLRRFGWIVPAYTMPADAEH 416 Seq ID #   1
UNIREF100_Q7XZU7      KEGIDATGRFDVLSKADGVPLVALRLKDSTN-FSVFDISENLRRFGWIVPAYTMPADAEH 415 Seq ID #  22
UNIREF100_Q9AQU4      REGIEATGRFEILSKEAGVPLVAFSLKDSGR-YTVFDISEHLRRFGWIVPAYTMPANAEH 417 Seq ID # 128
UNIREF100_Q6YSB2      REGIEATGRFEILSKEAGVPLVAFSLKDSGR-YTVFDISEHLRRFGWIVPAYTMPANAEH 413 Seq ID #  21
UNIREF100_A7P433      KEGLEKTGRFNIISKDNGVPLVAFSLKDNSC-HDEFEVADMLRRFGWIVPAYTMPPDAQH 413 Seq ID #  10
UNIREF100_Q07346      REGLEKTGRFNIISKELGVPLVAFSLKDNRQ-HNEFEISETLRRFGWIVPAYTMPPNAQH 413 Seq ID #   4
UNIREF100_O81102      REGLEKSGRFNIISKEIGVPLVAFSLKDNSQ-HNEFEISETLRRFGWIIPAYTMPPNAQH 413 Seq ID #  13
UNIREF100_Q8LKR4      REGIEKSGRFNIISKEIGVPLVAFSLKDNSQ-HNEFEISETLRRFGWIVPAYTMPPNAQH 413 Seq ID #  25
UNIREF100_Q9AT17      REGLEKSGRFNIISKEIGVPLVAFSLKDNSQ-HNEFEISETLRRFGWIIPAYTMPPNAQH 413 Seq ID #  30
UNIREF100_P93369      REGLEKSGRFNIISKELGVPLVAFSLKDNSQ-HNEFEISETLRRFGWIIPAYTMPPNAQH 413 Seq ID #  14
UNIREF100_Q1I1D8      KEGLEKTGRFNIVSKDEGVPLVAFSLKDNKR-HDEFEVAELLRRFGWIVPAYTMPADAQH 413 Seq ID #  16
UNIREF100_Q42521      REGLEKTERFNIVSKDEGVPLVAFSLKDSSC-HTEFEISDMLRRYGWIVPAYTMPPNAQH 413 Seq ID #   2
UNIREF100_Q94KK8      REGLEKTGRFNIVSKDEGVPLVAFSLKDNSR-HNEFEVSETLRRFGWIVPAYTMPADAQH 413 Seq ID #  27
UNIREF100_Q9ZPS3      RQGLEKTGRFKIVSKENGVPLVAFSLKDSSR-HNEFEVAHTLRRFGWIVPAYTMPADAQH 413 Seq ID # 129
UNIREF100_Q6Q4I2      REGLEKTGRFNIVSKENGVPLVAFSLKDSSR-HDEFEVAETLRRFGWIVPAYTMPADAQH 413 Seq ID #  19
UNIREF100_A0EJ88      KQGLEKTGKFNIVSKDKGVPLVAFSLKDNSL-HNEFEVSDMLRRFGWIVPAYTMPPDAQH 413 Seq ID #   6
UNIREF100_A5BI27      KEGLEKTGRFNIISKDNGVPLVAFSLKDNSC-HDEFEVADMLRRFGWIVPAYTMPPDAQH 407 Seq ID #   9
UNIREF100_Q6Q411      REGLEKTGRFNIVSKENGVPLVAFSLKDSSR-HNEFEVAETLRRFGWIVPAYTVPADAEH 413 Seq ID #  18
UNIREF100_O81101      REGIEKSGRFNIISKEIGVPLVAFSLKDNSQ-HNEFEISETLRRFGWIVLAYTMPPNAQH 413 Seq ID #  12
UNIREF100_Q6ASV4      KQGLEKTGRFNIVSKDNGVPLVAFSLKDSAR-HNEFEISDFLRRFGWIVPAYTMPPDAQH 413 Seq ID #  17
UNIREF100_Q42472      KEGIEKTERFNIVSKDQGVPVVAFSLKDHSF-HNEFEISEMLRRFGWIVPAYTMPADAQH 412 Seq ID #   3
UNIREF100_P54767      TEGITKMGRFDIVSKDVGVPVVAFSLRDSSK-YTVFEVSEHLRRFGWIVPAYTMPPDAEH 414 Seq ID # 130
UNIREF100_A2XEB3      KEGLVKTGRFDIVSKDEGVPLVAFSLKDRSR-HDEFEISDMLRRFGWIVPAYTMPPDAQH 413 Seq ID #   7
UNIREF100_Q84U04      KEGLVKTGRFDIVSKDEGVPLVAFSLKDRSR-HDEFEISDMLRRFGWIVPAYTMPPDAQH 413 Seq ID #  23
UNIREF100_Q944L6      KEGIEKTERFNIVSKDQGVPVVAFSLKDHSF-HNEFEISEMLRRFGWIVPAYTMPADVQH 412 Seq ID #  26
UNIREF100_Q6Q413      REGIEKTERFNIVSKEVGVPLVAFSLKDHSF-HNEFEISEMLRRFGWIVPAYTMPADAQH 413 Seq ID #  20
UNIREF100_Q9LSH2      REGIEMTGKFNIVSKDIGVPLVAFSLKDSSK-HTVFEIAESLRKFGWIIPAYTMPADAQH 412 Seq ID #  31
UNIREF100_Q8LFR4      REGIEMTGKFNIVSKDIGVPLVAFSLKDSSK-HTVFEIAESLRKFGWIIPAYTMPADAQH 412 Seq ID #  24
UNIREF100_Q9ZPS4      RQGLEKTGRFNIVSKENGVPLVAFSLKDSSR-HNEFEVAEMLRRFGWIVPAYTMPADAQH 413 Seq ID # 131
UNIREF100_A3AM59      KQGLEKTGRFNIVSKDNGVPLVAFSLKDSAR-HNEFEISDFLRRFGWIVPAYTMPPDAQH 382 Seq ID #   8
UNIREF100_Q01J81      REGLEKTGRFTIISKEEGVPLVAFTFKDGAG-AQAFRLSSGLRRYGWIVPAYTMPAALEH 415 Seq ID #  15
UNIREF100_Q9AR41      REGLEKTGRFTIISKEEGVPLVAFTFKDGAG-AQAFRLSSGLRRYGWIVPAYTMPAALEH 416 Seq ID #  29
UNIREF100_A7P434      REGLEKTGRFQIISKEKGVPVVAFAFKGNDRKNLAFGLSKALRNYGWIVPAYTMPANAEN 383 Seq ID #  11
                       :*:     :* ::**  ***:**: ::.        * ::  **.:***: ***:*.  ::
```

FIG. 2H

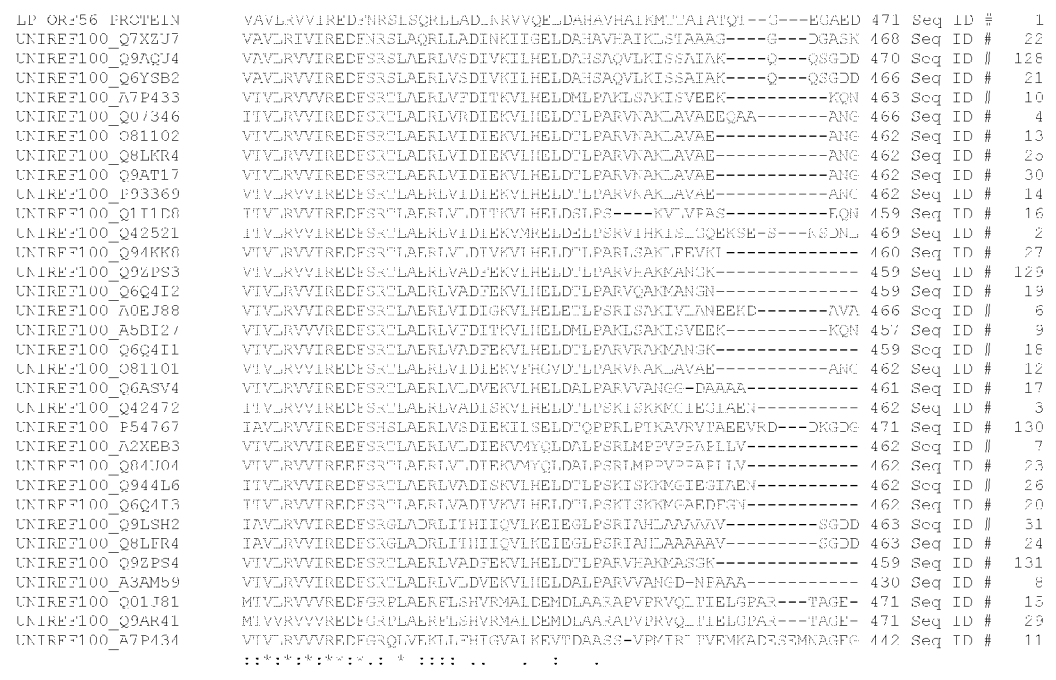

```
LP ORF56 PROTEIN      VAVLRVVIREDFNRSLSQRLLADLKRVVQELDAHAVHAIKMLTAIATQI--G---EGAED 471 Seq ID #   1
UNIREF100_Q7XZJ7      VAVLRIVIREDFNRSLAQRLLADINKIIGELDAHAVHAIKLSTAAAG----G---DGASK 468 Seq ID #  22
UNIREF100_Q9ACJ4      VAVLRVVIREDFSRSLAERLVSDIVKILHELDAHSAQVLKISSAIAK----Q---QSGDD 470 Seq ID # 128
UNIREF100_Q6YSB2      VAVLRVVIREDFSRSLAERLVSDIVKILHELDAHSAQVLKISSAIAK----Q---QSGDD 466 Seq ID #  21
UNIREF100_A7P433      VIVLRVVVREDFSRTLAERLVFDITKVLHELDMLPAKLSAKISVEEK----------KQN 463 Seq ID #  10
UNIREF100_Q07346      IIVLRVVIREDFSRTLADRLVRDIEKVLHELDTLPARVNAKLAVAEEQAA-------ANG 466 Seq ID #   4
UNIREF100 O81102      VIVLRVVIREDFSRTLAERLVIDIEKVLHELDTLPARVNAKLAVAE-----------ANG 462 Seq ID #  13
UNIREF100_Q8LKR4      VIVLRVVIREDFSRTLADRLVIDIEKVLHELDTLPARVNAKLAVAE-----------ANG 462 Seq ID #  25
UNIREF100 Q9AT17      VIVLRVVIREDFSRTLAERLVIDIEKVLHELDTLPARVNAKLAVAE-----------ANG 462 Seq ID #  30
UNIREF100_P93369      VIVLRVVIREDFSRTLAERLVIDIEKVLHELDTLPARVNAKLAVAE-----------ANG 462 Seq ID #  14
UNIREF100_Q1T1D8      ITVLRVVIREDFSRTLAERLVLDITKVLHELDSLPS----KVLVPAS----------EQN 459 Seq ID #  16
UNIREF100_Q42521      IIVLRVVIREDFSRTLAERLVIDIEKVMRELDELPSRVIHKISLGQEKSE-S---KSDNL 469 Seq ID #   2
UNIREF100_Q94KK8      VIVLRVVIREDFSRTLAERLVLDIVKVLHELDTLPARLSAKLFEVKI------------- 460 Seq ID #  27
UNIREF100_Q9ZPS3      VIVLRVVIREDFSRTLAERLVADFEKVLHELDTLPARVHAKMANGK-------------- 459 Seq ID # 129
UNIREF100_Q6Q4I2      VIVLRVVIREDFSRTLADRLVADFEKVLHELDTLPARVQAKMANGN-------------- 459 Seq ID #  19
UNIREF100 A0EJ88      VIVLRVVIREDFSRTLAERLVIDIGKVLHELETLPSRISAKIVLANEEKD-------AVA 466 Seq ID #   6
UNIREF100_A5BI27      VIVLRVVVREDFSRTLADRLVFDITKVLHELDMLPAKLSAKISVEEK----------KQN 457 Seq ID #   9
UNIREF100 Q6Q4I1      VIVLRVVIREDFSRTLAERLVADFEKVLHELDTLPARVRAKMANGK-------------- 459 Seq ID #  18
UNIREF100_O81101      VIVLRVVIREDFSRTLAERLVIDIEKVFHGVDTLPARVNAKLAVAE-----------ANG 462 Seq ID #  12
UNIREF100_Q6ASV4      VIVLRVVIREDFSRTLAERLVLDVEKVLHELDALPARVVANGG-DAAAA----------- 461 Seq ID #  17
UNIREF100_Q42472      IIVLRVVIREDFSRTLAERLVADISKVLHELDTLPSKISKKMGIEGIAEN---------- 462 Seq ID #   3
UNIREF100 P54767      IAVLRVVIREDFSHSLAERLVSDIEKILSELDTQPPRLPTKAVRVTAEEVRD---DKGDG 471 Seq ID # 130
UNIREF100_A2XEB3      VIVLRVVIREEFSRTLAERLVLDIEKVMYQLDALPSRLMPPVPPAPLLV----------- 462 Seq ID #   7
UNIREF100_Q84J04      VIVLRVVIREEFSRTLAERLVLDIEKVMYQLDALPSRLMPPVPPAPLLV----------- 462 Seq ID #  23
UNIREF100_Q944L6      IIVLRVVIREDFSRTLAERLVADISKVLHELDTLPSKISKKMGIEGIAEN---------- 462 Seq ID #  26
UNIREF100_Q6Q4T3      IIVLRVVIREDFSRTLAERLVADIVKVLHELDTLPSKISKKMGAEDFGN----------- 462 Seq ID #  20
UNIREF100_Q9LSH2      IAVLRVVIREDFSRGLADRLITHIIQVLKEIEGLPSRIAHLAAAAAV---------SGDD 463 Seq ID #  31
UNIREF100_Q8LFR4      IAVLRVVIREDFSRGLADRLITHIIQVLKEIEGLPSRIAHLAAAAAV---------SGDD 463 Seq ID #  24
UNIREF100 Q9ZPS4      VIVLRVVIREDFSRTLAERLVADFEKVLHELDTLPARVHAKMASGK-------------- 459 Seq ID # 131
UNIREF100_A3AM59      VIVLRVVIREDFSRTLADRLVLDVEKVLHELDALPARVVANGD-NPAAA----------- 430 Seq ID #   8
UNIREF100 Q01J81      MIVLRVVVREDFGRPLAERFLSHVRMALDEMDLAARAPVPRVQLPIELGPAR---TAGE- 471 Seq ID #  15
UNIREF100_Q9AR41      MIVVRVVVREDFGRPLAERFLSHVRMALDEMDLAARAPVPRVQLPIELGPAR---TAGE- 471 Seq ID #  29
UNIREF100_A7P434      VIVLRVVVREDFGRQLVEKLLFHTGVALKEVTDAASS-VPMTRLTVEMKADESEMNAGFG 442 Seq ID #  11
                      ::*:*:*:**:*.: * :::: ..   .  :   .
```

```
LP ORF56 PROTEIN    GVVTKKGVLDIEKEFAAACKDLVKNKKTGP----C-------  502 SEQ ID #    1
UNIREF100_Q7XZU7    SAVDAA---------TEAFKDLAGKKKAGV----C-------  490 SEQ ID #   22
UNIREF100_Q9AQU4    GVVTKKSVLETEREIFAYWRDQVKKKQTGI----C-------  501 Seq ID #  128
UNIREF100_Q6YSB2    GVVTKKSVLETEREIFAYWRDQVKKKQTGI----C-------  497 Seq ID #   21
UNIREF100_A7P433    GTILKKSVIETQREITDAWKKFVMAKKTNG---VC-------  495 Seq ID #   10
UNIREF100_Q07346    SEVHKKTDSEVQLEMITAWKKFVEEKKKKT-NRVC-------  500 Seq ID #    4
UNIREF100_O81102    SGVHKKTDREVQLEITTAWKKFVADKKKKT-NGVC-------  496 Seq ID #   13
UNIREF100_Q8LKR4    SGVHKKTDREVQLEITTAWKKFVADKKKKT-NGVC-------  496 Seq ID #   25
UNIREF100_Q9AT17    SGVHKKTDREVQLEITAAWKKFVADKKKKT-NGVC-------  496 Seq ID #   30
UNIREF100_P93369    SGVHKKTDREVQLEITTAWKKFVADKKKKT-NGVC-------  496 Seq ID #   14
UNIREF100_Q1I1D8    GRNGKKTEIETQREVTTYWRKFVSERKANNKNKIC-------  494 Seq ID #   16
UNIREF100_Q42521    MVTVKKSDIDKQRDIITGWKKFVADRKKTS--GIC-------  502 Seq ID #    2
UNIREF100_Q94KK8    VKNGKKFELEVQREVTNYWKKFVLARKAPV-C----------  491 Seq ID #   27
UNIREF100_Q9ZPS3    VNGVKKTPEETQREVTAYWKKLLETKKTNK-NTLC-------  493 Seq ID #  129
UNIREF100_Q6Q4I2    ANGVKKTEEETTREVTAYWKKFVEAKKSNK-NRIC-------  493 Seq ID #   19
UNIREF100_A0EJ88    AGKEKKDVQNETREIITAWRKLVVQRKKLN--GVC-------  499 Seq ID #    6
UNIREF100_A5BI27    GTILKKSVIETQREITDAWKKFVMAKKTNG---VC-------  489 Seq ID #    9
UNIREF100_Q6Q4I1    AKVVKQTEEETTREVTAYWKKFVETKKTNQ-NKIC-------  493 Seq ID #   18
UNIREF100_O81101    SGVHKKTDREVQLEITTAWLKFVADKKKKT-NGVC-------  496 Seq ID #   12
UNIREF100_Q6ASV4    --SASEREMEKQREVISLWKRAVLAKKKTN--GVC-------  492 Seq ID #   17
UNIREF100_Q42472    -VKEKKMEKEILMEVIVGWRKFVKERKKMN--GVC-------  494 Seq ID #    3
UNIREF100_P54767    LHHFHMDTVETQKDIIKHWRKIAGKKTSGV----C-------  502 Seq ID #  130
UNIREF100_A2XEB3    --VAKKSELETQRSVTEAWKKFVLAKR-TN--GVC-------  492 Seq ID #    7
UNIREF100_Q84U04    --VAKKSELETQRSVTEAWKKFVLAKR-TN--GVC-------  492 Seq ID #   23
UNIREF100_Q944L6    -VKEKKMEKEILMEVIVGWRKFVKERKKMN--GVC-------  494 Seq ID #   26
UNIREF100_Q6Q4I3    -VKGKKVDRDVLMEVIVGWRKFVKDRKKMN--GVC-------  494 Seq ID #   20
UNIREF100_Q9LSH2    EEVKVKTAKMSLEDITKYWKRLVEHKRNIV----C-------  494 Seq ID #   31
UNIREF100_Q8LFR4    EEVKVKTAKMSLEDITKYWKRLVEHKRNIV----C-------  494 Seq ID #   24
UNIREF100_Q9ZPS4    VNGVKKTPEETQREVTAYWKKFVDTKTDKN-GVPLVASITNQ  500 Seq ID #  131
UNIREF100_A3AM59    --SASEREMEKQREVISLWKRAVLAKKKTN--GVC-------  461 Seq ID #    8
UNIREF100_Q01J81    -----EASIRVVKSEAVPVRKSVPLVAGKT-KGVC-------  500 Seq ID #   15
UNIREF100_Q9AR41    -----EASIRVVKSEAVPVRKSVPLVAGKT-KGVC-------  500 Seq ID #   29
UNIREF100_A7P434    TLHIPAASVHWKHDKPETVDTQVPIMDGKT-KGVC-------  476 Seq ID #   11
```

FIG. 3A

Multiple Sequence Alignment

CLUSTAL (1.0) multiple sequence alignment

```
TP ORF56 PROTEIN      MVLTVA-ATAADTAEPLN-STFFATRYVRDQLPRYRMPENSIPKEAAYQTISDELMLDGN 58  Seq ID #   1
UNIREF100 Q7XZU7      MVVTVA-AIGPDTAEPLH-STTFASRYVRDQLPRYRMPENSIPKEAAYQIISDELMLDGN 58  Seq ID #  22
UNIREF100_Q9AQU4      MVVSVA-AIDSDTAQPVQYSTFFASRYVRDPLPRERMPEQSIPREAAYQIINDELMLDGN 59  Seq ID # 128
UNIREF100 Q6YSB2      MVLSHA-SSGRDDAVRCI----FATRYACETLPRERMPEQSIPREAAYQIINDELMLDGN 55  Seq ID #  21
UNIREF100_A7P433      MVLSKT-ASESDVSVHST----FASRYVKASLPREKLPENSIPKEAAYQIINDELMLDGN 55  Seq ID #  10
UNIREF100 Q07346      MVLSKT-VSQSDVSIHST----FASRYVRTSLPREKMPDNSIPKEAAYQIINDELMLDGN 55  Seq ID #   4
UNIREF100 O81102      MVLSKT-ASESDVSIHST----FASRYVRTSLPREKMPENSIPKEAAYQIINDELMLDGN 55  Seq ID #  13
UNIREF100 Q8LKR4      MVLSKT-ASESDVSIHST----FASRYVRTSLPREKMPENSIPKEAAYQIINDELMLDGN 55  Seq ID #  25
UNIREF100_Q9AT17      MVLSKT-ASESDVSIHST----FASRYVRTSLPREKMPENSIPKEAAYQIINDELMLDGN 55  Seq ID #  30
UNIREF100 P93369      MVLSKT-ASESDVSIHST----FASRYVRTSLPREKMPENSIPKEAAYQIINDELMLDGN 55  Seq ID #  14
UNIREF100_Q1I1D8      MVLSKT-ESESDESIHST----FASRYVRNSLPREIMPENSIPKEAAYQIINDELMLDGN 55  Seq ID #  16
UNIREF100 Q42521      MVLSHA-VSESDVSVHST----FASRYVRTSLPREKMPENSIPKEAAYQIINDELMLDGN 55  Seq ID #   2
UNIREF100_Q94KK8      MVLSKT-SSESDVSVHST----FASRYVRTSLPREEMAENSIPKEAAFQIINDELMLDGN 55  Seq ID #  27
UNIREF100 Q9ZPS3      MVLSKT-VSESDVSIHST----FASRYVRNSLPREIMPENSIPKEAAYQIINDELMLDGN 55  Seq ID # 129
UNIREF100_Q6Q4I2      MVLSKT-ASESDVSIHST----FASRYVRTSLPREIMPENSIPKEAAYQIINDELMLDGN 55  Seq ID #  19
UNIREF100 A0EJ88      MVLSKT-ASESDVSVHST----FASRYVRASLPREKMPENSIPKEAAFQIINDELMLDGN 55  Seq ID #   6
UNIREF100_A5BT27      MVLSKT-ASESDVSVHST----FASRYVKASLPREKLPENSIPKEAAYQIINDELMLDGN 55  Seq ID #   9
UNIREF100 Q6Q4I1      MVLSKT-ASGIDVSVHST----FASRYVRNSLPREIMPENSIPKEAAYQIINDELMLDGN 55  Seq ID #  18
UNIREF100 O81101      MVLSKT-ASESDVSVHST----FASRYVRTSLPREKMPENSIPKEAAYQIINDELMLDGN 55  Seq ID #  12
UNIREF100 Q6ASV4      MVLSHG-VSGSDESVHST----FASRYVRTSLPRERMPEQSIPKEAAYQIINDELMLDGN 55  Seq ID #  17
UNIREF100_Q42472      MVLTKT-ATND-ESVCTM----FGSRYVRTTLPKYEIGENSIPKDAAYQIIKDELMLDGN 54  Seq ID #   3
UNIREF100 P54767      MVLTTTSIRDSEESLHCI----FASRYVQEPLPKEKMPKKSMPKEAAYQIVNDELMLDGN 56  Seq ID # 130
UNIREF100_A2XEB3      MVLSKA-VSESDMSVHST----FASRYVRASLPRYRMPENSIPKEAAYQIINDELMLDGN 55  Seq ID #   7
UNIREF100_Q84UC4      MVLSKA-VSESDMSVHST----FASRYVRASLPRYRMPENSIPKEAAYQIINDELMLDGN 55  Seq ID #  23
UNIREF100_Q944L6      MVLTKT-ATND-ESVCTM----FGSRYVRTTLPKYEIGENSIPKDAAYQIIKDELMLDGN 54  Seq ID #  26
UNIREF100 Q6Q4I3      MVLSRA-AIESGENVCST----FGSRYVRTALPKHKIGESSIPKEAAYQIIKDELMLDGN 55  Seq ID #  20
UNIREF100_Q9LSH2      ---MVL-ATNSDSDEHLH--STFASRYVRAVVPREKMPDHCMPKDAAYQVINDELMLDGN 54  Seq ID #  31
UNIREF100_Q8LFR4      ---MVL-ATNSDSDEHLH--STFASRYVRAVVPREKMPDHCMPKDAAYQVINDELMLDGN 54  Seq ID #  24
UNIREF100_Q9ZPS4      MVLSKT-ASKSDDSTHST----FASRYVRNSTSREEIPKNSIPKEAAYQIINDELKFDGN 55  Seq ID # 131
UNIREF100 A3AM59      ------------------------------------MPEQSIPKEAAYQIINDELMLDGN 24  Seq ID #   8
UNIREF100_Q01J81      MVLTHVEAVEEGSEAAAA---VFASRYVQDPVPRYILGERSISKDAAYQIVHDELLLDSS 57  Seq ID #  15
UNIREF100_Q9AR41      MVLTHVEAVEEGSEAAAA---VFASRYVQDPVPRYILGERSISKDAAYQIVHDELLLDSS 57  Seq ID #  29
UNIREF100_A7P434      ------------------------------------MPEKSIPKEAAYQIVHDELLLDGL 24  Seq ID #  11
                                                          :  .  .:.::**:*::  ***  :*.
```

FIG. 3B

```
LP ORF56 PROTEIN      PRLNLASFVTTRMEPFVGKLIMDSVNKNYVDMDEYPVTTELQNRCVNMIAHLFNAPIKEE 118 Seq ID #   1
UNIREF100_Q7XZU7      PRLNLASFVTTWMEPECGKLIMDSVNKNYVDMDEYPVTTELQDRCVNMIAHLFNAPTGED 118 Seq ID #  22
UNIREF100_Q9AQU4      PRLNLASFVTTWMEPECDKLIMDSVNKNYVDMDEYPVTTELQNRCVNMIAHLFNAPIKED 119 Seq ID # 128
UNIREF100_Q6YSB2      PRLNLASFVTTWMEPECDKLIMDSVNKNYVDMDEYPVTTELQNRCVNMIAHLFNAPIKED 115 Seq ID #  21
UNIREF100_A7P433      PRLNLASFVTTWMEPECDKLMMAAINKNYVDMDEYPVTTELQNRCVNIIAHLFNAPLEDS 115 Seq ID #  10
UNIREF100_Q07346      PRLNLASFVTTWMEPECDKLMMDSINKNYVDMDEYPVTTELQNRCVNMIAHLFNAPLEDG 115 Seq ID #   4
UNIREF100_O81102      PRLNLASFVTTWMEPECNKLMMDSINKNYVDMDEYPVTTELQNRCVNMIAHLFNAPLGDG 115 Seq ID #  13
UNIREF100_Q8LKR4      PRLNLASFVTTWMEPECNTLMMDSINKNYVDMDEYPVTTELQNRCVNMIAHLFNAPLGDG 115 Seq ID #  25
UNIREF100_Q9AT17      PRLNLASFVTTWMEPECNKLMMDSINKNYVDMGEYPVTTELQNRCVNMIAHLFNAPLGDG 115 Seq ID #  30
UNIREF100_P93369      PRLNLASFVTTWMEPECNKLMMDSINKNYVDMDEYPVTTELQNRCVNMIAHLFNAPLGDG 115 Seq ID #  14
UNIREF100_Q1T1D8      PRLNLASFVTTWMEPECDKLMMAATNKNYVDMDEYPVTTELQNRCVNTTARLFNAPLEDS 115 Seq ID #  16
UNIREF100_Q42521      PRLNLASFVTTWMEPECDKLIMSSINKNYVDMDEYPVTTELQNRCVNMIAHLFNAPLEEA 115 Seq ID #   2
UNIREF100_Q94KK8      PRLNLASFVTTWMEPECDKLMMDSINKNYVDMDEYPVTTELQNRCVNMIARLFNAPLEEK 115 Seq ID #  27
UNIREF100_Q9ZPS3      PRLNLASFVTTWMEPECDKLMMESINKNYVDMDEYPVTTELQNRCVNMIARLFNAPLGDG 115 Seq ID # 129
UNIREF100_Q6Q4I2      PRLNLASFVTTWMEPECDKLMMESINKNYVDMDEYPVTTELQNRCVNMIARLFNAPLGDG 115 Seq ID #  19
UNIREF100_A0EJ88      PRLNLASFVTTWMEPECDKLTTASTNKNYVDMDEYPVTTELQNRCVNMTAHLFNAPLGDS 115 Seq ID #   6
UNIREF100_A5BI27      PRLNLASFVTTWMEPECDKLMMAAINKNYVDMDEYP------NRCVNIIAHLFNAPLEDS 109 Seq ID #   9
UNIREF100_Q6Q411      PRLNLASFVTTWMEPECDKLMMESINKNYVDMDEYPVTTELQNRCVNMIARLFNAPLGDG 115 Seq ID #  18
UNIREF100_O81101      PRLNLASFVTTWMEPECNTLMMDSINKNYVDMDEYPVTTELQNRCVNMIAHLFNAPLGDG 115 Seq ID #  12
UNIREF100_Q6ASV4      PRLNLASFVTTWMEPECDKLIQASVNKNYVDMDEYPVTTELQNRCVNMIAHLFNAPLGDS 115 Seq ID #  17
UNIREF100_Q42472      PRLNLASFVTTWMEPECDKLTMDSTNKNYVDMDEYPVTTELQNRCVNTTARLFNAPLEES 114 Seq ID #   3
UNIREF100_P54767      PRLNLASFVSTWMEPECDKLIMSSINKNYVDMDEYPVTTELQNRCVNMLAHLFHAPVGDD 116 Seq ID # 130
UNIREF100_A2XEB3      PRLNLASFVTTWMEPECDKLIMAAINKNYVDMDEYPVTTELQNRCVNMIAHLFHAPLGED 115 Seq ID #   7
UNIREF100_Q84U04      PRLNLASFVTTWMEPECDKLIMAAINKNYVDMDEYPVTTELQNRCVNMIAHLFHAPLGED 115 Seq ID #  23
UNIREF100_Q944I6      PRLNLASFVTTWMEPECDKLIMDSINKNYVDMDEYPVTTELQNRCVNIIARLFNAPLEES 114 Seq ID #  26
UNIREF100_Q6Q4I3      PRLNLASFVTTWMEPECDKLIMESINKNYVDMDEYPVTTELQNRCVNMIARLFNAPLEET 115 Seq ID #  20
UNIREF100_Q9LSH2      PRLNLASFVTTWMEPECDKLIMDSVNKNYVDMDEYPVTTELQNRCVNMIANLFHAPVGED 114 Seq ID #  31
UNIREF100_Q8LFR4      PRLNLASFVTTWMEPECDKLIMDSVNKNYVDMDEYPVTTELQNRCVNMIAKFFHAPVGED 114 Seq ID #  24
UNIREF100_Q9ZPS4      PRLNLASFVTTWMEPECDKLMMESINKNKVEMDQYPVTTDLQNRCVNMIARLFNAPLGDG 115 Seq ID # 131
UNIREF100_A3AM59      PRLNLASFVTTWMEPECDKLTQASVNKNYVDMDEYPVTTELQNRCVNMTAHLFNAPLGDS 84  Seq ID #   8
UNIREF100_Q01J81      PRLNLASFVTTWMEPECDRLILEAINKNYADMDEYPVTTELQNRCVNIIARLFNAPVGDG 117 Seq ID #  15
UNIREF100_Q9AR41      PRLNLASFVTTWMEPECDRLILEAINKNYADMDEYPVTTELQNRCVNIIARLFNAPVGDG 117 Seq ID #  29
UNIREF100_A7P434      PRLNLATFVTTWMEPECDKLMAEAINKNYVDMDEYPVTTELQNRCVNMIAKLFNAPSADQ 84  Seq ID #  11
                      ******:**:* **** . *:  ::*** .:*.:**      :****::*.:*:**  :
```

FIG. 3C

```
LP ORF56 PROTEIN       ET-AIGVATVGSSEAIMLAGLAFKRKWANKRKEEGKPYDKPNIVTGANVQVCWEKFARYF 177 Seq ID #   1
UNIREF100_Q7XZU7       ET-AIGVSTVGSSEAIMLAGLAFKRKWANKMKEQGKPCDKPNIVTGANVQVCWEKFARYF 177 Seq ID #  22
UNIREF100_Q9AQU4       ET-AIGVGTVGSSEAIMLAGLAFKRKWQNKRKEQGKPCDKPNIVTGANVQVCWEKFARYF 178 Seq ID # 128
UNIREF100 Q6YSB2       ET-AIGVGTVGSSEAIMLAGLAFKRKWQNKRKEQGKPCDKPNIVTGANVQVCWEKFARYF 174 Seq ID #  21
UNIREF100 A7P433       EA-AVGVGTVGSSEAIMLAGLAFKRKWQNKRKAEGKPYDKPNIVTGANVQVCWEKFARYF 174 Seq ID #  10
UNIREF100_Q07346       ET-AVGVGTVGSSEAIMLAGLAFKRKWQNKMKAQGKPCDKPNIVTGANVQVCWEKFARYF 174 Seq ID #   4
UNIREF100_O81102       ET-AVGVGTVGSSEAIMLAGLAFKRKWQNKMKAQGKPCDKPNIVTGANVQVCWEKFARYF 174 Seq ID #  13
UNIREF100_Q8LKR4       ET-AVGVGTVGSSEAIMLAGLAFKRKWQNKMKAQGKPFDKPNIVTGANVQVCWEKFARYF 174 Seq ID #  25
UNIREF100_Q9AT17       ET-AVGVGTVGSSEAIMLAGLAFKRKWQNKMKAQGKPCDKPNIVTGANVQVCWEKFARYF 174 Seq ID #  30
UNIREF100 P93369       ET-AVGVGTVGSSEAIMLAGLAFKRKWQNKMKAQGKPCDKPNIVTGANVQVCWEKFARYF 174 Seq ID #  14
UNIREF100 Q111J8       ET-AVGVGTVGSSEAIMLAGLAFKRKWQNKRKAEGKPFDKPNIVTGANVQVCWEKFARYF 174 Seq ID #  16
UNIREF100_Q42521       ET-AVGVGTVGSSEAIMLAGLAFKRKWQNKRKAEGKPVDKPNIVTGANVQVCWEKFARYF 174 Seq ID #   2
UNIREF100_Q94KK8       ET-AVGVGTVGSSEAIMLAGLAFKRNWQNKRKAEGKPYNKPNIVTGANVQVCWEKFANYF 174 Seq ID #  27
UNIREF100_Q9ZPS3       EA-AVGVGTVGSSEAIMLAGLAFKRQWQNKRKAQGLPYDKPNIVTGANVQVCWEKFARYF 174 Seq ID # 129
UNIREF100_Q6Q4I2       EA-AVGVGTVGSSEAIMLAGLAFKRQWQNKRKAQGLPYDKPNIVTGANVQVCWEKFARYF 174 Seq ID #  19
UNIREF100_A0EJ88       ET-AVGVGTVGSSEAIMLAGLAFKRKWQNKRKAEGKPYDKPNIVTGANVQVCWEKFARYF 174 Seq ID #   6
UNIREF100_A5BI27       EA-AVGVGTVGSSEAIMLAGLAFKRKWQNKRKAEGKPYDKPNIVTGANVQVCWEKFARYF 168 Seq ID #   9
UNIREF100_Q6Q4I1       EA-AVGVGTVGSSEAIMLAGLAFKRQWQNKRKAQGLPYDKPNIVTGANVQVCWEKFARYF 174 Seq ID #  18
UNIREF100_O81101       ET-AVGVGTVGSSEAIMLAGLAFKRKWQNKMKAQGKPFDKPNIVTGANVQVCWEKFARYF 174 Seq ID #  12
UNIREF100_Q6ASV4       ET-AVGVGTVGSSEAIMLAGLAFKRRWQNKMKAAGKPCDKPNIVTGANVQVCWEKFARYF 174 Seq ID #  17
UNIREF100_Q42472       ET-AVGVGTVGSSEAIMLAGLAFKRKWQNKRKAEGKPYDKPNIVTGANVQVCWEKFARYF 173 Seq ID #   3
UNIREF100_P54767       ET-AVGVGTVGSSEAIMLAGLAFKRKWQSKRKAEGKPFDKPNIVTGANVQVCWEKFARYF 175 Seq ID # 130
UNIREF100_A2XEB3       ET-AVGVGTVGSSEAIMLAGLAFKRRWQNKRKAEGKPFDKPNIITGANVQVCWEKFARYF 174 Seq ID #   7
UNIREF100_Q84JC4       ET-AVGVGTVGSSEAIMLAGLAFKRRWQNKRKAEGKPFDKPNIITGANVQVCWEKFARYF 174 Seq ID #  23
UNIREF100 Q944L6       ET-AVGVGTVGSSEAIMLAGLAFKRKWQNKRKAEGKPYDKPNIVTGANVQVCWEKFARYF 173 Seq ID #  26
UNIREF100 Q6Q413       ET-AMGVGTVGSSEAIMLAGLAFKRNWQNKRKAEGKPYDKPNIVTGANVQVCWEKFARYF 174 Seq ID #  20
UNIREF100_Q9LSH2       EA-ATGCGTVGSSEAIMLAGLAFKRKWQHRRKAQGLPTDKPNIVTGANVQVCWEKFARYF 173 Seq ID #  31
UNIREF100_Q8LFR4       EA-ATGCGTVGSSEAIMLAGLAFKRKWQHRRKAQGLPTDKPNIVTGANVQVCWEKFARYF 173 Seq ID #  24
UNIREF100_Q9ZPS4       EA-AIGVGTVGSSEAVMLAGLAFKRQWQNKRKALGLPYDRPNIVTGANIQVCLEKFARYF 174 Seq ID # 131
UNIREF100_A3AM59       ET-AVGVGTVGSSEAIMLAGLAFKRRWQNKMKAAGKPCDKPNIVTGANVQVCWEKFARYF 143 Seq ID #   8
UNIREF100_Q01J81       EK-AVGVGTVGSSEAIMLAGLAFKRRWQNRRKAAGKPHDKPNIVTGANVQVCWEKFARYF 176 Seq ID #  15
UNIREF100 Q9AR41       EK-AVGVGTVGSSEAIMLAGLAFKRRWQNRRKAAGKPHDKPNIVTGANVQVCWEKFARYF 176 Seq ID #  29
UNIREF100_A7P434       TKQAVGVGTVGSSEAMMLAGLAFKKKWQNKRKAQKKPFDKPNIVTGANVQVCWEKFARYF 144 Seq ID #  11
                          *:*  .*******:********:.*   : *    *  ::***:****:***  ****.**
```

FIG. 3D

```
LP ORF56 PROTEIN     EVELKEVKLTEGYYVMDPLKAVEMVDENTICVAAILGSTLTGEYEDVKLLNDLLVEKNKK 237 Seq ID #   1
UNIREF100_Q7XZU7     EVELKEVKLTEGYYVMDPKKAVEMVDENTICVAAILGSTLTGEYEDVKLLNDLLVEKNKE 237 Seq ID #  22
UNIREF100_Q9AQU4     EVELKEVKLSEGYYVMDPVKAVEMVDENTICVAAILGSTLTGEFEDVKLLNNLLTEKNKE 238 Seq ID # 128
UNIREF100_Q6YSB2     EVELKEVKLSEGYYVMDPVKAVEMVDENTICVAAILGSTLTGEFEDVKLLNNLLTEKNKE 234 Seq ID #  21
UNIREF100_A7P433     EVELKEVKLRDGYYVMDPEKAVEMVDENTICVAAILGSTLNGEFEDVKLLNDLLVEKNKQ 234 Seq ID #  10
UNIREF100_Q07346     EVELKEVKLSEGYYVMDPEKAVEMVDENTICVAAILGSTLNGEFEDVKRLNDLLVEKNKE 234 Seq ID #   4
UNIREF100_O81102     EVELKEVKLSDGYYVMDPEKAVEMVDENTICVAAILGSTLNGEFEDVKRLNDLLIEKNKE 234 Seq ID #  13
UNIREF100_Q8LKR4     EVELKEVKLSDGYYVMDPEKAVEMVDENTICVAAILGSTLNGEFEDVKRLNDLLTEKNKE 234 Seq ID #  25
UNIREF100_Q9AT17     EVELKEVKLSDGYYVMDPEKAVEMVDENTICVAAILGSTLNGEFEDVKRLNDLLIEKNKE 234 Seq ID #  30
UNIREF100_P93369     EVELKEVKLSDGYYVMDPEKAVEMVDENTICVAAILGSTLNGEFEDVKRLNDLLIEKNKE 234 Seq ID #  14
UNIREF100_Q1I1D8     EVELKEVKLSEGYYVMDPAKAVEMVDENTICVAAILGSTLNGEFEDVKLLNDLLTEKNKE 234 Seq ID #  16
UNIREF100_Q42521     EVELKEVKLSEGYYVMDPQQAVDMVDENTICVAAILGSTLNGEFEDVKLLNDLLVEKNKE 234 Seq ID #   2
UNIREF100_Q94KK8     EVELKEVKLREGYYVMDPVQAVEMVDENTICVAAILGSTLNGEFEDVKLLNDLLIEKNKQ 234 Seq ID #  27
UNIREF100_Q9ZPS3     EVELKEVNLREDYYVMDPVKAVEMVDENTICVAAILGSTLTGEFEDVKLLNDLLVEKNKQ 234 Seq ID # 129
UNIREF100_Q6Q4I2     EVELKEVKLREGYYVMDPEKAVEMVDENTICVAAILGSTLTGEFEDVKLLNDLLVEKNKQ 234 Seq ID #  19
UNIREF100_A0EJ88     EVELKEVKLSDGYYVMDPEKAVQMVDENTICVAAILGSTLNGEFEDVKLLNDLLVEKNKS 234 Seq ID #   6
UNIREF100_A5BI27     EVELKEVKLRDGYYVMDPEKAVEMVDENTICVAAILGSTLNGEFEDVKLLNDLLVEKNKQ 228 Seq ID #   9
UNIREF100_Q6Q4I1     EVELKEVKLREGYYVMDPEKAVEMVDENTICVAAILGSTLTGEFEDVKLLNDLLVEKNKQ 234 Seq ID #  18
UNIREF100_O81101     EVELKEVKLSDGYYVMDPEKAVEMVDENTICVAAILGSTLNGEFEDVKRLNDLLIEKNKE 234 Seq ID #  12
UNIREF100_Q6ASV4     EVELKEVKLSDGYYVMDPAKAVDMVDENTICVAAILGSTLNGEFEDVKLLNDLLTKKNAE 234 Seq ID #  17
UNIREF100_Q42472     EVELKEVNLSEGYYVMDPDKAAEMVDENTICVAAILGSTLNGEFEDVKRLNDLLVKKNEE 233 Seq ID #   3
UNIREF100_P54767     EVELKEVKLKEGYYVMDPAKAVEIVDENTICVAAILGSTLTGEFEDVKLLNELLTKKNKE 235 Seq ID # 130
UNIREF100_A2XEB3     EVELKEVKLRDGYYVMDPEKAVDMVDENTICVAAILGSTLNGEFEDVKLLNDLLDKKNKE 234 Seq ID #   7
UNIREF100_Q84JC4     EVELKEVKLRDGYYVMDPEKAVDMVNENTICVAAILGSTLNGEFEDVKLLNDLLDKKNKE 234 Seq ID #  23
UNIREF100_Q944L6     EVELKEVNLSEGYYVMDPDKAAEMVDENTICVAAILGSTLNGEFEDVKRLNDLLVKKNEE 233 Seq ID #  26
UNIREF100_Q6Q4I3     EVELKEVKLSEGYYVMDPDKAAEMVDENTICVAAILGSTLNGEFEDVKRLNDLLVKKNEE 234 Seq ID #  20
UNIREF100_Q9LSH2     EVELKEVKLSEDYYVMDPAKAVEMVDENTICVAAILGSTLTGEFEDVKQLNDLLAEKNAE 233 Seq ID #  31
UNIREF100_Q8LFR4     EVELKEVKLSEDYYVMDPAKAVEMVDENTICVAAILGSTLTGEFEDVKQLNDLLAEKNAE 233 Seq ID #  24
UNIREF100_Q9ZPS4     EVELKEVKLREGYYVMDPDKAVEMVDENTICVVAILGSTLTGEFEDVKLLNDLLVEKNKK 234 Seq ID # 131
UNIREF100_A3AM39     EVELKEVKLSDGYYVMDPAKAVDMVDENTICVAAILGSTLNGEFEDVKLLNDLLTKKNAE 203 Seq ID #   8
UNIREF100_Q01J81     EVELKEVKLTEGCYVMDPVKAVDMVDENTICVAAILGSTLTGEFEDVRRLNDLLAAKNKR 236 Seq ID #  15
UNIREF100_Q9AR41     EVELKEVKLTEGCYVMDPVKAVDMVDENTICVAAILGSTLTGEFEDVRRLNDLLAAKNKR 236 Seq ID #  29
UNIREF100_A7P434     EVELKEVKLREGYYVMDPVKAVEMVDENTICVAAILGSTFNGEFEDVKLLNDLLTQKNKR 204 Seq ID #  11
                     *******:* :. ***** :*.::*:******.******:.**:***: ** **  **
```

FIG. 3E

```
LP ORF56 PROTEIN      TGFNVPIHVDAASGGFIAPFLHPELEWDFRLPLVKSINVSGHKYGLVYPGVGWVIWRSKD 297 Seq ID #   1
UNIREF100_Q7XZU7      TGWNVPIHVDAASGGFIAPFLQPELEWDFRLPLVKSINVSGHKYGLVYPGVGWVIWRSKD 297 Seq ID #  22
UNIREF100_Q9AQU4      TGWDVPIHVDAASGGFIAPFLYPELEWDFRLPLVKSINVSGHKYGLVYPGVGWVIWRSKE 298 Seq ID # 128
UNIREF100_Q6YSB2      TGWDVPIHVDAASGGFIAPFLYPELEWDFRLPLVKSINVSGHKYGLVYPGVGWVIWRSKE 294 Seq ID #  21
UNIREF100_A7P433      TGWDTPIHVDAASGGFIAPFLYPELEWDFRLPLVKSINVSGHKYGLVYAGIGWVVWRSKE 294 Seq ID #  10
UNIREF100_Q07346      TGWDTPIHVDAASGGFIAPFLYPELEWDFRLPLVKSINVSGHKYGLVYAGIGWVVWRNKD 294 Seq ID #   4
UNIREF100_O81102      TGWDTPIHVDAASGGFIAPFLYPELEWDFRLPLVKSINVSGHKYGLVYAGIGWAIWRNKE 294 Seq ID #  13
UNIREF100_Q8LKR4      TGWDTPIHVDAASGGFIAPFLYPELEWDFRLPLVKSINVSGHKYGLVYAGIGWAIWRNKE 294 Seq ID #  25
UNIREF100_Q9AT17      TGWDTPIHVDAASGGFIAPFLYPELEWDFRLPLVKSINVSGHKYGLVYAGIGWAIWRNKE 294 Seq ID #  30
UNIREF100_P93369      TGWDTPIHVDAASGEFIAPFLYPELEWDFRLPLVKSINVSGHKYGLVYAGIGWAIWRNKE 294 Seq ID #  14
UNIREF100_Q1I1D8      TGWDTPIHVDAASGGFIAPFLYPELEWDFRLPLVKSINVSGHKYGLVYAGIGWVVWRNKE 294 Seq ID #  16
UNIREF100_Q42521      TGWDTPIHVDAASGGFIAPFLYPELEWDFRLPLVKSINVSGHKYGLVYAGIGWVIWRNKE 294 Seq ID #   2
UNIREF100_Q94KK8      TGWNTPIHVDAASGGFIAPFLYPELEWDFRLPLVKSINVSGHKYGLVYAGIGWVIWRTKQ 294 Seq ID #  27
UNIREF100_Q9ZPS3      TGWDTPIHVDAASGGFIAPFLYPELEWDFRLPLVKSINVSGHKYGLVYAGIGWVVWRTKT 294 Seq ID # 129
UNIREF100_Q6Q4I2      TGWDTGIHVDAASGGFIAPFLYPELEWDFRLPLVKSINVSGHKYGLVYAGIGWVVWRTKS 294 Seq ID #  19
UNIREF100_A0EJ88      TGWDTPIHVDAASGGFIAPFIYPELEWDFRLPLVKSINVSGHKYGLVYAGIGWVIWRNKE 294 Seq ID #   6
UNIREF100_A5BT27      XGWDTPIHVDAASGGFIAPFLYPELEWDFRLPLVKSINVSGHKYGLVYAGIGWVVWRSKE 288 Seq ID #   9
UNIREF100_Q6Q4I1      TGWDTGNHVDAASGGFIAPFLYPELEWDFRLPLVKSINVSGHKYGLVYAGIGWVVWRTKS 294 Seq ID #  18
UNIREF100_O81101      TGWDTPIHVDAASGGFIAPFLYPELEWDFRLPLEKSINVSGHKYGLVYAGIGWAIWRNKE 294 Seq ID #  12
UNIREF100_Q6ASV4      TGWDTPIHVDAASGGFIAPFLYPELEWDFRLPLVKSINVSGHKYGLVYAGIGWCIWRSKE 294 Seq ID #  17
UNIREF100_Q42472      TGWNTPIHVDAASGGFIAPFIYPELEWDFRLPLVKSINVSGHKYGLVYAGIGWVVWRAAE 293 Seq ID #   3
UNIREF100_P54767      TGWETPIHVDAASGGFIAPFLWPDLEWDFRLPLVKSINVSGHKYGLVYAGVGWVIWRSKE 295 Seq ID # 130
UNIREF100_A2XEB3      TGWETPIHVDAASGGFIAPFLYPELEWDFRLPWVKSINVSGHKYGLVYAGIGWCIWRNKE 294 Seq ID #   7
UNIREF100_Q84U04      TGWETPIHVDAASGGFIAPFLYPELEWDFRLPWVKSINVSGHKYGLVYAGIGWCIWRNKE 294 Seq ID #  23
UNIREF100_Q944L6      TGWNTPIHVDAASGGFIAPFIYPELEWDFRLPLVKSINVSGHKYGLVYAGIGWVVWRAAE 293 Seq ID #  26
UNIREF100_Q6Q4I3      TGWNTPIHVDAASGGFIAPFIYPELEWDFRLPLVKSINVSGHKYGLVYAGIGWVVWRTQQ 294 Seq ID #  20
UNIREF100_Q9LSH2      TGWETPIHVDAASGGFIAPFLYPDLEWDFRLPWVKSINVSGHKYGLVYAGVGWVVWRTKD 293 Seq ID #  31
UNIREF100_Q8LFR4      TGWETPIHVDAASGGFIAPFLYPDLEWDFRLPWVKSINVSGHKYGLVYAGVGWVVWRTKD 293 Seq ID #  24
UNIREF100_Q9ZPS4      TGWDTPIHVDAASGGFIAPFLYPDLEWDFRLPLVKSINVSGHKYGLVYAGIGWVVWRTKT 294 Seq ID # 131
UNIREF100_A3AM59      TGWDTPIHVDAASGGFIAPFLYPELEWDFRLPLVKSINVSGHKYGLVYAGIGWCIWRSKE 263 Seq ID #   8
UNIREF100_Q01J81      TGWDTPIHVDAASGGFIAPFIYPELEWDFRLPLVKSINVSGHKYGLVYAGVGWVIWRNKE 296 Seq ID #  15
UNIREF100_Q9AR41      TGWDTPIHVDAASGGFIAPFIYPELEWDFRLPLVKSINVSGHKYGLVYAGVGWVIWRNKE 296 Seq ID #  29
UNIREF100_A7P434      TGWDTPIHVDAASGGFVAPFLYPELEWDFRLPLVKSINVSGHKYGLVYAGVGWAIWRSKE 264 Seq ID #  11
                       *::.   ******* *:***: *:*********   **************.*:** :**
```

FIG. 3F

```
IP ORF56 PROTEIN      DLPGELIFHINYLGTDQPTFTLNFSKGASQIIAQYYQLIRLGFEGYKHIMENCQANATAL 357 Seq ID #   1
UNIREF100_Q7XZU7      DLPEELIFHINYLGADQPTFTLNFSKGQ-QIIAQYYQLIRLGFEGYKHIMENCKLNAAVL 356 Seq ID #  22
UNIREF100_Q9AQU4      DLPEELIFHINYLGTDQPTFTLNFSKGSSQIIAQYYQLIRLGFEGYKNIMQNCMENTAIL 358 Seq ID # 128
UNIREF100_Q6YSB2      DLPEELIFHINYLGTDQPTFTLNFSKGSSQIIAQYYQLIRLGFEGYKNIMQNCMENTAIL 354 Seq ID #  21
UNIREF100_A7P433      DLPEELIFHINYLGADQPTFTLNFSKGSSQVIAQYYQLIRLGFEGYRNVMENCQENAMAL 354 Seq ID #  10
UNIREF100_Q07346      DLPDELIFHINYLGADQPTFTLNFSKGSSQVIAQYYQLIRLGYEGYKNVMENCQENASVL 354 Seq ID #   4
UNIREF100_O81102      DLPDELIFHINYLGADQPTFTLNFSKGSSQVIAQYYQLIRLGFEGYKNVMENCQENARVL 354 Seq ID #  13
UNIREF100_Q8LKR4      DLPDELIFHINYLGADQPTFTLNFSKGSSQVIAQYYQLIRLGFEGYKNVMENCQENARVL 364 Seq ID #  26
UNIREF100_Q9AT17      DLPDELIFHINYLGADQPTFTLNFSKGSSQVIAQYYQLIRLGFEGYKNVMENCQENARVL 354 Seq ID #  30
UNIREF100_P93369      DLPDELIFHINYLGADQPTFTLNFSKGSSQVIAQYYQLIRLGFEGYKNVMENCQENARVL 354 Seq ID #  14
UNIREF100_Q1I1D8      DLPEELIFHINYLGADQPTFTLNFSKGSSQVIAQYYQLIRLGFEGYRNVMENCHENAMVL 364 Seq ID #  16
UNIREF100_Q42521      DLPEELIFHINYLGADQPTFTLNFSKGSSQVIAQYYQLIRLGHEGYRNVMENCRENMIVL 354 Seq ID #   2
UNIREF100_Q94KK8      DLPEELIFHINYLGADQPTFTLNFSKGSSQVIAQYYQLIRLGYEGYRNVMENCRENAIVL 354 Seq ID #  27
UNIREF100_Q9ZPS3      DLPDELIFHINYLGADQPTFTLNFSKGSSQVIAQYYQLIRLGFEGYRNVMDNCRENMMVL 354 Seq ID # 129
UNIREF100_Q6Q4I2      DLPDELIFHINYLGADQPTFTLNFSKGSSQVIAQYYQLIRLGFEGYRNVMDNCRENMMVL 354 Seq ID #  19
UNIREF100_A0EJ88      DLPEELIFHINYLGADQPTFTLNFSKGSSQVIAQYYQLIRLGYEGYKNVMENCRDNMLVL 354 Seq ID #   6
UNIREF100_A5B127      DLPEELIFHINYLGADQPTFTLNFSKGSSQVIAQYYQLIRLGFEGYRNVMENCQENAMAL 348 Seq ID #   9
UNIREF100_Q6Q4T1      DLPDELIFHINYLGADQPTFTLNFSKGSSQVIAQYYQLIRLGFEGYRNVMDNCRENMMVL 354 Seq ID #  18
UNIREF100_O81101      DLPDELIFHINYLGADQPTFTLNFSKGSSQVIAQYYQLIRLGFEGYKNVMENCQENARVL 354 Seq ID #  12
UNIREF100_Q6ASV4      DLPEELIFHINYLGADQPTFTLNFSKGSSQVIAQYYQLIRLGFEGYKNIMENCQENAMVL 354 Seq ID #  17
UNIREF100_Q42472      DLPEELIFHINYLGADQPTFTLNFSKGSSQIIAQYYQLIRLGFEGYKNVMENCILNMVVL 353 Seq ID #   3
UNIREF100_P54767      DLPDELVFHINYLGSDQPTFTLNFSKGSYQIIAQYYQLIRLGFEGYKNVMKNCLSNAKVL 355 Seq ID # 130
UNIREF100_A2XEB3      DLPEELIFHINYLGADQPTFTLNFSKGSSQVIAQYYQLIRHGFEGYRNIMENCHENAMVL 354 Seq ID #   7
UNIREF100_Q84UC4      DLPEELIFHINYLGTDQPTFTLNFSKGSSQVIAQYYQLIRHGFEGYRNIMENCHLNAMVL 364 Seq ID #  23
UNIREF100_Q944L6      DLPEELIFHINYLGADQPTFTLNFSKGSSQIIAQYYQLIRLGFEGYKNVMENCIENMVVL 353 Seq ID #  26
UNIREF100_Q6Q413      DLPDELIFHINYLGADQPTFTLNFSKGSSQIIAQYYQLIRLGFEGYKNVMENCRENMVVL 354 Seq ID #  20
UNIREF100_Q9LSH2      DLPEELVFHINYLGADQPTFTLNFSKGSSQIIAQYYQFIRLGFEGYKNIMENCMDNARRL 353 Seq ID #  31
UNIREF100_Q8LFR4      DLPEELVFHINYLGADQPTFTLNFSKGSSQIIAQYYQFIRLGFEGYKNIMENCMDNARRL 353 Seq ID #  24
UNIREF100_Q9ZPS4      DLPDELIFHINYLGADQPTFTLNFSKGSSQVIAQYYQLIRLGFEGYRNVMDNCRENMMVL 354 Seq ID # 131
UNIREF100_A3AM69      DLPEELIFHINYLGADQPTFTLNFSKGSSQVIAQYYQLIRLGFEGYKNIMENCQENAMVL 323 Seq ID #   8
UNIREF100_Q01J81      DLPEELIFHINYLGADQPTFTLNFSKGSSQIIAQYYQFLRLGFEGYKSVMKNCMESARTL 356 Seq ID #  15
UNIREF100_Q9AR41      DLPEELIFHINYLGADQPTFTLNFSKGSSQIIAQYYQFLRLGFEGYKSVMKNCMESARTL 356 Seq ID #  29
UNIREF100_A7P434      ELPEELIFHINYLGGDEPTFTLNFSKGN-QVIAQYYQFLRMGFEGYKKVMSNCMESARIL 323 Seq ID #  11
                      :** **:******* *:*********  *:******::* *.***: :*.**  .   *
```

FIG. 4

```
LP ORF56 PROTEIN      EGAEDGVVTKKGVLDIEKEFAAACKDLVKNKKTGP----C------- 502 Seq ID #   1
UNIREF100_Q7XZU7      DGASKSAVDAA---------TEAFKDLAGKKKAGV----C------- 490 Seq ID #  22
UNIREF100_Q9AQU4      QSGDDGVVTKKSVLETEREIFAYWRDQVKKKQTGI----C------- 501 Seq ID # 128
UNIREF100_Q6YSB2      QSGDDGVVTKKSVLETEREIFAYWRDQVKKKQTGI----C------- 497 Seq ID #  21
UNIREF100_A7P433      --KQNGTILKKSVIETQREITDAWKKFVMAKKTNG---VC------- 495 Seq ID #  10
UNIREF100_Q07346      --ANGSEVHKKTDSEVQLEMITAWKKFVEEKKKKT-NRVC------- 500 Seq ID #   4
UNIREF100_O81102      --ANGSGVHKKTDREVQLEITTAWKKFVADKKKKT-NGVC------- 496 Seq ID #  13
UNIREF100_Q8LKR4      --ANGSGVHKKTDREVQLEITTAWKKFVADKKKKT-NGVC------- 496 Seq ID #  25
UNIREF100_Q9AT17      --ANGSGVHKKTDREVQLEITAAWKKFVADKKKKT-NGVC------- 496 Seq ID #  30
UNIREF100_P93369      --ANGSGVHKKTDREVQLEITTAWKKFVADKKKKT-NGVC------- 496 Seq ID #  14
UNIREF100_Q1I1D8      --EQNGRNGKKTEIETQREVTTYWRKFVSERKANNKNKIC------- 494 Seq ID #  16
UNIREF100_Q42521      KSDNLMVTVKKSDIDKQRDIITGWKKFVADRKKTS--GIC------- 502 Seq ID #   2
UNIREF100_Q94KK8      -----VKNGKKFELEVQREVTKYWKKFVLARKAPV-C---------- 491 Seq ID #  27
UNIREF100_Q9ZPS3      -----VNGVKKTPEETQREVTAYWKKLLETKKTNK-NTIC------- 493 Seq ID # 129
UNIREF100_Q6Q4I2      -----ANGVKKTEEETTREVTAYWKKFVEAKKSNK-NRIC------- 493 Seq ID #  19
UNIREF100_ACEJ88      --AVAAGKEKKDVQNETREIITAWRKLVVQRKKLN--GVC------- 499 Seq ID #   6
UNIREF100_A5BI27      --KQNGTILKKSVIETQREITDAWKKFVMAKKTNG---VC------- 489 Seq ID #   9
UNIREF100_Q6Q4I1      -----AKVVKQTEEETTREVTAYWKKFVETKKTNQ-NKIC------- 493 Seq ID #  18
UNIREF100_O81101      --ANGSGVHKKTDREVQLEITTAWLKFVADKKKKT-NGVC------- 496 Seq ID #  12
UNIREF100_Q6ASV4      -------SASEREMEKQREVISLWKRAVLAKKKTN--GVC------- 492 Seq ID #  17
UNIREF100_Q42472      ------VKEKKMEKEILMEVIVGWRKFVKERKKMN--GVC------- 494 Seq ID #   3
UNIREF100_P54767      DKGDGLHHFHMDTVETQKDLIKHWRKIAGKKTSGV----C------- 502 Seq ID # 130
UNIREF100_A2XEB3      -------VAKKSELETQRSVTEAWKKFVLAKR-TN--GVC------- 492 Seq ID #   7
UNIREF100_Q84J04      -------VAKKSELETQRSVTEAWKKFVLAKR-TN--GVC------- 492 Seq ID #  23
UNIREF100_Q944L6      ------VKEKKMEKEILMEVIVGWRKFVKERKKMN--GVC------- 494 Seq ID #  26
UNIREF100_Q6Q4I3      ------VKGKKVDRDVLMEVIVGWRKFVKDRKKMN--GVC------- 494 Seq ID #  20
UNIREF100_Q9LSH2      -SGDDEEVKVKTAKMSLEDITKYWKRLVEHKRNIV----C------- 494 Seq ID #  31
UNIREF100_Q8LFR4      -SGDDEEVKVKTAKMSLEDITKYWKRLVEHKRNIV----C------- 494 Seq ID #  24
UNIREF100_Q9ZPS4      -----VNGVKKTPEETQREVTAYWKKFVDTKTDKN-GVPLVASTPNQ 500 Seq ID # 131
UNIREF100_A3AM59      -------SASEREMEKQREVISLWKRAVLAKKKTN--GVC------- 461 Seq ID #   8
UNIREF100_Q01J81      TAGE------EASIRVVKSEAVPVRKSVPLVAGKT-KGVC------- 500 Seq ID #  15
UNIREF100_Q9AR41      TAGE------EASIRVVKSEAVPVRKSVPLVAGKT-KGVC------- 500 Seq ID #  29
UNIREF100_A7P434      KAGEGTLHIPAASVHWKHDKPETVDTQVPIMDGKT-KGVC------- 476 Seq ID #  11
```

FIG. 10A

| | | | |
|---|---|---|---|
| Q84UC4 | MVLSKAVSESD--MSVHS--IFASRYVRASLPR---------------------YRMPEN | 35 | Seq ID # 23 |
| AAP79441 | MVLSKAVSESD--MSVHS--IFASRYVRASLPR---------------------YRMPEN | 35 | Seq ID # 111 |
| A2XEB3 | MVLSKAVSESD--MSVHS--IFASRYVRASLPR---------------------YRMPEN | 35 | Seq ID # 7 |
| Q6ASV4 | MVLSHGVSGSD--ESVHS--IFASRYVRTSLPR---------------------FRMPEQ | 35 | Seq ID # 17 |
| AAM47304 | MVLSHGVSGSD--ESVHS--IFASRYVRTSLPRHARSPLSRAPLAPIDSVIDWEFRMPEQ | 56 | Seq ID # 124 |
| AAT77842 | MVLSHGVSGSD--ESVHS--IFASRYVRTSLPR---------------------FRMPEQ | 35 | Seq ID # 126 |
| A3AM59 | ------------------------------------------------------MPEQ | 4 | Seq ID # 8 |
| Q7XZU7 | MVVTVAATCPDTAEILHS-TIFASRYVRDQLPR---------------------YRMPEN | 38 | Seq ID # 22 |
| AAP46640 | MVVTVAATGPDTAEILHS-TIFASRYVRDQLPR---------------------YRMPEN | 38 | Seq ID # 127 |
| LpORF | MVLTVAATAADTAEPLNS-TFFATRYVRDQLPR---------------------YRMPEN | 38 | Seq ID # 1 |
| Q6YSB2 | MVLSHASSGRDDAVRCT----FATRYACETLPR---------------------FRMPEQ | 35 | Seq ID # 21 |
| XP_482841 | MVLSHASSCRDDAVRCT----FATRYACETLPR---------------------FRMPEQ | 35 | Seq ID # 99 |
| AAL83983 | ---------------------------------------------------------- | | Seq ID # 121 |
| XP_482840 | MVVSVAATDSDTAQPVQYSTFFASRYVRDPLPR---------------------FRMPEQ | 39 | Seq ID # 113 |
| Q9AQU4 | MVVSVAATDSDTAQPVQYSTFFASRYVRDPLPR---------------------FRMPEQ | 39 | Seq ID # 128 |
| XP_462650 | MALSTAQTC----ESMHS-SIFASRYVRTALPR---------------------FRMPEK | 34 | Seq ID # 97 |
| Q01J81 | MVLTHVEAVEECSEAAAA--VFASRYVQDPVPR---------------------YELCER | 37 | Seq ID # 15 |
| XP_462654 | MVLTHVEAVEECSEAAAA--VFASRYVQDPVPR---------------------YELCER | 37 | Seq ID # 123 |
| Q9AR41 | MVLTHVEAVEECSEAAAA--VFASRYVQDPVPR---------------------YELCER | 37 | Seq ID # 28 |
| BAB32871 | MVLTHVEAVEECSEAAAA--VFASRYVQDPVPR---------------------YELCER | 37 | Seq ID # 125 |

FIG. 10B

| | | | |
|---|---|---|---|
| Q84UC4 | SIPKEAAYQIINDELMLDGNPRLNLASFVTTWMEPECDKLIMAAINKNYVDMDEYPVTTE | 95 | Seq ID # 23 |
| AAP79441 | SIPKEAAYQIINDELMLDGNPRLNLASFVTTWMEPECDKLIMAAINKNYVDMDEYPVTTE | 95 | Seq ID # 111 |
| A2XEB3 | SIPKEAAYQIINDELMLDGNPRLNLASFVTTWMEPECDKLIMAAINKNYVDMDEYPVTTE | 95 | Seq ID # 7 |
| Q6ASV4 | SIPKEAAYQIINDELMLDGNPRLNLASFVTTWMEPECDKLIQASVNKNYVDMDEYPVTTE | 95 | Seq ID # 17 |
| AAM47304 | SIPKEAAYQIINDELMLDGNPRLNLASFVTTWMEPECDKLIQASVNKNYVDMDEYPVTTE | 11 | Seq ID # 1246 |
| AAT77842 | SIPKEAAYQIINDELMLDGNPRLNLASFVTTWMEPECDKLIQASVNKNYVDMDEYPVTTE | 95 | Seq ID # 126 |
| A3AM59 | SIPKEAAYQIINDELMLDGNPRLNLASFVTTWMEPECDKLIQASVNKNYVDMDEYPVTTE | 64 | Seq ID # 8 |
| Q7XZU7 | SIPKEAAYQIISDELMLDGNPRLNLASFVTTWMEPECGKLIMDSVNKNYVDMDEYPVTTE | 98 | Seq ID # 22 |
| AAP46640 | SIPKEAAYQIISDELMLDGNPRLNLASFVTTWMEPECGKLIMDSVNKNYVDMDEYPVTTE | 98 | Seq ID # 127 |
| LpORF | SIPKEAAYQIISDELMLDGNPRLNLASFVTTRMEPEVGKLIMDSVNKNYVDMDEYPVTTE | 98 | Seq ID # 1 |
| Q6YSB2 | SIPREAAYQIINDELMLDGNPRLNLASFVTTWMEPECDKLIMDSVNKNYVDMDEYPVTTE | 95 | Seq ID # 21 |
| XP_482841 | SIPREAAYQIINDELMLDGNPRLNLASFVTTWMEPECDKLIMDSVNKNYVDMDEYPVTTE | 95 | Seq ID # 99 |
| AAL83983 | ------------------------------------------------------------ | | Seq ID # 121 |
| XP_482840 | SIPREAAYQIINDELMLDGNPRLNLASFVTTWMEPECDKLIMDSVNKNYVDMDEYPVTTE | 99 | Seq ID # 113 |
| Q9AQU4 | SIPREAAYQIINDELMLDGNPRLNLASFVTTWMEPECDKLIMDSVNKNYVDMDEYPVTTE | 99 | Seq ID # 128 |
| XP_462650 | SIPKDAAYQIINDELMLDGNPRLNLASFVTTWMEPECDKLMMAAINKNYVDMDEYPVTTE | 94 | Seq ID # 97 |
| Q01J81 | SISKDAAYQIVHDELLLDSSPRLNLASFVTTWMEPECDRLILEAINKNYADMDEYPVTTE | 97 | Seq ID # 15 |
| XP_462654 | SISKDAAYQIVHDELLLDSSPRLNLASFVTTWMEPECDRLILEAINKNYADMDEYPVTTE | 97 | Seq ID # 123 |
| Q9AR41 | SISKDAAYQIVHDELLLDSSPRLNLASFVTTWMEPECDRLILEAINKNYADMDEYPVTTE | 97 | Seq ID # 28 |
| BAB32871 | SISKDAAYQIVHDELLLDSSPRLNLASFVTTWMEPECDRLILEAINKNYADMDEYPVTTE | 97 | Seq ID # 125 |

FIG. 10C

| | | | |
|---|---|---|---|
| Q84U04 | LQNRCVNMIAHLFHAPLGEDETAVGVGTVGSSEAIMLAGLAFKRRWQNKRKAEGKPFDKP | 155 | Seq ID # 23 |
| AAP79441 | LQNRCVNMIAHLFHAPLGEDETAVGVGTVGSSEAIMLAGLAFKRRWQNKRKAEGKPFDKP | 155 | Seq ID # 111 |
| A2XEB3 | LQNRCVNMIAHLFHAPLGEDETAVGVGTVGSSEAIMLAGLAFKRRWQNKRKAEGKPFDKP | 155 | Seq ID # 7 |
| Q6ASV4 | LQNRCVNMIAHLFNAPLGDSETAVGVGTVGSSEAIMLAGLAFKRRWQNKMKAAGKPCDKP | 155 | Seq ID # 17 |
| AAM47304 | LQNRCVNMIAHLFNAPLGDSETAVGVGTVGSSEAIMLAGLAFKRRWQNKMKAAGKPCDKP | 176 | Seq ID # 124 |
| AAT77842 | LQNRCVNMIAHLFNAPLGDSETAVGVGTVGSSEAIMLAGLAFKRRWQNKMKAAGKPCDKP | 155 | Seq ID # 126 |
| A3AM59 | LQNRCVNMIAHLFNAPLGDSETAVGVGTVGSSEAIMLAGLAFKRRWQNKMKAAGKPCDKP | 124 | Seq ID # 8 |
| Q7XZU7 | LQDRCVNMIAHLFNAPIGEDETAIGVSTVGSSEAIMLAGLAFKRKWANKMKEQGKPCDKP | 158 | Seq ID # 22 |
| AAP46640 | LQDRCVNMIAHLFNAPIGEDETAIGVSTVGSSEAIMLAGLAFKRKWANKMKEQGKPCDKP | 158 | Seq ID # 127 |
| LpORF | LQNRCVNMIAHLFNAPIKEEETAIGVATVGSSEAIMLAGLAFKRKWANKRKEEGKPYDKP | 158 | Seq ID # 1 |
| Q6YSB2 | LQNRCVNMIAHLFNAPIKEDETAIGVGTVGSSEAIMLAGLAFKRKWQNKRKEQGKPCDKP | 155 | Seq ID # 21 |
| XP_482841 | LQNRCVNMIAHLFNAPIKEDETAIGVGTVGSSEAIMLAGLAFKRKWQNKRKEQGKPCDKP | 155 | Seq ID # 99 |
| AAL83983 | ------------------------------------------------------------ | | Seq ID # 121 |
| XP_482840 | LQNRCVNMIAHLFNAPIKEDETAIGVGTVGSSEAIMLAGLAFKRKWQNKRKEQGKPCDKP | 159 | Seq ID # 113 |
| Q9AQU4 | LQNRCVNMIAHLFNAPIKEDETAIGVGTVGSSEAIMLAGLAFKRKWQNKRKEQGKPCDKP | 159 | Seq ID # 128 |
| XP_462650 | LQNRCVNMIAHLFNAPIGDDETAVGVGTVGSSEAIMLAGLAFKRKWQNRMKAEGKPHDKP | 154 | Seq ID # 97 |
| Q01J81 | LQNRCVNIIARLFNAPVGDGEKAVGVGTVGSSEAIMLAGLAFKRRWQNRRKAAGKPHDKP | 157 | Seq ID # 15 |
| XP_462654 | LQNRCVNIIARLFNAPVGDGEKAVGVGTVGSSEAIMLAGLAFKRRWQNRRKAAGKPHDKP | 157 | Seq ID # 123 |
| Q9AR41 | LQNRCVNIIARLFNAPVGDGEKAVGVGTVGSSEAIMLAGLAFKRRWQNRRKAAGKPHDKP | 157 | Seq ID # 28 |
| BAB32871 | LQNRCVNIIARLFNAPVGDGEKAVGVGTVGSSEAIMLAGLAFKRRWQNRRKAAGKPHDKP | 157 | Seq ID # 125 |

FIG. 10D

| | | | |
|---|---|---|---|
| Q84U04 | NIIIGANVQVCWEKFARYFEVELKEVKLRDGYYVMDPEKAVDMVNENTICVAAILGSTLN | 215 | Seq ID # 23 |
| AAP79441 | NIIIGANVQVCWEKFARYFEVELKEVKLRDGYYVMDPEKAVDMVNENTICVAAILGSTLN | 215 | Seq ID # 111 |
| A2XEB3 | NIIIGANVQVCWEKFARYFEVELKEVKLRDGYYVMDPEKAVDMVDENTICVAAILGSTLN | 215 | Seq ID # 7 |
| Q6ASV4 | NIVIGANVQVCWEKFARYFEVELKEVKLSDGYYVMDPAKAVDMVDENTICVAAILGSTLN | 215 | Seq ID # 17 |
| AAM47304 | NIVIGANVQVCWEKFARYFEVELKEVKLSDGYYVMDPAKAVDMVDENTICVAAILGSTLN | 236 | Seq ID # 124 |
| AAT77842 | NIVIGANVQVCWEKFARYFEVELKEVKLSDGYYVMDPAKAVDMVDENTICVAAILGSTLN | 215 | Seq ID # 126 |
| A3AM59 | NIVIGANVQVCWEKFARYFEVELKEVKLSDGYYVMDPAKAVDMVDENTICVAAILGSTLN | 184 | Seq ID # 8 |
| Q7XZU7 | NIVIGANVQVCWEKFARYFEVELKEVKLTEGYYVMDPKKAVEMVDENTICVAAILGSTLT | 218 | Seq ID # 22 |
| AAP46640 | NIVIGANVQVCWEKFARYFEVELKEVKLTEGYYVMDPKKAVEMVDENTICVAAILGSTLT | 218 | Seq ID # 127 |
| LpORF | NIVIGANVQVCWEKFARYFEVELKEVKLTEGYYVMDPLKAVEMVDENTICVAAILGSTLT | 218 | Seq ID # 1 |
| Q6YSB2 | NIVIGANVQVCWEKFARYFEVELKEVKLSEGYYVMDPVKAVEMVDENTICVAAILGSTLT | 215 | Seq ID # 21 |
| XP_482841 | NIVIGANVQVCWEKFARYFEVELKEVKLSEGYYVMDPVKAVEMVDENTICVAAILGSTLT | 215 | Seq ID # 99 |
| AAL83983 | ------------------------------------------------------------ | | Seq ID # 121 |
| XP_482840 | NIVIGANVQVCWEKFARYFEVELKEVKLSEGYYVMDPVKAVEMVDENTICVAAILGSTLT | 219 | Seq ID # 113 |
| Q9AQU4 | NIVIGANVQVCWEKFARYFEVELKEVKLSEGYYVMDPVKAVEMVDENTICVAAILGSTLT | 219 | Seq ID # 128 |
| XP_462650 | NIVIGANVQVCWEKFARYFEVELKEVKLTQGYYVMNPEKAVEMVDENTICVAAILGSTLN | 214 | Seq ID # 97 |
| Q01J81 | NIVIGANVQVCWEKFARYFEVELKEVKLTEGCYVMDPVKAVDMVDENTICVAAILGSTLT | 217 | Seq ID # 15 |
| XP_462654 | NIVIGANVQVCWEKFARYFEVELKEVKLTEGCYVMDPVKAVDMVDENTICVAAILGSTLT | 217 | Seq ID # 123 |
| Q9AR41 | NIVIGANVQVCWEKFARYFEVELKEVKLTEGCYVMDPVKAVDMVDENTICVAAILGSTLT | 217 | Seq ID # 28 |
| BAB32871 | NIVIGANVQVCWEKFARYFEVELKEVKLTEGCYVMDPVKAVDMVDENTICVAAILGSTLT | 217 | Seq ID # 125 |

FIG. 10E

```
Q84U04       GEFEDVKLLNDLLDKKNKETGWETPIHVDAASGGFIAPFLYPELEWDFRLPWVKSINVSG 275 Seq ID #  23
AAP79441     GEFEDVKLLNDLLDKKNKETGWETPIHVDAASGGFIAPFLYPELEWDFRLPWVKSINVSG 275 Seq ID # 111
A2XEB3       GEFEDVKLLNDLLDKKNKETGWETPIHVDAASGGFIAPFLYPELEWDFRLPWVKSINVSG 275 Seq ID #   7
Q6ASV4       GEFEDVKLLNDLLTKKNAETGWDTPIHVDAASGGFIAPFLYPELEWDFRLPLVKSINVSG 275 Seq ID #  17
AAM47304     GEFEDVKLLNDLLTKKNAETGWDTPIHVDAASGGFIAPFLYPELEWDFRLPLVKSINVSG 296 Seq ID # 124
AAT77842     GEFEDVKLLNDLLTKKNAETGWDTPIHVDAASGGFIAPFLYPELEWDFRLPLVKSINVSG 275 Seq ID # 126
A3AM59       GEFEDVKLLNDLLTKKNAETGWDTPIHVDAASGGFIAPFLYPELEWDFRLPLVKSINVSG 244 Seq ID #   8
Q7XZU7       GEYEDVKLLNDLLVEKNKETGWNVPIHVDAASGGFIAPFLQPELEWDFRLPLVKSINVSG 278 Seq ID #  22
AAP46640     GEYEDVKLLNDLLVEKNKETGWNVPIHVDAASGGFIAPFLQPELEWDFRLPLVKSINVSG 278 Seq ID # 127
LpORF        GEYEDVKLLNDLLVEKNKKTGENVPIHVDAASGGFIAPFLHPELEWDFRLPLVKSINVSG 278 Seq ID #   1
Q6YSB2       GEFEDVKLLNNLLTEKNKETGWDVPIHVDAASGGFIAPFLYPELEWDFRLPLVKSINVSG 275 Seq ID #  21
XP_482841    GEFEDVKLLNNLLTEKNKETGWDVPIHVDAASGGFIAPFLYPELEWDFRLPLVKSINVSG 275 Seq ID #  99
AAL83983     GEFEDVKLLNNLLTEKNKETGWDVPIHVDAASGGFIAPFLYPELEWDFRLPLVKSINVSG 60  Seq ID # 121
XP_482840    GEFEDVKLLNNLLTEKNKETGWDVPIHVDAASGGFIAPFLYPELEWDFRLPLVKSINVSG 279 Seq ID # 113
Q9AQU4       GEFEDVKLLNNLLTEKNKETGWDVPIHVDAASGGFIAPFLYPELEWDFRLPLVKSINVSG 279 Seq ID # 128
XP_462650    GEFEDVKMLNDLLTAKNAETGWNTPIHVDAASGGFIAPFIYPELEWDFRLPLVKSINVSG 274 Seq ID #  97
Q01J81       GEFEDVRRLNDLLAAKNKRTGWDTPIHVDAASGGFIAPFIYPELEWDFRLPLVKSINVSG 277 Seq ID #  15
XP_462654    GEFEDVRRLNDLLAAKNKRTGWDTPIHVDAASGGFIAPFIYPELEWDFRLPLVKSINVSG 277 Seq ID # 123
Q9AR41       GEFEDVRRLNDLLAAKNKRTGWDTPIHVDAASGGFIAPFIYPELEWDFRLPLVKSINVSG 277 Seq ID #  28
BAB32871     GEFEDVRRLNDLLAAKNKRTGWDTPIHVDAASGGFIAPFIYPELEWDFRLPLVKSINVSG 277 Seq ID # 125
             **:***: **:**  ** .**::.***************: ********** ********
```

FIG. 10F

```
Q84U04       HKYGLVYAGIGWCIWRNKEDLPEELIFHINYLGTDQPIFTLNFSKGSSQVIAQYYQLIRH 335 Seq ID #  23
AAP79441     HKYGLVYAGIGWCIWRNKEDLPEELIFHINYLGTDQPIFTLNFSKGSSQVIAQYYQLIRH 335 Seq ID # 111
A2XEB3       HKYGLVYAGIGWCIWRNKEDLPEELIFHINYLGADQPIFTLNFSKGSSQVIAQYYQLIRH 335 Seq ID #   7
Q6ASV4       HKYGLVYAGIGWCIWRSKEDLPEELIFHINYLGADQPIFTLNFSKGSSQVIAQYYQLIRL 335 Seq ID #  17
AAM47304     HKYGLVYAGIGWCIWRSKEDLPEELIFHINYLGADQPIFTLNFSKGSSQVIAQYYQLIRL 356 Seq ID # 124
AAT77842     HKYGLVYAGIGWCIWRSKEDLPEELIFHINYLGADQPIFTLNFSKGSSQVIAQYYQLIRL 335 Seq ID # 126
A3AM59       HKYGLVYAGIGWCIWRSKEDLPEELIFHINYLGADQPIFTLNFSKGSSQVIAQYYQLIRL 304 Seq ID #   8
Q7XZU7       HKYGLVYPGVGWVIWRSKDDLPEELIFHINYLGADQPIFTLNFSKGQ-QIIAQYYQLIRL 337 Seq ID #  22
AAP46640     HKYGLVYPGVGWVIWRSKDDLPEELIFHINYLGADQPIFTLNFSKGQ-QIIAQYYQLIRL 337 Seq ID # 127
LpORF        HKYGLVYPGVGWVIWRSKDDLPGELIFHINYLGTDQPIFTLNFSKGASQIIAQYYQLIRL 338 Seq ID #   1
Q6YSB2       HKYGLVYPGVGWVIWRSKEDLPEELIFHINYLGTDQPIFTLNFSKGSSQIIAQYYQLIRL 335 Seq ID #  21
XP_482841    HKYGLVYPGVGWVIWRSKEDLPEELIFHINYLGTDQPIFTLNFSKGSSQIIAQYYQLIRL 335 Seq ID #  99
AAL83983     HKYGLVYPGVGWVIWRSKEDLPEELIFHINYLGTDQPIFTLNFSKGSSQIIAQYYQLIRL 120 Seq ID # 121
XP_482840    HKYGLVYPGVGWVIWRSKEDLPEELIFHINYLGTDQPIFTLNFSKGSSQIIAQYYQLIRL 339 Seq ID # 113
Q9AQU4       HKYGLVYPGVGWVIWRSKEDLPEELIFHINYLGTDQPIFTLNFSKGSSQIIAQYYQLIRL 339 Seq ID # 128
XP_462650    HKYGLVYAGVGWVIWRNKEDLPDELIFHINYLGADQPIFTLNFSKGSNQIIAQYYQLIRL 334 Seq ID #  97
Q01J81       HKYGLVYAGVGWVIWRNKEDLPEELIFHINYLGADQPIFTLNFSKGSSQIIAQYYQFLRL 337 Seq ID #  15
XP_462654    HKYGLVYAGVGWVIWRNKEDLPEELIFHINYLGADQPIFTLNFSKGSSQIIAQYYQFLRL 337 Seq ID # 123
Q9AR41       HKYGLVYAGVGWVIWRNKEDLPEELIFHINYLGADQPIFTLNFSKGSSQIIAQYYQFLRL 337 Seq ID #  28
BAB32871     HKYGLVYAGVGWVIWRNKEDLPEELIFHINYLGADQPIFTLNFSKGSSQIIAQYYQFLRL 337 Seq ID # 125
             *******.*:** ***.*:*** **********:***********  *:******::*
```

FIG. 10G

```
Q84U04        GFEGYRNIMENCHENAMVLKEGLVKTGRFDIVSKDEGVPLVAFSLKDRSRHDEFEISDML 395 Seq ID #  23
AAP79441      GFEGYRNIMENCHENAMVLKEGLVKTGRFDIVSKDEGVPLVAFSLKDRSRHDEFEISDML 395 Seq ID # 111
A2XEB3        GFEGYRNIMENCHENAMVLKEGLVKTGRFDIVSKDEGVPLVAFSLKDRSRHDEFEISDML 395 Seq ID #   7
Q6ASV4        GFEGYKNIMENCQENAMVLKQGLEKTGRFNIVSKDNGVPLVAFSLKDSARHNEFEISDFL 395 Seq ID #  17
AAM47304      GFEGYKNIMENCQENAMVLKQGLEKTGRFNIVSKDNGVPLVAFSLKDSARHNEFEISDFL 416 Seq ID # 124
AAT77842      GFEGYKNIMENCQENAMVLKQGLEKTGRFNIVSKDNGVPLVAFSLKDSARHNEFEISDFL 395 Seq ID # 126
A3AM59        GFEGYKNIMENCQENAMVLKQGLEKTGRFNIVSKDNGVPLVAFSLKDSARHNEFEISDFL 364 Seq ID #   8
Q7XZU7        GFEGYKHIMENCKLNAAVLKEGIDATGRFDVLSKADGVPLVAIRLKDSTNFSVEDISENL 397 Seq ID #  22
AAP46640      GFEGYKHIMENCKLNAAVLKEGIDATGRFDVLSKADGVPLVAIRLKDSTNFSVEDISENL 397 Seq ID # 127
LpORF         GFEGYKIIMENCQANATALREGLEATGRFDILSKEDGVPLVAIRLKDSSKFSVEDISENL 398 Seq ID #   1
Q6YSB2        GFEGYKNIMQNCMENTAILREGIEATGRFEILSKEAGVPLVAFSLKDSGRYTVEDISEHL 395 Seq ID #  21
XP_482841     GFEGYKNIMQNCMENTAILREGIEATGRFEILSKEAGVPLVAFSLKDSGRYTVEDISEHL 395 Seq ID #  99
AAL83983      GFEGYKNIMQNCMETPAILREGIEATGRFEILSKEAGVPLVAFSLKASGRYTVEDISEHL 180 Seq ID # 121
XP_482840     GFEGYKNIMQNCMENTAILREGIEATGRFEILSKEAGVPLVAFSLKDSGRYTVEDISEHL 399 Seq ID # 113
Q9AQU4        GFEGYKNIMQNCMENTAILREGIEATGRFEILSKEAGVPLVAFSLKDSGRYTVEDISEHL 399 Seq ID # 128
XP_462650     GFEGYKDIMQNCRDNATVIREGTEKTGHFDVVSKDSGVPLVAFSLKDSSRYTVEEVAESL 394 Seq ID #  97
Q0IJ81        GFEGYKSVMKNCMESARTLREGLEKTGRFEIISKEEGVPLVAFTEKDGAGAQAERLSSGL 397 Seq ID #  15
XP_462654     GFEGYKSVMKNCMESARTLREGLEKTGRFEIISKEEGVPLVAFTEKDGAGAQAERLSSGL 397 Seq ID # 123
Q9AR41        GFEGYKSVMKNCMESARTLREGLEKTGRFEIISKEEGVPLVAFTEKDGAGAQAERLSSGL 397 Seq ID #  28
BAB32871      GFEGYKSVMKNCMESARTLREGLEKTGRFEIISKEEGVPLVAFTEKDGAGAQAERLSSGL 397 Seq ID # 125
              *****: :*:**  ..  *::*:  **:* ::**  ******: :*        * ::. *
```

FIG. 10H

```
Q84U04        RRFGWIVPAYTMPPDAQHVTVLRVVIREDFSRTLAERLVLDIEKVMYQLDALPSRLMPPV 455 Seq ID #  23
AAP79441      RRFGWIVPAYTMPPDAQHVTVLRVVIREDFSRTLAERLVLDIEKVMYQLDALPSRLMPPV 455 Seq ID # 111
A2XEB3        RRFGWIVPAYTMPPDAQHVTVLRVVIREDFSRTLAERLVLDIEKVMYQLDALPSRLMPPV 455 Seq ID #   7
Q6ASV4        RRFGWIVPAYTMPPDAQHVTVLRVVIREDFSRTLAERLVLDVEKVLHELDALPARVVANG 455 Seq ID #  17
AAM47304      RRFGWIVPAYTMPPDAQHVTVLRVVIREDFSRTLAERLVLDVEKVLHELDALPARVVANG 476 Seq ID # 124
AAT77842      RRFGWIVPAYTMPPDAQHVTVLRVVIREDFSRTLAERLVLDVEKVLHELDALPARVVANG 455 Seq ID # 126
A3AM59        RRFGWIVPAYTMPPDAQHVTVLRVVIREDFSRTLAERLVLDVEKVLHELDALPARVVANG 424 Seq ID #   8
Q7XZU7        RRFGWIVPAYTMPADAEHVAVLRIVIREDFNRSLAQRLLADINKIICELDAHAVHAIKLS 457 Seq ID #  22
AAP46640      RRFGWIVPAYTMPADAEHVAVLRIVIREDFNRSLAQRLLADINKIICELDAHAVHAIKLS 457 Seq ID # 127
LpORF         RRFGWIVPAYTMPADAEHVAVLRVVIREDFNRSLSQRLLADINRVVQELDAHAVHAIKMT 458 Seq ID #   1
Q6YSB2        RRFGWIVPAYTMPANAEHVAVLRVVIREDFSRSLAERLVSDIVKILHELDAHSAQVLKIS 455 Seq ID #  21
XP_482841     RRFGWIVPAYTMPANAEHVAVLRVVIREDFSRSLAERLVSDIVKILHELDAHSAQVLKIS 455 Seq ID #  99
AAL83983      RRFGWIVPAYTMPANAEHVAILRVVIREDFSRSLAERLVSDIVKILHELDAHSAQVLKIS 240 Seq ID # 121
XP_482840     RRFGWIVPAYTMPANAEHVAVLRVVIREDFSRSLAERLVSDIVKILHELDAHSAQVLKIS 459 Seq ID # 113
Q9AQU4        RRFGWIVPAYTMPANAEHVAVLRVVIREDFSRSLAERLVSDIVKILHELDAHSAQVLKIS 459 Seq ID # 128
XP_462650     RRFGWIVPAYTMPADAEHVAVMRVVIREDFSRGLAERLLTDLIKTVADMDAHAVKKAAAH 454 Seq ID #  97
Q0IJ81        RRYGWIVPAYTMPAALEHMTVLRVVVREDFGRPLAERFLSHVRMALDEMDLAARAPVPRV 457 Seq ID #  15
XP_462654     RRYGWIVPAYTMPAALEHMTVLRVVVREDFGRPLAERFLSHVRMALDEMDLAARAPVPRV 457 Seq ID # 123
Q9AR41        RRYGWIVPAYTMPAALEHMTVVRVVVREDFGRPLAERFLSHVRMALDEMDLAARAPVPRV 457 Seq ID #  28
BAB32871      RRYGWIVPAYTMPAALEHMTVVRVVVREDFGRPLAERFLSHVRMALDEMDLAARAPVPRV 457 Seq ID # 125
              **:*********.  :*::::*:*:**:*.* *::*:: .:    : ::*   .
```

FIG. 10I

```
Q84U04          PPAPLL--------VVAKKSELETQRSVTEAWKKFVLAKR-TNGVC- 492 Seq ID #  23
AAP79441        PPAPLL--------VVAKKSELETQRSVTEAWKKFVLAKR-TNGVC- 492 Seq ID # 111
A2XEB3          PPAPLL--------VVAKKSELETQRSVTEAWKKFVLAKR-TNGVC- 492 Seq ID #   7
Q6ASV4          GDAAAA--------SASER-EMEKQREVISLWKRAVLAKKKTNGVC- 492 Seq ID #  17
AAM47304        GDAAAA--------SASER-EMEKQREVISLWKRAVLAKKKTNGVC- 513 Seq ID # 124
AAT77842        GDAAAA--------SASER-EMEKQREVISLWKRAVLAKKKTNGVC- 492 Seq ID # 126
A3AM59          DNPAAA--------SASER-EMEKQREVISLWKRAVLAKKKTNGVC- 461 Seq ID #   8
Q7XZU7          TAAAG--GDGASKSAVDAA---------TEAFKDLAGKKK--AGVC- 490 Seq ID #  22
AAP46640        TAAAG--GDGASKSAVDAA---------TEAFKDLAGKKK--AGVC- 490 Seq ID # 127
LpORF           TAIATQTGEGAEDGVVTKKGVLDIEKEFAAACKDLVKNKK--TGPC- 502 Seq ID #   1
Q6YSB2          SAIAKQ--QSGDDGVVTKKSVLETEREIFAYWRDQVKKKQ--TGIC- 497 Seq ID #  21
XP_482841       SAIAKQ--QSGDDGVVTKKSVLETEREIFAYWRDQVKKKQ--TGIC- 497 Seq ID #  99
AAL83983        SAIAKQ--QSGDDGAVTKKSVLETEREIFAYWRDQVKKKQ--TGIC- 282 Seq ID # 121
XP_482840       SAIAKQ--QSGDDGVVTKKSVLETEREIFAYWRDQVKKKQ--TGIC- 501 Seq ID # 113
Q9AQU4          SAIAKQ--QSCDDGVVTKKSVLETEREIFAYWRDQVKKKQ--TGIC- 501 Seq ID # 128
XP_462650       P---------------AKKTVREIEKEVTTYWRSFVARKK--SSLVC 484 Seq ID #  97
Q01J81          QLTIELG---PARTAGEEASIRVVKSEAVPVRKSVPLVAGKTKGVC- 500 Seq ID #  15
XP_462654       QLTIELG---PARTAGEEASIRVVKSEAVPVRKSVPLVAGKTKGVC- 500 Seq ID # 123
Q9AR41          QLTIELG---PARTAGEEASIRVVKSEAVPVRKSVPLVAGKTKGVC- 500 Seq ID #  28
BAB32871        QLTIELG---PARTAGEEASIRVVKSEAVPVRKSVPLVAGKTKGVC- 500 Seq ID # 125
                                                :          .
```

FIG. 11A

| | | | |
|---|---|---|---|
| P93369 | MVLSKTA--SESDVSIHST-FASRYVRTSLPRFKMPENSIPKEAAYQIINDELMLDGNPR | 57 | Seq ID # 14 |
| AAB40608 | MVLSKTA--SESDVSIHST-FASRYVRTSLPRFKMPENSIPKEAAYQIINDELMLDGNPR | 57 | Seq ID # 118 |
| AAC24195 | MVLSKTA--SESDVSIHST-FASRYVRTSLPRFKMPENSIPKEAAYQIINDELMLDGNPR | 57 | Seq ID # 117 |
| O81102 | MVLSKTA--SESDVSIHST-FASRYVRTSLPRFKMPENSIPKEAAYQIINDELMLDGNPR | 57 | Seq ID # 13 |
| Q9AT17 | MVLSKTA--SESDVSIHST-FASRYVRTSLPRFKMPENSIPKEAAYQIINDELMLDGNPR | 57 | Seq ID # 30 |
| AAK18620 | MVLSKTA--SESDVSIHST-FASRYVRTSLPRFKMPENSIPKEAAYQIINDELMLDGNPR | 57 | Seq ID # 107 |
| O81101 | MVLSKTA--SESDVSVHST-FASRYVRTSLPRFKMPENSIPKEAAYQIINDELMLDGNPR | 57 | Seq ID # 12 |
| AAC39483 | MVLSKTA--SESDVSVHST-FASRYVRTSLPRFKMPENSIPKEAAYQIINDELMLDGNPR | 57 | Seq ID # 115 |
| Q8LKR4 | MVLSKTA--SESDVSIHST-FASRYVRTSLPRFKMPENSIPKEAAYQIINDELMLDGNPR | 57 | Seq ID # 25 |
| AAM48129 | MVLSKTA--SESDVSIHST-FASRYVRTSLPRFKMPENSIPKEAAYQIINDELMLDGNPR | 57 | Seq ID # 109 |
| Q07346 | MVLSKTV--SQSDVSIHST-FASRYVRTSLPRFKMPDNSIPKEAAYQIINDELMLDGNPR | 57 | Seq ID # 4 |
| A48767 | MVLSKTV--SQSDVSIHST-FASRYVRTSLPRFKMPDNSIPKEAAYQIINDELMLDGNPR | 57 | Seq ID # 120 |
| A5B127 | MVLSKTA--SESDVSVHST-FASRYVKASLPRFKLPENSIPKEAAYQIINDELMLDGNPR | 57 | Seq ID # 9 |
| A7P433 | MVLSKTA--SESDVSVHST-FASRYVKASLPRFKLPENSIPKEAAYQIINDELMLDGNPR | 57 | Seq ID # 10 |
| Q1I1D8 | MVLSKTF--SESDESIHST-FASRYVRNSLPRFTMPENSIPKEAAYQIINDELMLDGNPR | 57 | Seq ID # 16 |
| Q6Q4T1 | MVLSKTA--SGTDVSVHST-FASRYVRNSLPRFEMPENSIPKEAAYQIINDELMLDGNPR | 57 | Seq ID # 18 |
| AAS79671 | MVLSKTA--SGTDVSVHST-FASRYVRNSLPRFEMPENSIPKEAAYQIINDELMLDGNPR | 57 | Seq ID # 100 |
| Q6Q4I2 | MVLSKTA--SESDVSIHST-FASRYVRTSLPRFEMPENSIPKEAAYQIINDELMLDGNPR | 57 | Seq ID # 19 |
| AAS79670 | MVLSKTA--SESDVSIHST-FASRYVRTSLPRFEMPENSIPKEAAYQIINDELMLDGNPR | 57 | Seq ID # 101 |
| AAM70569 | MVLSKTV--SESDVSIHST-FASRYVRNSLPRFEMPENSIPKEAAYQIINDELMLDGNPR | 57 | Seq ID # 104 |
| BAC42751 | MVLSKTA--SKSDDSIHST-FASRYVRNSLSRFEIPKNSIPKEAAYQIINDELKFDGNPR | 57 | Seq ID # 105 |
| Q94KK8 | MVLSKTS--SESDVSVHST-FASRYVRTSLPRFEMAENSIPKEAAFQIINDELMLDGNPR | 57 | Seq ID # 27 |
| AAK38667 | MVLSKTS--SESDVSVHST-FASRYVRTSLPRFEMAENSIPKEAAFQIINDELMLDGNPR | 57 | Seq ID # 106 |
| Q42521 | MVLSHAV--SESDVSVHST-FASRYVRTSLPRFKMPENSIPKEAAYQIINDELMLDGNPR | 57 | Seq ID # 2 |
| AAN46801 | MVLSHAV--SESDVSVHST-FASRYVRTSLPRFKMPENSIPKEAAYQIINDELMLDGNPR | 57 | Seq ID # 98 |
| AAA93132 | MVLSHAV--SESDVSVHST-FASRYVRTSLPRFKMPENSIPKEAAYQIINDELMLDGNPR | 57 | Seq ID # 119 |
| A0EJ88 | MVLSKTA--SESDVSVHST-FASRYVRASLPRFKMPENSIPKEAAFQIINDELMLDGNPR | 57 | Seq ID # 6 |
| Q944L6 | MVLTKTA--TND-ESVCTM-FGSRYVRTLLPKYEIGENSIPKDAAYQIIKDELMLDGNPR | 56 | Seq ID # 26 |
| AAL16126 | MVLTKTA--TND-ESVCTM-FGSRYVRTLLPKYEIGENSIPKDAAYQIIKDELMLDGNPR | 56 | Seq ID # 114 |
| Q42472 | MVLTKTA--TND-ESVCTM-FGSRYVRTLLPKYEIGENSIPKDAAYQIIKDELMLDGNPR | 56 | Seq ID # 3 |
| AAM70582 | MVLTKTA--TND-ESVCTM-FGSRYVRTLLPKYEIGENSIPKDAAYQIIKDELMLDGNPR | 56 | Seq ID # 116 |
| AAL91148 | ------------------------------------------------------------ | | Seq ID # 112 |
| Q6Q4I3 | MVLSRAA--TESGENVCST-FGSRYVRTALPKHKIGESSIPKEAAYQIIKDELMLDGNPR | 57 | Seq ID # 20 |
| AAS79669 | MVLSRAA--TESGENVCST-FGSRYVRTALPKHKIGESSIPKEAAYQIIKDELMLDGNPR | 57 | Seq ID # 102 |
| AAP85548 | --------------------------------------------------------GNPR | 4 | Seq ID # 108 |
| P54767 | MVLTTTSI-RDSEESLHCT-FASRYVQEPLPKFKMPKKSMPKEAAYQIVNDELMLDGNPR | 58 | Seq ID # 5 |
| CAA56812 | MVLTTTSI-RDSEESLHCT-FASRYVQEPLPKFKMPKKSMPKEAAYQIVNDELMLDGNPR | 58 | Seq ID # 122 |
| Q8LER4 | MVLATNS---DSDEHLHST-FASRYVRAVVPRFKMPDHCMPKDAAYQVINDELMLDGNPR | 56 | Seq ID # 24 |
| AAM61251 | MVLATNS---DSDEHLHST-FASRYVRAVVPRFKMPDHCMPKDAAYQVINDELMLDGNPR | 56 | Seq ID # 110 |
| Q9LSH2 | MVLATNS---DSDEHLHST-FASRYVRAVVPRFKMPDHCMPKDAAYQVINDELMLDGNPR | 56 | Seq ID # 31 |
| BAB02870 | MVLATNS---DSDEHLHST-FASRYVRAVVPRFKMPDHCMPKDAAYQVINDELMLDGNPR | 56 | Seq ID # 103 |
| **LpORF** | MVLTVAATAADTAEPLNSTFFATRYVRDQLPRYRMPENSIPKEAAYQIISDELMLDGNPR | 60 | Seq ID # 1 |
| A7P434 | ----------------------------------MPEKSIPKEAAYQIVHDELLLDGLPR | 26 | Seq ID # 11 |

FIG. 11B

| | | | |
|---|---|---|---|
| P93369 | LNLASFVTTWMEPECNKLMMDSINKNYVDMDEYPVTTELQNRCVNMIAHLFNAP-LGDGE | 116 | Seq ID # 14 |
| AAB40608 | LNLASFVTTWMEPECNKLMMDSINKNYVDMDEYPVTTELQNRCVNMIAHLFNAP-LGDGE | 116 | Seq ID # 118 |
| AAC24195 | LNLASFVTTWMEPECNKLMMDSINKNYVDMDEYPVTTELQNRCVNMIAHLFNAP-LGDGE | 116 | Seq ID # 117 |
| O81102 | LNLASFVTTWMEPECNKLMMDSINKNYVDMDEYPVTTELQNRCVNMIAHLFNAP-LGDGE | 116 | Seq ID # 13 |
| Q9AT17 | LNLASFVTTWMEPECNKLMMDSINKNYVDMGEYPVTTELQNRCVNMIAHLFNAP-LGDGE | 116 | Seq ID # 30 |
| AAK18620 | LNLASFVTTWMEPECNKLMMDSINKNYVDMGEYPVTTELQNRCVNMIAHLFNAP-LGDGE | 116 | Seq ID # 107 |
| O81101 | LNLASFVTTWMEPECNTLMMDSINKNYVDMDEYPVTTELQNRCVNMIAHLFNAP-LGDGE | 116 | Seq ID # 12 |
| AAC39483 | LNLASFVTTWMEPECNTLMMDSINKNYVDMDEYPVTTELQNRCVNMIAHLFNAP-LGDGE | 116 | Seq ID # 115 |
| Q8LKR4 | LNLASFVTTWMEPECNTLMMDSINKNYVDMDEYPVTTELQNRCVNMIAHLFNAP-LGDGE | 116 | Seq ID # 25 |
| AAM48129 | LNLASFVTTWMEPECNTLMMDSINKNYVDMDEYPVTTELQNRCVNMIAHLFNAP-LGDGE | 116 | Seq ID # 109 |
| Q07346 | LNLASFVTTWMEPECDKLMMDSINKNYVDMDEYPVTTELQNRCVNMIAHLFNAP-LEDGE | 116 | Seq ID # 4 |
| A48767 | LNLASFVTTWMEPECDKLMMDSINKNYVDMDEYPVTTELQNRCVNMIAHLFNAP-LEDGE | 116 | Seq ID # 120 |
| A5B127 | LNLASFVTTWMEPECDKLMMAAINKNYVDMDEYP------NRCVNIIAHLFNAP-LEDSE | 110 | Seq ID # 9 |
| A7P433 | LNLASFVTTWMEPECDKLMMAAINKNYVDMDEYPVTTELQNRCVNIIAHLFNAP-LEDSE | 116 | Seq ID # 10 |
| Q1I1D8 | LNLASFVTTWMEPECDKLMMAAINKNYVDMDEYPVTTELQNRCVNIIARLFNAP-LEDSE | 116 | Seq ID # 16 |
| Q6Q4I1 | LNLASFVTTWMEPECDKLMMESINKNYVDMDEYPVTTELQNRCVNMIARLFNAP-LGDGE | 116 | Seq ID # 18 |
| AAS79671 | LNLASFVTTWMEPECDKLMMESINKNYVDMDEYPVTTELQNRCVNMIARLFNAP-LGDGE | 116 | Seq ID # 100 |
| Q6Q4I2 | LNLASFVTTWMEPECDKLMMESINKNYVDMDEYPVTTELQNRCVNMIARLFNAP-LGDGE | 116 | Seq ID # 19 |
| AAS79670 | LNLASFVTTWMEPECDKLMMESINKNYVDMDEYPVTTELQNRCVNMIARLFNAP-LGDGE | 116 | Seq ID # 101 |
| AAM70569 | LNLASFVTTWMEPECDKLMMESINKNYVDMDEYPVTTELQNRCVNMIARLFNAP-LGDGE | 116 | Seq ID # 104 |
| BAC42751 | LNLASFVTTWMEPECDKLMMESINKNNVEMDQYPVTTDLQNRCVNMIARLFNAP-LGDGE | 116 | Seq ID # 105 |
| Q94KK8 | LNLASFVTTWMEPECDKLMMDSINKNYVDMDEYPVTTELQNRCVNMIARLFNAP-LEEKE | 116 | Seq ID # 27 |
| AAK38667 | LNLASFVTTWMEPECDKLMMDSINKNYVDMDEYPVTTELQNRCVNMIARLFNAP-LEEKE | 116 | Seq ID # 106 |
| Q42521 | LNLASFVTTWMEPECDKLIMSSINKNYVDMDEYPVTTELQNRCVNMIAHLFNAP-LEEAE | 116 | Seq ID # 2 |
| AAN46801 | LNLASFVTTWMEPECDKLIMSSINKNYVDMDEYPVTTELQNRCVNMIAHLFNAP-LEEAE | 116 | Seq ID # 98 |
| AAA93132 | LNLASFVTTWMEPECDKLIMSSINKNYVDMDEYPVTTELQNRCVNMIAHLFNAP-LEEAE | 116 | Seq ID # 119 |
| A0EJ88 | LNLASFVTTWMEPECDKLIIASINKNYVDMDEYPVTTELQNRCVNMIAHLFNAP-LGDSE | 116 | Seq ID # 6 |
| Q944L6 | LNLASFVTTWMEPECDKLIMDSINKNYVDMDEYPVTTELQNRCVNIIARLFNAP-LEESE | 115 | Seq ID # 26 |
| AAL16126 | LNLASFVTTWMEPECDKLIMDSINKNYVDMDEYPVTTELQNRCVNIIARLFNAP-LEESE | 115 | Seq ID # 114 |
| Q42472 | LNLASFVTTWMEPECDKLIMDSINKNYVDMDEYPVTTELQNRCVNIIARLFNAP-LEESE | 115 | Seq ID # 3 |
| AAM70582 | LNLASFVTTWMEPECDKLIMDSINKNYVDMDEYPVTTELQNRCVNIIARLFNAP-LEESE | 115 | Seq ID # 116 |
| AAL91148 | -------------------MDSINKNYVDMDEYPVTTELQNRCVNIIARLFNAP-LEESE | 40 | Seq ID # 112 |
| Q6Q4I3 | LNLASFVTTWMEPECDKLIMESINKNYVDMDEYPVTTELQNRCVNMIARLFNAP-LEETE | 116 | Seq ID # 20 |
| AAS79669 | LNLASFVTTWMEPECDKLIMESINKNYVDMDEYPVTTELQNRCVNMIARLFNAP-LEETE | 116 | Seq ID # 102 |
| AAP85548 | LNLASFVTTWMEPECDKLIMAAINKNYVDMDEYPVTTELQNRCVNMIAHLFNAP-LEETE | 63 | Seq ID # 108 |
| P54767 | LNLASFVSTWMEPECDKLIMSSINKNYVDMDEYPVTTELQNRCVNMLAHLFHAP-VGDDE | 117 | Seq ID # 5 |
| CAA56812 | LNLASFVSTWMEPECDKLIMSSINKNYVDMDEYPVTTELQNRCVNMLAHLFHAP-VGDDE | 117 | Seq ID # 122 |
| Q8LFR4 | LNLASFVTTWMEPECDKLIMDSVNKNYVDMDEYPVTTELQNRCVNMIANFFHAP-VGEDE | 115 | Seq ID # 24 |
| AAM61251 | LNLASFVTTWMEPECDKLIMDSVNKNYVDMDEYPVTTELQNRCVNMIANFFHAP-VGEDE | 115 | Seq ID # 110 |
| Q9LSH2 | LNLASFVTTWMEPECDKLIMDSVNKNYVDMDEYPVTTELQNRCVNMIANLFHAP-VGEDE | 115 | Seq ID # 31 |
| BAB02870 | LNLASFVTTWMEPECDKLIMDSVNKNYVDMDEYPVTTELQNRCVNMIANLFHAP-VGEDE | 115 | Seq ID # 103 |
| LpCRF | LNLASFVTTRMEPEVGKLIMDSVNKNYVDMDEYPVTTELQNRCVNMIAHLFNAP-IKEEE | 119 | Seq ID # 1 |
| A7P434 | LNLATFVTTWMEPECDKLMAEAINKNYVDMDEYPVTTELQNRCVNMIAKLFNAPSADQTK | 86 | Seq ID # 11 |
| | ::*** *:*.:** *****::*.:*:** : : | | |

FIG. 11C

```
P93369      TAVGVGTVGSSEAIMLAGLAFKRKWQNKMKAQGKPCDKPNIVTGANVQVCWEKFARYFEV 176 Seq ID #  14
AAB40608    TAVGVGTVGSSEAIMLAGLAFKRKWQNKMKAQGKPCDKPNIVTGANVQVCWEKFARYFEV 176 Seq ID # 118
AAC24195    TAVGVGTVGSSEAIMLAGLAFKRKWQNKMKAQGKPCDKPNIVTGANVQVCWEKFARYFEV 176 Seq ID # 117
O81102      TAVGVGTVGSSEAIMLAGLAFKRKWQNKMKAQGKPCDKPNIVTGANVQVCWEKFARYFEV 176 Seq ID #  13
Q9AT17      TAVGVGTVGSSEAIMLAGLAFKRKWQNKMKAQGKPCDKPNIVTGANVQVCWEKFARYFEV 176 Seq ID #  30
AAK18620    TAVGVGTVGSSEAIMLAGLAFKRKWQNKMKAQGKPCDKPNIVTGANVQVCWEKFARYFEV 176 Seq ID # 107
O81101      TAVGVGTVGSSEAIMLAGLAFKRKWQNKMKAQGKPFDKPNIVTGANVQVCWEKFARYFEV 176 Seq ID #  12
AAC39483    TAVGVGTVGSSEAIMLAGLAFKRKWQNKMKAQGKPFDKPNIVTGANVQVCWEKFARYFEV 176 Seq ID # 115
Q8LKR4      TAVGVGTVGSSEAIMLAGLAFKRKWQNKMKAQGKPFDKPNIVTGANVQVCWEKFARYFEV 176 Seq ID #  25
AAM48129    TAVGVGTVGSSEAIMLAGLAFKRKWQNKMKAQGKPFDKPNIVTGANVQVCWEKFARYFEV 176 Seq ID # 109
Q07346      TAVGVGTVGSSEAIMLAGLAFKRKWQNKMKAQGKPCDKPNIVTGANVQVCWEKFARYFEV 176 Seq ID #   4
A48767      TAVGVGTVGSSEAIMLAGLAFKRKWQNKMKAQGKPCDKPNIVTGANVQVCWEKFARYFEV 176 Seq ID # 120
A5BI27      AAVGVGTVGSSEAIMLAGLAFKRKWQNKRKAEGKPYDKPNIVTGANVQVCWEKFARYFEV 170 Seq ID #   9
A7P433      AAVGVGTVGSSEAIMLAGLAFKRKWQNKRKAEGKPYDKPNIVTGANVQVCWEKFARYFEV 176 Seq ID #  10
Q1I1D8      TAVGVGTVGSSEAIMLAGLAFKRKWQNKRKAEGKPFDKPNIVTGANVQVCWEKFARYFEV 176 Seq ID #  16
Q6Q411      AAVGVGTVGSSEAIMLAGLAFKRQWQNKRKAQGLPYDKPNIVTGANVQVCWEKFARYFEV 176 Seq ID #  18
AAS79671    AAVGVGTVGSSEAIMLAGLAFKRQWQNKRKAQGLPYDKPNIVTGANVQVCWEKFARYFEV 176 Seq ID # 100
Q6Q412      AAVGVGTVGSSEAIMLAGLAFKRQWQNKRKAQGLPYDKPNIVTGANVQVCWEKFARYFEV 176 Seq ID #  19
AAS79670    AAVGVGTVGSSEAIMLAGLAFKRQWQNKRKAQGLPYDKPNIVTGANVQVCWEKFARYFEV 176 Seq ID # 101
AAM70569    AAVGVGTVGSSEAIMLAGLAFKRQWQNKRKAQGLPYDKPNIVTGANVQVCWEKFARYFEV 176 Seq ID # 104
BAC42751    AATGVGTVGSSEAVMLAGLAFKRQWQNKRKALGLPYDRPNIVTGANTQVCLEKFARYFEV 176 Seq ID # 105
Q94KK8      TAVGVGTVGSSEAIMLAGLAFKRNWQNKRKAEGKPYNKPNIVTGANVQVCWEKFANYFEV 176 Seq ID #  27
AAK38667    TAVGVGTVGSSEAIMLAGLAFKRNWQNKRKAEGKPYNKPNIVTGANVQVCWEKFANYFEV 176 Seq ID # 106
Q42521      TAVGVGTVGSSEAIMLAGLAFKRKWQNKRKAEGKPVDKPNIVTGANVQVCWEKFARYFEV 176 Seq ID #   2
AAN46801    TAVGVGTVGSSEAIMLAGLAFKRKWQNKRKAEGKPVDKPNIVTGANVQVCWEKFARYFEV 176 Seq ID #  98
AAA93132    TAVGVGTVGSSEAIMLAGLAFKRKWQNKRKAEGKPVDKPNIVTGANVQVCWEKFARYFEV 176 Seq ID # 119
A0EJ88      TAVGVGTVGSSEAIMLAGLAFKRKWQNKRKAEGKPYDKPNIVTGANVQVCWEKFARYFEV 176 Seq ID #   6
Q944L6      TAVGVGTVGSSEAIMLAGLAFKRKWQNKRKAEGKPYDKPNIVTGANVQVCWEKFARYFEV 175 Seq ID #  26
AAL16126    TAVGVGTVGSSEAIMLAGLAFKRKWQNKRKAEGKPYDKPNIVTGANVQVCWEKFARYFEV 175 Seq ID # 114
Q42472      TAVGVGTVGSSEAIMLAGLAFKRKWQNKRKAEGKPYDKPNIVTGANVQVCWEKFARYFEV 175 Seq ID #   3
AAM70582    TAVGVGTVGSSEAIMLAGLAFKRKWQNKRKAEGKPYDKPNIVTGANVQVCWEKFARYFEV 175 Seq ID # 116
AAL91148    TAVGVGTVGSSEAIMLAGLAFKRKWQNKRKAEGKPYDKPNIVTGANVQVCWEKFARYFEV 100 Seq ID # 112
Q6Q4I3      TAMGVGTVGSSEAIMLAGLAFKRNWQNKRKAEGKPYDKPNIVTGANVQVCWEKFARYFEV 176 Seq ID #  20
AAS79669    TAMGVGTVGSSEAIMLAGLAFKRNWQNKRKAEGKPYDKPNIVTGANVQVCWEKFARYFEV 176 Seq ID # 102
AAP85548    AAVGVGTVGSSEAIMLAGLAFKRKWQNRRKQEGKPYDKPNIVTGANVQVCWEKFARYFEV 123 Seq ID # 108
P54767      TAVGVGTVGSSEAIMLAGLAFKRKWQSKRKAEGKPFDKPNIVTGANVQVCWEKFARYFEV 177 Seq ID #   5
CAA56812    TAVGVGTVGSSEAIMLAGLAFKRKWQSKRKAEGKPFDKPNIVTGANVQVCWEKFARYFEV 177 Seq ID # 122
Q8LFR4      AAIGCGTVGSSEAIMLAGLAFKRKWQHRRKAQGLPIDKPNIVTGANVQVCWEKFARYFEV 175 Seq ID #  24
AAM61251    AAIGCGTVGSSEAIMLAGLAFKRKWQHRRKAQGLPIDKPNIVTGANVQVCWEKFARYFEV 175 Seq ID # 110
Q9LSH2      AAIGCGTVGSSEAIMLAGLAFKRKWQHRRKAQGLPIDKPNIVTGANVQVCWEKFARYFEV 175 Seq ID #  31
BAB02870    AAIGCGTVGSSEAIMLAGLAFKRKWQHRRKAQGLPIDKPNIVTGANVQVCWEKFARYFEV 175 Seq ID # 103
LpORF       TAIGVATVGSSEAIMLAGLAFKRKWANKRKEEGKPYDKPNIVTGANVQVCWEKFARYFEV 179 Seq ID #   1
A7P434      QAVGVGTVGSSEAMMLAGLAFKKKWQNKRKAQKKPFDKPNIVTGANVQVCWEKFARYFEV 146 Seq ID #  11
             *:* .*******:********::*  : *     * ::********:*** ****.****
```

FIG. 11D

```
P93369      ELKEVKLSDGYYVMDPEKAVEMVDENTICVAAILGSTLNGEFEDVKRLNDLLIEKNKETG 236 Seq ID #  14
AAB40608    ELKEVKLSDGYYVMDPEKAVEMVDENTICVAAILGSTLNGEFEDVKRLNDLLIEKNKETG 236 Seq ID # 118
AAC24195    ELKEVKLSDGYYVMDPEKAVEMVDENTICVAAILGSTLNGEFEDVKRLNDLLIEKNKETG 236 Seq ID # 117
O81102      ELKEVKLSDGYYVMDPEKAVEMVDENTICVAAILGSTLNGEFEDVKRLNDLLIEKNKETG 236 Seq ID #  13
Q9AT17      ELKEVKLSDGYYVMDPEKAVEMVDENTICVAAILGSTLNGDFEDVKRLNDLLIEKNKETG 236 Seq ID #  30
AAK18620    ELKEVKLSDGYYVMDPEKAVEMVDENTICVAAILGSTLNGDFEDVKRLNDLLIEKNKETG 236 Seq ID # 107
O81101      ELKEVKLSDGYYVMDPEKAVEMVDENTICVAAILGSTLNGEFEDVKRLNDLLIEKNKETG 236 Seq ID #  12
AAC39433    ELKEVKLSDGYYVMDPEKAVEMVDENTICVAAILGSTLNGEFEDVKRLNDLLIEKNKETG 236 Seq ID # 115
Q8LKR4      ELKEVKLSDGYYVMDPEKAVEMVDENTICVAAILGSTLNGEFEDVKRLNDLLIEKNKETG 236 Seq ID #  25
AAM48129    ELKEVKLSDGYYVMDPEKAVEMVDENTICVAAILGSTLNGEFEDVKRLNDLLIEKNKETG 236 Seq ID # 109
Q07346      ELKEVKLSEGYYVMDPEKAVEMVDENTICVAAILGSTLNGDFEDVKRLNDLLVEKNKETG 236 Seq ID #   4
A48767      ELKEVKLSEGYYVMDPEKAVEMVDENTICVAAILGSTLNGEFEDVKRLNDLLVEKNKETG 236 Seq ID # 120
A5B 27      ELKEVKLRDGYYVMDPEKAVEMVDENTICVAAILGSTLNGEFEDVKLLNDLLVEKNKQXG 230 Seq ID #   9
A7P433      ELKEVKLRDGYYVMDPEKAVEMVDENTICVAAILGSTLNGEFEDVKLLNDLLVEKNKQTG 236 Seq ID #  10
Q1I1D8      ELKEVKLSEGYYVMDPAKAVEMVDENTICVAAILGSTLNGEFEDVKLLNDLLTEKNKETG 236 Seq ID #  16
Q6Q4I1      ELKEVKLREGYYVMDPEKAVEMVDENTICVAAILGSTLTGDFEDVKLLNDLLVEKNKQTG 236 Seq ID #  18
AAS79671    ELKEVKLREGYYVMDPEKAVEMVDENTICVAAILGSTLTGEFEDVKLLNDLLVEKNKQTG 236 Seq ID # 100
Q6Q4I2      ELKEVKLREGYYVMDPEKAVEMVDENTICVAAILGSTLTGEFEDVKLLNDLLVEKNKQTG 236 Seq ID #  19
AAS79670    ELKEVKLREGYYVMDPEKAVEMVDENTICVAAILGSTLTGEFEDVKLLNDLLVEKNKQTG 236 Seq ID # 101
AAM70569    ELKEVNLREDYYVMDPVKAVEMVDENTICVAAILGSTLTGEFEDVKLLNDLLVEKNKQTG 236 Seq ID # 104
BAC42751    ELKEVKLREGYYVMDPDKAVEMVDENTICVVAILGSTLTGDFEDVKLLNDLLVEKNKKTG 236 Seq ID # 105
Q94KK8      ELKEVKLREGYYVMDPVQAVEMVDENTICVAAILGSTLNGDFEDVKLLNDLLIEKNKQTG 236 Seq ID #  27
AAK38667    ELKEVKLREGYYVMDPVQAVEMVDENTICVAAILGSTLNGEFEDVKLLNDLLIEKNKQTG 236 Seq ID # 106
Q42521      ELKEVKLSEGYYVMDPQQAVDMVDENTICVAAILGSTLNGEFEDVKLLNDLLVEKNKETG 236 Seq ID #   2
AAN46801    ELKEVKLSEGYYVMDPQQAVDMVDENTICVAAILGSTLNGEFEDVKLLNDLLVEKNKETG 236 Seq ID #  98
AAA93132    ELKEVKLSEGYYVMDPQQAVDMVDENTICVAAILGSTLNGDFEDVKLLNDLLVEKNKETG 236 Seq ID # 119
A0EJ88      ELKEVKLSDGYYVMDPEKAVQMVDENTICVAAILGSTLNGDFEDVKLLNDLLVEKNKSTG 236 Seq ID #   6
Q944L6      ELKEVNLSEGYYVMDPDKAAEMVDENTICVAAILGSTLNGEFEDVKRLNDLLVKKNEETG 235 Seq ID #  26
AAL16126    ELKEVNLSEGYYVMDPDKAAEMVDENTICVAAILGSTLNGEFEDVKRLNDLLVKKNEETG 235 Seq ID # 114
Q42472      ELKEVNLSEGYYVMDPDKAAEMVDENTICVAAILGSTLNGEFEDVKRLNDLLVKKNEETG 235 Seq ID #   3
AAM70582    ELKEVNLSEGYYVMDPDKAAEMVDENTICVAAILGSTLNGEFEDVKRLNDLLVKKNEETG 235 Seq ID # 116
AAL91148    ELKEVNLSEGYYVMDPDKAAEMVDENTICVAAILGSTLNGDFEDVKRLNDLLVKKNEETG 160 Seq ID # 112
Q6Q4I3      ELKEVKLSEGYYVMDPDKAAEMVDENTICVAAILGSTLNGEFEDVKRLNDLLVKKNEETG 236 Seq ID #  20
AAS79669    ELKEVKLSEGYYVMDPDKAAEMVDENTICVAAILGSTLNGEFEDVKRLNDLLVKKNEETG 236 Seq ID # 102
AAP85548    ELKEVKLRDDYYVMDPEKAVELVDENTICVAAILGSTLNGEFEDVKRLNDLLIEKNKITG 183 Seq ID # 108
P54767      ELKEVKLKEGYYVMDPAKAVEIVDENTICVAAILGSTLTGEFEDVKLLNELLTKKNKETG 237 Seq ID #   5
CAA56812    ELKEVKLKEGYYVMDPAKAVEIVDENTICVAAILGSTLTGEFEDVKLLNELLTKKNKETG 237 Seq ID # 122
Q8LFR4      ELKEVKLSEDYYVMDPAKAVEMVDENTICVAAILGSTLTGEFEDVKQLNDLLAEKNAETG 235 Seq ID #  24
AAM61251    ELKEVKLSEDYYVMDPAKAVEMVDENTICVAAILGSTLTGEFEDVKQLNDLLAEKNAETG 235 Seq ID # 110
Q9LSH2      ELKEVKLSEDYYVMDPAKAVEMVDENTICVAAILGSTLTGEFEDVKQLNDLLAEKNAETG 235 Seq ID #  31
BAB02870    ELKEVKLSEDYYVMDPAKAVEMVDENTICVAAILGSTLTGEFEDVKQLNDLLAEKNAETG 235 Seq ID # 103
LpORF       ELKEVKLTEGYYVMDPLKAVEMVDENTICVAAILGSTLTGEYEDVKLLNDLLVEKNKKTG 239 Seq ID #   1
A7P434      ELKEVKLREGYYVMDPVKAVEMVDENTICVAAILGSTFNGEFEDVKLLNTLLTQKNKRTG 206 Seq ID #  11
            *****:* :.****** :*.::********.******:.**:**** ** ** :**   *
```

FIG. 11E

```
P93369      WDTPIHVDAASGEFIAPFLYPELEWDERLPLVKSINVSGHKYGLVYAGIGWAIWRNKEDL 296 Seq ID #  14
AAB40608    WDTPIHVDAASGEFIAPFLYPELEWDERLPLVKSINVSGHKYGLVYAGIGWAIWRNKEDL 296 Seq ID # 118
AAC24195    WDTPIHVDAASGGFIAPFLYPELEWDERLPLVKSINVSGHKYGLVYAGIGWAIWRNKEDL 296 Seq ID # 117
O81102      WDTPIHVDAASGGFIAPFLYPELEWDERLPLVKSINVSGHKYGLVYAGIGWAIWRNKEDL 296 Seq ID #  13
Q9AT17      WDTPIHVDAASGGFIAPFLYPELEWDERLPLVKSINVSGHKYGLVYAGIGWAIWRNKEDL 296 Seq ID #  30
AAK18620    WDTPIHVDAASGGFIAPFLYPELEWDERLPLVKSINVSGHKYGLVYAGIGWAIWRNKEDL 296 Seq ID # 107
O81101      WDTPIHVDAASGGFIAPFLYPELEWDERLPLEKSINVSGHKYGLVYAGIGWAIWRNKEDL 296 Seq ID #  12
AAC39483    WDTPIHVDAASGGFIAPFLYPELEWDERLPLEKSINVSGHKYGLVYAGIGWAIWRNKEDL 296 Seq ID # 115
Q8LKR4      WDTPIHVDAASGGFIAPFLYPELEWDERLPLVKSINVSGHKYGLVYAGIGWAIWRNKEDL 296 Seq ID #  25
AAM48129    WDTPIHVDAASGGFIAPFLYPELEWDERLPLVKSINVSGHKYGLVYAGIGWAIWRNKEDL 296 Seq ID # 109
Q07346      WDTPIHVDAASGGFIAPFIYPELEWDERLPLVKSINVSGHKYGLVYAGIGWVVWRNKDDL 296 Seq ID #   4
A48767      WDTPIHVDAASGGFIAPFIYPELEWDERLPLVKSINVSGHKYGLVYAGIGWVVWRNKDDL 296 Seq ID # 120
A5BI27      WDTPIHVDAASGGFIAPFLYPELEWDERLPLVKSINVSGHKYGLVYAGIGWVVWRSKEDL 290 Seq ID #   9
A7P433      WDTPIHVDAASGGFIAPFLYPELEWDERLPLVKSINVSGHKYGLVYAGIGWVVWRSKEDL 296 Seq ID #  10
Q1I1D8      WDTPIHVDAASGGFIAPFLYPELEWDERLPLVKSINVSGHKYGLVYAGIGWVVWRNKEDL 296 Seq ID #  16
Q6Q4I1      WDTGNHVDAASGGFIAPFLYPELEWDERLPLVKSINVSGHKYGLVYAGIGWVVWRTKSDL 296 Seq ID #  18
AAS79671    WDTGNHVDAASGGFIAPFLYPELEWDERLPLVKSINVSGHKYGLVYAGIGWVVWRTKSDL 296 Seq ID # 100
Q6Q4I2      WDTGIHVDAASGGFIAPFLYPELEWDERLPLVKSINVSGHKYGLVYAGIGWVVWRTKSDL 296 Seq ID #  19
AAS79670    WDTGIHVDAASGGFIAPFLYPELEWDERLPLVKSINVSGHKYGLVYAGIGWVVWRTKSDL 296 Seq ID # 101
AAM70569    WDTPIHVDAASGGFIAPFLYPELEWDERLPLVKSINVSGHKYGLVYAGIGWVVWRTKTDL 296 Seq ID # 104
BAC42751    WDTPIHVDAASGGFIAPFLYPDLEWDERLPLVKSINVSGHKYGLVYAGIGWVVWRTKTDL 296 Seq ID # 105
Q94KK8      WNTPIHVDAASGGFIAPFLYPELEWDERLPLVKSINVSGHKYGLVYAGIGWVIWRTKQDL 296 Seq ID #  27
AAK38667    WNTPIHVDAASGGFIAPFLYPELEWDERLPLVKSINVSGHKYGLVYAGIGWVIWRTKQDL 296 Seq ID # 106
Q42521      WDTPIHVDAASGGFIAPFLYPELEWDERLPLVKSINVSGHKYGLVYAGIGWVIWRNKEDL 296 Seq ID #   2
AAN46801    WDTPIHVDAASGGFIAPFLYPELEWDERLPLVKSINVSGHKYGLVYAGIGWVIWRNKEDL 296 Seq ID #  98
AAA93132    WDTPIHVDAASGGFIAPFLYPELEWDERLPLVKSINVSGHKYGLVYAGIGWVIWRNKEDL 296 Seq ID # 119
A0-U88      WDTPIHVDAASGGFIAPFLYPELEWDERLPLVKSINVSGHKYGLVYAGIGWVIWRNKEDL 296 Seq ID #   6
Q944L6      WNTPIHVDAASGGFIAPFIYPELEWDERLPLVKSINVSGHKYGLVYAGIGWVVWRAAEDL 295 Seq ID #  26
AAL16726    WNTPIHVDAASGGFIAPFIYPELEWDERLPLVKSINVSGHKYGLVYAGIGWVVWRAAEDL 295 Seq ID # 114
Q42472      WNTPIHVDAASGGFIAPFIYPELEWDERLPLVKSINVSGHKYGLVYAGIGWVVWRAAEDL 295 Seq ID #   3
AAM70582    WNTPIHVDAASGGFIAPFIYPELEWDERLPLVKSINVSGHKYGLVYAGIGWVVWRAAEDL 295 Seq ID # 116
AAL91148    WNTPIHVDAASGGFIAPFIYPELEWDERLPLVKSINVSGHKYGLVYAGIGWVVWRAAEDL 220 Seq ID # 112
Q6Q4I3      WNTPIHVDAASGGFIAPFIYPELEWDERLPLVKSINVSGHKYGLVYAGIGWVVWRTQQDL 296 Seq ID #  20
AAS79669    WNTPIHVDAASGGFIAPFIYPELEWDERLPLVKSINVSGHKYGLVYAGIGWVVWRTQQDL 296 Seq ID # 102
AAP85548    WDTPIHVDAASGGFIAPFIYPELEWDERLQLVKSINVSGHKYGLVYAGIGWVIWRSKQDL 243 Seq ID # 108
P54767      WETPIHVDAASGGFIAPFLWPDLEWDERLPLVKSINVSGHKYGLVYAGVGWVIWRSKEDL 297 Seq ID #   5
CAA56812    WETPIHVDAASGGFIAPFLWPDLEWDERLPLVKSINVSGHKYGLVYAGVGWVIWRSKEDL 297 Seq ID # 122
Q8LFR4      WETPIHVDAASGGFIAPFLYPDLEWDERLPWVKSINVSGHKYGLVYAGVGWVVWRTKDDL 295 Seq ID #  24
AAM61251    WETPIHVDAASGGFIAPFLYPDLEWDERLPWVKSINVSGHKYGLVYAGVGWVVWRTKDDL 295 Seq ID # 110
Q9LSH2      WETPIHVDAASGGFIAPFLYPDLEWDERLPWVKSINVSGHKYGLVYAGVGWVVWRTKDDL 295 Seq ID #  31
BAB02870    WETPIHVDAASGGFIAPFLYPDLEWDERLPWVKSINVSGHKYGLVYAGVGWVVWRTKDDL 295 Seq ID # 103
LpORF       FNVPIHVDAASGGFIAPFLHPELEWDERLPLVKSINVSGHKYGLVYPGVGWVIWRSKDDL 299 Seq ID #   1
A7P434      WDTPIHVDAASGGIVAPFLYPELEWDERLPLVKSINVSGHKYGLVYAGVGWAIWRSKEEL 266 Seq ID #  11
            ::.  ******* *:***: *:*******   **************.*:**.:**   :*
```

FIG. 11F

```
P93369          PDELIFHINYLGADQPTFTLNFSKGSSQVIAQYYQLIRLGFEGYKNVMENCQENARVLRE 356 Seq ID #  14
AAB40608        PDELIFHINYLGADQPTFTLNFSKGSSQVIAQYYQLIRLGFEGYKNVMENCQENARVLRE 356 Seq ID # 118
AAC24195        PDELIFHINYLGADQPTFTLNFSKGSSQVIAQYYQLIRLGFEGYKNVMENCQENARVLRE 356 Seq ID # 117
O81102          PDELIFHINYLGADQPTFTLNFSKGSSQVIAQYYQLIRLGFEGYKNVMENCQENARVLRE 356 Seq ID #  13
Q9AT17          PDELIFHINYLGADQPTFTLNFSKGSSQVIAQYYQLIRLGFEGYKNVMENCQENARVLRE 356 Seq ID #  30
AAK18620        PDELIFHINYLGADQPTFTLNFSKGSSQVIAQYYQLIRLGFEGYKNVMENCQENARVLRE 356 Seq ID # 107
O81101          PDELIFHINYLGADQPTFTLNFSKGSSQVIAQYYQLIRLGFEGYKNVMENCQENARVLRE 356 Seq ID #  12
AAC39483        PDELIFHINYLGADQPTFTLNFSKGSSQVIAQYYQLIRLGFEGYKNVMENCQENARVLRE 356 Seq ID # 115
Q8LKR4          PDELIFHINYLGADQPTFTLNFSKGSSQVIAQYYQLIRLGFEGYKNVMENCQENARVLRE 356 Seq ID #  25
AAM48129        PDELIFHINYLGADQPTFTLNFSKGSSQVIAQYYQLIRLGFEGYKNVMENCQENARVLRE 356 Seq ID # 109
Q07346          PDELIFHINYLGADQPTFTLNFSKGSSQVIAQYYQLIRLGYEGYKNVMENCQENASVLRE 356 Seq ID #   4
A48767          PDELIFHINYLGADQPTFTLNFSKGSSQVIAQYYQLIRLGYEGYKNVMENCQENASVLRE 356 Seq ID # 120
A5BI27          PEELIFHINYLGADQPTFTLNFSKGSSQVIAQYYQLIRLGFEGYRNVMENCQENAMALKE 350 Seq ID #   9
A7P433          PEELIFHINYLGADQPTFTLNFSKGSSQVIAQYYQLIRLGFEGYRNVMENCQENAMALKE 356 Seq ID #  10
Q1I1D8          PEELIFHINYLGADQPTFTLNFSKGSSQVIAQYYQLIRLGFEGYRNVMENCHENAMVLKE 356 Seq ID #  16
Q6Q4I1          PDELIFHINYLGADQPTFTLNFSKGSSQVIAQYYQLIRLGFEGYRNVMDNCRENMMVLRE 356 Seq ID #  18
AAS79671        PDELIFHINYLGADQPTFTLNFSKGSSQVIAQYYQLIRLGFEGYRNVMDNCRENMMVLRE 356 Seq ID # 100
Q6Q4I2          PDELIFHINYLGADQPTFTLNFSKGSSQVIAQYYQLIRLGFEGYRNVMDNCRENMMVLRE 356 Seq ID #  19
AAS79670        PDELIFHINYLGADQPTFTLNFSKGSSQVIAQYYQLIRLGFEGYRNVMDNCRENMMVLRE 356 Seq ID # 101
AAM70569        PDELIFHINYLGADQPTFTLNFSKGSSQVIAQYYQLIRLGFEGYRNVMDNCRENMMVLRQ 356 Seq ID # 104
BAC42751        PDELIFHINYLGADQPTFTLNFSKGSSQVIAQYYQLIRLGFEGYRNVMDNCRENMMVLRQ 356 Seq ID # 105
Q94KK8          PEELIFHINYLGADQPTFTLNFSKGSSQVIAQYYQLIRLGYEGYRNVMENCRENAIVLRE 356 Seq ID #  27
AAK38667        PEELIFHINYLGADQPTFTLNFSKGSSQVIAQYYQLIRLGYEGYRNVMENCRENAIVLRE 356 Seq ID # 106
Q42521          PEELIFHINYLGADQPTFTLNFSKGSSQVIAQYYQLIRLGHEGYRNVMENCRENMIVLRE 356 Seq ID #   2
AAN46801        PEELIFHINYLGADQPTFTLNFSKGSSQVIAQYYQLIRLGHEGYRNVMENCRENMIVLRE 356 Seq ID #  98
AAA93132        PEELIFHINYLGADQPTFTLNFSKGSSQVIAQYYQLIRLGHEGYRNVMENCRENMIVLRE 356 Seq ID # 119
A0EJ88          PEELIFHINYLGADQPTFTLNFSKGSSQVIAQYYQLIRLGYEGYKNVMENCRDNMLVLKQ 356 Seq ID #   6
Q944L6          PEELIFHINYLGADQPTFTLNFSKGSSQIIAQYYQLIRLGFEGYKNVMENCIENMVVLKE 355 Seq ID #  26
AAL16126        PEELIFHINYLGADQPTFTLNFSKGSSQIIAQYYQLIRLGFEGYKNVMENCIENMVVLKE 355 Seq ID # 114
Q42472          PEELIFHINYLGADQPTFTLNFSKGSSQIIAQYYQLIRLGFEGYKNVMENCIENMVVLKE 355 Seq ID #   3
AAM70582        PEELIFHINYLGADQPTFTLNFSKGSSQIIAQYYQLIRLGFEGYKNVMENCIENMVVLKE 355 Seq ID # 116
AAL91148        PEELIFHINYLGADQPTFTLNFSKGSSQIIAQYYQLIRLGFEGYKNVMENCIENMVVLKE 280 Seq ID # 112
Q6Q4I3          PDELIFHINYLGADQPTFTLNFSKGSSQIIAQYYQLIRLGFEGYKNVMENCRENMVVLRE 356 Seq ID #  20
AAS79669        PDELIFHINYLGADQPTFTLNFSKGSSQIIAQYYQLIRLGFEGYKNVMENCRENMVVLRE 356 Seq ID # 102
AAP85548        PEELIFHINYLGADQPTFTLNFSKGSSQVIAQYYQLIRLGFEGYRNVMENCRDNMLVLKE 303 Seq ID # 108
P54767          PDELVFHINYLGSDQPTFTLNFSKGSYQIIAQYYQLIRLGFEGYKNVMKNCLSNAKVLTE 357 Seq ID #   5
CAA56812        PDELVFHINYLGSDQPTFTLNFSKGSYQIIAQYYQLIRLGFEGYKNVMKNCLSNAKVLTE 357 Seq ID # 122
Q8LFR4          PEELVFHINYLGADQPTFTLNFSKGSSQIIAQYYQFIRLGFEGYKNIMENCMDNARRLRE 355 Seq ID #  24
AAM61251        PEELVFHINYLGADQPTFTLNFSKGSSQIIAQYYQFIRLGFEGYKNIMENCMDNARRLRE 355 Seq ID # 110
Q9LSH2          PEELVFHINYLGADQPTFTLNFSKGSSQIIAQYYQFIRLGFEGYKNIMENCMDNARRLRE 355 Seq ID #  31
BAB02870        PEELVFHINYLGADQPTFTLNFSKGSSQIIAQYYQFIRLGFEGYKNIMENCMDNARRLRE 355 Seq ID # 103
LpORF           PGELIFHINYLGTDQPTFTLNFSKGASQIIAQYYQLIRLGFEGYKHIMENCQANATALRE 359 Seq ID #   1
A7P434          PEELIFHINYLGGDEPTFTLNFSKG-NQVIAQYYQFLRMGFEGYKKVMSNCMESARILRE 325 Seq ID #  11
                * **:******* *:**********  *:******::*:*.***:::*.**  .   * :
```

FIG. 11G

```
P93369      GLEKSGRFNIISKEIGVPLVAFSLK-DNSQHNEFEISETLRRFGWIIPAYTMPPNAQHVT 415 Seq ID #  14
AAB40608    GLEKSGRFNIISKEIGVPLVAFSLK-DNSQHNEFEISETLRRFGWIIPAYTMPPNAQHVT 415 Seq ID # 118
AAC24195    GLEKSGRFNIISKEIGVPLVAFSLK-DNSQHNEFEISETLRRFGWIIPAYTMPPNAQHVT 415 Seq ID # 117
O81102      GLEKSGRFNIISKEIGVPLVAFSLK-DNSQHNEFEISETLRRFGWIIPAYTMPPNAQHVT 415 Seq ID #  13
Q9AT17      GLEKSGRFNIISKEIGVPLVAFSLK-DNSQHNEFEISETLRRFGWIIPAYTMPPNAQHVT 415 Seq ID #  30
AAK18620    GLEKSGRFNIISKEIGVPLVAFSLK-DNSQHNEFEISETLRRFGWIIPAYTMPPNAQHVT 415 Seq ID # 107
O81101      GIEKSGRFNIISKEIGVPLVAFSLK-DNSQHNEFEISETLRRFGWIVLAYTMPPNAQHVT 415 Seq ID #  12
AAC39483    GIEKSGRFNIISKEIGVPLVAFSLK-DNSQHNEFEISETLRRFGWIVLAYTMPPNAQHVT 415 Seq ID # 115
Q8LKR4      GIEKSGRFNIISKEIGVPLVAFSLK-DNSQHNEFEISETLRRFGWIVPAYTMPPNAQHVT 415 Seq ID #  25
AAM48129    GIEKSGRFNIISKEIGVPLVAFSLK-DNSQHNEFEISETLRRFGWIVPAYTMPPNAQHVT 415 Seq ID # 109
Q07346      GLEKTGRFNIISKEIGVPLVAFSLK-DNRQHNEFEISETLRRFGWIVPAYTMPPNAQHIT 415 Seq ID #   4
A48767      GLEKTGRFNIISKEIGVPLVAFSLK-DNRQHNEFEISETLRRFGWIVPAYTMPPNAQHIT 415 Seq ID # 120
A5BI27      GLEKTGRFNIISKDNGVPLVAFSLK-DNSCHDEFEVADMLRRFGWIVPAYTMPPDAQHVT 409 Seq ID #   9
A7P433      GLEKTGRFNIISKDNGVPLVAFSLK-DNSCHDEFEVADMLRRFGWIVPAYTMPPDAQHVT 415 Seq ID #  10
Q1I1D8      GLEKTGRFNIVSKDEGVPLVAFSLK-DNKRHDEFEVAELLRRFGWIVPAYTMPADAQHIT 415 Seq ID #  16
Q6Q4I1      GLEKTGRFNIVSKENGVPLVAFSLK-DSSRHNEFEVAETLRRFGWIVPAYTVPADAEHVT 415 Seq ID #  18
AAS79671    GLEKTGRFNIVSKENGVPLVAFSLK-DSSRHNEFEVAETLRRFGWIVPAYTVPADAEHVT 415 Seq ID # 100
Q6Q4I2      GLEKTGRFNIVSKENGVPLVAFSLK-DSSRHDEFEVAETLRRFGWIVPAYTMPADAQHVT 415 Seq ID #  19
AAS79670    GLEKTGRFNIVSKENGVPLVAFSLK-DSSRHDEFEVAETLRRFGWIVPAYTMPADAQHVT 415 Seq ID # 101
AAM70569    GLEKTGRFKIVSKENGVPLVAFSLK-DSSRHNEFEVAHTLRRFGWIVPAYTMPADAQHVT 415 Seq ID # 104
BAC42751    GLEKTGRFNIVSKENGVPLVAFSLK-DSSRHNEFEVAEMLRRFGWIVPAYTMPADAQHVT 415 Seq ID # 105
Q94KK8      GLEKTGRFNIVSKDEGVPLVAFSLK-DNSRHNEFEVSETLRRFGWIVPAYTMPADAQHVT 415 Seq ID #  27
AAK38667    GLEKTGRFNIVSKDEGVPLVAFSLK-DNSRHNEFEVSETLRRFGWIVPAYTMPADAQHVT 415 Seq ID # 106
Q42521      GLEKTERFNIVSKDEGVPLVAFSLK-DSSCHTEFEISDMLRRYGWIVPAYTMPPNAQHIT 415 Seq ID #   2
AAN46801    GLEKTERFNIVSKDEGVPLVAFSLK-DSSCHTEFEISDMLRRYGWIVPAYTMPPNAQHIT 415 Seq ID #  98
AAA93132    GLEKTERFNIVSKDEGVPLVAFSLK-DSSCHTEFEISDMLRRYGWIVPAYTMPPNAQHIT 415 Seq ID # 119
A0EJ88      GLEKTGKFNIVSKDKGVPLVAFSLK-DNSLHNEFEVSDMLRRFGWIVPAYTMPPDAQHVT 415 Seq ID #   6
Q944L6      GIEKTERFNIVSKDQGVPVVAFSLK-DHSFHNEFEISEMLRRFGWIVPAYTMPADVQHIT 414 Seq ID #  26
AAL16126    GIEKTERFNIVSKDQGVPVVAFSLK-DHSFHNEFEISEMLRRFGWIVPAYTMPADVQHIT 414 Seq ID # 114
Q42472      GIEKTERFNIVSKDQGVPVVAFSLK-DHSFHNEFEISEMLRRFGWIVPAYTMPADAQHIT 414 Seq ID #   3
AAM70582    GIEKTERFNIVSKDQGVPVVAFSLK-DHSFHNEFEISEMLRRFGWIVPAYTMPADAQHIT 414 Seq ID # 116
AAL91148    GIEKTERFNIVSKDQGVPVVAFSLK-DHSFHNEFEISEMLRRFGWIVPAYTMPADAQHIT 339 Seq ID # 112
Q6Q4I3      GIEKTERFNIVSKEVGVPLVAFSLK-DHSFHNEFEISEMLRRFGWIVPAYTMPADAQHIT 415 Seq ID #  20
AAS79669    GIEKTERFNIVSKEVGVPLVAFSLK-DHSFHNEFEISEMLRRFGWIVPAYTMPADAQHIT 415 Seq ID # 102
AAP85548    GLEKTGRFSIVSKDNGVPLVAFTLK-DHTHFDEFQISDFLRRFGWIVPAYTMPPDAQHVT 362 Seq ID # 108
P54767      GITKMGRFDIVSKDVGVPVVAFSLR-DSSKYTVFEVSEHLRRFGWIVPAYTMPPDAEHIA 416 Seq ID #   5
CAA56812    GITKMGRFDIVSKDVGVPVVAFSLR-DSSKYTVFEVSEHLRRFGWIVPAYTMPPDAEHIA 416 Seq ID # 122
Q8LFR4      GIEMTGKFNIVSKDIGVPLVAFSLK-DSSKHTVFEIAESLRKFGWIIPAYTMPADAQHIA 414 Seq ID #  24
AAM61251    GIEMTGKFNIVSKDIGVPLVAFSLK-DSSKHTVFEIAESLRKFGWIIPAYTMPADAQHIA 414 Seq ID # 110
Q9LSH2      GIEMTGKFNIVSKDIGVPLVAFSLK-DSSKHTVFEIAESLRKFGWIIPAYTMPADAQHIA 414 Seq ID #  31
BAB02870    GIEMTGKFNIVSKDIGVPLVAFSLK-DSSKHTVFEIAESLRKFGWIIPAYTMPADAQHIA 414 Seq ID # 103
LpORF       GLEATGRFDILSKEDGVPLVAIRLK-DSSKFSVFDISENLRRFGWIVPAYTMPADAEHVA 418 Seq ID #   1
A7P434      GLEKTGRFQIISKEKGVPVVAFAFKGNDRKNLAFGLSKALRNYGWIVPAYTMPANAENVT 385 Seq ID #  11
            *:    :*.*:**: ***:**: :: :      * ::. **.:***: ***:*.:.::::
```

FIG. 11H

```
P93369          VLRVVIREDFSRTLAERLVIDIEKVLHELDTLPARVN-------AKLAVAE--------A 460 Seq ID #  14
AAB40608        VLRVVIREDFSRTLAERLVIDIEKVLHELDTLPARVN-------AKLAVAE--------A 460 Seq ID # 118
AAC24195        VLRVVIREDFSRTLAERLVIDIEKVLHELDTLPARVN-------AKLAVAE--------A 460 Seq ID # 117
O81102          VLRVVIREDFSRTLAERLVIDIEKVLHELDTLPARVN-------AKLAVAE--------A 460 Seq ID #  13
Q9AT17          VLRVVIREDFSRTLAERLVIDIEKVLHELDTLPARVN-------AKLAVAE--------A 460 Seq ID #  30
AAK18620        VLRVVIREDFSRTLAERLVIDIEKVLHELDTLPARVN-------AKLAVAE--------A 460 Seq ID # 107
O81101          VLRVVIREDFSRTLAERLVIDIEKVFHGVDTLPARVN-------AKLAVAE--------A 460 Seq ID #  12
AAC39483        VLRVVIREDFSRTLAERLVIDIEKVFHGVDTLPARVN-------AKLAVAE--------A 460 Seq ID # 115
Q8LKR4          VLRVVIREDFSRTLAERLVIDIEKVLHELDTLPARVN-------AKLAVAE--------A 460 Seq ID #  25
AAM48129        VLRVVIREDFSRTLAERLVIDIEKVLHELDTLPARVN-------AKLAVAE--------A 460 Seq ID # 109
Q07346          VLRVVIREDFSRTLAERLVRDIEKVLHELDTLPARVN-------AKLAVAEEQA----AA 464 Seq ID #   4
A48767          VLRVVIREDFSRTLAERLVRDIEKVLHELDTLPARVN-------AKLAVAEEQA----AA 464 Seq ID # 120
A5B127          VLRVVVREDFSRTLAERLVFDITKVLHELDMLPAKLS-------AKISVEEKK------- 455 Seq ID #   9
A7P433          VLRVVVREDFSRTLAERLVFDITKVLHELDMLPAKLS-------AKISVEEKK------- 461 Seq ID #  10
Q1I1D8          VLRVVIREDFSRTLAERLVLDITKVLHELDSLPS-----------KVLVPASE------- 457 Seq ID #  16
Q6Q4I1          VLRVVIREDFSRTLAERLVADFEKVLHELDTLPARVR-------AKMANGK--------- 459 Seq ID #  18
AAS79671        VLRVVIREDFSRTLAERLVADFEKVLHELDTLPARVR-------AKMANGK--------- 459 Seq ID # 100
Q6Q4I2          VLRVVIREDFSRTLAERLVADFEKVLHELDTLPARVQ-------AKMANGN--------- 459 Seq ID #  19
AAS79670        VLRVVIREDFSRTLAERLVADFEKVLHELDTLPARVQ-------AKMANGN--------- 459 Seq ID # 101
AAM70569        VLRVVIREDFSRTLAERLVADFEKVLHELDTLPARVH-------AKMANGK--------- 459 Seq ID # 104
BAC42751        VLRVVIREDFSRTLAERLVADFEKVLHELDTLPARVH-------AKMASGK--------- 459 Seq ID # 105
Q94KK8          VLRVVIREDFSRTLAERLVLDIVKVLHELDTLPARLS-------AKLEEVKL-------- 460 Seq ID #  27
AAK38667        VLRVVIREDFSRTLAERLVLDIVKVLHELDTLPARLS-------AKLEEVKL-------- 460 Seq ID # 106
Q42521          VLRVVIREDFSRTLAERLVIDIEKVMRELDELPSRVI-------HKISLGQEKSESNSDN 468 Seq ID #   2
AAN46801        VLRVVIREDFSRTLAERLVIDIEKVMRELDELPSRVI-------HKISLGQEKSESNSDN 468 Seq ID #  98
AAA93132        VLRVVIREDFSRTLAERLVIDIEKVMRELDELPSRVI-------HKISLGQEKSESNSDN 468 Seq ID # 119
A0EJ88          VLRVVIREDFSRTLAERLVIDIGKVLHELETLPSRIS-------AKIVLANEEK----DA 464 Seq ID #   6
Q944L6          VLRVVIREDFSRTLAERLVADISKVLHELDTLPSKIS-------KKMGIEGIAE------ 461 Seq ID #  26
AAL16126        VLRVVIREDFSRTLAERLVADISKVLHELDTLPSKIS-------KKMGIEGIAE------ 461 Seq ID # 114
Q42472          VLRVVIREDFSRTLAERLVADISKVLHELDTLPSKIS-------KKMGIEGIAE------ 461 Seq ID #   3
AAM70582        VLRVVIREDFSRTLAERLVADISKVLHELDTLPSKIS-------KKMGIEGIAE------ 461 Seq ID # 116
AAL91148        VLRVVIREDFSRTLAERLVADISKVLHELDTLPSKIS-------KKMGIEGIAK------ 386 Seq ID # 112
Q6Q4I3          VLRVVIREDFSRTLAERLVADIVKVLHELDTLPSKIS-------KKMGAEDFG------- 461 Seq ID #  20
AAS79669        VLRVVIREDFSRTLAERLVADIVKVLHELDTLPSKIS-------KKMGAEDFG------- 461 Seq ID # 102
AAP85548        VLRVVIREDFSRTLAERLVSDVEKVLHELDSLPARVISSTT---VTLSAEENGK------ 413 Seq ID # 108
P54767          VLRVVIREDFSHSLAERLVSDIEKILSELDTQPPRLPTKAVRVTAEEVRDDKGD------ 470 Seq ID #   5
CAA56812        VLRVVIREDFSHSLAERLVSDIEKILSELDTQPPRLPTKAVRVTAEEVRDDKGD------ 470 Seq ID # 122
Q8LER4          VLRVVIREDFSRGLADRLITHIIQVLKEIEGLPSRIAHLAA--AAAVSGDDEEV------ 466 Seq ID #  24
AAM61251        VLRVVIREDFSRGLADRLITHIIQVLKEIEGLPSRIAHLAA--AAAVSGDDEEV------ 466 Seq ID # 110
Q9LSH2          VLRVVIREDFSRGLADRLITHIIQVLKEIEGLPSRIAHLAA--AAAVSGDDEEV------ 466 Seq ID #  31
BAB02870        VLRVVIREDFSRGLADRLITHIIQVLKEIEGLPSRIAHLAA--AAAVSGDDEEV------ 466 Seq ID # 103
LpORF           VLRVVIREDFNRSLSQRLLADINRVVQELDAHAVHAIKMT----TAIATQTGEG-----A 469 Seq ID #   1
A7P434          VLRVVVREDFGRQLVEKLLFHIGVALKEVTDAASSVPMIR--LTVEMKADESEMNAGEGT 443 Seq ID #  11
                *****:****.: * ::*: ..   .  :   .
```

FIG. 11I

```
P93369       NGSGVHKKTDREVQLEIITAWKKFVADKKKKTN------GVC-- 496 Seq ID #  14
AAB40608     NGSGVHKKTDREVQLEIITAWKKFVADKKKKTN------GVC-- 496 Seq ID # 118
AAC24195     NGSGVHKKTDREVQLEIITAWKKFVADKKKKTN------GVC-- 496 Seq ID # 117
O81102       NGSGVHKKTDREVQLEIITAWKKFVADKKKKTN------GVC-- 496 Seq ID #  13
Q9AT17       NGSGVHKKTDREVQLEIIAAWKKFVADKKKKTN------GVC-- 496 Seq ID #  30
AAK18620     NGSGVHKKTDREVQLEIIAAWKKFVADKKKKTN------GVC-- 496 Seq ID # 107
O81101       NGSGVHKKTDREVQLEIITAWLKFVADKKKKTN------GVC-- 496 Seq ID #  12
AAC39483     NGSGVHKKTDREVQLEIITAWLKFVADKKKKTN------GVC-- 496 Seq ID # 115
Q8LKR4       NGSGVHKKTDREVQLEIITAWKKFVADKKKKTN------GVC-- 496 Seq ID #  25
AAM48129     NGSGVHKKTDREVQLEIITAWKKFVADKKKKTN------GVC-- 496 Seq ID # 109
Q07346       NGSEVHKKTDSEVQLEMITAWKKFVEEKKKKTN------RVC-- 500 Seq ID #   4
A48767       NGSEVHKKTDSEVQLEMITAWKKFVEEKKKKTN------RVC-- 500 Seq ID # 120
A5BI27       QNGTILKKSVIETQREIIDAWKKFVMAKKTNG--------VC-- 489 Seq ID #   9
A7P433       QNGTILKKSVIETQREIIDAWKKFVMAKKTNG--------VC-- 495 Seq ID #  10
Q1I1D8       QNGRNGKKTEIETQREVITYWRKFVSERKANNKN-----KIC-- 494 Seq ID #  16
Q6Q4I1       --AKVVKQTEEETTREVIAYWKKFVEIKKTNQN------KIC-- 493 Seq ID #  18
AAS79671     --AKVVKQTEEETTREVIAYWKKFVEIKKTNQN------KIC-- 493 Seq ID # 100
Q6Q4I2       --ANGVKKTEEETTREVIAYWKKFVEAKKSNKN------RIC-- 493 Seq ID #  19
AAS79670     --ANGVKKTEEETTREVIAYWKKFVEAKKSNKN------RIC-- 493 Seq ID # 101
AAM70569     --VNGVKKTPEETQREVIAYWKKLLEIKKTNKN------TIC-- 493 Seq ID # 104
BAC42751     --VNGVKKTPEETQREVIAYWKKFVDI-KTDKNGVPLVASITNQ 500 Seq ID # 105
Q94KK8       --VKNGKKFELEVQREVINYWKKFVLARKAPVC----------- 491 Seq ID #  27
AAK38667     --VKNGKKFELEVQREVINYWKKFVLARKAPVC----------- 491 Seq ID # 106
Q42521       LMVTVKKSDID-KQRDIITGWKKFVADRKKTSC-------IC-- 502 Seq ID #   2
AAN46801     LMVTVKKSDID-KQRDIITGWKKFVADRKKTSC-------IC-- 502 Seq ID #  98
AAA93132     LMVTVKKSDID-KQRDIITGWKKFVADRKKTSG-------IC-- 502 Seq ID # 119
A0EJ88       VAAGKEKKDVQNETREIITAWRKLVVQRKKLNG-------VC-- 499 Seq ID #   6
Q944L6       --NVKEKKMEKEILMEVIVGWRKFVKERKK-------MNGVC-- 494 Seq ID #  26
AAL16126     --NVKEKKMEKEILMEVIVGWRKFVKERKK-------MNGVC-- 494 Seq ID # 114
Q42472       --NVKEKKMEKEILMEVIVGWRKFVKERKK-------MNGVC-- 494 Seq ID #   3
AAM70582     --NVKEKKMEKEILMEVIVGWRKFVKERKK-------MNGVC-- 494 Seq ID # 116
AAL91148     --NVKEKKMEKEILMEVIVGWRKFVKERKK-------MNGVC-- 419 Seq ID # 112
Q6Q4I3       --NVKGKKVDRDVLMEVIVGWRKFVKDRKK-------MNGVC-- 494 Seq ID #  20
AAS79669     --NVKGKKVDRDVLMEVIVGWRKFVKDRKK-------MNGVC-- 494 Seq ID # 102
AAP85548     --VVVAKKNPMETQREIIAIWKKFVLERKKNNDK---MNGVC-- 450 Seq ID # 108
P54767       -GLHHFHMDTVETQKDIIKHWRKIAGKKTS---------GVC-- 502 Seq ID #   5
CAA56812     -GLHHFHMDTVETQKDIIKHWRKIAGKKTS---------GVC-- 502 Seq ID # 122
Q8LFR4       -KVKTAKMS----LEDIIKYWKRLVEHKRN---------IVC-- 494 Seq ID #  24
AAM61251     -KVKTAKMS----LEDIIKYWKRLVEHKRN---------IVC-- 494 Seq ID # 110
Q9LSH2       -KVKTAKMS----LEDIIKYWKRLVEHKRN---------IVC-- 494 Seq ID #  31
BAB02870     -KVKTAKMS----LEDIIKYWKRLVEHKRN---------IVC-- 494 Seq ID # 103
LpORF        EDGVVTKKGVLDIEKEFAAACKDLVKNKKT---------GPC-- 502 Seq ID #   1
A7P434       LHTPAASVHWKHDKPETVDTQVPIMDCKTK---------GVC-- 476 Seq ID #  11
                            :       :
```

POLYNUCLEOTIDES AND METHODS FOR THE IMPROVEMENT OF PLANTS

RELATED APPLICATIONS

This application claims priority to U.S. Provisional Application Ser. No. 60/982,862, filed Oct. 26, 2007, which is hereby incorporated by reference in its entirety.

SEQUENCE LISTING

The present application is being filed along with a Sequence Listing in electronic format. The Sequence Listing is provided as a file entitled AJPARK44_001AUS.txt, created Oct. 24, 2008, which is 403 Kb in size. The information in the electronic format of the Sequence Listing is incorporated herein by reference in its entirety.

TECHNICAL FIELD

The present invention relates to compositions and methods for producing plants with increased seed yield.

BACKGROUND ART

As the population of the world increases, a major goal of agricultural research is to improve the grain yield of crop plant species.

Such improvements have until recently depended on selective breeding of plants for desirable characteristics. However for many plants the heterogeneous genetic compliments produced in off-spring do not result in the same desirable traits as those of their parents, thus limiting the effectiveness of selective breeding approaches.

Advances in molecular biology now make it possible to genetically manipulate the germplasm of both plants and animals. Genetic engineering of plants involves the isolation and manipulation of genetic material and the subsequent introduction of such material into a plant. This technology has led to the development of plants that are capable of expressing pharmaceuticals and other chemicals, plants with increased pest resistance, increased stress tolerance, and plants that express other beneficial traits.

Improvements in the grain yield of plant crop plants may be achieved by developing plants that produce more seed or grain than the equivalent wild-type plants.

Thus, there exists a need for plants with increased seed yield relative to their normally cultivated counterparts.

It is an object of the invention to provide improved compositions and/or methods for developing plant varieties with improved seed or grain seed yield or at least to provide the public with a useful choice.

SUMMARY OF THE INVENTION

In a first aspect the invention provides a method for producing a plant with altered seed yield, the method comprising transformation of a plant with:

a) a polynucleotide encoding of a polypeptide with the amino acid sequence of SEQ ID NO:1 or a variant of the polypeptide, wherein the variant is capable of modulating seed yield in a plant;
b) a polynucleotide comprising a fragment, of at least 15 nucleotides in length, of the polynucleotide of a), or
c) a polynucleotide comprising a compliment, of at least 15 nucleotides in length, of the polynucleotide of a).

In one embodiment the variant has at least 70% sequence identity to a polypeptide with the amino acid sequence of SEQ ID NO: 1.

Preferably the variant is derived from a plant species and comprises the sequence of SEQ ID NO: 32.

In one embodiment the variant is from a monocotyledonous species and comprises the sequence of SEQ ID NO: 33.

In a preferred embodiment the variant comprises an amino acid sequence selected from any one of SEQ ID NO: 2-31.

In a preferred embodiment the polypeptide or variant is a glutamate decarboxylase.

In a preferred embodiment the polynucleotide of a) encodes a polypeptide with the amino acid sequence of SEQ ID NO: 1.

In a preferred embodiment the plant is transformed with a genetic construct containing the polynucleotide.

In a further aspect the invention provides a method of producing a plant with altered seed yield, the method comprising transformation of a plant cell or plant with:

a) a polynucleotide comprising the nucleotide sequence of SEQ ID NO: 34, or a variant thereof, wherein the variant encodes a polypeptide capable of modulating seed yield in a plant;
b) a polynucleotide comprising a fragment, of at least 15 nucleotides in length, of the polynucleotide of a), or
c) a polynucleotide comprising a complement, of at least 15 nucleotides in length, of the polynucleotide of a).

In a one embodiment the variant comprises the sequence of any one of SEQ ID NO: 35 to 65.

In a preferred embodiment the polynucleotide or variant in a) encodes a polypeptide which is a glutamate decarboxylase.

In a further embodiment the polynucleotide of a) comprises the sequence of SEQ ID NO: 34.

In a further embodiment the polynucleotide of a) comprises the coding sequence of SEQ ID NO: 34.

In a preferred embodiment the plant is transformed with a genetic construct containing the polynucleotide.

Preferably the plant produced by the method of the invention has increased seed yield relative to a suitable control plant.

In a further embodiment the method for producing a plant with altered seed yield comprises transformation of a plant cell, or plant with a genetic construct capable or altering expression of a polypeptide which modulates seed yield.

In one embodiment, the method results in a plant with decreased seed yield, relative to a suitable control, due to transformation of a plant cell or plant, with a genetic construct capable of down-regulating expression of a polypeptide which positively modulates seed yield.

In a preferred embodiment, the method results in a plant with increased seed yield, relative to a suitable control, due to transformation of a plant cell or plant, with a genetic construct capable of up-regulating expression of a polypeptide which positively modulates seed yield.

In a further aspect the invention provides a plant cell or plant produced by a method of the invention.

Preferably the plant produced by the method of the invention has increased seed yield relative to a suitable control plant.

In a further aspect the invention provides an isolated polynucleotide having at least 75% sequence identity to a nucleotide sequence that encodes a polypeptide comprising an amino acid sequence selected of SEQ ID NO: 1, wherein the polynucleotide encodes a polypeptide capable of modulating seed yield in a plant.

In one embodiment said nucleotide sequence comprises the sequence of SEQ ID NO: 34.

In a further embodiment said nucleotide sequence comprises the full-length coding sequence of SEQ ID NO:34.

In a further aspect the invention provides a polynucleotide encoding a polypeptide with at least 70% identity to the amino acid sequence of SEQ ID NO: 1.

Preferably the polypeptide is capable of modulating seed yield in a plant.

Preferably the polypeptide is a glutamate decarboxylase.

In a further aspect the invention provides an isolated polynucleotide that encodes a polypeptide comprising an amino acid sequence SEQ ID NO: 1.

In a further embodiment the polynucleotide comprises the sequence of SEQ ID NO: 34.

In a further embodiment the polynucleotide comprises the full-length coding sequence of SEQ ID NO: 34.

In a further aspect the invention provides an isolated polynucleotide comprising the sequence of SEQ ID NO: 34 or a variant thereof, wherein the variant is from ryegrass or fescue, and encodes a polypeptide capable of modulating seed yield in a plant.

In one embodiment the polypeptide is a glutamate decarboxylase.

In one embodiment the isolated polynucleotide comprises the sequence of SEQ ID NO: 34.

In a further aspect the invention provides an isolated polypeptide having at least 83% sequence identity to the amino acid sequence of SEQ ID NO: 1, wherein the polypeptide is capable of modulating seed yield in a plant.

In one embodiment the isolated polypeptide of comprises the amino acid sequence of SEQ ID NO: 1.

In a further aspect the invention provides an isolated polynucleotide encoding a polypeptide of the invention.

In a further aspect the invention provides an isolated polynucleotide comprising:

a) a polynucleotide comprising a fragment, of at least 15 nucleotides in length, of a polynucleotide of the invention;
b) a polynucleotide comprising a complement, of at least 15 nucleotides in length, of the polynucleotide of the invention; or
c) a polynucleotide comprising a sequence, of at least 15 nucleotides in length, capable of hybridising to the polynucleotide of the invention.

In a further aspect the invention provides a genetic construct which comprises a polynucleotide of the invention.

In one embodiment the genetic construct is an expression construct.

In one embodiment the construct comprises a promoter operably linked to the polynucleotide.

In a further embodiment the construct comprises a terminator operably linked to the polynucleotide.

Preferably the promoter, the terminator, or both is/are derived from a different source than the polynucleotide.

In one embodiment the different source is a different species.

In a further aspect the invention provides a vector comprising a genetic construct or expression construct of the invention.

In a further aspect the invention provides a host cell genetically modified to express a polynucleotide of the invention, or a polypeptide of the invention.

In a further aspect the invention provides a host cell comprising a genetic construct or expression construct of the invention.

In a further aspect the invention provides a plant cell genetically modified to express a polynucleotide of the invention, or a polypeptide of the invention.

In a further aspect the invention provides a plant cell which comprises a genetic construct of the invention or the expression construct of the invention.

In a further aspect the invention provides a plant which comprises a plant cell of the invention.

In a further aspect the invention provides a method for selecting a plant with altered seed yield relative to suitable contrast, the method comprising testing of a plant for altered expression of a polynucleotide of the invention.

In a further aspect the invention provides a method for selecting a plant with altered seed yield relative to a suitable control, the method comprising testing of a plant for altered expression of a polypeptide of the invention.

In a further aspect the invention provides a plant cell or plant produced by the method of the invention.

In a further aspect the invention provides a plant selected by the method of the invention.

In a further aspect the invention provides a population or group of plants selected by the method of the invention.

In a further aspect the invention provides an antibody raised against a polypeptide of the invention.

The polynucleotides and polynucleotide variants of the invention may be derived from any species and/or may be produced synthetically or recombinantly.

In one embodiment the polynucleotide or variant, is derived from a plant species.

In a further embodiment the polynucleotide or variant, is derived from a gymnosperm plant species.

In a further embodiment the polynucleotide or variant, is derived from an angiosperm plant species.

In a further embodiment the polynucleotide or variant, is derived from a from dicotyledonuous plant species.

In a further embodiment the polynucleotide or variant, is derived from a monocotylenouous plant species.

The polypeptide and polypeptide variants, of the invention may be derived from any species and/or may be produced synthetically or recombinantly.

In one embodiment the polypeptide or variant, is derived from a plant species.

In a further embodiment the polypeptide or variant, is derived from a gymnosperm plant species.

In a further embodiment the polypeptide or variant, is derived from an angiosperm plant species.

In a further embodiment the polypeptide or variant, is derived from a from dicotyledonuous plant species.

In a further embodiment the polypeptide or variant, is derived from a monocotylenouous plant species.

The plant cells and plants, of the invention may be derived from any species.

In one embodiment the plant cell or plant, is derived from a gymnosperm plant species.

In a further embodiment the plant cell or plant, is derived from an angiosperm plant species.

In a further embodiment the plant cell or plant, is derived from a from dicotyledonuous plant species.

In a further embodiment the plant cell or plant, is derived from a monocotylenouous plant species.

Preferred dicotyledonous genera include: *Amygdalus, Anacardium, Arachis, Brassica, Cajanus, Cannabis, Carthamus, Carya, Ceiba, Cicer, Cocos, Coriandrum, Coronilla, Cossypium, Crotalaria, Dolichos, Elaeis, lycine, Gossypium, Helianthus, Lathyrus, Lens, Lespedeza, Linum, Lotus, Lupinus, Macadamia, Medicago, Melilotus, Mucuna, Olea, Onobrychis, Ornithopus, Papaver, Phaseolus, Phoenix, Pistacia, Pisum, Prunus, Pueraria, Ribes, Ricinus, Sesamum, Theobroma, Trifolium, Trigonella, Vicia* and *Vigna.*

Preferred dicotyledonous species include: *Amygdalus communis, Anacardium occidentale, Arachis hypogaea, Arachis hypogea, Brassica napus* Rape, *Brassica nigra. Brassica campestris, Cajanus cajan, Cajanus indicus, Cannabis sativa, Carthamus tinctorius, Carya illinoinensis, Ceiba pentandra, Cicer arietinum, Cocos nucifera, Coriandrum sativum, Coronilla varia, Cossypium hirsutum, Crotalaria juncea, Dolichos lablab, Elaeis guineensis, Gossypium arboreum, Gossypium nanking, Gossypium barbadense, Gossypium herbaceum, Gossypium hirsutum, Glycine max, Glycine ussuriensis, Glycine gracilis, Helianthus annus, Lathyrus angustifolius, Lathyrus luteus, Lathyrus mutabilis, Lathyrus sericea, Lathyrus striata, Lathyrus uliginosus, Lathyrus sativus, Lens culinaris, Lespedeza stipulacea, Linum usitatissimum, Lotus corniculatus, Lupinus albus, Medicago arabica, Medicago arborea, Medicago falcate, Medicago hispida, Medicago officinalis, Medicago sativa, Medicago tribuloides, Macadamia integrifolia, Melilotus albus, Mucuna pruriens, Olea europaea, Onobrychis viciifolia, Ornithopus sativus, Phaseolus aureus, Phaseolus aureus cerasifera, Phaseolus aureus cerasus, Phaseolus aureus coccineus, Phaseolus aureus domestica, Phaseolus aureus lunatus, Phaseolus aureus maheleb, Phaseolus aureus mungo, Phaseolus aureus persica, Phaseolus aureus pseudocerasus, Phaseolus aureus vulgaris, Papaver somniferum, Phaseolus acutifolius, Phoenix dactylifera, Pistacia vera, Pisum sativum, Prunus amygdalus, Prunus armeniaca, Pueraria thunbergiana, Ribes nigrum, Ribes rubrum, Ribes grossularia, Ricinus communis, Sesamum indicum, Trifolium augustifolium, Trifolium diffusum, Trifolium hybridum, Trifolium incarnatum, Trifolium ingrescens, Trifolium pratense, Trifolium repens, Trifolium resupinatum, Trifolium subterraneum, Theobroma cacao, Trifolium alexandrinum, Trigonella foenumgraecum, Vigna angustifolia, Vigna atropurpurea, Vigna calcarata, Vigna dasycarpa, Vigna ervilia, Vigna oxycoccos, Vigna pannonica, Vigna sesquipedalis, Vigna sinensis, Vigna villosa, Vicia faba, Vicia native* and *Vigna angularis.*

Preferred monocotyledonous genera include: *Agropyron, Allium, Alopecurus, Andropogon, Arrhenatherum, Asparagus, Avena, Bambusa, Bothrichloa, Bouteloua, Bromus, Cenchrus, Chloris, Cymbopogon, Cynodon, Dactylis, Dichanthium, Digitaria, Eleusine, Elymus, Eragrostis, Fagopyrum, Festuca, Hordeum, Lolium, Otyza, Panicum, Paspalum, Pennisetum, Phalaris, Phleum, Poa, Saccharum, Secale, Setaria, Sorghastrum, Sorghum, Triticum, Vanilla,* x *Triticosecale* and *Zea.*

Preferred monocotyledonous species include: *Agropyron desertorum, Agropyron elongatum, Agropyron spicatum, Agropyron trachycaulum, Agropyron trichophorum, Allium fistulosum, Allium. sativum, Alopecurus pratensis, Andropogon gerardi, Arrhenatherum elatius, Asparagus officinalis, Avena sativa, Bambusa vulgaris, Bothrichloa barbinodis, Bothrichloa ischaemum, Bouteloua curipendula, Bouteloua gracilis, Bromus erectus, Cenchrus ciliaris, Chloris gayana, Cymbopogon nardus, Cynodon dactylon, Dactylis glomerata, Dichanthium annulatum, Digitaria decumbens, Eleusine coracan, Elymus angustus, Eragrostis curvula, Eragrostis* tef, *Fagopyrum esculentum, Fagopyrum tataricum, Festuca arundinacea, Hordeum distichum, Hordeum vulgare, Lolium. perenne, Lolium multiflorum, Oryza sativa, Panicum italicium, Panicum maximum, Panicum miliaceum, Paspalum dilatatum, Pennisetum clandestinum, Pennisetum glaucum, Phalaris arundinacea, Phleum bertolinii, Poa fendleriana, Poa nemoralis, Saccharum robustum, Saccharum sinense, Secale cereale, Setaria sphacelata, Sorghastrum nutans, Sorghum dochna, Sorghum halepense, Sorghum bicolor, Triticum aestivum, Triticum dicoccum,* X *Triticosecale, Zea mays, Agropyron cristatum, Agropyron intermedium, Agropyron smithii, Allium ascalonicum, Allium cepa, Allium chinense, Allium porrum, Allium schoenoprasum, Avena nuda, Bambusa vulgaris, Bothrichloa saccharoides, Bouteloua eriopoda, Bromus inermis, Bromus riparius, Dactylis aristatum, Dactylis sericeum, Digitaria smutsii, Elymus junceus, Festuca ovina, Festuca pratensis, Festuca rubra, Panicum purpurascens, Panicum virgatum, Paspalum notatum, Pennisetum purpureum, Pennisetum spicatum, Phleum pratense, Poa pratensis, Saccharum officinarum, Saccharum spontaneum, Sorghum sudanense, Triticum durum, Triticum monococcum, Vanilla fragrans* and *Zea mays.*

Preferred plants are from the genera *Lolium* and *Trifolium*. Particularly preferred are the species *Lolium perenne* and *Trifolium repens.*

Particularly preferred monocotyledonous plant species are: *Lolium perenne* and *Oryza sativa.*

The term "plant" is intended to include a whole plant, any part of a plant, propagules and progeny of a plant.

The term 'propagule' means any part of a plant that may be used in reproduction or propagation, either sexual or asexual, including seeds and cuttings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be better understood with reference to the accompanying drawings in which:

FIG. 1 shows the output summary of a BLASTP search of the uniref100 database (version 2.0MP-WashU [4 May 2006]) in which the ORF56 polypeptide was used as a seed sequence.

FIGS. 2A-2I show "Prettyplot" alignments of polypeptides (SEQ ID NO: 1 to 31) including ORF56 and variants thereof and illustrates a consensus region identified by the applicants which is present in all of the sequences.

FIGS. 3A-3F show "Prettyplot" alignments of polypeptides of the invention, including ORF56 SEQ ID NO:1 and sequences from all variants of SEQ ID NO:1 and illustrates a consensus GAD region identified by the applicants which is present in all of the such sequences.

FIG. 4 shows another "Prettyplot" alignment of polypeptides of the invention, including ORF 56 SEQ ID NO: 1 and sequence variants SEQ ID NO:2-31 and illustrates a consensus CaM region identified by the applicants which is present in all of the such sequences.

FIG. 7A. Plant height measurements from experiment 1. FIG. 7B. Plant tiller measurements from experiment 1. FIG. 7C. Plant height measurements from experiment 2. FIG. 7D. Plant tiller measurements from experiment 2.

FIG. 8A, Seed yield per plant in different ORF56 T1 lines. FIG. 8B Total number of seeds per plant in different ORF56 T1 lines. FIG. 8C Average mass of an individual seed in each ORF56 T1 line. FIG. 8D Binomial distribution for seed yields in different ORF56 T1 lines. FIG. 8E Shift in seed yield distribution in the different ORF56 T1 lines.

FIGS. 10A-10I show alignments of the ORF56 polypeptide sequence (SEQ ID NO: 1) and all of the other variants sequences disclosed that are from monocotyledonous species. The position of a completely conserved motif within the GAD region is shown. The sequence of the completely conserved motif is shown in SEQ ID NO: 32.

FIGS. 11A-11I show alignments of the ORF56 polypeptide sequence (SEQ ID NO: 1) and all of the other variant sequences disclosed that are from dicotyledonous species. The position of a completely conserved motif within the GAD region is shown. This sequence motif is completely conserved in all of the dicotyledonous sequences and all of the monocotyledonous sequences (see FIGS. 10A-10I) and is shown on SEQ ID NO: 33.

DETAILED DESCRIPTION

Figure 5:
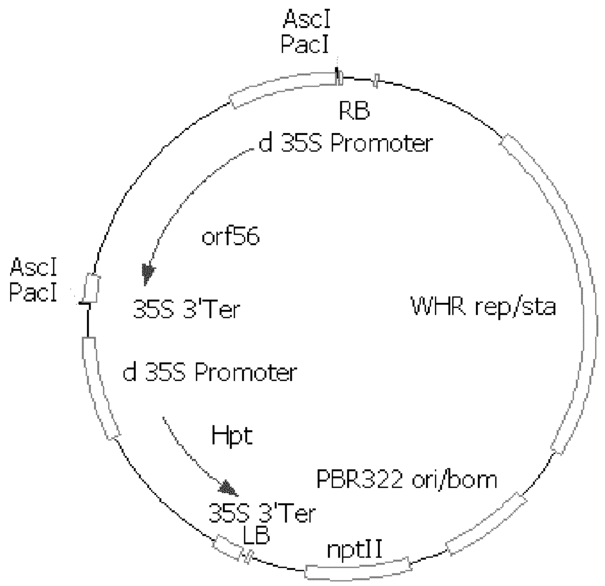
FIG. 5 shows a map of an over-expression vector, for plant transformation, comprising ORF56 cloned in sense orientation (SEQ ID NO:66).

Methods and compositions that can be used for, among other things, producing plants with altered seed yield are disclosed herein. In some embodiments, the methods include transforming a plant with a genetic construct including one or more polynucleotides disclosed herein. In some embodiments, isolated polypeptides, polynucleotides, constructs, vectors and methods useful for producing plants with altered seed yield are provided. In some embodiments, plant cells and plants transformed to contain and express the polypeptides, polynucleotides and constructs disclosed herein are provided. In some embodiments, plants produced by the disclosed methods are provided.

General Definitions

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that is capable of specific hybridization to a target of interest, e.g., a sequence that is at least 15 nucleotides in length. The fragments of the invention comprise 15 nucleotides, preferably at least 20 nucleotides, more preferably at least 30 nucleotides, more preferably at least 50 nucleotides, more preferably at least 50 nucleotides and most preferably at least 60 nucleotides of contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods of the invention.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a specified polynucleotide sequence. Identity is found over a comparison window of at least 20 nucleotide positions, preferably at least 50 nucleotide positions, more preferably at least 100 nucleotide positions, and most preferably over the entire length of the specified polynucleotide sequence.

Polynucleotide sequence identity can be determined in the following manner. The subject polynucleotide sequence is compared to a candidate polynucleotide sequence using BLASTN (from the BLAST suite of programs, version 2.2.5 [Nov 2002]) in b12seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI on the world wide web at ftp://ftp.ncbi.nih.gov/blast/. The default parameters of b12seq are utilized except that filtering of low complexity parts should be turned off The identity of polynucleotide sequences may be examined using the following unix command line parameters:

bl2seq -i nucleotideseq1 -j nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice,P. Longden,I. and Bleasby,A. EMBOSS: The European Molecular Biology Open Software Suite, Trends in Genetics June 2000, vol 16, No 6. pp.276-277) which can be obtained via the world wide web at http://www.hgmp.mrc.ac.uk/Software/EMBOSS/. The European Bioinformatics Institute server also provides the facility to perform EMBOSS-needle global alignments between two sequences on line at http://www.ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp://ftp.ncbi.nih.gov/blast/).

The similarity of polynucleotide sequences may be examined using the following unix command line parameters:

bl2seq -i nucleotideseq1 -j nucleotideseq2 -F F -p tblastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$, more preferably less than $1\times10^{-100}$, more preferably less than $1\times10^{-110}$, and most preferably less than $1\times10^{-120}$ when compared with any one of the specifically identified sequences.

Alternatively, variant polynucleotides of the present invention hybridize to a specified polynucleotide sequence, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing). Tm for polynucleotide molecules greater than about 100 bases can be calculated by the formula Tm=81.5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. Dec. 6, 1991; 254 (5037):1497-500) Tm values are higher than those for DNA-DNA or DNA-RNA hybrids, and can be calculated using the formula described in Giesen et al., Nucleic Acids Res. Nov. 1, 1998; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available b12seq program from the BLAST suite of programs (version 2.2.5 [Nov 2002]) from NCBI on the world wide web at ftp://ftp.ncbi.nih.gov/blast via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in b12seq, which is publicly available from NCBI on the world wide web at ftp://ftp.ncbi.nih.gov/blast/. The default parameters of b12seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http://www.ebi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

Use of BLASTP as described above is preferred for use in the determination of polypeptide variants according to the present invention.

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available b12seq program from the BLAST suite of programs (version 2.2.5 [Nov 2002]) from NCBI on the world wide web at ftp://ftp.ncbi.nih.gov/blast/. The similarity of polypeptide sequences may be examined using the following unix command line parameters:

b12seq -i peptideseq1 -j peptideseq2 -F F p blastp

Variant polypeptide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$, more preferably less than $1\times10^{-100}$, more preferably less than $1\times10^{-110}$, more preferably less than $1\times10^{-120}$ more preferably less than $1\times10^{-130}$, more preferably less than $1\times10^{-140}$, more preferably less than $1\times10^{-150}$, more preferably less than $1\times10^{-160}$ more preferably less than $1\times10^{-170}$, more preferably less than $1\times10^{-180}$, more preferably less than $1\times10^{-190}$, more preferably less than $1\times10^{-200}$, more preferably less than $1\times10^{-210}$, more preferably less than $1\times10^{-220}$, and most preferably less than $1\times10^{-222}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli*.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter functional in the host cell into which the construct will be transformed, b) the polynucleotide to be expressed, and c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors.

A "transgene" is a polynucleotide that is taken from one organism and introduced into a different organism by transformation. The transgene may be derived from the same species or from a different species as the species of the organism into which the transgene is introduced.

An "inverted repeat" is a sequence that is repeated, where the second half of the repeat is in the complementary strand, e.g.,

```
(5')GATCTA . . . TAGATC(3')

(3')CTAGAT . . . ATCTAG(5')
```

Read-through transcription will produce a transcript that undergoes complementary base-pairing to form a hairpin structure provided that there is a 3-5 bp spacer between the repeated regions.

A "transgenic plant" refers to a plant which contains new genetic material as a result of genetic manipulation or transformation. The new genetic material may be derived from a plant of the same species as the resulting transgenic plant or from a different species.

The terms "to alter expression of" and "altered expression" of a polynucleotide or polypeptide of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

The term "seed yield" refers to the size and/or mass and/or number of seed or grain produced by a plant. Thus a plant with increased seed yield has increased size and/or mass and/or number of seed or grain relative to a suitable control plant at the same age or an equivalent developmental stage. Conversely, a plant with decreased seed yield has increased size and/or mass and/or number of seed or grain relative to a suitable control plant the same age or an equivalent development stage.

Suitable control plants may include non-transformed plants of the same species and variety, or plants of the same species or variety transformed with a control construct.

The term "altered" with reference to seed yield is intended to encompass either a decrease or increase in seed yield.

The term "modulating" with reference to seed yield is intended to encompass either decreasing or increasing seed yield.

The invention provides methods for producing and/or selecting plants with altered seed yield relative to suitable control plants, including plants with both increased and decreased seed yield and plants produced by such methods.

The invention provides a polynucleotide (SEQ ID NO: 34) encoding a polypeptide (SEQ ID NO:1) which modulates seed yield in plants. The invention provides polynucleotide variants of SEQ ID NO:34 (SEQ ID NO: 35 to 65) which encode polypeptide variants of SEQ ID NO: 1 (SEQ ID NO:2 to 31). The applicants have also identified a consensus polypeptide sequence (SEQ ID NO: 32) present in SEQ ID NO: 1 to 31 and a second consensus polypeptide sequence (SEQ ID NO:33) present in the sequences from monocotyledonous plants selected from within SEQ ID NO:1 to 31.

Methods for Isolating or Producing Polynucleotides

The polynucleotide molecules of the invention can be isolated by using a variety of techniques known to those of ordinary skill in the art. By way of example, such polynucleotides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides, of the invention or useful in the methods of the invention, include use of all, or portions of, the polynucleotides set forth herein as hybridization probes. The technique of hybridizing labeled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion and oligonucleotide synthesis.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species. Variants (including orthologues) may be identified by the methods described.

Methods for Identifying Variants

Physical Methods

Variant polynucleotides may be identified using PCR-based methods (Mullis et al., Eds. 1994 The Polymerase Chain Reaction, Birkhauser). Typically, the polynucleotide sequence of a primer, useful to amplify variant polynucleotide molecules PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

Polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp://ftp.ncbi.nih.gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with DbCLUSTAL (Thompson J.D., Plewnial F., Thierry J.-C. and Poch O. (2000) Rapid and reliable global multiple alignments of protein sequences detected by database searches. Nucleic Acid Research, Vol.28, No 15: 2919-2926, on the world wide web at http://www.ebi.ac.uk/cgi-bin/dbclustal/submit) or CLUSTALW (Thompson, J.D., Higgins, D.G. and Gibson, T.J. (1994) CLUSTALW: improving the sensitivity of progressive multiple sequence alignment through sequence weighting, positions-specific gap penalties and weight matrix choice. Nucleic Acids Research, 22:4673-4680, on the world wide web at http://www-igbmc.u-strasbg.fr/BioInfo/ClustalW/Top.html or T-COFFEE (Cedric Notredame, Desmond G. Higgins, Jaap Heringa, T-Coffee: A novel method for fast and accurate multiple sequence alignment, J. Mol. Biol. (2000) 302: 205-217))or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco, Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention may also be purified from natural sources using a variety of techniques that are well known in the art (e.g. Deutscher, 1990, Ed, Methods in Enzymology, Vol. 182, *Guide to Protein Purification*).

Alternatively the polypeptides and variant polypeptides of the invention may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Constructs and Vectors

The invention provides a host cell which comprises a genetic construct or vector of the invention. Host cells may be derived from, for example, bacterial, fungal, insect, mammalian or plant organisms.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Host cells of the invention may also be useful in methods for production of an enzymatic product generated by an expressed polypeptide of the invention. Such methods may involve culturing the host cells of the invention in a medium suitable for expression of a recombinant polypeptide of the invention, optionally in the presence of additional enzymatic substrate for the expressed polypeptide of the invention. The enzymatic product produced may then be separated from the host cells or medium by a variety of art standard methods.

Methods for Producing Plant Cells and Plants Comprising Constructs and Vectors

The invention further provides plant cells which comprise a genetic construct of the invention, and plant cells modified to alter expression of a polynucleotide or polypeptide of the invention. Plants comprising such cells also form an aspect of the invention.

Production of plants altered in seed yield may be achieved through methods of the invention. Such methods may involve the transformation of plant cells and plants, with a construct designed to alter expression of a polynucleotide or polypeptide capable of modulating seed yield in such plant cells and plants. Such methods also include the transformation of plant cells and plants with a combination of constructs designed to alter expression of one or more polypeptides or polypeptides capable of modulating seed yield in such plant cells and plants.

Methods for transforming plant cells, plants and portions thereof with polynucleotides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of strategies for genetically manipulating plants are available (e.g. Birch, 1997, Ann Rev Plant Phys Plant Mol Biol, 48, 297). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detest presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zin gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenbert. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide of the invention may include an antisense copy of a polynucleotide of the invention. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3'     (coding strand)
3'CUAGAU 5'     mRNA

3'CTAGAT 5'     (antisense strand)
5'GAUCUCG 3'    antisense RNA
```

Genetic constructs designed for gene silencing may also include an inverted repeat. An 'inverted repeat' is a sequence that is repeated where the second half of the repeat is in the complementary strand, e.g.,

```
5'-GATCTA . . . TAGATC-3'

3'-CTAGAT . . . ATCTAG-5'
```

The transcript formed may undergo complementary base pairing to form a hairpin structure. Usually a spacer of at least 3-5 bp between the repeated region is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polypeptides effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve over-expression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257)

Pre-transcriptional silencing may be brought about through mutation of the gene itself or its regulatory elements. Such mutations may include point mutations, frameshifts, insertions, deletions and substitutions.

The following are representative publications disclosing genetic transformation protocols that can be used to genetically transform the following plant species: Rice (Alam et al., 1999, Plant Cell Rep. 18, 572); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073, 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416,011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); brassica (U.S. Pat. Nos. 5,188,958; 5,463,174 and 5,750,871); and cereals (U.S. Pat. No. 6,074,877). Other species are contemplated and suitable methods and protocols are available to in the scientific literature for use by those skilled in the art.

Several further methods known in the art may be employed to alter expression of a nucleotide and/or polypeptide of the invention. Such methods include but are not limited to Tilling (Till et al., 2003, Methods Mol Biol, 2%, 205), so called "Deletagene" technology (Li et al., 2001, Plant Journal 27(3), 235) and the use of artificial transcription factors such as synthetic zinc finger transcription factors. (e.g. Jouvenot et al., 2003, Gene Therapy 10, 513). Additionally antibodies or fragments thereof, targeted to a particular polypeptide may also be expressed in plants to modulate the activity of that polypeptide (Jobling et al., 2003, Nat. Biotechnol., 21(1), 35). Transposon tagging approaches may also be applied. Additionally peptides interacting with a polypeptide of the invention may be identified through technologies such as phase-display (Dyax Corporation). Such interacting peptides may be expressed in or applied to a plant to affect activity of a polypeptide of the invention. Use of each of the above approaches in alteration of expression of a nucleotide and/or polypeptide of the invention is specifically contemplated.

Methods for Selecting Plants

Methods are also provided for selecting plants with altered seed yield. Such methods involve testing of plants for altered for the expression of a polynucleotide or polypeptide of the invention. Such methods may be applied at a young age or early developmental stage when the altered seed yield may not necessarily be visible, to accelerate breeding programs directed toward improving seed yield.

The expression of a polynucleotide, such as a messenger RNA, is often used as an indicator of expression of a corresponding polypeptide. Exemplary methods for measuring the expression of a polynucleotide include but are not limited to Northern analysis, RT-PCR and dot-blot analysis (Sambrook et al., Molecular Cloning: A Laboratory Manual, 2nd Ed. Cold Spring Harbor Press, 1987). Polynucleotides or portions of the polynucleotides of the invention are thus useful as probes or primers, as herein defined, in methods for the identification of plants with altered seed yield. The polypeptides of the invention may be used as probes in hybridization experiments, or as primers in PCR based experiments, designed to identify such plants.

Alternatively antibodies may be raised against polypeptides of the invention. Methods for raising and using antibodies are standard in the art (see for example: Antibodies, A Laboratory Manual, Harlow A Lane, Eds, Cold Spring Harbour Laboratory, 1998). Such antibodies may be used in methods to detect altered expression of polypeptides which modulate seed yield in plants. Such methods may include ELISA (Kemeny, 1991, A Practical Guide to ELISA, NY Pergamon Press) and Western analysis (Towbin & Gordon, 1994, J Immunol Methods, 72, 313).

These approaches for analysis of polynucleotide or polypeptide expression and the selection of plants with altered expression are useful in conventional breeding programs designed to produce varieties with altered seed yield.

Plants

The plants of the invention may be grown and either self-ed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

Seed yield in a plant may also be altered through methods of the invention. Such methods may involve the transformation of plant cells and plants, with a construct of the invention designed to alter expression of a polynucleotide or polypeptide which modulates seed yield in such plant cells and plants. Such methods also include the transformation of plant cells and plants with a combination of the construct of the invention and one or more other constructs designed to alter expression of one or more polynucleotides or polypeptides which modulates seed yield in plants.

Exemplary methods for assessing seed yield in plants are provided in Boyes D C et al., 2001, Plant Cell. 13(7):1499-510; Lancashire P. D et al., 1991, Ann. Appl. Biol. 119: 560-601, and in Example 1 below.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

EXAMPLE

The invention will now be illustrated with reference to the following non-limiting example.

Example 1

Altered Seed Yield by In-Plant Expression of a Polynucleotide of the Invention

ORF56

A polynucleotide designated ORF56 (SEQ ID NO:34) was identified in a ViaLactia Biosciences Ltd proprietary ryegrass (*Lolium perenne*) GeneThresher (Orion Genomics) genomic library.

ORF56 appears to encode a polypeptide (SEQ ID NO:1) which is a glutamate decarboxylase (GAD). GAD catalyses the reaction of glutamate into carbon dioxide and gamma-aminobutyrate (GABA). GAD is believed to be essential for cytosolic pH regulation as well as basic morphological development. The synthesis of GABA is highly regulated under normal growth conditions and in response to stresses such as cold, heat, water or mechanical (Bouche et al 2004; Mayer et al 1990: Patterson and Graham 1987; Wallace et al. 1984). It has been shown that GABA stimulates ethylene production in sunflower, apparently by causing increases in ACC synthase mRNA accumulation, ACC levels, ACC oxidase mRNA levels and ACC oxidase activity, suggesting that GABA may play a role in signaling (Kathiresan et al 1997). High GABA has been reported to impair pollen tube growth, and consequently seed set, while lower levels are reported to be stimulatory (Updegraff and Preuss 2004). The glutamate decarboxylase encoded by ORF56 contains two major domains, the GAD catalytic domain and a second Calmodulin binding domain (CaM). CaM has been shown to stimulate GAD activity by binding to a C-terminal 'extension' not found in prokaryotes such as *E. coli* or mammalian forms of GAD. Truncation of this domain results in shorter, more branched plants with delayed greening and lacking pollen (Baum et al 1996; Akama and Takaiwa 2007). Post-translational modifications of GAD may account for different phenotypes observed. GAD is a monomer in aqueous solutions. Normally, the binding of a Trp residue in the hydrophobic region of the peptide to the C-terminal domain of CaM (boxed residue in FIG. 4) initiates the peptide complex formation. Subsequently, the N-terminal lobe of CaM binds to the hydrophobic and positively charged residues of the region of the peptide 10-12 residues away from the Trp residue (Yuan and Vogel 1998). However, in perennial ryegrass, SEQ ID: 1, the CaM binding domain, lacks the hydrophobic residue Trp, but instead is replaced with a polar but non-charged Cys residue in a hydrophobic setting. The negative charges in perennial ryegrass CaM domain are also disposed in such a way that interaction of the N-terminal lobe of CaM with the region either N- or C-terminal to the GAD would not be energetically favourable, thereby facilitating binding of a second or multiple GAD peptides to the hydrophobic surface in the N-terminal region of CaM. This essentially results in the dimerization or multimerization of the GAD-$Ca^{2+}$—CaM complex. There are possibilities for the GAD such dimerization, which seems to be induced by $Ca^{2+}$—CaM binding (Yuan and Vogel 1998). In plants, there is evidence for the oligomerization of petunia GAD and it appears that only oligomerized GAD seem to be active in petunia (Baum et al 1996). In addition, various isoforms of active GAD extracted from barley were reported to have a mass of ~256 kDa and ~120 kDa (Inatomi and Slaughter 1975). The activity of the barley GADs were also reported to exhibit a reversible inhibition in the presence of 2-Mercaptoethanol. Given these evidences, it is not unreasonable to expect the Cys residue, at the normally Trp residue position in the CaM domain, to play a role in stabilizing the dimerized GAD-$Ca^{2+}$—CaM complex.

ORF56 Variants

The polypeptide sequence encoded by the ORF56 was used as seed sequence to perform WU-blastp search against uniref100 database (2.0MP-WashU [4 May 2006]) to identify variants of ORF56. The WU-blastp output summary is shown in FIG. 1. A cut-off e value of less than or equal to 5.5e-169, was identified as distinguishing variants of ORF56 from unrelated proteins, based upon assessment of the associated score value and annotations in the public database. Selected variant sequences were aligned using the DbCLUSTAL (Thompson J. D., Plewnial F., Thierry J.-C. and Poch O.: 2000), which is an interface to the popular multiple alignment program ClustalW. Aligned sequences were visualised using another EMBOSS tool called Prettyplot as shown in FIG. 2.

The variant polypeptide sequences of ORF56 are listed as SEQ ID NO:2-31 in the sequence listing. The corresponding polynucleotide sequences are listed as SEQ ID NO: 35-65.

All but four of the variant polypeptide sequences appear to have both a proper GAD catalytic domain and a proper CaM binding domain. Four of the sequences (polypeptide SEQ ID NO: 11, 15, 22 and 29; polynucleotide SEQ ID NO:61 to 66) appear to have a proper GAD catalytic domain with a variant CaM binding domain.

A conserved GAD polypeptide sequence region present in ORF56 and all of the identified variants of ORF 56 was identified using Prettyplot alignment as shown in FIG. 3.

A further conserved CaM polypeptide sequence region present in polypeptide sequences SEQ ID NO: 1-31 was also identified using Prettyplot alignment as shown in FIG. 4.

A completely conserved polypeptide sequence motif was identified in the GAD region in all of the variant sequences, and is shown on SEQ ID NO: 32.

A completely conserved polypeptide sequence motif was also identified in the GAD region in all of the variant sequences that are from monocotyledonous species and is shown in SEQ ID NO: 33.

Construction of a Vector for Over-Expression of ORF56 Via Plant Transformation

A vector for over-expression ORF56 was produced by standard molecular biology techniques. A map of the binary vector is shown in FIG. 5. The sequence of the vector is shown in SEQ ID NO: 66.

Plant Transformation

*Agrobacterium tumefaciens* strains can be transformed with binary plasmid DNA using either a freeze/thaw (Chen et. at 1994) or electroporation method (den Dulk-Ras A and Hooykaas P J.). Purified plasmid DNA of ORF56 was introduced into *Agrobacterium* strain EHA105 by electroporation and the suspension was incubated at 26° C. for 30 minutes. A small aliquot was plated on AB minimal medium (Schmidt-Eisenlohr et. al 1999) containing Kanamycin at 100 mg/L. Plates were incubated at 26° C. for 3 days and single colonies were tested for presence of the plasmid using construct specific primers and transformation confirmed.

*Agrobacterium* cultures were grown in AG minimal medium containing 100 mg/L kanamycin at 26° C. with shaking (200 rpm). The *Agrobacterium* suspensions were pelleted at 5,000 rpm for 5 minutes, washed once in basal MS medium containing 1% glucose and 3% sucrose, pH 5.2, and re-suspended in same medium containing 200 μM acetosyringone to $OD_{600}$ 0.6-0.8.

Figure 6:
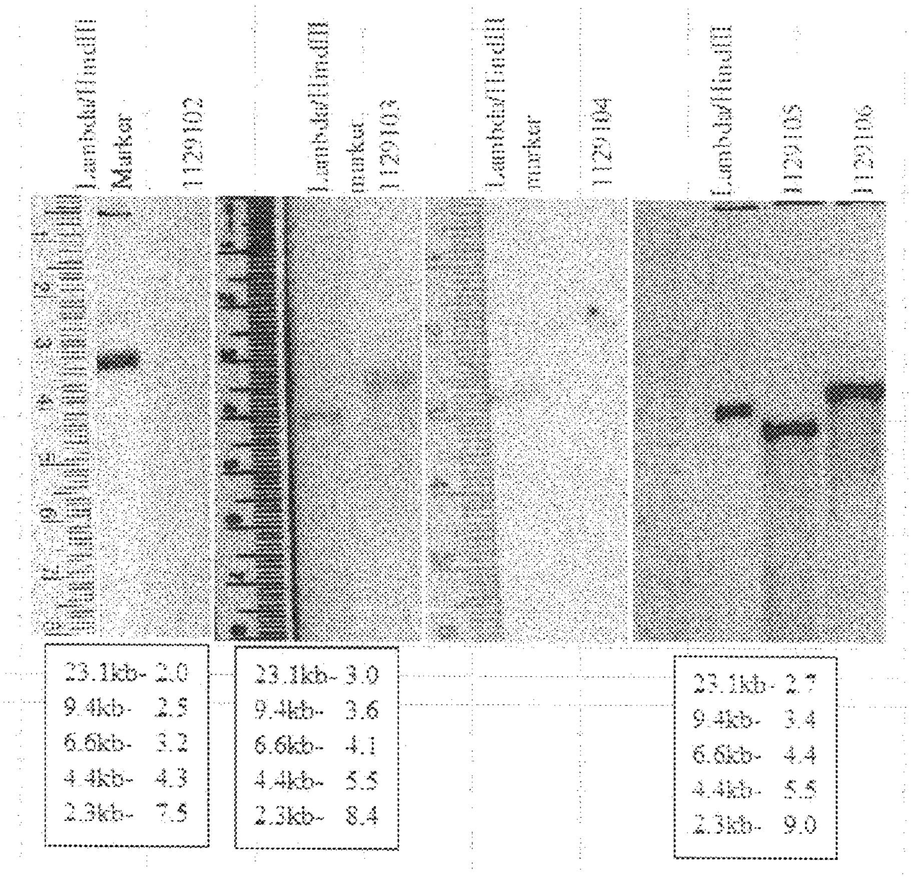
FIG. 6 shows a DNA gel-blot analysis on genomic DNA from ORF56 T0 transgenic plants digested with a restriction enzyme and probed with a fragment of ORF56 coding sequence to determine gene copy number and to identify independent transformation events.

A. tumefaciens containing the binary vector ORF56 were used to co-cultivate at least 1,000 immature rice (*Oryza sativa*) cv. Nipponbare embryos. Immature seeds from rice were washed in sterile water and then surface sterilized with sodium hypochlorite containing 1.25% active chlorine with 10 μL Tween® 20 for 20 minutes. After sterilization, the seeds were washed several times with sterile water and blotted dry on sterile filter paper (3M). The seeds were dehusked manually using sterile pair of forceps and the embryo dissected out with sterile knife. The isolated embryos were immersed in *Agrobacterium* suspension for 30 minutes with continuous shaking at 100 rpm in a 10 mL culture tube. The excess liquid was drained off and the embryos blotted on to sterile filter paper before placing them on to co-cultivation medium containing MS medium (Murashige and Skoog, 1964) supplemented with 3% sucrose, 1% glucose, 2 mg/L 2,4-D, 0.1 mg/L BA, 400 μM acetosyringone, pH 5.2 for 4 days in dark. After co-cultivation, the calli forming embryos were subcultured once every two weeks on selection medium consisting of MS medium supplemented with 3% sucrose, 1% glucose, 2 mg/L 2,4-D (2,4-dichlorophenoxy acetic acid), 0.1 mg/L BA (benzyl adenine) and containing 50 mg/L hygromycin and 300 mg/L timentin™ (ticarcillin+clavulanic acid) till at-least 30 healthy calli showing green spots indicative of healthy shoot emergence was achieved. Calli containing the green spots were transferred to selection medium lacking 2,4-D to regenerate a minimum of 10 transformed plants. Regenerated plants were rooted and then transplanted to six inch pots containing soil and plants grown in greenhouse. DNA gel-blot analysis was carried out (FIG. 6) to determine gene copy number and identify five independent transformation events. T1 seeds were harvested from the transformed plants (T0).

T1 Plant Phenotyping

Thirty seeds from Southern positive T0 plants were sown in individual cups containing cocopeat and twenty healthy plants out of them were transplanted in the green house.

These plants were arranged using a CRD using the random numbers from a random table.

T1 plant phenotyping was carried out in two separate experiments. The first experiment involved progeny lines from T0 events 1129105 and 1129106 and Nipponbare (a wild-type control), and the second experiment involved progeny lines from T0 events 1129102, 1129103 and 112904 and Nipponbare (a wild-type control.)

Phenotypic Analysis of T0 Lines

The physiological state of T0 plants is presented in Table 1; below.

TABLE 1

Physiological measurements of T0 lines

| T0 line | Pollen fertility | Productive Tillers/Total Number of Tillers | Plant height (cms) | Seed yield |
|---|---|---|---|---|
| 1129102 | 72.2% | 9/9 | 64.3 | 30 |
| 1129103 | 91.5% | 14/15 | 69.6 | 30 |
| 1129104 | 79.7% | 9/9 | 65.6 | 50 |
| 1129105 | 85.6% | 8/8 | 84.2 | 130 |
| 1129106 | 81.5% | 7/7 | 75.5 | 160 |

Phenotypic Analysis of T1 Lines

Figure 7A:
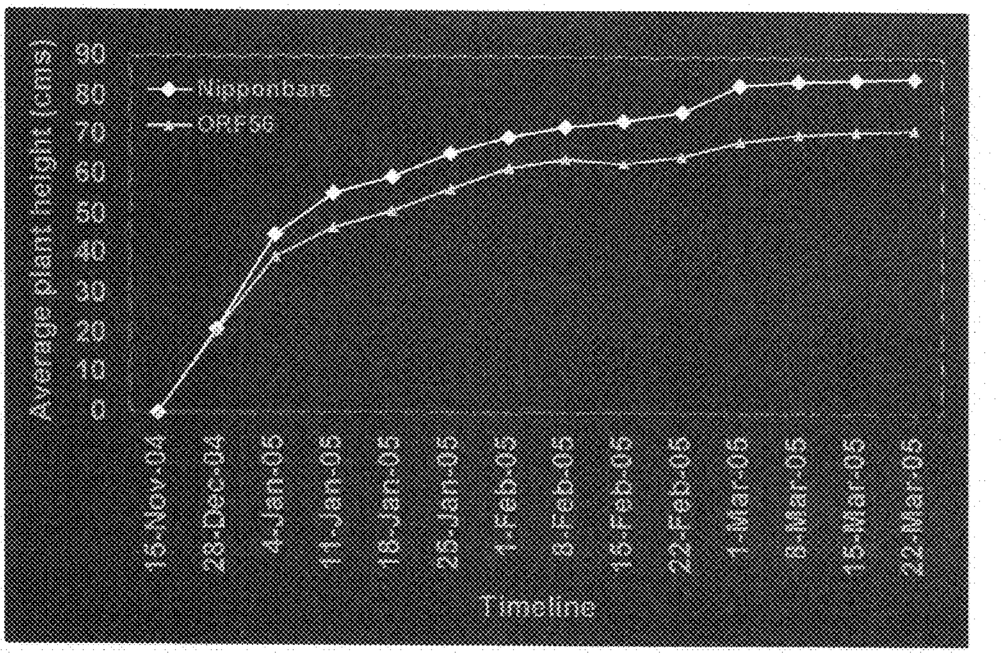
FIGS. 7A-7D show the growth parameters observed for transgenic ORF56 T1 plant lines compared to the best performing wild type control (Nipponbare).
Figure 7B:
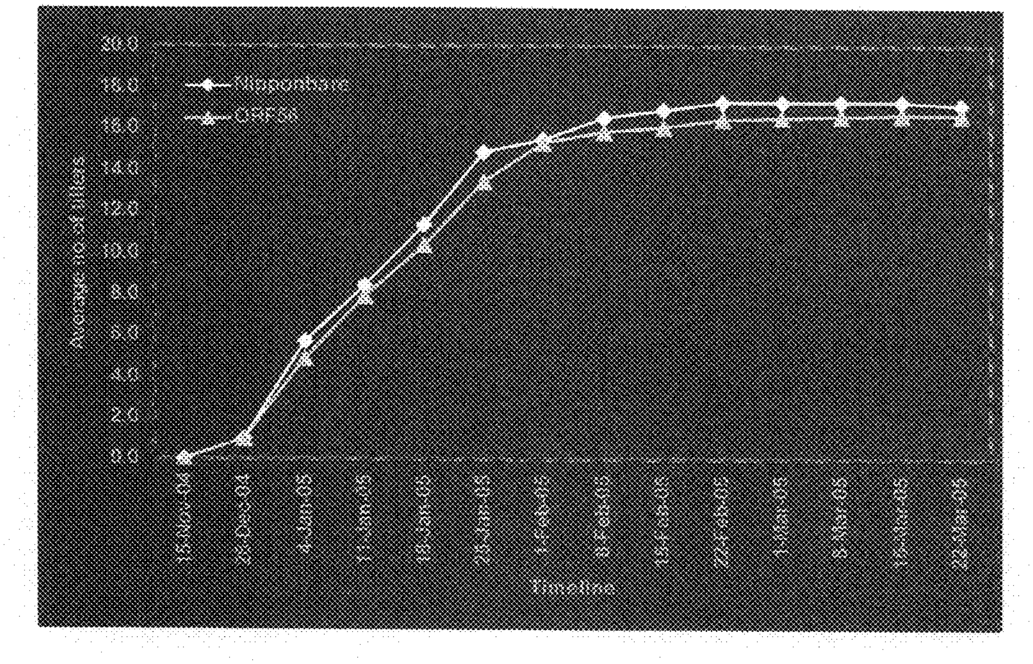
Figure 7C:
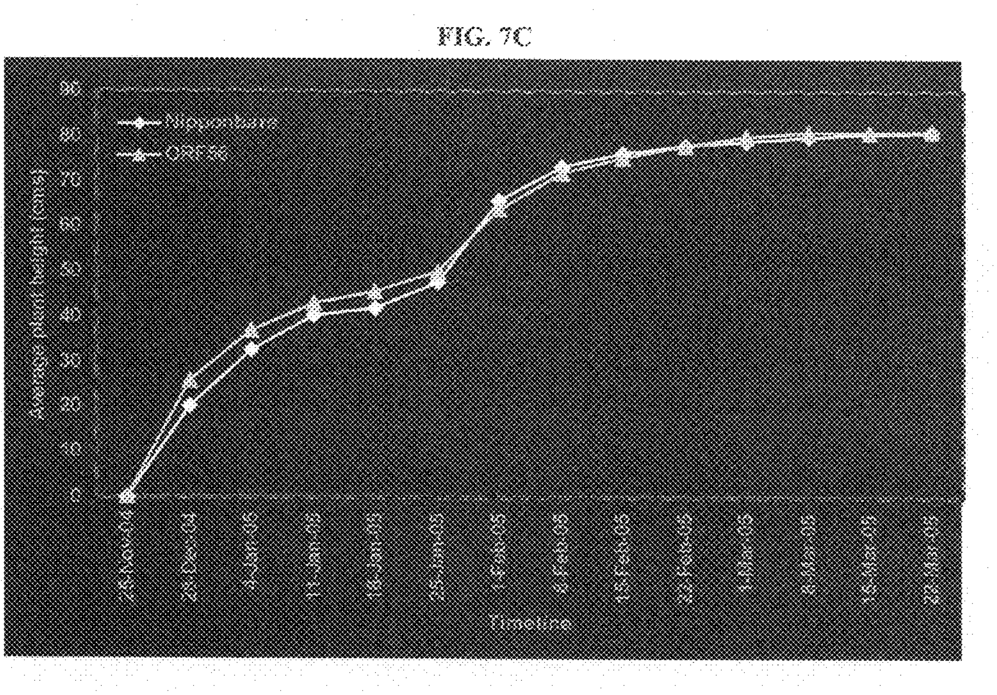
Figure 7D:
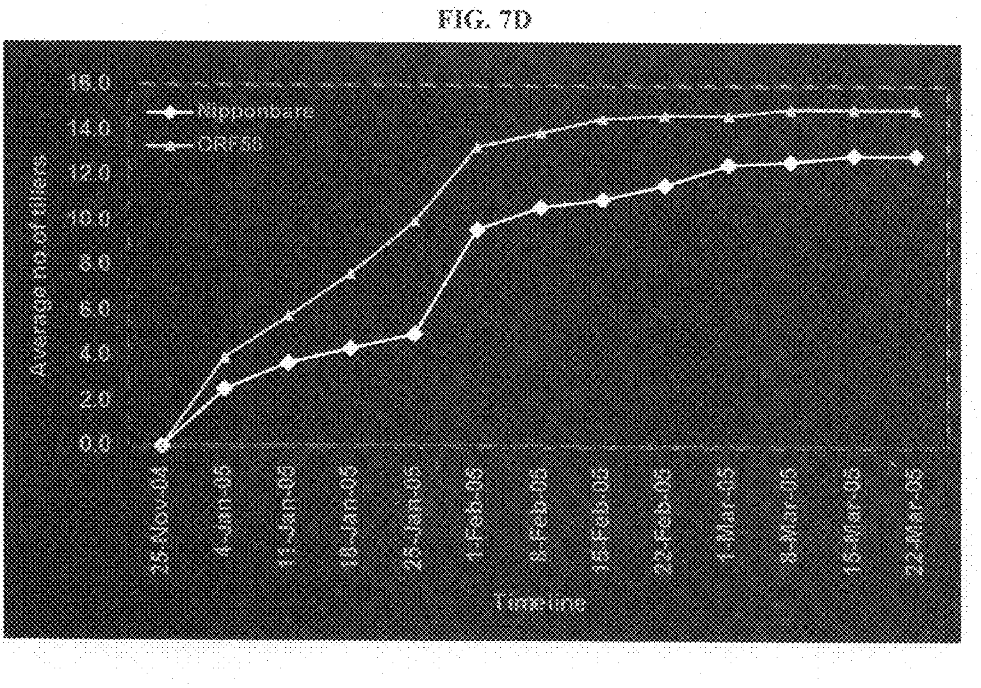

Plants height and tiller numbers were measured once every week post-transplanting until seed set was achieved. FIGS. 7*a, b, c* and *d* depict the growth parameters observed for these plants. Transgenic ORF56 plants (T1) were not different in terms of plant height and tillering capacity based upon standard statistical analysis. Transgenic ORF56 plants can be said to be normal in all aspects assessed (data not shown) except for seed yield, which was found in one of the plant progenies analysed to be as high as 3.55 times the normal seed yield.

Figure 8A:
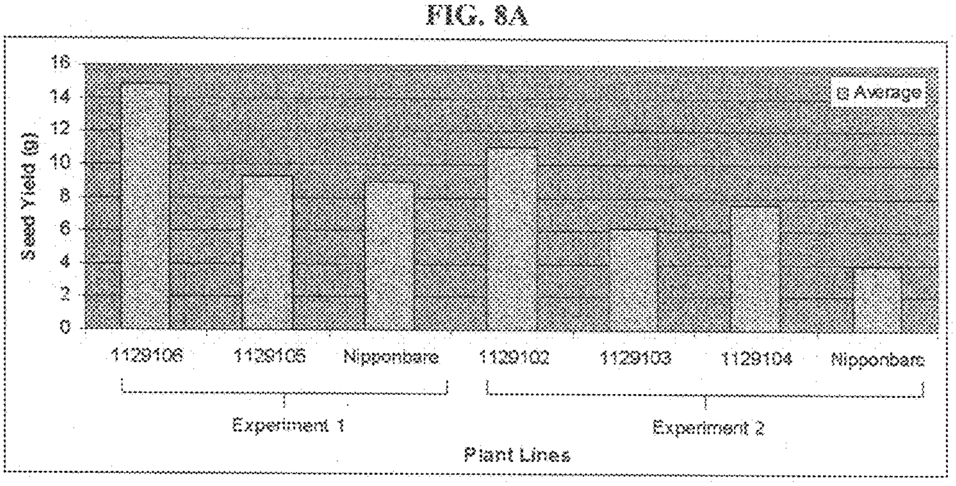
FIGS. 8A-8E show the seed and grain characteristics for transgenic ORF56 T1 plant lines compared to the best performing wild type control (Nipponbare).
Figure 8B:
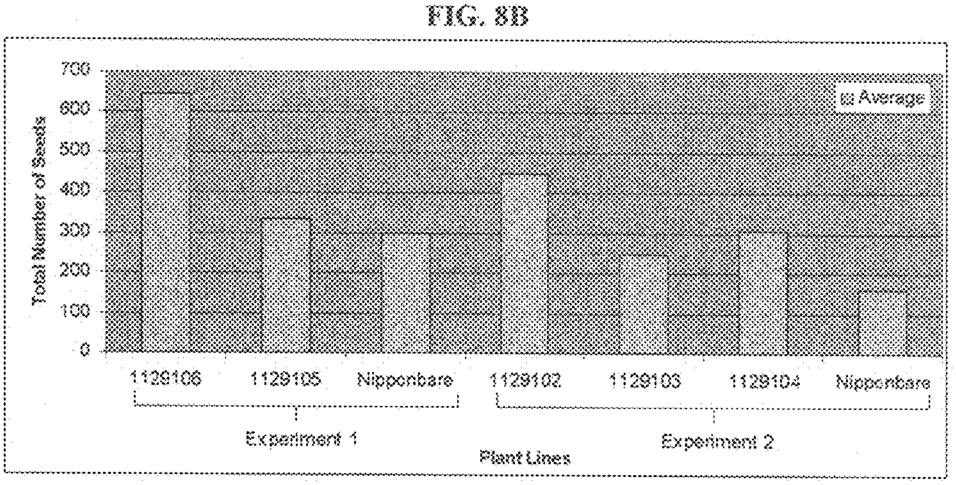
Figure 8C:
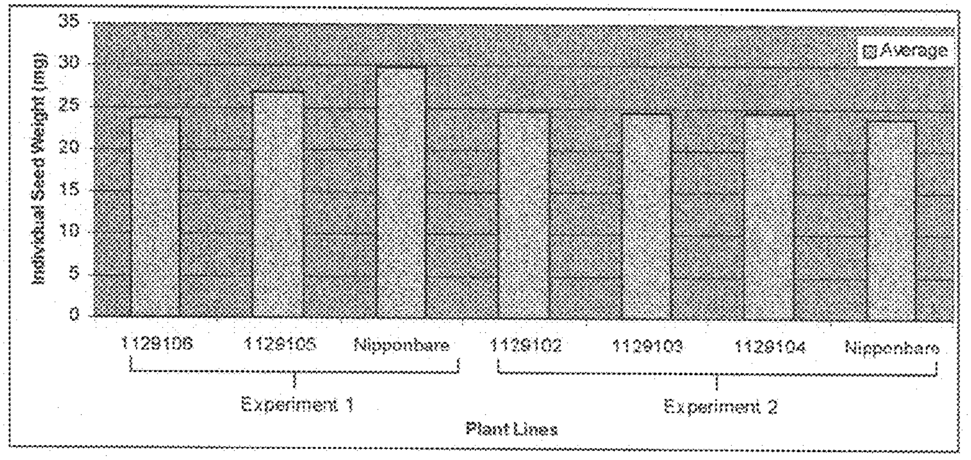
Figure 8D:
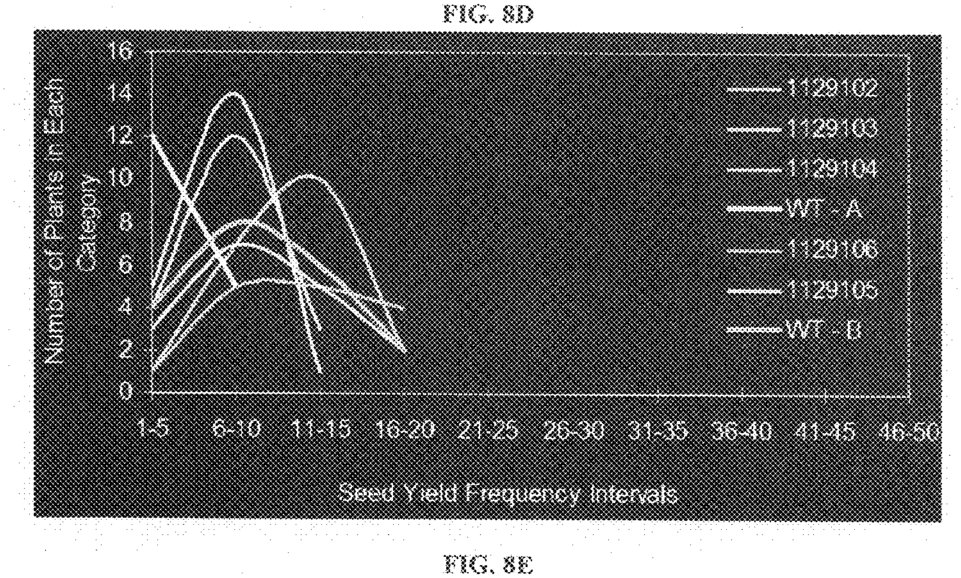
Figure 8E:
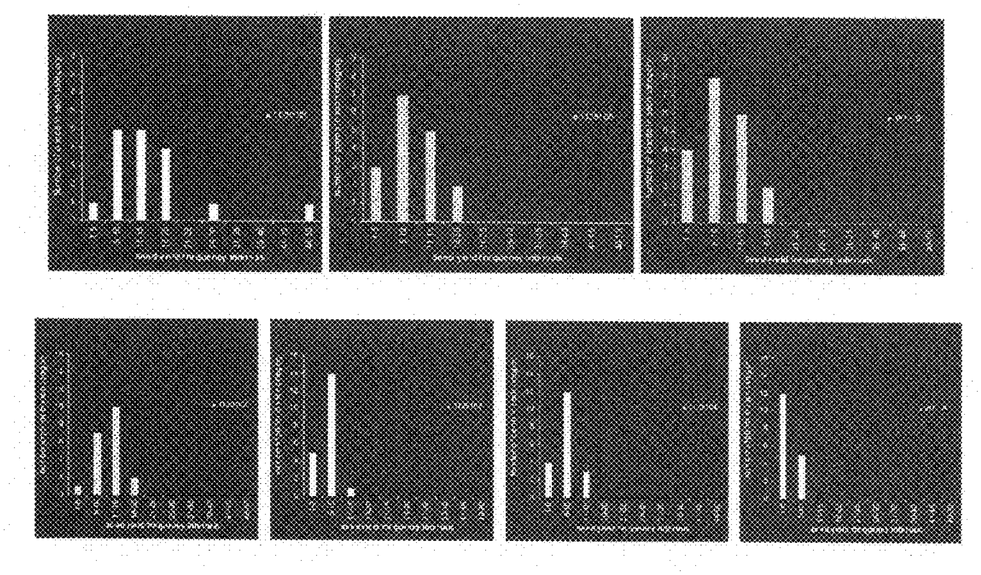

FIGS. 8*a, b, c, d,* and *e* describe the seed yield per plant, total number of seeds per plant, average mass of an individual seed in each line, binomial distribution for seed yields in different lines and shift in seed yield distribution in the lines analysed. It is evident from this analysis that the increase in seed yield is the result of an increase in seed number rather than an increase in individual seed weight (FIGS. 8*a, b* and *c*). Given that the analysis was carried out using the segregating population in T1, it is not surprising that a shift is observed in the binomial distribution for seed yield trait in the transgenic populations investigated (FIGS. 8*d* and *e*). Conventional breeding techniques, such as single seed descent, can fix the trait for enhanced seed yield.

Figure 9:
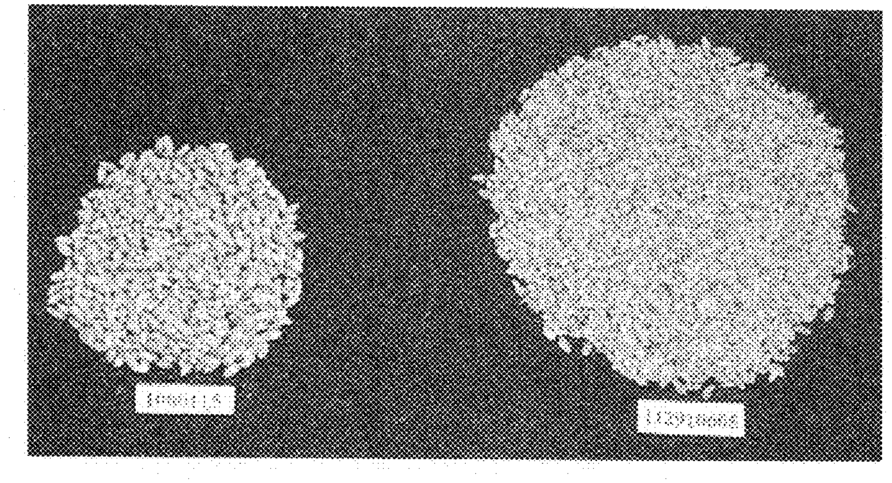
FIG. 9 shows the seeds/grain harvested from the best yielding control plant (Nipponbare) and ORF56 T1 plant.

The seed yield from the best seed yielding plant from wild-type Nipponbare and the T1 ORF56 plant is presented in FIG. 9.

References

Adams et al. 1991, *Science* 252:1651-1656.

Akama, K and Takaiwa (2007) J Exp Bot.: 58 (10) 2699-2707.

Baum G, Lev-Yadun S, Fridmann Y, Arazi T, Katsnelson H, Zik M, and Fromm H (1996) EMBO J.: 15 (12) 2988-2996.

Bouche N, Fait A, Zik M, Fromm H. (2004) Plant Mol Biol.; 55 (3): 315-25.

Chen H, Nelson R S, Sherwood J L. (1994) Biotechniques;16 (4): 664-8, 670.

Chen et al. 2002, Nucleic Acids Res. 31:101-105 den Dulk-Ras A, Hooykaas P J. (1995) Methods Mol Biol.; 55: 63-72.

Inatomi, K and Slaughter, J C (1975) Biochem J. 147: 479-484.

Kathiresan A, Tung P, Chinnappa C C, Reid D M (1997) Plant Physiol. 115: 129-135.

Lee et al. 2003, *PNAS* 99:12257-12262

Lee and Lee, 2003 *Plant Physiol.* 132: 517-529

Mayer R R, Cherry J H, Rhodes D (1990) Plant Physiol. 94: 796-810.

Murashige T, Skoog F (1962) Physiol Plant 15: 473-497

Patterson B D, Graham D (1987) In (D D Davies ed) “The Biochemistry of Plants”, Vol 12, Academic Press, New York, pp. 153-199.

Richmond and Somerville 2000, *Current Opinion in Plant Biology.* 3:108-116

Ruan et al. 2004, *Trends in Biotechnology* 22: 23-30.

Schmidt-Eisenlohr H, Domke N, Angerer C, Wanner G, Zambryski P C, Baron C. (1999) J. Bacteriol.; 181 (24): 7485-92.

Sun et al. 2004, *BMC Genomics* 5: 1.1-1.4

Thompson, J. D., Higgins, D. G. and Gibson, T. J. (1994) CABIOS, 10, 19-29.

Updegraff E, Preuss D (2004) in International *Arabidopsis* Conference, Germany

Velculescu et al. 1995, *Science* 270: 484-487

Wallace W, Secor J, Schrader L E (1984) Plant Physiol. 75: 170-175.

Yuan, T and Vogel, H J (1998) J Biol. Chem. 273 (46) 30328-30335.

The above examples illustrate practice of the invention. It will be appreciated by those skilled in the art that numerous variations and modifications may be made without departing from the spirit and scope of the invention.

Summary Of Sequences

| SEQ ID NO: | Sequence type | Information | Species |
|---|---|---|---|
| 1 | polypeptide | ORF 56 | *Lolium perenne* |
| 2 | polypeptide | UniRef100_Q42521 Glutamate decarboxylase 1 | *Arabidopsis thaliana* |

-continued

| SEQ ID NO: | Sequence type | Information | Species |
|---|---|---|---|
| 3 | polypeptide | UniRef100_Q42472 Glutamate decarboxylase 2 | *Arabidopsis thaliana* |
| 4 | polypeptide | UniRef100_Q07346 Glutamate decarboxylase | *Petunia hybrida* |
| 5 | polypeptide | UniRef100_P54767 Glutamate decarboxylase | *Lycopersicon esculentum* |
| 6 | polypeptide | UniRef100_A0EJ88 Glutamate decarboxylase | *Populus tremula* x *Populus alba* |
| 7 | polypeptide | UniRef100_A2XEB3 Putative uncharacterized protein | *Oryza sativa* subsp. *indica* |
| 8 | polypeptide | UniRef100_A3AM59 Putative uncharacterized protein | *Oryza sativa* subsp. *japonica* |
| 9 | polypeptide | UniRef100_A5BI27 Putative uncharacterized protein | *Vitis vinifera* |
| 10 | polypeptide | UniRef100_A7P433 Chromosome chr1 scaffold_5, whole genome shotgun sequence | *Vitis vinifera* |
| 11 | polypeptide | UniRef100_A7P434 Chromosome chr1 scaffold_5, whole genome shotgun sequence | *Vitis vinifera* |
| 12 | polypeptide | UniRef100_O81101 Glutamate decarboxylase isozyme 2 | *Nicotiana tabacum* |
| 13 | polypeptide | UniRef100_O81102 Glutamate decarboxylase isozyme 1 | *Nicotiana tabacum* |
| 14 | polypeptide | UniRef100_P93369 Glutamate decarboxylase | *Nicotiana tabacum* |
| 15 | polypeptide | UniRef100_Q01J81 OSIGBa0152K17.6 | *Oryza sativa* |
| 16 | polypeptide | UniRef100_Q1I1D8 Glutamate decarboxylase | *Citrus sinensis* |
| 17 | polypeptide | UniRef100_Q6ASV4 Putative glutamate decarboxylase isozyme | *Oryza sativa* subsp. *japonica* |
| 18 | polypeptide | UniRef100_Q6Q4I1 Glutamate decarboxylase 4b | *Brassica juncea* |
| 19 | polypeptide | UniRef100_Q6Q4I2 Glutamate decarboxylase 4a | *Brassica juncea* |
| 20 | polypeptide | UniRef100_Q6Q4I3 Glutamate decarboxylase 2 | *Brassica juncea* |
| 21 | polypeptide | UniRef100_Q6YSB2 | *Oryza sativa* subsp. *japonica* |
| 22 | polypeptide | UniRef100_Q7XZU7 GAD1 | *Hordeum vulgare* |
| 23 | polypeptide | UniRef100_Q84U04 Glutamate decarboxylase | *Oryza sativa* subsp. *japonica* |
| 24 | polypeptide | UniRef100_Q8LFR4 Glutamate decarboxylase, putative | *Arabidopsis thaliana* |
| 25 | polypeptide | UniRef100_Q8LKR4 Glutamate decarboxylase | *Nicotiana tabacum* |
| 26 | polypeptide | UniRef100_Q944L6 At1g65960/F12P19_12 | *Arabidopsis thaliana* |
| 27 | polypeptide | UniRef100_Q94KK8 Glutamate decarboxylase isozyme 3 | *Nicotiana tabacum* |
| 28 | polypeptide | UniRef100_Q9AR41 Glutamate decaroxylase | *Oryza sativa* subsp. *japonica* |
| 29 | polypeptide | UniRef100_Q9AR41 Glutamate decarboxylase | *Oryza sativa* subsp. *japonica* |
| 30 | polypeptide | UniRef100_Q9AT17 Glutamate decarboxylase isozyme 1 | *Nicotiana tabacum* |
| 31 | polypeptide | UniRef100_Q9LSH2 Glutamate dearboxylase | *Arabidopsis thaliana* |
| 32 | polypeptide | GAD plant consensus | Artificial |
| 33 | polypeptide | CaM monocot plant consensus | Artificial |

-continued

| SEQ ID NO: | Sequence type | Information | Species |
|---|---|---|---|
| 34 | polynucleotide | ORF 56 | *Lolium perenne* |
| 35 | polynucleotide | XP_462650.10 | *Oryza sativa* |
| 36 | polynucleotide | AAN46801.1 | *Arabidopsis thaliana* |
| 37 | polynucleotide | XP_482841.1 | *Oryza sativa* |
| 38 | polynucleotide | AAS79671.1 | *Brassica juncea* |
| 39 | polynucleotide | AAS79670.1 | *Brassica juncea* |
| 40 | polynucleotide | AAS79669.1 | *Brassica juncea* |
| 41 | polynucleotide | BAB02870.1 | *Arabidopsis thaliana* |
| 42 | polynucleotide | AAM70569.1 | *Arabidopsis thaliana* |
| 43 | polynucleotide | BAC42751.1 | *Arabidopsis thaliana* |
| 44 | polynucleotide | AAK38667.1\|AF353615_1 | *Nicotiana tabacum* |
| 45 | polynucleotide | AAK18620.1\|AF352732_1 | *Nicotiana tabacum* |
| 46 | polynucleotide | AAP85548.1 | *Glycine Max* |
| 47 | polynucleotide | AAM48129.1\|AF506366_1 | *Nicotiana tabacum* |
| 48 | polynucleotide | AAM61251.1 | *Arabidopsis thaliana* |
| 49 | polynucleotide | AAP79441.1 | *Oryza sativa* |
| 50 | polynucleotide | AAL91148.1 | *Arabidopsis thaliana* |
| 51 | polynucleotide | XP_482840.1 | *Oryza sativa* |
| 52 | polynucleotide | AAL16126.1\|AF428294_1 | *Arabidopsis thaliana* |
| 53 | polynucleotide | AAC39483.1 | *Nicotiana tabacum* |
| 54 | polynucleotide | AAM70582.1 | *Arabidopsis thaliana* |
| 55 | polynucleotide | AAC24195.1 | *Nicotiana tabacum* |
| 56 | polynucleotide | AAB40608.1 | *Nicotiana tabacum* |
| 57 | polynucleotide | AAA93132.1 | *Arabidopsis thaliana* |
| 58 | polynucleotide | A48767 | *Petunia hybrida* |
| 59 | polynucleotide | AAL83983.1 | *Oryza sativa* |
| 60 | polynucleotide | CAA56812.1 | *Lycopersicon esculentum* |
| 61 | polynucleotide | XP_462654.1 | *Oryza sativa* |
| 62 | polynucleotide | AAM7304.1\|AF377946_6 | *Oryza sativa* |
| 63 | polynucleotide | BAB32871.1 | *Oryza sativa* |
| 64 | polynucleotide | AAT77842.1 | *Oryza sativa* |
| 65 | polynucleotide | AAP46640.1 | *Hordeum vulgare* |
| 66 | polynucleotide | vector | Artificial |
| 67 | polynucleotide | U10034.1\|codes AAA93132 and UniRef100_Q42521 | *Arabidopsis thaliana* |
| 68 | polynucleotide | U46665.1\|codes AAC33485 and UniRef100_Q42472 | *Arabidopsis thaliana* |
| 69 | polynucleotide | L16797.1 codes AAA33709 and UniRef100_Q07346 | *Petunia* x *hybrida* |
| 70 | polynucleotide | X80840.1\|codes CAA56812 and UniRef100_P54767 | *Solanum lycopersicum* |
| 71 | polynucleotide | DQ125945.1\|codes ABA18652 and UniRef100_A0EJ88 | *Populus tremula* x *Populus alba* |
| 72 | polynucleotide | CM000128.1\|codes EAY89173 and UniRef100_A2XEB3 | *Oryza sativa Indica* |
| 73 | polynucleotide | CM000140.1\|codes EAZ28398 and UniRef100_A3AM59 | *Oryza sativa Japonica* |
| 74 | polynucleotide | AM460203.2\|codes CAN67952 and UniRef100_A5BI27 | *Vitis vinifera* |
| 75 | polynucleotide | CU459222.1\|codes CAO42441 and UniRef100_A7P433 | *Vitis vinifera* |
| 76 | polynucleotide | CU459222.1\|codes CAO42442 and UniRef100_A7P434 | *Vitis vinifera* |
| 77 | polynucleotide | AF020424.1\|codes AAC39483 and UniRef100_O81101 | *Nicotiana tabacum* |
| 78 | polynucleotide | AF020425.1\|codes AAC24195 and UniRef100_O81102 | *Nicotiana tabacum* |
| 79 | polynucleotide | U54774.1\|codes AAB40608 and UniRef100_P93369 | *Nicotiana tabacum* |
| 80 | polynucleotide | CR855179.1\|codes CAH67194 and UniRef100_Q01J81 | *Oryza sativa* |
| 81 | polynucleotide | DQ001727.1\|codes AAZ05070 and UniRef100_Q1I1D8 | *Citrus sinensis* |
| 82 | polynucleotide | DP000009.2\|codes ABF98584 and UniRef100_Q6ASV4 | *Oryza sativa Japonica* |

-continued

| SEQ ID NO: | Sequence type | Information | Species |
|---|---|---|---|
| 83 | polynucleotide | AY559320.1\|codes AAS79671 and UniRef100_Q6Q4I1 | *Brassica juncea* |
| 84 | polynucleotide | AY559319.1\|codes AAS79670 and UniRef100_Q6Q4I2 | *Brassica juncea* |
| 85 | polynucleotide | AY559318.1\|codes AAS79669 and UniRef100_Q6Q4I3 | *Brassica juncea* |
| 86 | polynucleotide | AP006461.3\|codes BAD10771 and UniRef100_Q6YSB2 | *Oryza sativa Japonica* |
| 87 | polynucleotide | AF521177.1\|codes AAP46640 and UniRef100_Q7XZU7 | *Hordeum vulgare* |
| 88 | polynucleotide | AY318775.1\|codes AAP79441 and UniRef100_Q84U04 | *Oryza sativa Japonica* |
| 89 | polynucleotide | AY084689.1\|codes AAM61251 and UniRef100_Q8LFR4 | *Arabidopsis thaliana* |
| 90 | polynucleotide | AF506366.1\|codes AAM48129 and UniRef100_Q8LKR4 | *Nicotiana tabacum* |
| 91 | polynucleotide | AF428294.1\|codes AAL16126 and UniRef100_Q944L6 | *Arabidopsis thaliana* |
| 92 | polynucleotide | AF353615.1\|codes AAK38667 and UniRef100_Q94KK8 | *Nicotiana tabacum* |
| 93 | polynucleotide | AB056061.1\|codes BAB32869 and UniRef100_Q9AR41 | *Oryza sativa Japonica* |
| 94 | polynucleotide | AB056061.1\|codes BAB32869 and UniRef100_Q9AR41 | *Oryza sativa Japonica* |
| 95 | polynucleotide | AF352732.1\|codes AAK18620 and UniRef100_Q9AT17 | *Nicotiana tabacum* |
| 96 | polynucleotide | AB026646.1\|codes BAB02870 and UniRef100_Q9LSH2 | *Arabidopsis thaliana* |
| 97 | polypeptide | XP_462650 | *Oryza sativa* |
| 98 | polypeptide | AAN46801.1 | *Arabidopsis thaliana* |
| 99 | polypeptide | XP_482841.1 | *Oryza sativa* |
| 100 | polypeptide | AAS79671.1 | *Brassica juncea* |
| 101 | polypeptide | AAS79670.1 | *Brassica juncea* |
| 102 | polypeptide | AAS79669.1 | *Brassica juncea* |
| 103 | polypeptide | BAB02870.1 | *Arabidopsis thaliana* |
| 104 | polypeptide | AAM70569.1 | *Arabidopsis thaliana* |
| 105 | polypeptide | BAC42751.1 | *Arabidopsis thaliana* |
| 106 | polypeptide | AAK38667.1\|AF353615_1 | *Nicotiana tabacum* |
| 107 | polypeptide | AAK18620.1\|AF352732_1 | *Nicotiana tabacum* |
| 108 | polypeptide | AAP85548.1 | *Glycine max* |
| 109 | polypeptide | AAM48129.1\|AF506366_1 | *Nicotiana tabacum* |
| 110 | polypeptide | AAM61251.1 | *Arabidopsis thaliana* |
| 111 | polypeptide | AAP79441.1 | *Oryza sativa* |
| 112 | polypeptide | AAL91148.1 | *Arabidopsis thaliana* |
| 113 | polypeptide | XP_482840.1 | *Oryza sativa* |
| 114 | polypeptide | AAL16126.1\|AF428294_1 | *Arabidopsis thaliana* |
| 115 | polypeptide | AAC39483.1 | *Nicotiana tabacum* |
| 116 | polypeptide | AAM70582.1 | *Arabidopsis thaliana* |
| 117 | polypeptide | AAC24195.1 | *Nicotiana tabacum* |
| 118 | polypeptide | AAB40608.1 | *Nicotiana tabacum* |
| 119 | polypeptide | AAA93132.1 | *Arabidopsis thaliana* |
| 120 | polypeptide | A48767 | *Petunia* x *hybrida* |
| 121 | polypeptide | AAL83983.1 | *Oryza sativa* |
| 122 | polypeptide | CAA56812.1 | *Lycopersicon esculentum* |
| 123 | polypeptide | XP_46254.1 | *Oryza sativa* |
| 124 | polypeptide | AAM47304.1\|AF377946_6 | *Oryza sativa* |

-continued

| SEQ ID NO: | Sequence type | Information | Species |
|---|---|---|---|
| 125 | polypeptide | BAB32871.1 | *Oryza sativa* |
| 126 | polypeptide | AAT77842.1 | *Oryza sativa* |
| 127 | polypeptide | AAP46640.1 | *Hordeum vulgare* |

Incorporation By Reference

All references cited herein, including patents, patent applications, papers, text books, and the like, and the references cited therein, to the extent that they are not already, are hereby incorporated herein by reference in their entirety. To the extent that any of the definitions or terms provided in the references incorporated by reference differ from the terms and discussion provided herein, the present terms and definitions control.

What is claimed is:

1. A method for producing a plant with altered seed yield, the method comprising transformation of a plant with:
   a) a polynucleotide encoding of a polypeptide with at least 95% sequence identity to the amino acid sequence of SEQ ID NO: 1.

2. The method of claim 1 in which the polypeptide is derived from a plant species and comprises the amino acid sequence of SEQ ID NO: 32.

3. The method of claim 1 or 2 in which the polypeptide is derived from a monocotyledonous species and comprises the amino acid sequence of SEQ ID NO: 33.

4. The method of claim 1 in which the polypeptide is a glutamate decarboxylase.

5. The method of claim 1 in which the polynucleotide of a) encodes a polypeptide with the amino acid sequence of SEQ ID NO: 1.

6. A method of producing a plant with altered seed yield, the method comprising transformation of a plant cell or plant with:
   a) a polynucleotide comprising a sequence with at least 95% sequence identity to the coding sequence of SEQ ID NO: 34.

7. The method of claim 6 in which the polynucleotide has at least 95% sequence identity to SEQ ID NO: 34.

8. The method of any one of claims 6 to 7 in which the polypeptide is a glutamate decarboxylase.

9. The method of claim 6 in which the polynucleotide of a) comprises the sequence of SEQ ID NO: 34.

10. The method of claim 6 in which the polynucleotide of a) comprises the coding sequence of SEQ ID NO: 34.

11. The method of claims 1 or 6 in which the plant produced has increased seed yield relative to a suitable control plant.

12. A plant produced by the method of claims 1 or 6.

13. An isolated polynucleotide encoding a polypeptide with at least 95% sequence identity to the amino acid sequence of SEQ ID NO: 1.

14. The isolated polynucleotide of claim 13 wherein the polypeptide is a glutamate decarboxylase.

15. The isolated polynucleotide of claim 13 comprising the sequence of SEQ ID NO: 34.

16. The isolated polynucleotide of claim 13 comprising the coding sequence of SEQ ID NO: 34.

17. A genetic construct which comprises a polynucleotide of any one of claims 13 to 16.

18. A host cell comprising a genetic construct of claim 17.

19. A plant cell which comprises a genetic construct of claim 17.

20. A host cell genetically modified to express a polynucleotide of any one of claims 13 to 16.

21. A plant cell genetically modified to express a polynucleotide of any one of claims 13 to 16, or a polypeptide encoded by the polynucleotide.

22. A plant which comprises a plant cell of claim 21.

23. A method for selecting a plant with altered seed yield relative to suitable control plant, the method comprising testing of a plant for altered expression of a polynucleotide of any one of claims 13 to 16.

24. A group of plants selected by the method of claim 23.

25. A genetic construct including a polynucleotide consisting of at least one of a) a fragment, of at least 50 nucleotides in length, of a polynucleotide of any one of claims 13 to 16;

b) a complement, of at least 50 nucleotides in length, of the polynucleotide of any one of claims 13 to 16; or c) a sequence, of at least 50 nucleotides in length, capable of hybridising to the polynucleotide of any one of claims 13 to 16 in 0.2×SSC, 0.1% SDS at 65° C.

26. The genetic construct of claim 25 comprising a promoter sequence operably linked to the polynucleotide.

27. The genetic construct of claim 25 comprising a terminator sequence operably linked to the polynucleotide.

* * * * *

SEQUENCE LISTING

```
<160> NUMBER OF SEQ ID NOS: 131

<210> SEQ ID NO 1
<211> LENGTH: 502
<212> TYPE: PRT
<213> ORGANISM: Lolium perenne

<400> SEQUENCE: 1

Met Val Leu Thr Val Ala Ala Thr Ala Ala Asp Thr Ala Glu Pro Leu
1               5                   10                  15

Asn Ser Thr Phe Phe Ala Thr Arg Tyr Val Arg Asp Gln Leu Pro Arg
            20                  25                  30

Tyr Arg Met Pro Glu Asn Ser Ile Pro Lys Glu Ala Ala Tyr Gln Ile
        35                  40                  45

Ile Ser Asp Glu Leu Met Leu Asp Gly Asn Pro Arg Leu Asn Leu Ala
    50                  55                  60

Ser Phe Val Thr Thr Arg Met Glu Pro Glu Val Gly Lys Leu Ile Met
65                  70                  75                  80

Asp Ser Val Asn Lys Asn Tyr Val Asp Met Asp Glu Tyr Pro Val Thr
                85                  90                  95

Thr Glu Leu Gln Asn Arg Cys Val Asn Met Ile Ala His Leu Phe Asn
            100                 105                 110

Ala Pro Ile Lys Glu Glu Glu Thr Ala Ile Gly Val Ala Thr Val Gly
        115                 120                 125

Ser Ser Glu Ala Ile Met Leu Ala Gly Leu Ala Phe Lys Arg Lys Trp
    130                 135                 140

Ala Asn Lys Arg Lys Glu Glu Gly Lys Pro Tyr Asp Lys Pro Asn Ile
145                 150                 155                 160

Val Thr Gly Ala Asn Val Gln Val Cys Trp Glu Lys Phe Ala Arg Tyr
                165                 170                 175

Phe Glu Val Glu Leu Lys Glu Val Lys Leu Thr Glu Gly Tyr Tyr Val
            180                 185                 190

Met Asp Pro Leu Lys Ala Val Glu Met Val Asp Glu Asn Thr Ile Cys
        195                 200                 205

Val Ala Ala Ile Leu Gly Ser Thr Leu Thr Gly Glu Tyr Glu Asp Val
    210                 215                 220

Lys Leu Leu Asn Asp Leu Leu Val Glu Lys Asn Lys Lys Thr Gly Phe
225                 230                 235                 240

Asn Val Pro Ile His Val Asp Ala Ala Ser Gly Gly Phe Ile Ala Pro
                245                 250                 255

Phe Leu His Pro Glu Leu Glu Trp Asp Phe Arg Leu Pro Leu Val Lys
            260                 265                 270
```

```
Ser Ile Asn Val Ser Gly His Lys Tyr Gly Leu Val Tyr Pro Gly Val
        275                 280                 285

Gly Trp Val Ile Trp Arg Ser Lys Asp Asp Leu Pro Gly Glu Leu Ile
    290                 295                 300

Phe His Ile Asn Tyr Leu Gly Thr Asp Gln Pro Thr Phe Thr Leu Asn
305                 310                 315                 320

Phe Ser Lys Gly Ala Ser Gln Ile Ile Ala Gln Tyr Tyr Gln Leu Ile
                325                 330                 335

Arg Leu Gly Phe Glu Gly Tyr Lys His Ile Met Glu Asn Cys Gln Ala
            340                 345                 350

Asn Ala Thr Ala Leu Arg Glu Gly Leu Glu Ala Thr Gly Arg Phe Asp
        355                 360                 365

Ile Leu Ser Lys Glu Asp Gly Val Pro Leu Val Ala Ile Arg Leu Lys
    370                 375                 380

Asp Ser Ser Lys Phe Ser Val Phe Asp Ile Ser Glu Asn Leu Arg Arg
385                 390                 395                 400

Phe Gly Trp Ile Val Pro Ala Tyr Thr Met Pro Ala Asp Ala Glu His
                405                 410                 415

Val Ala Val Leu Arg Val Val Ile Arg Glu Asp Phe Asn Arg Ser Leu
            420                 425                 430

Ser Gln Arg Leu Leu Ala Asp Ile Asn Arg Val Val Gln Glu Leu Asp
        435                 440                 445

Ala His Ala Val His Ala Ile Lys Met Thr Thr Ala Ile Ala Thr Gln
    450                 455                 460

Thr Gly Glu Gly Ala Glu Asp Gly Val Val Thr Lys Lys Gly Val Leu
465                 470                 475                 480

Asp Ile Glu Lys Glu Phe Ala Ala Ala Cys Lys Asp Leu Val Lys Asn
                485                 490                 495

Lys Lys Thr Gly Pro Cys
            500
```

<210> SEQ ID NO 2
<211> LENGTH: 502
<212> TYPE: PRT
<213> ORGANISM: Arabidopsis thaliana

<400> SEQUENCE: 2

```
Met Val Leu Ser His Ala Val Ser Glu Ser Asp Val Ser Val His Ser
1               5                   10                  15

Thr Phe Ala Ser Arg Tyr Val Arg Thr Ser Leu Pro Arg Phe Lys Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Ile Met Ser Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Leu
            100                 105                 110

Glu Glu Ala Glu Thr Ala Val Gly Val Gly Thr Val Gly Ser Ser Glu
        115                 120                 125

Ala Ile Met Leu Ala Gly Leu Ala Phe Lys Arg Lys Trp Gln Asn Lys
```

```
    130                 135                 140

Arg Lys Ala Glu Gly Lys Pro Val Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Glu Gly Tyr Tyr Val Met Asp Pro
            180                 185                 190

Gln Gln Ala Val Asp Met Val Asp Glu Asn Thr Ile Cys Val Ala Ala
        195                 200                 205

Ile Leu Gly Ser Thr Leu Asn Gly Glu Phe Glu Asp Val Lys Leu Leu
    210                 215                 220

Asn Asp Leu Leu Val Glu Lys Asn Lys Glu Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Ile Trp Arg Asn Lys Glu Asp Leu Pro Glu Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

His Glu Gly Tyr Arg Asn Val Met Glu Asn Cys Arg Glu Asn Met Ile
            340                 345                 350

Val Leu Arg Glu Gly Leu Glu Lys Thr Glu Arg Phe Asn Ile Val Ser
        355                 360                 365

Lys Asp Glu Gly Val Pro Leu Val Ala Phe Ser Leu Lys Asp Ser Ser
    370                 375                 380

Cys His Thr Glu Phe Glu Ile Ser Asp Met Leu Arg Arg Tyr Gly Trp
385                 390                 395                 400

Ile Val Pro Ala Tyr Thr Met Pro Pro Asn Ala Gln His Ile Thr Val
                405                 410                 415

Leu Arg Val Val Ile Arg Glu Asp Phe Ser Arg Thr Leu Ala Glu Arg
            420                 425                 430

Leu Val Ile Asp Ile Glu Lys Val Met Arg Glu Leu Asp Glu Leu Pro
        435                 440                 445

Ser Arg Val Ile His Lys Ile Ser Leu Gly Gln Glu Lys Ser Glu Ser
    450                 455                 460

Asn Ser Asp Asn Leu Met Val Thr Val Lys Lys Ser Asp Ile Asp Lys
465                 470                 475                 480

Gln Arg Asp Ile Ile Thr Gly Trp Lys Lys Phe Val Ala Asp Arg Lys
                485                 490                 495

Lys Thr Ser Gly Ile Cys
            500


<210> SEQ ID NO 3
<211> LENGTH: 494
<212> TYPE: PRT
<213> ORGANISM: Arabidopsis thaliana

<400> SEQUENCE: 3
```

-continued

Met Val Leu Thr Lys Thr Ala Thr Asn Asp Glu Ser Val Cys Thr Met
1               5                   10                  15

Phe Gly Ser Arg Tyr Val Arg Thr Thr Leu Pro Lys Tyr Glu Ile Gly
            20                  25                  30

Glu Asn Ser Ile Pro Lys Asp Ala Ala Tyr Gln Ile Ile Lys Asp Glu
        35                  40                  45

Leu Met Leu Asp Gly Asn Pro Arg Leu Asn Leu Ala Ser Phe Val Thr
    50                  55                  60

Thr Trp Met Glu Pro Glu Cys Asp Lys Leu Ile Met Asp Ser Ile Asn
65                  70                  75                  80

Lys Asn Tyr Val Asp Met Asp Glu Tyr Pro Val Thr Thr Glu Leu Gln
                85                  90                  95

Asn Arg Cys Val Asn Ile Ile Ala Arg Leu Phe Asn Ala Pro Leu Glu
            100                 105                 110

Glu Ser Glu Thr Ala Val Gly Val Gly Thr Val Gly Ser Ser Glu Ala
        115                 120                 125

Ile Met Leu Ala Gly Leu Ala Phe Lys Arg Lys Trp Gln Asn Lys Arg
    130                 135                 140

Lys Ala Glu Gly Lys Pro Tyr Asp Lys Pro Asn Ile Val Thr Gly Ala
145                 150                 155                 160

Asn Val Gln Val Cys Trp Glu Lys Phe Ala Arg Tyr Phe Glu Val Glu
                165                 170                 175

Leu Lys Glu Val Asn Leu Ser Glu Gly Tyr Tyr Val Met Asp Pro Asp
            180                 185                 190

Lys Ala Ala Glu Met Val Asp Glu Asn Thr Ile Cys Val Ala Ala Ile
        195                 200                 205

Leu Gly Ser Thr Leu Asn Gly Glu Phe Glu Asp Val Lys Arg Leu Asn
    210                 215                 220

Asp Leu Leu Val Lys Lys Asn Glu Glu Thr Gly Trp Asn Thr Pro Ile
225                 230                 235                 240

His Val Asp Ala Ala Ser Gly Gly Phe Ile Ala Pro Phe Ile Tyr Pro
                245                 250                 255

Glu Leu Glu Trp Asp Phe Arg Leu Pro Leu Val Lys Ser Ile Asn Val
            260                 265                 270

Ser Gly His Lys Tyr Gly Leu Val Tyr Ala Gly Ile Gly Trp Val Val
        275                 280                 285

Trp Arg Ala Ala Glu Asp Leu Pro Glu Glu Leu Ile Phe His Ile Asn
    290                 295                 300

Tyr Leu Gly Ala Asp Gln Pro Thr Phe Thr Leu Asn Phe Ser Lys Gly
305                 310                 315                 320

Ser Ser Gln Ile Ile Ala Gln Tyr Tyr Gln Leu Ile Arg Leu Gly Phe
                325                 330                 335

Glu Gly Tyr Lys Asn Val Met Glu Asn Cys Ile Glu Asn Met Val Val
            340                 345                 350

Leu Lys Glu Gly Ile Glu Lys Thr Glu Arg Phe Asn Ile Val Ser Lys
        355                 360                 365

Asp Gln Gly Val Pro Val Val Ala Phe Ser Leu Lys Asp His Ser Phe
    370                 375                 380

His Asn Glu Phe Glu Ile Ser Glu Met Leu Arg Arg Phe Gly Trp Ile
385                 390                 395                 400

Val Pro Ala Tyr Thr Met Pro Ala Asp Ala Gln His Ile Thr Val Leu
                405                 410                 415

Arg Val Val Ile Arg Glu Asp Phe Ser Arg Thr Leu Ala Glu Arg Leu

```
            420                 425                 430

Val Ala Asp Ile Ser Lys Val Leu His Glu Leu Asp Thr Leu Pro Ser
        435                 440                 445

Lys Ile Ser Lys Lys Met Gly Ile Glu Gly Ile Ala Glu Asn Val Lys
    450                 455                 460

Glu Lys Lys Met Glu Lys Glu Ile Leu Met Glu Val Ile Val Gly Trp
465                 470                 475                 480

Arg Lys Phe Val Lys Glu Arg Lys Lys Met Asn Gly Val Cys
                485                 490


<210> SEQ ID NO 4
<211> LENGTH: 500
<212> TYPE: PRT
<213> ORGANISM: Petunia hybrida

<400> SEQUENCE: 4

Met Val Leu Ser Lys Thr Val Ser Gln Ser Asp Val Ser Ile His Ser
1               5                   10                  15

Thr Phe Ala Ser Arg Tyr Val Arg Thr Ser Leu Pro Arg Phe Lys Met
            20                  25                  30

Pro Asp Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Asp Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Leu
            100                 105                 110

Glu Asp Gly Glu Thr Ala Val Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140

Met Lys Ala Gln Gly Lys Pro Cys Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Glu Gly Tyr Tyr Val Met Asp Pro
            180                 185                 190

Glu Lys Ala Val Glu Met Val Asp Glu Asn Thr Ile Cys Val Ala Ala
        195                 200                 205

Ile Leu Gly Ser Thr Leu Asn Gly Glu Phe Glu Asp Val Lys Arg Leu
    210                 215                 220

Asn Asp Leu Leu Val Glu Lys Asn Lys Glu Thr Gly Trp Asp Thr Pro
225                 230                 235                 240

Ile His Val Asp Ala Ala Ser Gly Gly Phe Ile Ala Pro Phe Ile Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Asn Lys Asp Asp Leu Pro Asp Glu Leu Ile Phe His Ile
    290                 295                 300
```

-continued

Asn Tyr Leu Gly Ala Asp Gln Pro Thr Phe Thr Leu Asn Phe Ser Lys
305 310 315 320

Gly Ser Ser Gln Val Ile Ala Gln Tyr Tyr Gln Leu Ile Arg Leu Gly
325 330 335

Tyr Glu Gly Tyr Lys Asn Val Met Glu Asn Cys Gln Glu Asn Ala Ser
340 345 350

Val Leu Arg Glu Gly Leu Glu Lys Thr Gly Arg Phe Asn Ile Ile Ser
355 360 365

Lys Glu Ile Gly Val Pro Leu Val Ala Phe Ser Leu Lys Asp Asn Arg
370 375 380

Gln His Asn Glu Phe Glu Ile Ser Glu Thr Leu Arg Arg Phe Gly Trp
385 390 395 400

Ile Val Pro Ala Tyr Thr Met Pro Pro Asn Ala Gln His Ile Thr Val
405 410 415

Leu Arg Val Val Ile Arg Glu Asp Phe Ser Arg Thr Leu Ala Glu Arg
420 425 430

Leu Val Arg Asp Ile Glu Lys Val Leu His Glu Leu Asp Thr Leu Pro
435 440 445

Ala Arg Val Asn Ala Lys Leu Ala Val Ala Glu Glu Gln Ala Ala Ala
450 455 460

Asn Gly Ser Glu Val His Lys Lys Thr Asp Ser Glu Val Gln Leu Glu
465 470 475 480

Met Ile Thr Ala Trp Lys Lys Phe Val Glu Glu Lys Lys Lys Lys Thr
485 490 495

Asn Arg Val Cys
500

<210> SEQ ID NO 5
<211> LENGTH: 502
<212> TYPE: PRT
<213> ORGANISM: Lycopersicon esculentum

<400> SEQUENCE: 5

Met Val Leu Thr Thr Thr Ser Ile Arg Asp Ser Glu Glu Ser Leu His
1 5 10 15

Cys Thr Phe Ala Ser Arg Tyr Val Gln Glu Pro Leu Pro Lys Phe Lys
20 25 30

Met Pro Lys Lys Ser Met Pro Lys Glu Ala Ala Tyr Gln Ile Val Asn
35 40 45

Asp Glu Leu Met Leu Asp Gly Asn Pro Arg Leu Asn Leu Ala Ser Phe
50 55 60

Val Ser Thr Trp Met Glu Pro Glu Cys Asp Lys Leu Ile Met Ser Ser
65 70 75 80

Ile Asn Lys Asn Tyr Val Asp Met Asp Glu Tyr Pro Val Thr Thr Glu
85 90 95

Leu Gln Asn Arg Cys Val Asn Met Leu Ala His Leu Phe His Ala Pro
100 105 110

Val Gly Asp Asp Glu Thr Ala Val Gly Val Gly Thr Val Gly Ser Ser
115 120 125

Glu Ala Ile Met Leu Ala Gly Leu Ala Phe Lys Arg Lys Trp Gln Ser
130 135 140

Lys Arg Lys Ala Glu Gly Lys Pro Phe Asp Lys Pro Asn Ile Val Thr
145 150 155 160

Gly Ala Asn Val Gln Val Cys Trp Glu Lys Phe Ala Arg Tyr Phe Glu
165 170 175

-continued

Val Glu Leu Lys Glu Val Lys Leu Lys Glu Gly Tyr Tyr Val Met Asp
180 185 190

Pro Ala Lys Ala Val Glu Ile Val Asp Glu Asn Thr Ile Cys Val Ala
195 200 205

Ala Ile Leu Gly Ser Thr Leu Thr Gly Glu Phe Glu Asp Val Lys Leu
210 215 220

Leu Asn Glu Leu Leu Thr Lys Lys Asn Lys Glu Thr Gly Trp Glu Thr
225 230 235 240

Pro Ile His Val Asp Ala Ala Ser Gly Gly Phe Ile Ala Pro Phe Leu
245 250 255

Trp Pro Asp Leu Glu Trp Asp Phe Arg Leu Pro Leu Val Lys Ser Ile
260 265 270

Asn Val Ser Gly His Lys Tyr Gly Leu Val Tyr Ala Gly Val Gly Trp
275 280 285

Val Ile Trp Arg Ser Lys Glu Asp Leu Pro Asp Glu Leu Val Phe His
290 295 300

Ile Asn Tyr Leu Gly Ser Asp Gln Pro Thr Phe Thr Leu Asn Phe Ser
305 310 315 320

Lys Gly Ser Tyr Gln Ile Ile Ala Gln Tyr Tyr Gln Leu Ile Arg Leu
325 330 335

Gly Phe Glu Gly Tyr Lys Asn Val Met Lys Asn Cys Leu Ser Asn Ala
340 345 350

Lys Val Leu Thr Glu Gly Ile Thr Lys Met Gly Arg Phe Asp Ile Val
355 360 365

Ser Lys Asp Val Gly Val Pro Val Val Ala Phe Ser Leu Arg Asp Ser
370 375 380

Ser Lys Tyr Thr Val Phe Glu Val Ser Glu His Leu Arg Arg Phe Gly
385 390 395 400

Trp Ile Val Pro Ala Tyr Thr Met Pro Pro Asp Ala Glu His Ile Ala
405 410 415

Val Leu Arg Val Val Ile Arg Glu Asp Phe Ser His Ser Leu Ala Glu
420 425 430

Arg Leu Val Ser Asp Ile Glu Lys Ile Leu Ser Glu Leu Asp Thr Gln
435 440 445

Pro Pro Arg Leu Pro Thr Lys Ala Val Arg Val Thr Ala Glu Glu Val
450 455 460

Arg Asp Asp Lys Gly Asp Gly Leu His His Phe His Met Asp Thr Val
465 470 475 480

Glu Thr Gln Lys Asp Ile Ile Lys His Trp Arg Lys Ile Ala Gly Lys
485 490 495

Lys Thr Ser Gly Val Cys
500

<210> SEQ ID NO 6
<211> LENGTH: 499
<212> TYPE: PRT
<213> ORGANISM: Populus tremula x Populus alba

<400> SEQUENCE: 6

Met Val Leu Ser Lys Thr Ala Ser Glu Ser Asp Val Ser Val His Ser
1 5 10 15

Thr Phe Ala Ser Arg Tyr Val Arg Ala Ser Leu Pro Arg Phe Lys Met
20 25 30

Pro Glu Asn Ser Ile Pro Lys Glu Ala Ala Phe Gln Ile Ile Asn Asp

-continued

```
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Ile Ile Ala Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Leu
            100                 105                 110

Gly Asp Ser Glu Thr Ala Val Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140

Arg Lys Ala Glu Gly Lys Pro Tyr Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Asp Gly Tyr Tyr Val Met Asp Pro
            180                 185                 190

Glu Lys Ala Val Gln Met Val Asp Glu Asn Thr Ile Cys Val Ala Ala
        195                 200                 205

Ile Leu Gly Ser Thr Leu Asn Gly Glu Phe Glu Asp Val Lys Leu Leu
    210                 215                 220

Asn Asp Leu Leu Val Glu Lys Asn Lys Ser Thr Gly Trp Asp Thr Pro
225                 230                 235                 240

Ile His Val Asp Ala Ala Ser Gly Gly Phe Ile Ala Pro Phe Ile Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Ile Trp Arg Asn Lys Glu Asp Leu Pro Glu Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Tyr Glu Gly Tyr Lys Asn Val Met Glu Asn Cys Arg Asp Asn Met Leu
            340                 345                 350

Val Leu Lys Gln Gly Leu Glu Lys Thr Gly Lys Phe Asn Ile Val Ser
        355                 360                 365

Lys Asp Lys Gly Val Pro Leu Val Ala Phe Ser Leu Lys Asp Asn Ser
    370                 375                 380

Leu His Asn Glu Phe Glu Val Ser Asp Met Leu Arg Arg Phe Gly Trp
385                 390                 395                 400

Ile Val Pro Ala Tyr Thr Met Pro Pro Asp Ala Gln His Val Thr Val
                405                 410                 415

Leu Arg Val Val Ile Arg Glu Asp Phe Ser Arg Thr Leu Ala Glu Arg
            420                 425                 430

Leu Val Ile Asp Ile Gly Lys Val Leu His Glu Leu Glu Thr Leu Pro
        435                 440                 445

Ser Arg Ile Ser Ala Lys Ile Val Leu Ala Asn Glu Glu Lys Asp Ala
    450                 455                 460
```

Val Ala Ala Gly Lys Glu Lys Lys Asp Val Gln Asn Glu Thr Arg Glu
465 470 475 480

Ile Ile Thr Ala Trp Arg Lys Leu Val Val Gln Arg Lys Lys Leu Asn
485 490 495

Gly Val Cys

<210> SEQ ID NO 7
<211> LENGTH: 492
<212> TYPE: PRT
<213> ORGANISM: Oryza sativa subsp. indica

<400> SEQUENCE: 7

Met Val Leu Ser Lys Ala Val Ser Glu Ser Asp Met Ser Val His Ser
1 5 10 15

Thr Phe Ala Ser Arg Tyr Val Arg Ala Ser Leu Pro Arg Tyr Arg Met
20 25 30

Pro Glu Asn Ser Ile Pro Lys Glu Ala Ala Tyr Gln Ile Ile Asn Asp
35 40 45

Glu Leu Met Leu Asp Gly Asn Pro Arg Leu Asn Leu Ala Ser Phe Val
50 55 60

Thr Thr Trp Met Glu Pro Glu Cys Asp Lys Leu Ile Met Ala Ala Ile
65 70 75 80

Asn Lys Asn Tyr Val Asp Met Asp Glu Tyr Pro Val Thr Thr Glu Leu
85 90 95

Gln Asn Arg Cys Val Asn Met Ile Ala His Leu Phe His Ala Pro Leu
100 105 110

Gly Glu Asp Glu Thr Ala Val Gly Val Gly Thr Val Gly Ser Ser Glu
115 120 125

Ala Ile Met Leu Ala Gly Leu Ala Phe Lys Arg Arg Trp Gln Asn Lys
130 135 140

Arg Lys Ala Glu Gly Lys Pro Phe Asp Lys Pro Asn Ile Ile Thr Gly
145 150 155 160

Ala Asn Val Gln Val Cys Trp Glu Lys Phe Ala Arg Tyr Phe Glu Val
165 170 175

Glu Leu Lys Glu Val Lys Leu Arg Asp Gly Tyr Tyr Val Met Asp Pro
180 185 190

Glu Lys Ala Val Asp Met Val Asp Glu Asn Thr Ile Cys Val Ala Ala
195 200 205

Ile Leu Gly Ser Thr Leu Asn Gly Glu Phe Glu Asp Val Lys Leu Leu
210 215 220

Asn Asp Leu Leu Asp Lys Lys Asn Lys Glu Thr Gly Trp Glu Thr Pro
225 230 235 240

Ile His Val Asp Ala Ala Ser Gly Gly Phe Ile Ala Pro Phe Leu Tyr
245 250 255

Pro Glu Leu Glu Trp Asp Phe Arg Leu Pro Trp Val Lys Ser Ile Asn
260 265 270

Val Ser Gly His Lys Tyr Gly Leu Val Tyr Ala Gly Ile Gly Trp Cys
275 280 285

Ile Trp Arg Asn Lys Glu Asp Leu Pro Glu Glu Leu Ile Phe His Ile
290 295 300

Asn Tyr Leu Gly Ala Asp Gln Pro Thr Phe Thr Leu Asn Phe Ser Lys
305 310 315 320

Gly Ser Ser Gln Val Ile Ala Gln Tyr Tyr Gln Leu Ile Arg His Gly
325 330 335

-continued

```
Phe Glu Gly Tyr Arg Asn Ile Met Glu Asn Cys His Glu Asn Ala Met
            340                 345                 350

Val Leu Lys Glu Gly Leu Val Lys Thr Gly Arg Phe Asp Ile Val Ser
        355                 360                 365

Lys Asp Glu Gly Val Pro Leu Val Ala Phe Ser Leu Lys Asp Arg Ser
    370                 375                 380

Arg His Asp Glu Phe Glu Ile Ser Asp Met Leu Arg Arg Phe Gly Trp
385                 390                 395                 400

Ile Val Pro Ala Tyr Thr Met Pro Pro Asp Ala Gln His Val Thr Val
                405                 410                 415

Leu Arg Val Val Ile Arg Glu Glu Phe Ser Arg Thr Leu Ala Glu Arg
            420                 425                 430

Leu Val Leu Asp Ile Glu Lys Val Met Tyr Gln Leu Asp Ala Leu Pro
        435                 440                 445

Ser Arg Leu Met Pro Pro Val Pro Pro Ala Pro Leu Leu Val Val Ala
    450                 455                 460

Lys Lys Ser Glu Leu Glu Thr Gln Arg Ser Val Thr Glu Ala Trp Lys
465                 470                 475                 480

Lys Phe Val Leu Ala Lys Arg Thr Asn Gly Val Cys
                485                 490


<210> SEQ ID NO 8
<211> LENGTH: 461
<212> TYPE: PRT
<213> ORGANISM: Oryza sativa subsp. japonica

<400> SEQUENCE: 8

Met Pro Glu Gln Ser Ile Pro Lys Glu Ala Ala Tyr Gln Ile Ile Asn
1               5                   10                  15

Asp Glu Leu Met Leu Asp Gly Asn Pro Arg Leu Asn Leu Ala Ser Phe
            20                  25                  30

Val Thr Thr Trp Met Glu Pro Glu Cys Asp Lys Leu Ile Gln Ala Ser
        35                  40                  45

Val Asn Lys Asn Tyr Val Asp Met Asp Glu Tyr Pro Val Thr Thr Glu
    50                  55                  60

Leu Gln Asn Arg Cys Val Asn Met Ile Ala His Leu Phe Asn Ala Pro
65                  70                  75                  80

Leu Gly Asp Ser Glu Thr Ala Val Gly Val Gly Thr Val Gly Ser Ser
                85                  90                  95

Glu Ala Ile Met Leu Ala Gly Leu Ala Phe Lys Arg Arg Trp Gln Asn
            100                 105                 110

Lys Met Lys Ala Ala Gly Lys Pro Cys Asp Lys Pro Asn Ile Val Thr
        115                 120                 125

Gly Ala Asn Val Gln Val Cys Trp Glu Lys Phe Ala Arg Tyr Phe Glu
    130                 135                 140

Val Glu Leu Lys Glu Val Lys Leu Ser Asp Gly Tyr Tyr Val Met Asp
145                 150                 155                 160

Pro Ala Lys Ala Val Asp Met Val Asp Glu Asn Thr Ile Cys Val Ala
                165                 170                 175

Ala Ile Leu Gly Ser Thr Leu Asn Gly Glu Phe Glu Asp Val Lys Leu
            180                 185                 190

Leu Asn Asp Leu Leu Thr Lys Lys Asn Ala Glu Thr Gly Trp Asp Thr
        195                 200                 205

Pro Ile His Val Asp Ala Ala Ser Gly Gly Phe Ile Ala Pro Phe Leu
```

```
    210                 215                 220

Tyr Pro Glu Leu Glu Trp Asp Phe Arg Leu Pro Leu Val Lys Ser Ile
225                 230                 235                 240

Asn Val Ser Gly His Lys Tyr Gly Leu Val Tyr Ala Gly Ile Gly Trp
                245                 250                 255

Cys Ile Trp Arg Ser Lys Glu Asp Leu Pro Glu Glu Leu Ile Phe His
            260                 265                 270

Ile Asn Tyr Leu Gly Ala Asp Gln Pro Thr Phe Thr Leu Asn Phe Ser
        275                 280                 285

Lys Gly Ser Ser Gln Val Ile Ala Gln Tyr Tyr Gln Leu Ile Arg Leu
    290                 295                 300

Gly Phe Glu Gly Tyr Lys Asn Ile Met Glu Asn Cys Gln Glu Asn Ala
305                 310                 315                 320

Met Val Leu Lys Gln Gly Leu Glu Lys Thr Gly Arg Phe Asn Ile Val
                325                 330                 335

Ser Lys Asp Asn Gly Val Pro Leu Val Ala Phe Ser Leu Lys Asp Ser
            340                 345                 350

Ala Arg His Asn Glu Phe Glu Ile Ser Asp Phe Leu Arg Arg Phe Gly
        355                 360                 365

Trp Ile Val Pro Ala Tyr Thr Met Pro Pro Asp Ala Gln His Val Thr
    370                 375                 380

Val Leu Arg Val Val Ile Arg Glu Asp Phe Ser Arg Thr Leu Ala Glu
385                 390                 395                 400

Arg Leu Val Leu Asp Val Glu Lys Val Leu His Glu Leu Asp Ala Leu
                405                 410                 415

Pro Ala Arg Val Val Ala Asn Gly Asp Asn Pro Ala Ala Ala Ser Ala
            420                 425                 430

Ser Glu Arg Glu Met Glu Lys Gln Arg Glu Val Ile Ser Leu Trp Lys
        435                 440                 445

Arg Ala Val Leu Ala Lys Lys Lys Thr Asn Gly Val Cys
    450                 455                 460


<210> SEQ ID NO 9
<211> LENGTH: 489
<212> TYPE: PRT
<213> ORGANISM: Vitis vinifera
<220> FEATURE:
<221> NAME/KEY: misc_feature
<222> LOCATION: (229)..(229)
<223> OTHER INFORMATION: Xaa can be any naturally occurring amino acid

<400> SEQUENCE: 9

Met Val Leu Ser Lys Thr Ala Ser Glu Ser Asp Val Ser Val His Ser
1               5                   10                  15

Thr Phe Ala Ser Arg Tyr Val Lys Ala Ser Leu Pro Arg Phe Lys Leu
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Ala Ala Ile
65                  70                  75                  80

Asn Lys Asn Tyr Val Asp Met Asp Glu Tyr Pro Asn Arg Cys Val Asn
                85                  90                  95

Ile Ile Ala His Leu Phe Asn Ala Pro Leu Glu Asp Ser Glu Ala Ala
            100                 105                 110
```

```
Val Gly Val Gly Thr Val Gly Ser Ser Glu Ala Ile Met Leu Ala Gly
        115                 120                 125

Leu Ala Phe Lys Arg Lys Trp Gln Asn Lys Arg Lys Ala Glu Gly Lys
    130                 135                 140

Pro Tyr Asp Lys Pro Asn Ile Val Thr Gly Ala Asn Val Gln Val Cys
145                 150                 155                 160

Trp Glu Lys Phe Ala Arg Tyr Phe Glu Val Glu Leu Lys Glu Val Lys
                165                 170                 175

Leu Arg Asp Gly Tyr Tyr Val Met Asp Pro Glu Lys Ala Val Glu Met
            180                 185                 190

Val Asp Glu Asn Thr Ile Cys Val Ala Ala Ile Leu Gly Ser Thr Leu
        195                 200                 205

Asn Gly Glu Phe Glu Asp Val Lys Leu Leu Asn Asp Leu Leu Val Glu
    210                 215                 220

Lys Asn Lys Gln Xaa Gly Trp Asp Thr Pro Ile His Val Asp Ala Ala
225                 230                 235                 240

Ser Gly Gly Phe Ile Ala Pro Phe Leu Tyr Pro Glu Leu Glu Trp Asp
                245                 250                 255

Phe Arg Leu Pro Leu Val Lys Ser Ile Asn Val Ser Gly His Lys Tyr
            260                 265                 270

Gly Leu Val Tyr Ala Gly Ile Gly Trp Val Val Trp Arg Ser Lys Glu
        275                 280                 285

Asp Leu Pro Glu Glu Leu Ile Phe His Ile Asn Tyr Leu Gly Ala Asp
    290                 295                 300

Gln Pro Thr Phe Thr Leu Asn Phe Ser Lys Gly Ser Ser Gln Val Ile
305                 310                 315                 320

Ala Gln Tyr Tyr Gln Leu Ile Arg Leu Gly Phe Glu Gly Tyr Arg Asn
                325                 330                 335

Val Met Glu Asn Cys Gln Glu Asn Ala Met Ala Leu Lys Glu Gly Leu
            340                 345                 350

Glu Lys Thr Gly Arg Phe Asn Ile Ile Ser Lys Asp Asn Gly Val Pro
        355                 360                 365

Leu Val Ala Phe Ser Leu Lys Asp Asn Ser Cys His Asp Glu Phe Glu
    370                 375                 380

Val Ala Asp Met Leu Arg Arg Phe Gly Trp Ile Val Pro Ala Tyr Thr
385                 390                 395                 400

Met Pro Pro Asp Ala Gln His Val Thr Val Leu Arg Val Val Val Arg
                405                 410                 415

Glu Asp Phe Ser Arg Thr Leu Ala Glu Arg Leu Val Phe Asp Ile Thr
            420                 425                 430

Lys Val Leu His Glu Leu Asp Met Leu Pro Ala Lys Leu Ser Ala Lys
        435                 440                 445

Ile Ser Val Glu Glu Lys Lys Gln Asn Gly Thr Ile Leu Lys Lys Ser
    450                 455                 460

Val Ile Glu Thr Gln Arg Glu Ile Thr Asp Ala Trp Lys Lys Phe Val
465                 470                 475                 480

Met Ala Lys Lys Thr Asn Gly Val Cys
                485
```

<210> SEQ ID NO 10
<211> LENGTH: 495
<212> TYPE: PRT
<213> ORGANISM: Vitis vinifera -continued

<400> SEQUENCE: 10

```
Met Val Leu Ser Lys Thr Ala Ser Glu Ser Asp Val Ser Val His Ser
1               5                   10                  15

Thr Phe Ala Ser Arg Tyr Val Lys Ala Ser Leu Pro Arg Phe Lys Leu
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Ala Ala Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Ile Ile Ala His Leu Phe Asn Ala Pro Leu
            100                 105                 110

Glu Asp Ser Glu Ala Ala Val Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140

Arg Lys Ala Glu Gly Lys Pro Tyr Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Arg Asp Gly Tyr Tyr Val Met Asp Pro
            180                 185                 190

Glu Lys Ala Val Glu Met Val Asp Glu Asn Thr Ile Cys Val Ala Ala
        195                 200                 205

Ile Leu Gly Ser Thr Leu Asn Gly Glu Phe Glu Asp Val Lys Leu Leu
    210                 215                 220

Asn Asp Leu Leu Val Glu Lys Asn Lys Gln Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Ser Lys Glu Asp Leu Pro Glu Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Arg Asn Val Met Glu Asn Cys Gln Glu Asn Ala Met
            340                 345                 350

Ala Leu Lys Glu Gly Leu Glu Lys Thr Gly Arg Phe Asn Ile Ile Ser
        355                 360                 365

Lys Asp Asn Gly Val Pro Leu Val Ala Phe Ser Leu Lys Asp Asn Ser
    370                 375                 380

Cys His Asp Glu Phe Glu Val Ala Asp Met Leu Arg Arg Phe Gly Trp
385                 390                 395                 400

Ile Val Pro Ala Tyr Thr Met Pro Pro Asp Ala Gln His Val Thr Val
                405                 410                 415
```

```
Leu Arg Val Val Val Arg Glu Asp Phe Ser Arg Thr Leu Ala Glu Arg
            420                 425                 430

Leu Val Phe Asp Ile Thr Lys Val Leu His Glu Leu Asp Met Leu Pro
        435                 440                 445

Ala Lys Leu Ser Ala Lys Ile Ser Val Glu Glu Lys Lys Gln Asn Gly
    450                 455                 460

Thr Ile Leu Lys Lys Ser Val Ile Glu Thr Gln Arg Glu Ile Thr Asp
465                 470                 475                 480

Ala Trp Lys Lys Phe Val Met Ala Lys Lys Thr Asn Gly Val Cys
                485                 490                 495


<210> SEQ ID NO 11
<211> LENGTH: 476
<212> TYPE: PRT
<213> ORGANISM: Vitis vinifera

<400> SEQUENCE: 11

Met Pro Glu Lys Ser Ile Pro Lys Glu Ala Ala Tyr Gln Ile Val His
1               5                   10                  15

Asp Glu Leu Leu Leu Asp Gly Leu Pro Arg Leu Asn Leu Ala Thr Phe
            20                  25                  30

Val Thr Thr Trp Met Glu Pro Glu Cys Asp Lys Leu Met Ala Glu Ala
        35                  40                  45

Ile Asn Lys Asn Tyr Val Asp Met Asp Glu Tyr Pro Val Thr Thr Glu
    50                  55                  60

Leu Gln Asn Arg Cys Val Asn Met Ile Ala Lys Leu Phe Asn Ala Pro
65                  70                  75                  80

Ser Ala Asp Gln Thr Lys Gln Ala Val Gly Val Gly Thr Val Gly Ser
                85                  90                  95

Ser Glu Ala Met Met Leu Ala Gly Leu Ala Phe Lys Lys Lys Trp Gln
            100                 105                 110

Asn Lys Arg Lys Ala Gln Lys Lys Pro Phe Asp Lys Pro Asn Ile Val
        115                 120                 125

Thr Gly Ala Asn Val Gln Val Cys Trp Glu Lys Phe Ala Arg Tyr Phe
    130                 135                 140

Glu Val Glu Leu Lys Glu Val Lys Leu Arg Glu Gly Tyr Tyr Val Met
145                 150                 155                 160

Asp Pro Val Lys Ala Val Glu Met Val Asp Glu Asn Thr Ile Cys Val
                165                 170                 175

Ala Ala Ile Leu Gly Ser Thr Phe Asn Gly Glu Phe Glu Asp Val Lys
            180                 185                 190

Leu Leu Asn Thr Leu Leu Thr Gln Lys Asn Lys Arg Thr Gly Trp Asp
        195                 200                 205

Thr Pro Ile His Val Asp Ala Ala Ser Gly Gly Phe Val Ala Pro Phe
    210                 215                 220

Leu Tyr Pro Glu Leu Glu Trp Asp Phe Arg Leu Pro Leu Val Lys Ser
225                 230                 235                 240

Ile Asn Val Ser Gly His Lys Tyr Gly Leu Val Tyr Ala Gly Val Gly
                245                 250                 255

Trp Ala Ile Trp Arg Ser Lys Glu Glu Leu Pro Glu Glu Leu Ile Phe
            260                 265                 270

His Ile Asn Tyr Leu Gly Gly Asp Glu Pro Thr Phe Thr Leu Asn Phe
        275                 280                 285

Ser Lys Gly Asn Gln Val Ile Ala Gln Tyr Tyr Gln Phe Leu Arg Met
```

```
    290                 295                 300

Gly Phe Glu Gly Tyr Lys Lys Val Met Ser Asn Cys Met Glu Ser Ala
305                 310                 315                 320

Arg Ile Leu Arg Glu Gly Leu Glu Lys Thr Gly Arg Phe Gln Ile Ile
                325                 330                 335

Ser Lys Glu Lys Gly Val Pro Val Val Ala Phe Ala Phe Lys Gly Asn
            340                 345                 350

Asp Arg Lys Asn Leu Ala Phe Gly Leu Ser Lys Ala Leu Arg Asn Tyr
        355                 360                 365

Gly Trp Ile Val Pro Ala Tyr Thr Met Pro Ala Asn Ala Glu Asn Val
    370                 375                 380

Thr Val Leu Arg Val Val Val Arg Glu Asp Phe Gly Arg Gln Leu Val
385                 390                 395                 400

Glu Lys Leu Leu Phe His Ile Gly Val Ala Leu Lys Glu Val Thr Asp
                405                 410                 415

Ala Ala Ser Ser Val Pro Met Ile Arg Leu Thr Val Glu Met Lys Ala
            420                 425                 430

Asp Glu Ser Glu Met Asn Ala Gly Glu Gly Thr Leu His Ile Pro Ala
        435                 440                 445

Ala Ser Val His Trp Lys His Asp Lys Pro Glu Thr Val Asp Thr Gln
    450                 455                 460

Val Pro Ile Met Asp Gly Lys Thr Lys Gly Val Cys
465                 470                 475


<210> SEQ ID NO 12
<211> LENGTH: 496
<212> TYPE: PRT
<213> ORGANISM: Nicotiana tabacum

<400> SEQUENCE: 12

Met Val Leu Ser Lys Thr Ala Ser Glu Ser Asp Val Ser Val His Ser
1               5                   10                  15

Thr Phe Ala Ser Arg Tyr Val Arg Thr Ser Leu Pro Arg Phe Lys Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asn Thr Leu Met Met Asp Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Leu
            100                 105                 110

Gly Asp Gly Glu Thr Ala Val Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140

Met Lys Ala Gln Gly Lys Pro Phe Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Asp Gly Tyr Tyr Val Met Asp Pro
            180                 185                 190
```

-continued

```
Glu Lys Ala Val Glu Met Val Asp Glu Asn Thr Ile Cys Val Ala Ala
        195                 200                 205

Ile Leu Gly Ser Thr Leu Asn Gly Glu Phe Glu Asp Val Lys Arg Leu
    210                 215                 220

Asn Asp Leu Leu Ile Glu Lys Asn Lys Glu Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Glu Lys Ser Ile Asn
            260                 265                 270

Val Ser Gly His Lys Tyr Gly Leu Val Tyr Ala Gly Ile Gly Trp Ala
        275                 280                 285

Ile Trp Arg Asn Lys Glu Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Lys Asn Val Met Glu Asn Cys Gln Glu Asn Ala Arg
            340                 345                 350

Val Leu Arg Glu Gly Ile Glu Lys Ser Gly Arg Phe Asn Ile Ile Ser
        355                 360                 365

Lys Glu Ile Gly Val Pro Leu Val Ala Phe Ser Leu Lys Asp Asn Ser
    370                 375                 380

Gln His Asn Glu Phe Glu Ile Ser Glu Thr Leu Arg Arg Phe Gly Trp
385                 390                 395                 400

Ile Val Leu Ala Tyr Thr Met Pro Pro Asn Ala Gln His Val Thr Val
                405                 410                 415

Leu Arg Val Val Ile Arg Glu Asp Phe Ser Arg Thr Leu Ala Glu Arg
            420                 425                 430

Leu Val Ile Asp Ile Glu Lys Val Phe His Gly Val Asp Thr Leu Pro
        435                 440                 445

Ala Arg Val Asn Ala Lys Leu Ala Val Ala Glu Ala Asn Gly Ser Gly
    450                 455                 460

Val His Lys Lys Thr Asp Arg Glu Val Gln Leu Glu Ile Thr Thr Ala
465                 470                 475                 480

Trp Leu Lys Phe Val Ala Asp Lys Lys Lys Lys Thr Asn Gly Val Cys
                485                 490                 495


<210> SEQ ID NO 13
<211> LENGTH: 496
<212> TYPE: PRT
<213> ORGANISM: Nicotiana tabacum

<400> SEQUENCE: 13

Met Val Leu Ser Lys Thr Ala Ser Glu Ser Asp Val Ser Ile His Ser
1               5                   10                  15

Thr Phe Ala Ser Arg Tyr Val Arg Thr Ser Leu Pro Arg Phe Lys Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asn Lys Leu Met Met Asp Ser Ile
65                  70                  75                  80
```

-continued

```
Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Leu
            100                 105                 110

Gly Asp Gly Glu Thr Ala Val Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140

Met Lys Ala Gln Gly Lys Pro Cys Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Asp Gly Tyr Tyr Val Met Asp Pro
            180                 185                 190

Glu Lys Ala Val Glu Met Val Asp Glu Asn Thr Ile Cys Val Ala Ala
        195                 200                 205

Ile Leu Gly Ser Thr Leu Asn Gly Glu Phe Glu Asp Val Lys Arg Leu
    210                 215                 220

Asn Asp Leu Leu Ile Glu Lys Asn Lys Glu Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Ala
        275                 280                 285

Ile Trp Arg Asn Lys Glu Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Lys Asn Val Met Glu Asn Cys Gln Glu Asn Ala Arg
            340                 345                 350

Val Leu Arg Glu Gly Leu Glu Lys Ser Gly Arg Phe Asn Ile Ile Ser
        355                 360                 365

Lys Glu Ile Gly Val Pro Leu Val Ala Phe Ser Leu Lys Asp Asn Ser
    370                 375                 380

Gln His Asn Glu Phe Glu Ile Ser Glu Thr Leu Arg Arg Phe Gly Trp
385                 390                 395                 400

Ile Ile Pro Ala Tyr Thr Met Pro Pro Asn Ala Gln His Val Thr Val
                405                 410                 415

Leu Arg Val Val Ile Arg Glu Asp Phe Ser Arg Thr Leu Ala Glu Arg
            420                 425                 430

Leu Val Ile Asp Ile Glu Lys Val Leu His Glu Leu Asp Thr Leu Pro
        435                 440                 445

Ala Arg Val Asn Ala Lys Leu Ala Val Ala Glu Ala Asn Gly Ser Gly
    450                 455                 460

Val His Lys Lys Thr Asp Arg Glu Val Gln Leu Glu Ile Thr Thr Ala
465                 470                 475                 480

Trp Lys Lys Phe Val Ala Asp Lys Lys Lys Lys Thr Asn Gly Val Cys
                485                 490                 495
```

<210> SEQ ID NO 14
<211> LENGTH: 496
<212> TYPE: PRT
<213> ORGANISM: Nicotiana tabacum

<400> SEQUENCE: 14

```
Met Val Leu Ser Lys Thr Ala Ser Glu Ser Asp Val Ser Ile His Ser
1               5                   10                  15

Thr Phe Ala Ser Arg Tyr Val Arg Thr Ser Leu Pro Arg Phe Lys Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asn Lys Leu Met Met Asp Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Leu
            100                 105                 110

Gly Asp Gly Glu Thr Ala Val Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140

Met Lys Ala Gln Gly Lys Pro Cys Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Asp Gly Tyr Tyr Val Met Asp Pro
            180                 185                 190

Glu Lys Ala Val Glu Met Val Asp Glu Asn Thr Ile Cys Val Ala Ala
        195                 200                 205

Ile Leu Gly Ser Thr Leu Asn Gly Glu Phe Glu Asp Val Lys Arg Leu
    210                 215                 220

Asn Asp Leu Leu Ile Glu Lys Asn Lys Glu Thr Gly Trp Asp Thr Pro
225                 230                 235                 240

Ile His Val Asp Ala Ala Ser Gly Glu Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Ala
        275                 280                 285

Ile Trp Arg Asn Lys Glu Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Lys Asn Val Met Glu Asn Cys Gln Glu Asn Ala Arg
            340                 345                 350

Val Leu Arg Glu Gly Leu Glu Lys Ser Gly Arg Phe Asn Ile Ile Ser
        355                 360                 365

Lys Glu Ile Gly Val Pro Leu Val Ala Phe Ser Leu Lys Asp Asn Ser
    370                 375                 380
```

Gln His Asn Glu Phe Glu Ile Ser Glu Thr Leu Arg Arg Phe Gly Trp
385 390 395 400

Ile Ile Pro Ala Tyr Thr Met Pro Pro Asn Ala Gln His Val Thr Val
405 410 415

Leu Arg Val Val Ile Arg Glu Asp Phe Ser Arg Thr Leu Ala Glu Arg
420 425 430

Leu Val Ile Asp Ile Glu Lys Val Leu His Glu Leu Asp Thr Leu Pro
435 440 445

Ala Arg Val Asn Ala Lys Leu Ala Val Ala Glu Ala Asn Gly Ser Gly
450 455 460

Val His Lys Lys Thr Asp Arg Glu Val Gln Leu Glu Ile Thr Thr Ala
465 470 475 480

Trp Lys Lys Phe Val Ala Asp Lys Lys Lys Lys Thr Asn Gly Val Cys
485 490 495

<210> SEQ ID NO 15
<211> LENGTH: 500
<212> TYPE: PRT
<213> ORGANISM: Oryza sativa

<400> SEQUENCE: 15

Met Val Leu Thr His Val Glu Ala Val Glu Glu Gly Ser Glu Ala Ala
1 5 10 15

Ala Ala Val Phe Ala Ser Arg Tyr Val Gln Asp Pro Val Pro Arg Tyr
20 25 30

Glu Leu Gly Glu Arg Ser Ile Ser Lys Asp Ala Ala Tyr Gln Ile Val
35 40 45

His Asp Glu Leu Leu Leu Asp Ser Ser Pro Arg Leu Asn Leu Ala Ser
50 55 60

Phe Val Thr Thr Trp Met Glu Pro Glu Cys Asp Arg Leu Ile Leu Glu
65 70 75 80

Ala Ile Asn Lys Asn Tyr Ala Asp Met Asp Glu Tyr Pro Val Thr Thr
85 90 95

Glu Leu Gln Asn Arg Cys Val Asn Ile Ile Ala Arg Leu Phe Asn Ala
100 105 110

Pro Val Gly Asp Gly Glu Lys Ala Val Gly Val Gly Thr Val Gly Ser
115 120 125

Ser Glu Ala Ile Met Leu Ala Gly Leu Ala Phe Lys Arg Arg Trp Gln
130 135 140

Asn Arg Arg Lys Ala Ala Gly Lys Pro His Asp Lys Pro Asn Ile Val
145 150 155 160

Thr Gly Ala Asn Val Gln Val Cys Trp Glu Lys Phe Ala Arg Tyr Phe
165 170 175

Glu Val Glu Leu Lys Glu Val Lys Leu Thr Glu Gly Cys Tyr Val Met
180 185 190

Asp Pro Val Lys Ala Val Asp Met Val Asp Glu Asn Thr Ile Cys Val
195 200 205

Ala Ala Ile Leu Gly Ser Thr Leu Thr Gly Glu Phe Glu Asp Val Arg
210 215 220

Arg Leu Asn Asp Leu Leu Ala Ala Lys Asn Lys Arg Thr Gly Trp Asp
225 230 235 240

Thr Pro Ile His Val Asp Ala Ala Ser Gly Gly Phe Ile Ala Pro Phe
245 250 255

Ile Tyr Pro Glu Leu Glu Trp Asp Phe Arg Leu Pro Leu Val Lys Ser

-continued

```
            260                 265                 270

Ile Asn Val Ser Gly His Lys Tyr Gly Leu Val Tyr Ala Gly Val Gly
        275                 280                 285

Trp Val Ile Trp Arg Asn Lys Glu Asp Leu Pro Glu Glu Leu Ile Phe
    290                 295                 300

His Ile Asn Tyr Leu Gly Ala Asp Gln Pro Thr Phe Thr Leu Asn Phe
305                 310                 315                 320

Ser Lys Gly Ser Ser Gln Ile Ile Ala Gln Tyr Tyr Gln Phe Leu Arg
                325                 330                 335

Leu Gly Phe Glu Gly Tyr Lys Ser Val Met Lys Asn Cys Met Glu Ser
            340                 345                 350

Ala Arg Thr Leu Arg Glu Gly Leu Glu Lys Thr Gly Arg Phe Thr Ile
        355                 360                 365

Ile Ser Lys Glu Glu Gly Val Pro Leu Val Ala Phe Thr Phe Lys Asp
    370                 375                 380

Gly Ala Gly Ala Gln Ala Phe Arg Leu Ser Ser Gly Leu Arg Arg Tyr
385                 390                 395                 400

Gly Trp Ile Val Pro Ala Tyr Thr Met Pro Ala Ala Leu Glu His Met
                405                 410                 415

Thr Val Leu Arg Val Val Val Arg Glu Asp Phe Gly Arg Pro Leu Ala
            420                 425                 430

Glu Arg Phe Leu Ser His Val Arg Met Ala Leu Asp Glu Met Asp Leu
        435                 440                 445

Ala Ala Arg Ala Pro Val Pro Arg Val Gln Leu Thr Ile Glu Leu Gly
    450                 455                 460

Pro Ala Arg Thr Ala Gly Glu Glu Ala Ser Ile Arg Val Val Lys Ser
465                 470                 475                 480

Glu Ala Val Pro Val Arg Lys Ser Val Pro Leu Val Ala Gly Lys Thr
                485                 490                 495

Lys Gly Val Cys
            500


<210> SEQ ID NO 16
<211> LENGTH: 494
<212> TYPE: PRT
<213> ORGANISM: Citrus sinensis

<400> SEQUENCE: 16

Met Val Leu Ser Lys Thr Phe Ser Glu Ser Asp Glu Ser Ile His Ser
1               5                   10                  15

Thr Phe Ala Ser Arg Tyr Val Arg Asn Ser Leu Pro Arg Phe Thr Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Ala Ala Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Ile Ile Ala Arg Leu Phe Asn Ala Pro Leu
            100                 105                 110

Glu Asp Ser Glu Thr Ala Val Gly Val Gly Thr Val Gly Ser Ser Glu
        115                 120                 125
```

```
Ala Ile Met Leu Ala Gly Leu Ala Phe Lys Arg Lys Trp Gln Asn Lys
    130                 135                 140

Arg Lys Ala Glu Gly Lys Pro Phe Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Glu Gly Tyr Tyr Val Met Asp Pro
            180                 185                 190

Ala Lys Ala Val Glu Met Val Asp Glu Asn Thr Ile Cys Val Ala Ala
        195                 200                 205

Ile Leu Gly Ser Thr Leu Asn Gly Glu Phe Glu Asp Val Lys Leu Leu
    210                 215                 220

Asn Asp Leu Leu Thr Glu Lys Asn Lys Glu Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Asn Lys Glu Asp Leu Pro Glu Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Arg Asn Val Met Glu Asn Cys His Glu Asn Ala Met
            340                 345                 350

Val Leu Lys Glu Gly Leu Glu Lys Thr Gly Arg Phe Asn Ile Val Ser
        355                 360                 365

Lys Asp Glu Gly Val Pro Leu Val Ala Phe Ser Leu Lys Asp Asn Lys
    370                 375                 380

Arg His Asp Glu Phe Glu Val Ala Glu Leu Leu Arg Arg Phe Gly Trp
385                 390                 395                 400

Ile Val Pro Ala Tyr Thr Met Pro Ala Asp Ala Gln His Ile Thr Val
                405                 410                 415

Leu Arg Val Val Ile Arg Glu Asp Phe Ser Arg Thr Leu Ala Glu Arg
            420                 425                 430

Leu Val Leu Asp Ile Thr Lys Val Leu His Glu Leu Asp Ser Leu Pro
        435                 440                 445

Ser Lys Val Leu Val Pro Ala Ser Glu Gln Asn Gly Arg Asn Gly Lys
    450                 455                 460

Lys Thr Glu Ile Glu Thr Gln Arg Glu Val Thr Thr Tyr Trp Arg Lys
465                 470                 475                 480

Phe Val Ser Glu Arg Lys Ala Asn Asn Lys Asn Lys Ile Cys
                485                 490


<210> SEQ ID NO 17
<211> LENGTH: 492
<212> TYPE: PRT
<213> ORGANISM: Oryza sativa subsp. japonica

<400> SEQUENCE: 17

Met Val Leu Ser His Gly Val Ser Gly Ser Asp Glu Ser Val His Ser
1               5                   10                  15
```

-continued

```
Thr Phe Ala Ser Arg Tyr Val Arg Thr Ser Leu Pro Arg Phe Arg Met
            20                  25                  30

Pro Glu Gln Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Ile Gln Ala Ser Val
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Leu
            100                 105                 110

Gly Asp Ser Glu Thr Ala Val Gly Val Gly Thr Val Gly Ser Ser Glu
        115                 120                 125

Ala Ile Met Leu Ala Gly Leu Ala Phe Lys Arg Arg Trp Gln Asn Lys
    130                 135                 140

Met Lys Ala Ala Gly Lys Pro Cys Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Asp Gly Tyr Tyr Val Met Asp Pro
            180                 185                 190

Ala Lys Ala Val Asp Met Val Asp Glu Asn Thr Ile Cys Val Ala Ala
        195                 200                 205

Ile Leu Gly Ser Thr Leu Asn Gly Glu Phe Glu Asp Val Lys Leu Leu
    210                 215                 220

Asn Asp Leu Leu Thr Lys Lys Asn Ala Glu Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Cys
        275                 280                 285

Ile Trp Arg Ser Lys Glu Asp Leu Pro Glu Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Lys Asn Ile Met Glu Asn Cys Gln Glu Asn Ala Met
            340                 345                 350

Val Leu Lys Gln Gly Leu Glu Lys Thr Gly Arg Phe Asn Ile Val Ser
        355                 360                 365

Lys Asp Asn Gly Val Pro Leu Val Ala Phe Ser Leu Lys Asp Ser Ala
    370                 375                 380

Arg His Asn Glu Phe Glu Ile Ser Asp Phe Leu Arg Arg Phe Gly Trp
385                 390                 395                 400

Ile Val Pro Ala Tyr Thr Met Pro Pro Asp Ala Gln His Val Thr Val
                405                 410                 415

Leu Arg Val Val Ile Arg Glu Asp Phe Ser Arg Thr Leu Ala Glu Arg
            420                 425                 430
```

-continued

```
Leu Val Leu Asp Val Glu Lys Val Leu His Glu Leu Asp Ala Leu Pro
        435                 440                 445

Ala Arg Val Val Ala Asn Gly Gly Asp Ala Ala Ala Ala Ser Ala Ser
    450                 455                 460

Glu Arg Glu Met Glu Lys Gln Arg Glu Val Ile Ser Leu Trp Lys Arg
465                 470                 475                 480

Ala Val Leu Ala Lys Lys Lys Thr Asn Gly Val Cys
                485                 490


<210> SEQ ID NO 18
<211> LENGTH: 493
<212> TYPE: PRT
<213> ORGANISM: Brassica juncea

<400> SEQUENCE: 18

Met Val Leu Ser Lys Thr Ala Ser Gly Thr Asp Val Ser Val His Ser
1               5                   10                  15

Thr Phe Ala Ser Arg Tyr Val Arg Asn Ser Leu Pro Arg Phe Glu Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Glu Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala Arg Leu Phe Asn Ala Pro Leu
            100                 105                 110

Gly Asp Gly Glu Ala Ala Val Gly Val Gly Thr Val Gly Ser Ser Glu
        115                 120                 125

Ala Ile Met Leu Ala Gly Leu Ala Phe Lys Arg Gln Trp Gln Asn Lys
    130                 135                 140

Arg Lys Ala Gln Gly Leu Pro Tyr Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Arg Glu Gly Tyr Tyr Val Met Asp Pro
            180                 185                 190

Glu Lys Ala Val Glu Met Val Asp Glu Asn Thr Ile Cys Val Ala Ala
        195                 200                 205

Ile Leu Gly Ser Thr Leu Thr Gly Glu Phe Glu Asp Val Lys Leu Leu
    210                 215                 220

Asn Asp Leu Leu Val Glu Lys Asn Lys Gln Thr Gly Trp Asp Thr Gly
225                 230                 235                 240

Asn His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Thr Lys Ser Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320
```

```
Gly Ser Ser Gln Val Ile Ala Gln Tyr Tyr Gln Leu Ile Arg Leu Gly
                325                 330                 335

Phe Glu Gly Tyr Arg Asn Val Met Asp Asn Cys Arg Glu Asn Met Met
            340                 345                 350

Val Leu Arg Glu Gly Leu Glu Lys Thr Gly Arg Phe Asn Ile Val Ser
        355                 360                 365

Lys Glu Asn Gly Val Pro Leu Val Ala Phe Ser Leu Lys Asp Ser Ser
    370                 375                 380

Arg His Asn Glu Phe Glu Val Ala Glu Thr Leu Arg Arg Phe Gly Trp
385                 390                 395                 400

Ile Val Pro Ala Tyr Thr Val Pro Ala Asp Ala Glu His Val Thr Val
                405                 410                 415

Leu Arg Val Val Ile Arg Glu Asp Phe Ser Arg Thr Leu Ala Glu Arg
            420                 425                 430

Leu Val Ala Asp Phe Glu Lys Val Leu His Glu Leu Asp Thr Leu Pro
        435                 440                 445

Ala Arg Val Arg Ala Lys Met Ala Asn Gly Lys Ala Lys Val Val Lys
    450                 455                 460

Gln Thr Glu Glu Glu Thr Thr Arg Glu Val Thr Ala Tyr Trp Lys Lys
465                 470                 475                 480

Phe Val Glu Thr Lys Lys Thr Asn Gln Asn Lys Ile Cys
                485                 490


<210> SEQ ID NO 19
<211> LENGTH: 493
<212> TYPE: PRT
<213> ORGANISM: Brassica juncea

<400> SEQUENCE: 19

Met Val Leu Ser Lys Thr Ala Ser Glu Ser Asp Val Ser Ile His Ser
1               5                   10                  15

Thr Phe Ala Ser Arg Tyr Val Arg Thr Ser Leu Pro Arg Phe Glu Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Glu Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala Arg Leu Phe Asn Ala Pro Leu
            100                 105                 110

Gly Asp Gly Glu Ala Ala Val Gly Val Gly Thr Val Gly Ser Ser Glu
        115                 120                 125

Ala Ile Met Leu Ala Gly Leu Ala Phe Lys Arg Gln Trp Gln Asn Lys
    130                 135                 140

Arg Lys Ala Gln Gly Leu Pro Tyr Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Arg Glu Gly Tyr Tyr Val Met Asp Pro
            180                 185                 190

Glu Lys Ala Val Glu Met Val Asp Glu Asn Thr Ile Cys Val Ala Ala
```

-continued

```
        195                 200                 205

Ile Leu Gly Ser Thr Leu Thr Gly Glu Phe Glu Asp Val Lys Leu Leu
    210                 215                 220

Asn Asp Leu Leu Val Glu Lys Asn Lys Gln Thr Gly Trp Asp Thr Gly
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Thr Lys Ser Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Arg Asn Val Met Asp Asn Cys Arg Glu Asn Met Met
            340                 345                 350

Val Leu Arg Glu Gly Leu Glu Lys Thr Gly Arg Phe Asn Ile Val Ser
        355                 360                 365

Lys Glu Asn Gly Val Pro Leu Val Ala Phe Ser Leu Lys Asp Ser Ser
    370                 375                 380

Arg His Asp Glu Phe Glu Val Ala Glu Thr Leu Arg Arg Phe Gly Trp
385                 390                 395                 400

Ile Val Pro Ala Tyr Thr Met Pro Ala Asp Ala Gln His Val Thr Val
                405                 410                 415

Leu Arg Val Val Ile Arg Glu Asp Phe Ser Arg Thr Leu Ala Glu Arg
            420                 425                 430

Leu Val Ala Asp Phe Glu Lys Val Leu His Glu Leu Asp Thr Leu Pro
        435                 440                 445

Ala Arg Val Gln Ala Lys Met Ala Asn Gly Asn Ala Asn Gly Val Lys
    450                 455                 460

Lys Thr Glu Glu Glu Thr Thr Arg Glu Val Thr Ala Tyr Trp Lys Lys
465                 470                 475                 480

Phe Val Glu Ala Lys Lys Ser Asn Lys Asn Arg Ile Cys
                485                 490


<210> SEQ ID NO 20
<211> LENGTH: 494
<212> TYPE: PRT
<213> ORGANISM: Brassica juncea

<400> SEQUENCE: 20

Met Val Leu Ser Arg Ala Ala Thr Glu Ser Gly Glu Asn Val Cys Ser
1               5                   10                  15

Thr Phe Gly Ser Arg Tyr Val Arg Thr Ala Leu Pro Lys His Lys Ile
            20                  25                  30

Gly Glu Ser Ser Ile Pro Lys Glu Ala Ala Tyr Gln Ile Ile Lys Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Ile Met Glu Ser Ile
65                  70                  75                  80
```

-continued

```
Asn Lys Asn Tyr Val Asp Met Asp Glu Tyr Pro Val Thr Thr Glu Leu
                85                  90                  95

Gln Asn Arg Cys Val Asn Met Ile Ala Arg Leu Phe Asn Ala Pro Leu
            100                 105                 110

Glu Glu Thr Glu Thr Ala Met Gly Val Gly Thr Val Gly Ser Ser Glu
        115                 120                 125

Ala Ile Met Leu Ala Gly Leu Ala Phe Lys Arg Asn Trp Gln Asn Lys
    130                 135                 140

Arg Lys Ala Glu Gly Lys Pro Tyr Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Glu Gly Tyr Tyr Val Met Asp Pro
            180                 185                 190

Asp Lys Ala Ala Glu Met Val Asp Glu Asn Thr Ile Cys Val Ala Ala
        195                 200                 205

Ile Leu Gly Ser Thr Leu Asn Gly Glu Phe Glu Asp Val Lys Arg Leu
    210                 215                 220

Asn Asp Leu Leu Val Lys Lys Asn Glu Glu Thr Gly Trp Asn Thr Pro
225                 230                 235                 240

Ile His Val Asp Ala Ala Ser Gly Gly Phe Ile Ala Pro Phe Ile Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Thr Gln Gln Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Ile Ile Ala Gln Tyr Tyr Gln Leu Ile Arg Leu Gly
                325                 330                 335

Phe Glu Gly Tyr Lys Asn Val Met Glu Asn Cys Arg Glu Asn Met Val
            340                 345                 350

Val Leu Arg Glu Gly Ile Glu Lys Thr Glu Arg Phe Asn Ile Val Ser
        355                 360                 365

Lys Glu Val Gly Val Pro Leu Val Ala Phe Ser Leu Lys Asp His Ser
    370                 375                 380

Phe His Asn Glu Phe Glu Ile Ser Glu Met Leu Arg Arg Phe Gly Trp
385                 390                 395                 400

Ile Val Pro Ala Tyr Thr Met Pro Ala Asp Ala Gln His Ile Thr Val
                405                 410                 415

Leu Arg Val Val Ile Arg Glu Asp Phe Ser Arg Thr Leu Ala Glu Arg
            420                 425                 430

Leu Val Ala Asp Ile Val Lys Val Leu His Glu Leu Asp Thr Leu Pro
        435                 440                 445

Ser Lys Ile Ser Lys Lys Met Gly Ala Glu Asp Phe Gly Asn Val Lys
    450                 455                 460

Gly Lys Lys Val Asp Arg Asp Val Leu Met Glu Val Ile Val Gly Trp
465                 470                 475                 480

Arg Lys Phe Val Lys Asp Arg Lys Lys Met Asn Gly Val Cys
                485                 490
```

<210> SEQ ID NO 21
<211> LENGTH: 497
<212> TYPE: PRT
<213> ORGANISM: Oryza sativa subsp. japonica

<400> SEQUENCE: 21

```
Met Val Leu Ser His Ala Ser Ser Gly Arg Asp Asp Ala Val Arg Cys
1               5                   10                  15

Thr Phe Ala Thr Arg Tyr Ala Cys Glu Thr Leu Pro Arg Phe Arg Met
            20                  25                  30

Pro Glu Gln Ser Ile Pro Arg Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Ile Met Asp Ser Val
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Ile
            100                 105                 110

Lys Glu Asp Glu Thr Ala Ile Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140

Arg Lys Glu Gln Gly Lys Pro Cys Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Glu Gly Tyr Tyr Val Met Asp Pro
            180                 185                 190

Val Lys Ala Val Glu Met Val Asp Glu Asn Thr Ile Cys Val Ala Ala
        195                 200                 205

Ile Leu Gly Ser Thr Leu Thr Gly Glu Phe Glu Asp Val Lys Leu Leu
    210                 215                 220

Asn Asn Leu Leu Thr Glu Lys Asn Lys Glu Thr Gly Trp Asp Val Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Pro Gly Val Gly Trp Val
        275                 280                 285

Ile Trp Arg Ser Lys Glu Asp Leu Pro Glu Glu Leu Ile Phe His Ile
    290                 295                 300

Asn Tyr Leu Gly Thr Asp Gln Pro Thr Phe Thr Leu Asn Phe Ser Lys
305                 310                 315                 320

Gly Ser Ser Gln Ile Ile Ala Gln Tyr Tyr Gln Leu Ile Arg Leu Gly
                325                 330                 335

Phe Glu Gly Tyr Lys Asn Ile Met Gln Asn Cys Met Glu Asn Thr Ala
            340                 345                 350

Ile Leu Arg Glu Gly Ile Glu Ala Thr Gly Arg Phe Glu Ile Leu Ser
        355                 360                 365

Lys Glu Ala Gly Val Pro Leu Val Ala Phe Ser Leu Lys Asp Ser Gly
    370                 375                 380
```

-continued

```
Arg Tyr Thr Val Phe Asp Ile Ser Glu His Leu Arg Arg Phe Gly Trp
385                 390                 395                 400

Ile Val Pro Ala Tyr Thr Met Pro Ala Asn Ala Glu His Val Ala Val
                405                 410                 415

Leu Arg Val Val Ile Arg Glu Asp Phe Ser Arg Ser Leu Ala Glu Arg
            420                 425                 430

Leu Val Ser Asp Ile Val Lys Ile Leu His Glu Leu Asp Ala His Ser
        435                 440                 445

Ala Gln Val Leu Lys Ile Ser Ser Ala Ile Ala Lys Gln Gln Ser Gly
    450                 455                 460

Asp Asp Gly Val Val Thr Lys Lys Ser Val Leu Glu Thr Glu Arg Glu
465                 470                 475                 480

Ile Phe Ala Tyr Trp Arg Asp Gln Val Lys Lys Lys Gln Thr Gly Ile
                485                 490                 495

Cys


<210> SEQ ID NO 22
<211> LENGTH: 490
<212> TYPE: PRT
<213> ORGANISM: Hordeum vulgare

<400> SEQUENCE: 22

Met Val Val Thr Val Ala Ala Thr Gly Pro Asp Thr Ala Glu Thr Leu
1               5                   10                  15

His Ser Thr Thr Phe Ala Ser Arg Tyr Val Arg Asp Gln Leu Pro Arg
            20                  25                  30

Tyr Arg Met Pro Glu Asn Ser Ile Pro Lys Glu Ala Ala Tyr Gln Ile
        35                  40                  45

Ile Ser Asp Glu Leu Met Leu Asp Gly Asn Pro Arg Leu Asn Leu Ala
    50                  55                  60

Ser Phe Val Thr Thr Trp Met Glu Pro Glu Cys Gly Lys Leu Ile Met
65                  70                  75                  80

Asp Ser Val Asn Lys Asn Tyr Val Asp Met Asp Glu Tyr Pro Val Thr
                85                  90                  95

Thr Glu Leu Gln Asp Arg Cys Val Asn Met Ile Ala His Leu Phe Asn
            100                 105                 110

Ala Pro Ile Gly Glu Asp Glu Thr Ala Ile Gly Val Ser Thr Val Gly
        115                 120                 125

Ser Ser Glu Ala Ile Met Leu Ala Gly Leu Ala Phe Lys Arg Lys Trp
    130                 135                 140

Ala Asn Lys Met Lys Glu Gln Gly Lys Pro Cys Asp Lys Pro Asn Ile
145                 150                 155                 160

Val Thr Gly Ala Asn Val Gln Val Cys Trp Glu Lys Phe Ala Arg Tyr
                165                 170                 175

Phe Glu Val Glu Leu Lys Glu Val Lys Leu Thr Glu Gly Tyr Tyr Val
            180                 185                 190

Met Asp Pro Lys Lys Ala Val Glu Met Val Asp Glu Asn Thr Ile Cys
        195                 200                 205

Val Ala Ala Ile Leu Gly Ser Thr Leu Thr Gly Glu Tyr Glu Asp Val
    210                 215                 220

Lys Leu Leu Asn Asp Leu Leu Val Glu Lys Asn Lys Glu Thr Gly Trp
225                 230                 235                 240

Asn Val Pro Ile His Val Asp Ala Ala Ser Gly Gly Phe Ile Ala Pro
                245                 250                 255
```

```
Phe Leu Gln Pro Glu Leu Glu Trp Asp Phe Arg Leu Pro Leu Val Lys
            260                 265                 270

Ser Ile Asn Val Ser Gly His Lys Tyr Gly Leu Val Tyr Pro Gly Val
        275                 280                 285

Gly Trp Val Ile Trp Arg Ser Lys Asp Asp Leu Pro Glu Glu Leu Ile
    290                 295                 300

Phe His Ile Asn Tyr Leu Gly Ala Asp Gln Pro Thr Phe Thr Leu Asn
305                 310                 315                 320

Phe Ser Lys Gly Gln Gln Ile Ile Ala Gln Tyr Tyr Gln Leu Ile Arg
                325                 330                 335

Leu Gly Phe Glu Gly Tyr Lys His Ile Met Glu Asn Cys Lys Leu Asn
            340                 345                 350

Ala Ala Val Leu Lys Glu Gly Ile Asp Ala Thr Gly Arg Phe Asp Val
        355                 360                 365

Leu Ser Lys Ala Asp Gly Val Pro Leu Val Ala Ile Arg Leu Lys Asp
    370                 375                 380

Ser Thr Asn Phe Ser Val Phe Asp Ile Ser Glu Asn Leu Arg Arg Phe
385                 390                 395                 400

Gly Trp Ile Val Pro Ala Tyr Thr Met Pro Ala Asp Ala Glu His Val
                405                 410                 415

Ala Val Leu Arg Ile Val Ile Arg Glu Asp Phe Asn Arg Ser Leu Ala
            420                 425                 430

Gln Arg Leu Leu Ala Asp Ile Asn Lys Ile Ile Gly Glu Leu Asp Ala
        435                 440                 445

His Ala Val His Ala Ile Lys Leu Ser Thr Ala Ala Ala Gly Gly Asp
    450                 455                 460

Gly Ala Ser Lys Ser Ala Val Asp Ala Ala Thr Glu Ala Phe Lys Asp
465                 470                 475                 480

Leu Ala Gly Lys Lys Lys Ala Gly Val Cys
                485                 490


<210> SEQ ID NO 23
<211> LENGTH: 492
<212> TYPE: PRT
<213> ORGANISM: Oryza sativa subsp. japonica

<400> SEQUENCE: 23

Met Val Leu Ser Lys Ala Val Ser Glu Ser Asp Met Ser Val His Ser
1               5                   10                  15

Thr Phe Ala Ser Arg Tyr Val Arg Ala Ser Leu Pro Arg Tyr Arg Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Ile Met Ala Ala Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe His Ala Pro Leu
            100                 105                 110

Gly Glu Asp Glu Thr Ala Val Gly Val Gly Thr Val Gly Ser Ser Glu
        115                 120                 125

Ala Ile Met Leu Ala Gly Leu Ala Phe Lys Arg Arg Trp Gln Asn Lys
    130                 135                 140
```

```
Arg Lys Ala Glu Gly Lys Pro Phe Asp Lys Pro Asn Ile Ile Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Arg Asp Gly Tyr Tyr Val Met Asp Pro
            180                 185                 190

Glu Lys Ala Val Asp Met Val Asn Glu Asn Thr Ile Cys Val Ala Ala
        195                 200                 205

Ile Leu Gly Ser Thr Leu Asn Gly Glu Phe Glu Asp Val Lys Leu Leu
    210                 215                 220

Asn Asp Leu Leu Asp Lys Lys Asn Lys Glu Thr Gly Trp Glu Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Trp Val Lys Ser Ile Asn
            260                 265                 270

Val Ser Gly His Lys Tyr Gly Leu Val Tyr Ala Gly Ile Gly Trp Cys
        275                 280                 285

Ile Trp Arg Asn Lys Glu Asp Leu Pro Glu Glu Leu Ile Phe His Ile
    290                 295                 300

Asn Tyr Leu Gly Thr Asp Gln Pro Thr Phe Thr Leu Asn Phe Ser Lys
305                 310                 315                 320

Gly Ser Ser Gln Val Ile Ala Gln Tyr Tyr Gln Leu Ile Arg His Gly
                325                 330                 335

Phe Glu Gly Tyr Arg Asn Ile Met Glu Asn Cys His Glu Asn Ala Met
            340                 345                 350

Val Leu Lys Glu Gly Leu Val Lys Thr Gly Arg Phe Asp Ile Val Ser
        355                 360                 365

Lys Asp Glu Gly Val Pro Leu Val Ala Phe Ser Leu Lys Asp Arg Ser
    370                 375                 380

Arg His Asp Glu Phe Glu Ile Ser Asp Met Leu Arg Arg Phe Gly Trp
385                 390                 395                 400

Ile Val Pro Ala Tyr Thr Met Pro Pro Asp Ala Gln His Val Thr Val
                405                 410                 415

Leu Arg Val Val Ile Arg Glu Glu Phe Ser Arg Thr Leu Ala Glu Arg
            420                 425                 430

Leu Val Leu Asp Ile Glu Lys Val Met Tyr Gln Leu Asp Ala Leu Pro
        435                 440                 445

Ser Arg Leu Met Pro Pro Val Pro Pro Ala Pro Leu Leu Val Val Ala
    450                 455                 460

Lys Lys Ser Glu Leu Glu Thr Gln Arg Ser Val Thr Glu Ala Trp Lys
465                 470                 475                 480

Lys Phe Val Leu Ala Lys Arg Thr Asn Gly Val Cys
                485                 490


<210> SEQ ID NO 24
<211> LENGTH: 494
<212> TYPE: PRT
<213> ORGANISM: Arabidopsis thaliana

<400> SEQUENCE: 24

Met Val Leu Ala Thr Asn Ser Asp Ser Asp Glu His Leu His Ser Thr
1               5                   10                  15

Phe Ala Ser Arg Tyr Val Arg Ala Val Val Pro Arg Phe Lys Met Pro
```

-continued

```
            20                  25                  30

Asp His Cys Met Pro Lys Asp Ala Ala Tyr Gln Val Ile Asn Asp Glu
        35                  40                  45

Leu Met Leu Asp Gly Asn Pro Arg Leu Asn Leu Ala Ser Phe Val Thr
    50                  55                  60

Thr Trp Met Glu Pro Glu Cys Asp Lys Leu Ile Met Asp Ser Val Asn
65                  70                  75                  80

Lys Asn Tyr Val Asp Met Asp Glu Tyr Pro Val Thr Thr Glu Leu Gln
                85                  90                  95

Asn Arg Cys Val Asn Met Ile Ala Asn Phe Phe His Ala Pro Val Gly
            100                 105                 110

Glu Asp Glu Ala Ala Ile Gly Cys Gly Thr Val Gly Ser Ser Glu Ala
        115                 120                 125

Ile Met Leu Ala Gly Leu Ala Phe Lys Arg Lys Trp Gln His Arg Arg
    130                 135                 140

Lys Ala Gln Gly Leu Pro Ile Asp Lys Pro Asn Ile Val Thr Gly Ala
145                 150                 155                 160

Asn Val Gln Val Cys Trp Glu Lys Phe Ala Arg Tyr Phe Glu Val Glu
                165                 170                 175

Leu Lys Glu Val Lys Leu Ser Glu Asp Tyr Tyr Val Met Asp Pro Ala
            180                 185                 190

Lys Ala Val Glu Met Val Asp Glu Asn Thr Ile Cys Val Ala Ala Ile
        195                 200                 205

Leu Gly Ser Thr Leu Thr Gly Glu Phe Glu Asp Val Lys Gln Leu Asn
    210                 215                 220

Asp Leu Leu Ala Glu Lys Asn Ala Glu Thr Gly Trp Glu Thr Pro Ile
225                 230                 235                 240

His Val Asp Ala Ala Ser Gly Gly Phe Ile Ala Pro Phe Leu Tyr Pro
                245                 250                 255

Asp Leu Glu Trp Asp Phe Arg Leu Pro Trp Val Lys Ser Ile Asn Val
            260                 265                 270

Ser Gly His Lys Tyr Gly Leu Val Tyr Ala Gly Val Gly Trp Val Val
        275                 280                 285

Trp Arg Thr Lys Asp Asp Leu Pro Glu Glu Leu Val Phe His Ile Asn
    290                 295                 300

Tyr Leu Gly Ala Asp Gln Pro Thr Phe Thr Leu Asn Phe Ser Lys Gly
305                 310                 315                 320

Ser Ser Gln Ile Ile Ala Gln Tyr Tyr Gln Phe Ile Arg Leu Gly Phe
                325                 330                 335

Glu Gly Tyr Lys Asn Ile Met Glu Asn Cys Met Asp Asn Ala Arg Arg
            340                 345                 350

Leu Arg Glu Gly Ile Glu Met Thr Gly Lys Phe Asn Ile Val Ser Lys
        355                 360                 365

Asp Ile Gly Val Pro Leu Val Ala Phe Ser Leu Lys Asp Ser Ser Lys
    370                 375                 380

His Thr Val Phe Glu Ile Ala Glu Ser Leu Arg Lys Phe Gly Trp Ile
385                 390                 395                 400

Ile Pro Ala Tyr Thr Met Pro Ala Asp Ala Gln His Ile Ala Val Leu
                405                 410                 415

Arg Val Val Ile Arg Glu Asp Phe Ser Arg Gly Leu Ala Asp Arg Leu
            420                 425                 430

Ile Thr His Ile Ile Gln Val Leu Lys Glu Ile Glu Gly Leu Pro Ser
        435                 440                 445
```

```
Arg Ile Ala His Leu Ala Ala Ala Ala Ala Val Ser Gly Asp Asp Glu
    450                 455                 460

Glu Val Lys Val Lys Thr Ala Lys Met Ser Leu Glu Asp Ile Thr Lys
465                 470                 475                 480

Tyr Trp Lys Arg Leu Val Glu His Lys Arg Asn Ile Val Cys
                485                 490


<210> SEQ ID NO 25
<211> LENGTH: 496
<212> TYPE: PRT
<213> ORGANISM: Nicotiana tabacum

<400> SEQUENCE: 25

Met Val Leu Ser Lys Thr Ala Ser Glu Ser Asp Val Ser Ile His Ser
1               5                   10                  15

Thr Phe Ala Ser Arg Tyr Val Arg Thr Ser Leu Pro Arg Phe Lys Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asn Thr Leu Met Met Asp Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Leu
            100                 105                 110

Gly Asp Gly Glu Thr Ala Val Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140

Met Lys Ala Gln Gly Lys Pro Phe Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Asp Gly Tyr Tyr Val Met Asp Pro
            180                 185                 190

Glu Lys Ala Val Glu Met Val Asp Glu Asn Thr Ile Cys Val Ala Ala
        195                 200                 205

Ile Leu Gly Ser Thr Leu Asn Gly Glu Phe Glu Asp Val Lys Arg Leu
    210                 215                 220

Asn Asp Leu Leu Ile Glu Lys Asn Lys Glu Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Ala
        275                 280                 285

Ile Trp Arg Asn Lys Glu Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
```

-continued

```
                325                 330                 335

Phe Glu Gly Tyr Lys Asn Val Met Glu Asn Cys Gln Glu Asn Ala Arg
            340                 345                 350

Val Leu Arg Glu Gly Ile Glu Lys Ser Gly Arg Phe Asn Ile Ile Ser
        355                 360                 365

Lys Glu Ile Gly Val Pro Leu Val Ala Phe Ser Leu Lys Asp Asn Ser
    370                 375                 380

Gln His Asn Glu Phe Glu Ile Ser Glu Thr Leu Arg Arg Phe Gly Trp
385                 390                 395                 400

Ile Val Pro Ala Tyr Thr Met Pro Pro Asn Ala Gln His Val Thr Val
                405                 410                 415

Leu Arg Val Val Ile Arg Glu Asp Phe Ser Arg Thr Leu Ala Glu Arg
            420                 425                 430

Leu Val Ile Asp Ile Glu Lys Val Leu His Glu Leu Asp Thr Leu Pro
        435                 440                 445

Ala Arg Val Asn Ala Lys Leu Ala Val Ala Glu Ala Asn Gly Ser Gly
    450                 455                 460

Val His Lys Lys Thr Asp Arg Glu Val Gln Leu Glu Ile Thr Thr Ala
465                 470                 475                 480

Trp Lys Lys Phe Val Ala Asp Lys Lys Lys Lys Thr Asn Gly Val Cys
                485                 490                 495


<210> SEQ ID NO 26
<211> LENGTH: 494
<212> TYPE: PRT
<213> ORGANISM: Arabidopsis thaliana

<400> SEQUENCE: 26

Met Val Leu Thr Lys Thr Ala Thr Asn Asp Glu Ser Val Cys Thr Met
1               5                   10                  15

Phe Gly Ser Arg Tyr Val Arg Thr Thr Leu Pro Lys Tyr Glu Ile Gly
            20                  25                  30

Glu Asn Ser Ile Pro Lys Asp Ala Ala Tyr Gln Ile Ile Lys Asp Glu
        35                  40                  45

Leu Met Leu Asp Gly Asn Pro Arg Leu Asn Leu Ala Ser Phe Val Thr
    50                  55                  60

Thr Trp Met Glu Pro Glu Cys Asp Lys Leu Ile Met Asp Ser Ile Asn
65                  70                  75                  80

Lys Asn Tyr Val Asp Met Asp Glu Tyr Pro Val Thr Thr Glu Leu Gln
                85                  90                  95

Asn Arg Cys Val Asn Ile Ile Ala Arg Leu Phe Asn Ala Pro Leu Glu
            100                 105                 110

Glu Ser Glu Thr Ala Val Gly Val Gly Thr Val Gly Ser Ser Glu Ala
        115                 120                 125

Ile Met Leu Ala Gly Leu Ala Phe Lys Arg Lys Trp Gln Asn Lys Arg
    130                 135                 140

Lys Ala Glu Gly Lys Pro Tyr Asp Lys Pro Asn Ile Val Thr Gly Ala
145                 150                 155                 160

Asn Val Gln Val Cys Trp Glu Lys Phe Ala Arg Tyr Phe Glu Val Glu
                165                 170                 175

Leu Lys Glu Val Asn Leu Ser Glu Gly Tyr Tyr Val Met Asp Pro Asp
            180                 185                 190

Lys Ala Ala Glu Met Val Asp Glu Asn Thr Ile Cys Val Ala Ala Ile
        195                 200                 205
```

-continued

```
Leu Gly Ser Thr Leu Asn Gly Glu Phe Glu Asp Val Lys Arg Leu Asn
    210                 215                 220

Asp Leu Leu Val Lys Lys Asn Glu Glu Thr Gly Trp Asn Thr Pro Ile
225                 230                 235                 240

His Val Asp Ala Ala Ser Gly Gly Phe Ile Ala Pro Phe Ile Tyr Pro
                245                 250                 255

Glu Leu Glu Trp Asp Phe Arg Leu Pro Leu Val Lys Ser Ile Asn Val
            260                 265                 270

Ser Gly His Lys Tyr Gly Leu Val Tyr Ala Gly Ile Gly Trp Val Val
        275                 280                 285

Trp Arg Ala Ala Glu Asp Leu Pro Glu Glu Leu Ile Phe His Ile Asn
    290                 295                 300

Tyr Leu Gly Ala Asp Gln Pro Thr Phe Thr Leu Asn Phe Ser Lys Gly
305                 310                 315                 320

Ser Ser Gln Ile Ile Ala Gln Tyr Tyr Gln Leu Ile Arg Leu Gly Phe
                325                 330                 335

Glu Gly Tyr Lys Asn Val Met Glu Asn Cys Ile Glu Asn Met Val Val
            340                 345                 350

Leu Lys Glu Gly Ile Glu Lys Thr Glu Arg Phe Asn Ile Val Ser Lys
        355                 360                 365

Asp Gln Gly Val Pro Val Val Ala Phe Ser Leu Lys Asp His Ser Phe
    370                 375                 380

His Asn Glu Phe Glu Ile Ser Glu Met Leu Arg Arg Phe Gly Trp Ile
385                 390                 395                 400

Val Pro Ala Tyr Thr Met Pro Ala Asp Val Gln His Ile Thr Val Leu
                405                 410                 415

Arg Val Val Ile Arg Glu Asp Phe Ser Arg Thr Leu Ala Glu Arg Leu
            420                 425                 430

Val Ala Asp Ile Ser Lys Val Leu His Glu Leu Asp Thr Leu Pro Ser
        435                 440                 445

Lys Ile Ser Lys Lys Met Gly Ile Glu Gly Ile Ala Glu Asn Val Lys
    450                 455                 460

Glu Lys Lys Met Glu Lys Glu Ile Leu Met Glu Val Ile Val Gly Trp
465                 470                 475                 480

Arg Lys Phe Val Lys Glu Arg Lys Lys Met Asn Gly Val Cys
                485                 490


<210> SEQ ID NO 27
<211> LENGTH: 491
<212> TYPE: PRT
<213> ORGANISM: Nicotiana tabacum

<400> SEQUENCE: 27

Met Val Leu Ser Lys Thr Ser Ser Glu Ser Asp Val Ser Val His Ser
1               5                   10                  15

Thr Phe Ala Ser Arg Tyr Val Arg Thr Ser Leu Pro Arg Phe Glu Met
            20                  25                  30

Ala Glu Asn Ser Ile Pro Lys Glu Ala Ala Phe Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Asp Ser Ile
65                  70                  75                  80

Asn Lys Asn Tyr Val Asp Met Asp Glu Tyr Pro Val Thr Thr Glu Leu
                85                  90                  95
```

```
Gln Asn Arg Cys Val Asn Met Ile Ala Arg Leu Phe Asn Ala Pro Leu
            100                 105                 110

Glu Glu Lys Glu Thr Ala Val Gly Val Gly Thr Val Gly Ser Ser Glu
        115                 120                 125

Ala Ile Met Leu Ala Gly Leu Ala Phe Lys Arg Asn Trp Gln Asn Lys
    130                 135                 140

Arg Lys Ala Glu Gly Lys Pro Tyr Asn Lys Pro Asn Ile Val Thr Gly
145                 150                 155                 160

Ala Asn Val Gln Val Cys Trp Glu Lys Phe Ala Asn Tyr Phe Glu Val
                165                 170                 175

Glu Leu Lys Glu Val Lys Leu Arg Glu Gly Tyr Tyr Val Met Asp Pro
            180                 185                 190

Val Gln Ala Val Glu Met Val Asp Glu Asn Thr Ile Cys Val Ala Ala
        195                 200                 205

Ile Leu Gly Ser Thr Leu Asn Gly Glu Phe Glu Asp Val Lys Leu Leu
    210                 215                 220

Asn Asp Leu Leu Ile Glu Lys Asn Lys Gln Thr Gly Trp Asn Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Ile Trp Arg Thr Lys Gln Asp Leu Pro Glu Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Tyr Glu Gly Tyr Arg Asn Val Met Glu Asn Cys Arg Glu Asn Ala Ile
            340                 345                 350

Val Leu Arg Glu Gly Leu Glu Lys Thr Gly Arg Phe Asn Ile Val Ser
        355                 360                 365

Lys Asp Glu Gly Val Pro Leu Val Ala Phe Ser Leu Lys Asp Asn Ser
    370                 375                 380

Arg His Asn Glu Phe Glu Val Ser Glu Thr Leu Arg Arg Phe Gly Trp
385                 390                 395                 400

Ile Val Pro Ala Tyr Thr Met Pro Ala Asp Ala Gln His Val Thr Val
                405                 410                 415

Leu Arg Val Val Ile Arg Glu Asp Phe Ser Arg Thr Leu Ala Glu Arg
            420                 425                 430

Leu Val Leu Asp Ile Val Lys Val Leu His Glu Leu Asp Thr Leu Pro
        435                 440                 445

Ala Arg Leu Ser Ala Lys Leu Glu Glu Val Lys Leu Val Lys Asn Gly
    450                 455                 460

Lys Lys Phe Glu Leu Glu Val Gln Arg Glu Val Thr Asn Tyr Trp Lys
465                 470                 475                 480

Lys Phe Val Leu Ala Arg Lys Ala Pro Val Cys
                485                 490
```

```
<210> SEQ ID NO 28
<211> LENGTH: 501
```

```
<212> TYPE: PRT
<213> ORGANISM: Oryza sativa subsp. japonica

<400> SEQUENCE: 28

Met Val Val Ser Val Ala Ala Thr Asp Ser Asp Thr Ala Gln Pro Val
1               5                   10                  15

Gln Tyr Ser Thr Phe Phe Ala Ser Arg Tyr Val Arg Asp Pro Leu Pro
            20                  25                  30

Arg Phe Arg Met Pro Glu Gln Ser Ile Pro Arg Glu Ala Ala Tyr Gln
        35                  40                  45

Ile Ile Asn Asp Glu Leu Met Leu Asp Gly Asn Pro Arg Leu Asn Leu
    50                  55                  60

Ala Ser Phe Val Thr Thr Trp Met Glu Pro Glu Cys Asp Lys Leu Ile
65                  70                  75                  80

Met Asp Ser Val Asn Lys Asn Tyr Val Asp Met Asp Glu Tyr Pro Val
                85                  90                  95

Thr Thr Glu Leu Gln Asn Arg Cys Val Asn Met Ile Ala His Leu Phe
            100                 105                 110

Asn Ala Pro Ile Lys Glu Asp Glu Thr Ala Ile Gly Val Gly Thr Val
        115                 120                 125

Gly Ser Ser Glu Ala Ile Met Leu Ala Gly Leu Ala Phe Lys Arg Lys
    130                 135                 140

Trp Gln Asn Lys Arg Lys Glu Gln Gly Lys Pro Cys Asp Lys Pro Asn
145                 150                 155                 160

Ile Val Thr Gly Ala Asn Val Gln Val Cys Trp Glu Lys Phe Ala Arg
                165                 170                 175

Tyr Phe Glu Val Glu Leu Lys Glu Val Lys Leu Ser Glu Gly Tyr Tyr
            180                 185                 190

Val Met Asp Pro Val Lys Ala Val Glu Met Val Asp Glu Asn Thr Ile
        195                 200                 205

Cys Val Ala Ala Ile Leu Gly Ser Thr Leu Thr Gly Glu Phe Glu Asp
    210                 215                 220

Val Lys Leu Leu Asn Asn Leu Leu Thr Glu Lys Asn Lys Glu Thr Gly
225                 230                 235                 240

Trp Asp Val Pro Ile His Val Asp Ala Ala Ser Gly Gly Phe Ile Ala
                245                 250                 255

Pro Phe Leu Tyr Pro Glu Leu Glu Trp Asp Phe Arg Leu Pro Leu Val
            260                 265                 270

Lys Ser Ile Asn Val Ser Gly His Lys Tyr Gly Leu Val Tyr Pro Gly
        275                 280                 285

Val Gly Trp Val Ile Trp Arg Ser Lys Glu Asp Leu Pro Glu Glu Leu
    290                 295                 300

Ile Phe His Ile Asn Tyr Leu Gly Thr Asp Gln Pro Thr Phe Thr Leu
305                 310                 315                 320

Asn Phe Ser Lys Gly Ser Ser Gln Ile Ile Ala Gln Tyr Tyr Gln Leu
                325                 330                 335

Ile Arg Leu Gly Phe Glu Gly Tyr Lys Asn Ile Met Gln Asn Cys Met
            340                 345                 350

Glu Asn Thr Ala Ile Leu Arg Glu Gly Ile Glu Ala Thr Gly Arg Phe
        355                 360                 365

Glu Ile Leu Ser Lys Glu Ala Gly Val Pro Leu Val Ala Phe Ser Leu
    370                 375                 380

Lys Asp Ser Gly Arg Tyr Thr Val Phe Asp Ile Ser Glu His Leu Arg
385                 390                 395                 400
```

```
Arg Phe Gly Trp Ile Val Pro Ala Tyr Thr Met Pro Ala Asn Ala Glu
                405                 410                 415

His Val Ala Val Leu Arg Val Val Ile Arg Glu Asp Phe Ser Arg Ser
            420                 425                 430

Leu Ala Glu Arg Leu Val Ser Asp Ile Val Lys Ile Leu His Glu Leu
        435                 440                 445

Asp Ala His Ser Ala Gln Val Leu Lys Ile Ser Ser Ala Ile Ala Lys
    450                 455                 460

Gln Gln Ser Gly Asp Asp Gly Val Val Thr Lys Lys Ser Val Leu Glu
465                 470                 475                 480

Thr Glu Arg Glu Ile Phe Ala Tyr Trp Arg Asp Gln Val Lys Lys Lys
                485                 490                 495

Gln Thr Gly Ile Cys
            500
```

<210> SEQ ID NO 29
<211> LENGTH: 500
<212> TYPE: PRT
<213> ORGANISM: Oryza sativa subsp. japonica

<400> SEQUENCE: 29

```
Met Val Leu Thr His Val Glu Ala Val Glu Glu Gly Ser Glu Ala Ala
1               5                   10                  15

Ala Ala Val Phe Ala Ser Arg Tyr Val Gln Asp Pro Val Pro Arg Tyr
            20                  25                  30

Glu Leu Gly Glu Arg Ser Ile Ser Lys Asp Ala Ala Tyr Gln Ile Val
        35                  40                  45

His Asp Glu Leu Leu Leu Asp Ser Ser Pro Arg Leu Asn Leu Ala Ser
    50                  55                  60

Phe Val Thr Thr Trp Met Glu Pro Glu Cys Asp Arg Leu Ile Leu Glu
65                  70                  75                  80

Ala Ile Asn Lys Asn Tyr Ala Asp Met Asp Glu Tyr Pro Val Thr Thr
                85                  90                  95

Glu Leu Gln Asn Arg Cys Val Asn Ile Ile Ala Arg Leu Phe Asn Ala
            100                 105                 110

Pro Val Gly Asp Gly Glu Lys Ala Val Gly Val Gly Thr Val Gly Ser
        115                 120                 125

Ser Glu Ala Ile Met Leu Ala Gly Leu Ala Phe Lys Arg Arg Trp Gln
    130                 135                 140

Asn Arg Arg Lys Ala Ala Gly Lys Pro His Asp Lys Pro Asn Ile Val
145                 150                 155                 160

Thr Gly Ala Asn Val Gln Val Cys Trp Glu Lys Phe Ala Arg Tyr Phe
                165                 170                 175

Glu Val Glu Leu Lys Glu Val Lys Leu Thr Glu Gly Cys Tyr Val Met
            180                 185                 190

Asp Pro Val Lys Ala Val Asp Met Val Asp Glu Asn Thr Ile Cys Val
        195                 200                 205

Ala Ala Ile Leu Gly Ser Thr Leu Thr Gly Glu Phe Glu Asp Val Arg
    210                 215                 220

Arg Leu Asn Asp Leu Leu Ala Ala Lys Asn Lys Arg Thr Gly Trp Asp
225                 230                 235                 240

Thr Pro Ile His Val Asp Ala Ala Ser Gly Gly Phe Ile Ala Pro Phe
                245                 250                 255

Ile Tyr Pro Glu Leu Glu Trp Asp Phe Arg Leu Pro Leu Val Lys Ser
```

```
            260                 265                 270

Ile Asn Val Ser Gly His Lys Tyr Gly Leu Val Tyr Ala Gly Val Gly
        275                 280                 285

Trp Val Ile Trp Arg Asn Lys Glu Asp Leu Pro Glu Glu Leu Ile Phe
    290                 295                 300

His Ile Asn Tyr Leu Gly Ala Asp Gln Pro Thr Phe Thr Leu Asn Phe
305                 310                 315                 320

Ser Lys Gly Ser Ser Gln Ile Ile Ala Gln Tyr Tyr Gln Phe Leu Arg
                325                 330                 335

Leu Gly Phe Glu Gly Tyr Lys Ser Val Met Lys Asn Cys Met Glu Ser
            340                 345                 350

Ala Arg Thr Leu Arg Glu Gly Leu Glu Lys Thr Gly Arg Phe Thr Ile
        355                 360                 365

Ile Ser Lys Glu Glu Gly Val Pro Leu Val Ala Phe Thr Phe Lys Asp
    370                 375                 380

Gly Ala Gly Ala Gln Ala Phe Arg Leu Ser Ser Gly Leu Arg Arg Tyr
385                 390                 395                 400

Gly Trp Ile Val Pro Ala Tyr Thr Met Pro Ala Ala Leu Glu His Met
                405                 410                 415

Thr Val Val Arg Val Val Val Arg Glu Asp Phe Gly Arg Pro Leu Ala
            420                 425                 430

Glu Arg Phe Leu Ser His Val Arg Met Ala Leu Asp Glu Met Asp Leu
        435                 440                 445

Ala Ala Arg Ala Pro Val Pro Arg Val Gln Leu Thr Ile Glu Leu Gly
    450                 455                 460

Pro Ala Arg Thr Ala Gly Glu Glu Ala Ser Ile Arg Val Val Lys Ser
465                 470                 475                 480

Glu Ala Val Pro Val Arg Lys Ser Val Pro Leu Val Ala Gly Lys Thr
                485                 490                 495

Lys Gly Val Cys
            500


<210> SEQ ID NO 30
<211> LENGTH: 496
<212> TYPE: PRT
<213> ORGANISM: Nicotiana tabacum

<400> SEQUENCE: 30

Met Val Leu Ser Lys Thr Ala Ser Glu Ser Asp Val Ser Ile His Ser
1               5                   10                  15

Thr Phe Ala Ser Arg Tyr Val Arg Thr Ser Leu Pro Arg Phe Lys Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asn Lys Leu Met Met Asp Ser Ile
65                  70                  75                  80

Asn Lys Asn Tyr Val Asp Met Gly Glu Tyr Pro Val Thr Thr Glu Leu
                85                  90                  95

Gln Asn Arg Cys Val Asn Met Ile Ala His Leu Phe Asn Ala Pro Leu
            100                 105                 110

Gly Asp Gly Glu Thr Ala Val Gly Val Gly Thr Val Gly Ser Ser Glu
        115                 120                 125
```

```
Ala Ile Met Leu Ala Gly Leu Ala Phe Lys Arg Lys Trp Gln Asn Lys
    130                 135                 140

Met Lys Ala Gln Gly Lys Pro Cys Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Asp Gly Tyr Tyr Val Met Asp Pro
            180                 185                 190

Glu Lys Ala Val Glu Met Val Asp Glu Asn Thr Ile Cys Val Ala Ala
        195                 200                 205

Ile Leu Gly Ser Thr Leu Asn Gly Glu Phe Glu Asp Val Lys Arg Leu
    210                 215                 220

Asn Asp Leu Leu Ile Glu Lys Asn Lys Glu Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Ala
        275                 280                 285

Ile Trp Arg Asn Lys Glu Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Lys Asn Val Met Glu Asn Cys Gln Glu Asn Ala Arg
            340                 345                 350

Val Leu Arg Glu Gly Leu Glu Lys Ser Gly Arg Phe Asn Ile Ile Ser
        355                 360                 365

Lys Glu Ile Gly Val Pro Leu Val Ala Phe Ser Leu Lys Asp Asn Ser
    370                 375                 380

Gln His Asn Glu Phe Glu Ile Ser Glu Thr Leu Arg Arg Phe Gly Trp
385                 390                 395                 400

Ile Ile Pro Ala Tyr Thr Met Pro Pro Asn Ala Gln His Val Thr Val
                405                 410                 415

Leu Arg Val Val Ile Arg Glu Asp Phe Ser Arg Thr Leu Ala Glu Arg
            420                 425                 430

Leu Val Ile Asp Ile Glu Lys Val Leu His Glu Leu Asp Thr Leu Pro
        435                 440                 445

Ala Arg Val Asn Ala Lys Leu Ala Val Ala Glu Ala Asn Gly Ser Gly
    450                 455                 460

Val His Lys Lys Thr Asp Arg Glu Val Gln Leu Glu Ile Thr Ala Ala
465                 470                 475                 480

Trp Lys Lys Phe Val Ala Asp Lys Lys Lys Lys Thr Asn Gly Val Cys
                485                 490                 495


<210> SEQ ID NO 31
<211> LENGTH: 494
<212> TYPE: PRT
<213> ORGANISM: Arabidopsis thaliana

<400> SEQUENCE: 31

Met Val Leu Ala Thr Asn Ser Asp Ser Asp Glu His Leu His Ser Thr
1               5                   10                  15
```

-continued

```
Phe Ala Ser Arg Tyr Val Arg Ala Val Val Pro Arg Phe Lys Met Pro
            20                  25                  30

Asp His Cys Met Pro Lys Asp Ala Ala Tyr Gln Val Ile Asn Asp Glu
        35                  40                  45

Leu Met Leu Asp Gly Asn Pro Arg Leu Asn Leu Ala Ser Phe Val Thr
    50                  55                  60

Thr Trp Met Glu Pro Glu Cys Asp Lys Leu Ile Met Asp Ser Val Asn
65                  70                  75                  80

Lys Asn Tyr Val Asp Met Asp Glu Tyr Pro Val Thr Thr Glu Leu Gln
                85                  90                  95

Asn Arg Cys Val Asn Met Ile Ala Asn Leu Phe His Ala Pro Val Gly
            100                 105                 110

Glu Asp Glu Ala Ala Ile Gly Cys Gly Thr Val Gly Ser Ser Glu Ala
        115                 120                 125

Ile Met Leu Ala Gly Leu Ala Phe Lys Arg Lys Trp Gln His Arg Arg
    130                 135                 140

Lys Ala Gln Gly Leu Pro Ile Asp Lys Pro Asn Ile Val Thr Gly Ala
145                 150                 155                 160

Asn Val Gln Val Cys Trp Glu Lys Phe Ala Arg Tyr Phe Glu Val Glu
                165                 170                 175

Leu Lys Glu Val Lys Leu Ser Glu Asp Tyr Tyr Val Met Asp Pro Ala
            180                 185                 190

Lys Ala Val Glu Met Val Asp Glu Asn Thr Ile Cys Val Ala Ala Ile
        195                 200                 205

Leu Gly Ser Thr Leu Thr Gly Glu Phe Glu Asp Val Lys Gln Leu Asn
    210                 215                 220

Asp Leu Leu Ala Glu Lys Asn Ala Glu Thr Gly Trp Glu Thr Pro Ile
225                 230                 235                 240

His Val Asp Ala Ala Ser Gly Gly Phe Ile Ala Pro Phe Leu Tyr Pro
                245                 250                 255

Asp Leu Glu Trp Asp Phe Arg Leu Pro Trp Val Lys Ser Ile Asn Val
            260                 265                 270

Ser Gly His Lys Tyr Gly Leu Val Tyr Ala Gly Val Gly Trp Val Val
        275                 280                 285

Trp Arg Thr Lys Asp Asp Leu Pro Glu Glu Leu Val Phe His Ile Asn
    290                 295                 300

Tyr Leu Gly Ala Asp Gln Pro Thr Phe Thr Leu Asn Phe Ser Lys Gly
305                 310                 315                 320

Ser Ser Gln Ile Ile Ala Gln Tyr Tyr Gln Phe Ile Arg Leu Gly Phe
                325                 330                 335

Glu Gly Tyr Lys Asn Ile Met Glu Asn Cys Met Asp Asn Ala Arg Arg
            340                 345                 350

Leu Arg Glu Gly Ile Glu Met Thr Gly Lys Phe Asn Ile Val Ser Lys
        355                 360                 365

Asp Ile Gly Val Pro Leu Val Ala Phe Ser Leu Lys Asp Ser Ser Lys
    370                 375                 380

His Thr Val Phe Glu Ile Ala Glu Ser Leu Arg Lys Phe Gly Trp Ile
385                 390                 395                 400

Ile Pro Ala Tyr Thr Met Pro Ala Asp Ala Gln His Ile Ala Val Leu
                405                 410                 415

Arg Val Val Ile Arg Glu Asp Phe Ser Arg Gly Leu Ala Asp Arg Leu
            420                 425                 430
```

```
Ile Thr His Ile Ile Gln Val Leu Lys Glu Ile Glu Gly Leu Pro Ser
        435                 440                 445

Arg Ile Ala His Leu Ala Ala Ala Ala Ala Val Ser Gly Asp Asp Glu
    450                 455                 460

Glu Val Lys Val Lys Thr Ala Lys Met Ser Leu Glu Asp Ile Thr Lys
465                 470                 475                 480

Tyr Trp Lys Arg Leu Val Glu His Lys Arg Asn Ile Val Cys
                485                 490


<210> SEQ ID NO 32
<211> LENGTH: 14
<212> TYPE: PRT
<213> ORGANISM: Artificial
<220> FEATURE:
<223> OTHER INFORMATION: Motif

<400> SEQUENCE: 32

Lys Ser Ile Asn Val Ser Gly His Lys Tyr Gly Leu Val Tyr
1               5                   10


<210> SEQ ID NO 33
<211> LENGTH: 15
<212> TYPE: PRT
<213> ORGANISM: Artificial
<220> FEATURE:
<223> OTHER INFORMATION: Motif

<400> SEQUENCE: 33

Val Lys Ser Ile Asn Val Ser Gly His Lys Tyr Gly Leu Val Tyr
1               5                   10                  15


<210> SEQ ID NO 34
<211> LENGTH: 1704
<212> TYPE: DNA
<213> ORGANISM: Lolium perenne

<400> SEQUENCE: 34

catctccacg gcaccacctt tcctcgagct cgcggccgat tcccttcgct gcgcgcggcc      60

gacctgccgt cactgtctcc gtgcaagccg cgaccgcgac cgccagcaac catggttctc     120

actgtggcag cgaccgccgc ggacacggcc gagccgctca actccacctt cttcgccacc     180

cgctacgtcc gcgaccagct cccccggtac cggatgccgg agaactcgat ccccaaggag     240

gcggcgtacc agatcatcag cgacgagctc atgctcgacg gcaacccgcg cctcaacctc     300

gcatccttcg tcaccacccg gatggagccc gaggtcggca agctcatcat ggactccgtc     360

aacaagaact acgtcgacat ggacgagtac cccgtcacca ccgagctcca gaaccgttgt     420

gtaaatatga tagcccacct gttcaatgca ccgatcaagg aggaggagac agcaattgga     480

gttgcgacag tgggatcctc agaagcaata atgcttgcag gcctggcctt caagaggaag     540

tgggcaaata aaagaaagga ggaggggaag ccatatgaca aacctaacat tgttactggt     600

gcaaatgttc aggtttgctg ggaaaaattt gctagatatt ttgaagtaga attgaaggag     660

gtcaagttaa ctgaaggata ctatgtcatg gatcctttga aagctgttga aatggtggat     720

gagaacacta tatgtgttgc agccatcttg ggatctactc tcactggaga gtatgaagat     780

gttaaactat tgaatgacct gcttgtggaa aagaacaaga aaacagggtt taatgtgccg     840

atccatgttg atgctgcaag tggaggattt atagcccctt ttcttcaccc tgagcttgag     900

tgggacttca ggctaccatt ggtgaagagc atcaatgtta gtgggcacaa gtatggcctc     960

gtctaccctg gtgttggatg ggtcatctgg cggagcaaag acgatttgcc tggagaactc    1020
```

```
attttccata taaactacct gggaacagat cagcccacat tcacattgaa cttctccaaa   1080

ggtgctagcc agatcattgc gcaatactat caactgatac gcctaggctt cgagggatat   1140

aagcacatca tggagaattg ccaggccaat gcaaccgcgc tgagggaggg cttagaggca   1200

accgggcgat tcgacatcct gtccaaagag gacggtgtgc ccctagtggc catccggctc   1260

aaggacagct ccaaattcag cgtgttcgac atctccgaga acctgaggag gtttggctgg   1320

attgtgcctg cctacaccat gcctgcggac gcagagcacg tggctgtcct ccgcgtcgtc   1380

atcagggagg acttcaaccg cagcctctcc cagcggctcc tcgccgacat caacagggtc   1440

gtgcaggagc tagatgccca cgcggtccat gccattaaga tgaccactgc tatcgcgaca   1500

caaaccggcg agggtgctga ggatggcgtg gtgaccaaga agggcgttct ggacatcgag   1560

aaggagttcg ccgcggcctg caaggacctg gtaaagaaca agaagactgg accctgctga   1620

agggcatgcc ggcacagtac gcacgtacgt actatatgta tctatttttc ctggagtata   1680

tctgaaccgt gaatacctgg ctcc                                          1704
```

```
<210> SEQ ID NO 35
<211> LENGTH: 1455
<212> TYPE: DNA
<213> ORGANISM: Oryza sativa

<400> SEQUENCE: 35

atggcgctgt cgacggcgca gacaggggag tcgatgcact cctcgacgtt cgcgtcgcgg     60

tacgtgcgca cggcgctgcc gaggttcagg atgccggaga agtcgatccc caaggacgcg    120

gcgtaccaga tcatcaacga cgagctgatg ctcgacggca acccgcgcct gaacctggcg    180

tccttcgtca ccacgtggat ggagcccgag tgcgacaagc tcatgatggc cgccatcaac    240

aagaactacg tcgacatgga tgagtacccc gtcaccaccg agctccagaa ccggtgcgtg    300

aacatgatcg cgcatctgtt caacgcgccg atcggggacg acgagacggc ggtcggggtg    360

ggcacggtgg ggtcgtcgga ggccatcatg ctggcggggc tggcgttcaa gaggaagtgg    420

cagaacagga tgaaggccga ggggaagccc cacgacaagc ccaacatcgt gacgggggcc    480

aacgtgcagg tgtgctggga gaagttcgcg cgctacttcg aggtggagct caaggaggtg    540

aagctgaccc aagggtacta cgtgatgaac ccggagaagg ccgtggagat ggtcgacgag    600

aacaccatct gcgtcgccgc catcctcggc tccaccctca acggcgagtt cgaggacgtc    660

aagatgctca acgacctcct caccgccaag aacgccgaga cagggtggaa cacgccgatc    720

catgtggacg cggcgagcgg cgggttcatc gcgccgttca tctacccgga gctggagtgg    780

gacttccggc tgccgctggt gaagagcatc aacgtcagcg gccacaagta cgggctcgtc    840

tacgccggcg tcgggtgggt catctggcgc aacaaggagg acctccccga tgagctcatc    900

ttccacatca actacctcgg cgccgaccag ccaaccttca cgctcaactt ctccaaagga    960

tcgaaccaga taattgcgca gtattaccag ctcattcgtc tcggattcga ggggtacaag   1020

gacatcatgc agaactgccg ggacaacgcg acggtgctcc gggaggggat cgagaagacg   1080

ggccacttcg acgtggtgtc caaggactcc ggcgtgccgc tggtggcctt ctccctcaag   1140

gactcgtcgc ggtacacggt gttcgaggtg gccgagagcc tccgccgctt cggctggatc   1200

gtgccggcgt acaccatgcc cgccgacgct gagcacgtcg ccgtgatgcg cgtcgtcatc   1260

cgcgaggact tcagccgcgg cctcgccgag cgcctcatca ccgacctcac caagacggtg   1320

gccgatatgg acgcccacgc cgtcaagaag gccgccgccg agccggccaa gaagaccgtg   1380
```

cgggagatag agaaggaggt gaccacctac tggcggagtt tcgtcgccag gaagaagagc 1440
agcctcgtct gctga 1455

<210> SEQ ID NO 36
<211> LENGTH: 1509
<212> TYPE: DNA
<213> ORGANISM: Arabidopsis thaliana

<400> SEQUENCE: 36
atggtgctct cccacgccgt atcggagtcg gacgtctccg tccactccac attcgcatca 60
cgttacgtcc gtacttcact tcctaggttc aagatgccgg aaaactcgat tcctaaggaa 120
gcggcgtatc agatcatcaa cgacgagctg atgcttgacg ggaatccacg gttgaactta 180
gcctcctttg tgacgacatg gatggagcct gagtgtgata aactcatcat gtcctccatc 240
aacaagaact atgttgacat ggacgagtac cccgtcacca ccgaacttca gaaccgatgt 300
gtgaacatga ttgcacatct attcaatgca ccgttagaag aggcggagac cgccgtcgga 360
gtaggaaccg ttggatcatc ggaggccata atgttggccg gtttggcctt caagcgtaaa 420
tggcagaaca agcgcaaagc tgaaggcaaa cccgtcgata aacccaacat tgtcaccgga 480
gccaatgttc aagtgtgttg ggagaaattc gctaggtact ttgaggttga acttaaggaa 540
gtgaaattga gtgaaggata ctatgtgatg gaccctcaac aagctgttga tatggttgat 600
gagaacacca tttgtgttgc ggccattctt ggttccactc ttaatggaga attcgaagat 660
gttaaactct tgaacgatct cttggtcgaa aagaacaaag aaaccggatg ggatacacca 720
atccacgtgg atgcggcaag tggaggattc attgcaccgt ttttgtatcc ggaattggaa 780
tgggacttta gacttccctt ggtgaagagt atcaatgtga gtggtcacaa gtatggactt 840
gtgtacgcag ggattggttg ggtgatctgg agaaacaaag aggatttgcc tgaggaactc 900
atcttccata tcaattatct tggtgctgac caacccacct ttactctcaa tttctccaaa 960
ggttcaagtc aagtcattgc tcaatactac caacttatcc gattgggcca cgagggttac 1020
agaaatgtga tggagaattg cagagagaat atgatcgtcc taagggaagg acttgagaag 1080
acagaaaggt tcaacatcgt ctcaaaggac gagggagtgc cacttgtcgc tttctccttg 1140
aaagatagca gctgtcacac tgagttcgaa atctccgaca tgcttcgcag gtatggatgg 1200
atagtgccgg cctacacaat gcctccaaat gcacaacaca tcactgttct tcgtgtggtt 1260
atcagagaag atttctcgag aacactcgct gagagacttg tgatcgatat agagaaagtg 1320
atgcgtgagc tcgatgagct tccttcgaga gtgattcaca aaatatcact tggacaagag 1380
aagagtgaat ctaacagcga taacttgatg gtcacggtga agaagagcga tatcgacaag 1440
cagagagata tcatcactgg ctggaagaag tttgtcgccg acaggaagaa gacgagtggt 1500
atctgctaa 1509

<210> SEQ ID NO 37
<211> LENGTH: 1732
<212> TYPE: DNA
<213> ORGANISM: Oryza sativa

<400> SEQUENCE: 37
acttcgattg gttccaccgc gcctaccgag tttcccttgc taggcagtag agagagtctg 60
tgatcgagag agaagaggat cgagcagcta gcaagccggc gggcgccatg gtgctctcgc 120
acgcgagctc cggccgggac gacgccgtgc gctgcacctt cgcgacgcgc tacgcctgcg 180
agacgctgcc gcggttcagg atgccggagc agtcgatccc gagggaggcg gcgtaccaga 240

```
tcatcaacga cgagctgatg ctggacggga acccgcggct gaacctggcg tccttcgtca    300

ccacgtggat ggagcccgag tgcgacaagc tcatcatgga ctccgttaac aagaactacg    360

tcgacatgga cgagtaccct gtcaccacgg agctccagaa ccgttgtgtg aatatgatag    420

ctcacctgtt caatgcacca atcaaggagg atgaaacagc tattggagtt gggacggtgg    480

gatcctcaga agcaattatg cttgcaggac tggcattcaa gaggaagtgg caaaacaaac    540

ggaaggaaca ggggaagcca tgtgacaaac ccaacattgt tactggtgct aatgttcagg    600

tttgctggga gaaatttgcc agatattttg aagtagaact gaaggaggtt aagctcagtg    660

aaggatacta tgtcatggat cctgtaaagg ctgttgaaat ggtggatgag aacactatat    720

gcgttgcggc catcttgggc tctactctca ctggagagtt tgaggatgtt aagttattga    780

ataatctcct aacagaaaag aataaggaaa ctgggtggga tgtgccaatt catgttgatg    840

cagcaagtgg aggatttata gcaccttttc tataccctga gcttgaatgg gacttcaggc    900

taccactggt gaagagcatc aatgtcagtg ggcacaagta tggccttgtg tatccaggtg    960

ttggttgggt catttggcga agcaaagagg atttgcctga agaactcatt ttccatataa   1020

actatctggg gacagaccag ccgacgttca ctctgaactt ctccaaaggt tccagccaga   1080

taatcgcaca gtactatcaa ctaatacgcc tgggattcga gggatacaag aacatcatgc   1140

agaattgcat ggagaacaca gcaatactaa gggaaggcat agaggcgact ggtcgattcg   1200

aaatcctctc caaggaggcc ggtgtgccct tggtggcgtt ctcgctcaag gacagcggca   1260

ggtacaccgt gttcgacatc tccgagcacc tgaggaggtt cggctggatc gtgccggcgt   1320

acaccatgcc ggccaacgcc gagcacgtcg ccgtcctccg cgtcgtcatc agggaggact   1380

tcagccggag cctcgccgag cggctcgtct cggacatcgt caagatcctg cacgagctgg   1440

acgcccattc ggcccaggtg ctgaagatct ccagcgccat cgcgaagcag caatcgggcg   1500

acgatggcgt ggtcaccaag aagagcgtcc tggagaccga gagggagatc ttcgcgtact   1560

ggagggacca ggtgaagaag aagcagaccg gaatctgcta gtgtggctct gtgagaaatg   1620

cttgaataac gtggcatgct cgatttgtgc atgggatggc cggatcggat gggactgact   1680

ggcggtgtac ggacatggct gcccttgttc ttatgttgaa ctgttgatgt ag           1732
```

<210> SEQ ID NO 38
<211> LENGTH: 1730
<212> TYPE: DNA
<213> ORGANISM: Brassica juncea

<400> SEQUENCE: 38

```
gacacattct ttaactacaa acaaaaacat tacaaaccta taattcaaag ttcttataaa     60

cttcgagtga attgaaagac gatggttttg tctaagacag cttctggaac tgatgtttcc    120

gtccattcaa cttttgcttc tcgttatgtc cgcaactcgc tccctcgatt cgagatgcct    180

gagaactcca tcccgaagga agcagcgtac cagatcatca acgatgagct aatgctcgac    240

ggtaacccta ggctaaatct agcctccttc gtgactacgt ggatggagcc agagtgtgac    300

aagctcatga tggaatctat caacaagaac tacgttgaca tggacgagta ccctgtcacc    360

accgagcttc agaaccgatg tgtcaacatg attgcgcgtc tctttaacgc gccgctaggt    420

gacggtgagg ctgcggttgg tgtcggcacc gtgggatcgt ctgaggcgat tatgttggcc    480

gggttggctt ttaagagaca gtggcagaac aagcgtaagg cccaagggct tccttatgat    540

aagcctaata tcgtaaccgg agctaatgtt caggtttgct gggagaaatt cgcaaggtat    600
```

```
ttcgaggtgg aacttaagga agtgaagctg agagaaggat actacgtgat ggaccctgaa    660
aaggcagtcg aaatggtaga cgagaacacc atttgtgtcg cagccatcct cggttcgacg    720
ctaaccggag aattcgaaga cgttaagctc ctcaatgacc tcctagtcga gaaaaacaag    780
caaaccggat gggatactgg gaatcacgtg gacgcagcaa gtggtgggtt tattgcaccg    840
ttcttgtatc cggagctgga gtgggatttc cggttaccat tggttaagag cataaatgtt    900
agtggccaca aatacggtct ggtttatgct ggaatcggtt gggttgtgtg gagaaccaaa    960
tctgatttgc ctgatgaact tatcttccac atcaattatc ttggcgctga tcaacccacc   1020
ttcactctca acttctccaa gggttcgagt caagtgattg ctcagtacta ccaactgatt   1080
cgtcttggat tcgagggata tcgtaacgtg atggataatt gtcgtgaaaa catgatggtc   1140
ctaagagaag gactagagaa aacgggacgt ttcaacattg tctccaaaga aaacggtgtt   1200
ccgttagtgg cgtttttctct aaaagacagt agccgccaca atgagttcga agtggcggaa   1260
actctccgcc gctttggatg gatcgttccg gcctacacgg tgccagcgga tgcagaacat   1320
gtcaccgtcc tccgagtggt gattcgagaa gatttctctc gaaccttagc tgagagattg   1380
gttgcagact ttgagaaggt tcttcacgag ctcgatacac ttccggccag ggttcgcgcc   1440
aagatggcta atggaaaagc taaagttgtt aaacagacgg aggaggagac gacgagggaa   1500
gttacggcat attggaagaa gtttgtggag acaaagaaga ctaaccagaa caagatttgc   1560
taataaagaa aaattaatga gttgatattt tgttgttttg tctctaatta agctactttt   1620
aaatcctttt cttccatcct agtcggatca tttctggttt caaattatcc ttttttttatg   1680
atccgatgtt gatttttggt atttggaata aatttaaaca tatacgttta              1730
```

<210> SEQ ID NO 39
<211> LENGTH: 1701
<212> TYPE: DNA
<213> ORGANISM: Brassica juncea

<400> SEQUENCE: 39

```
gaaattcttc aacaacaaac aataacatta catataatcc ctctctactc tttcttttgt     60
tcattcaaag aagatggttt tgtctaagac agcttcggaa tctgatgttt caatccattc    120
aacttttgct tctcgttacg tccgcacctc tctcccacga tttgagatgc ctgagaactc    180
gatcccaaag gaagcagcgt accaaatcat caacgacgag ctaatgctcg acggtaaccc    240
aaggctaaat ctagcctcct tcgtgaccac gtggatggag ccagagtgcg acaagctcat    300
gatggaatcc atcaacaaga actacgtcga catggacgag taccctgtca ccaccgagct    360
tcagaaccga tgcgtcaaca tgatcgcgcg tctcttcaac gcgccgctag gtgacggcga    420
ggctgcggtt ggcgtcggca ccgtgggatc gtcggaggcg attatgttgg ctggattggc    480
ctttaagaga cagtggcaga ataagcgtaa ggctcaaggg cttccttatg ataagcccaa    540
tatcgttacc ggagccaatg ttcaggtttg ctgggagaag tttgcaaggt atttcgaggt    600
ggagcttaaa gaagttaagc taagagaagg atactacgtg atggacccag agaaggcggt    660
cgaaatggta gacgagaaca caatctgtgt tgcagccatc ctcggttcca ctctaacagg    720
agaattcgaa gacgttaagc tccttaacga cctcctagtc gagaaaaaca agcaaaccgg    780
atgggatacg gggatccatg tggacgcagc gagtggtggg tttattgctc ctttcttgta    840
tccagagctg gagtgggatt tccggttacc attggttaag agcataaatg tgagtggtca    900
caaatacggt ttggtttacg ctggaatcgg ttgggttgta tggagaacca aatccgattt    960
gcctgatgaa cttatcttcc atatcaacta tcttggcgct gaccaaccga ccttcactct   1020
```

```
caacttctcc aaaggttcaa gtcaagtgat tgctcagtac taccagctga ttcgtcttgg   1080

attcgaggga tatcgcaacg tgatggataa ttgccgtgaa aatatgatgg tcctaagaga   1140

aggattagag aagacaggac gtttcaacat agtctcaaaa gaaaacggtg ttccgttagt   1200

ggcattttct ttaaaagaca gtagtcgcca cgacgagttc gaagtggccg agactctccg   1260

tcgctttggg tggattgttc cggcctacac gatgcccgcg gatgctcaac atgtcaccgt   1320

cctccgagtg gtgattcgag aagatttctc tcgaactttg gctgagagat tggtcgcaga   1380

cttcgagaag gttctccacg agctcgatac gcttccggcg agggttcagg ccaagatggc   1440

taacggaaac gctaacggtg ttaagaagac ggaagaggaa acgacgaggg aagttactgc   1500

gtattggaag aagtttgtgg aagcaaagaa gagtaacaag aacaggattt gctaatgaaa   1560

tttaatgaac taatgttctg ctgttttatc cctaataatg ctccatttga aacccttttc   1620

ttccatgcta gctgctcgga ttactttggt ttcaaatttt ttttcatgat ttgatgttga   1680

tgagttataa ttttcatgta c                                             1701


<210> SEQ ID NO 40
<211> LENGTH: 1707
<212> TYPE: DNA
<213> ORGANISM: Brassica juncea

<400> SEQUENCE: 40

gatattcttc ttcctcctcc cactaccaaa aaagaaagaa agatggttct aagtcgagcg     60

gccaccgaaa gtggcgaaaa tgtttgctcg acgttcggat ctcgctatgt ccgcaccgca    120

ctgcccaagc ataagattgg tgagagctcg atcccgaagg aggctgcgta tcagatcata    180

aaagatgagc tgatgcttga tggtaacccg aggctgaacc tggcttcgtt tgtgacgaca    240

tggatggagc cagagtgtga caaactcatc atggaatcta tcaacaagaa ctacgtcgac    300

atggacgagt accctgtcac taccgaactc cagaaccgat gtgtaaacat gatagctcgg    360

ctgttcaatg cgccgcttga ggaaactgag accgccatgg gagtaggcac tgttgggtct    420

tcggaagcca tcatgttagc cggattggcc ttcaaaagga attggcagaa caaacgcaaa    480

gctgagggta aaccctatga caaacccaac attgtcaccg gagccaatgt tcaagtgtgc    540

tgggagaaat tcgctaggta cttcgaggtg gagctaaaag aagtgaagct tagtgaaggt    600

tactacgtga tggatccgga taaagcagct gaaatggtag acgagaatac aatctgtgtt    660

gctgccatac ttggttctac actcaacggt gagttcgaag acgtcaagcg ccttaatgac    720

ttgctggtca agaaaaacga agagactggc tggaacactc caatccacgt tgacgcagca    780

agtggaggct tcatagctcc gtttatctac cctgagttgg aatgggactt taggcttcct    840

ttggtgaaga gtatcaatgt gagtggtcat aagtatgggc tggtctatgc tggtattggc    900

tgggtcgtgt ggaggacaca acaggatttg cctgatgagc tcatctttca tattaactat    960

cttggtgctg atcaacccac atttactctc aatttctcca agggatcgag ccaaattatt   1020

gctcaatatt atcagctcat tcgtcttggc ttcgagggct acaagaacgt gatggagaac   1080

tgcagagaga acatggtggt tctgagagaa gggatcgaga aaacagagcg tttcaacata   1140

gtctcaaagg aggtaggagt tccactcgta gccttctccc tcaaggacca cagtttccac   1200

aacgagttcg aaatctcaga gatgctacgc cgtttcggct ggattgtccc ggcttacaca   1260

atgcctgcgg atgcgcaaca catcacagtt ctgcgtgttg tcatcaggga agatttctca   1320

agaacacttg cggagagact tgtggctgat attgtgaagg tgcttcacga gctcgacacc   1380
```

ttgccttcca agatatctaa gaagatggga gcagaggatt tcggaaacgt gaaagggaag 1440
aaggtggata gggatgttct gatggaagtc attgttggat ggaggaagtt tgtgaaggac 1500
aggaagaaga tgaatggtgt gtgttgatct gaagtgtctt gtggtttgtg tttgaatgta 1560
tcgtcgtcta ataaataaaa tgaagtatgt gtgtgaggac ttgtggtttg atgaaagagt 1620
tgtgtctggt atctatttga gacgataatt aattttggat tctgttgtat gcttgaagag 1680
tcttttaaat aatattatca tattact 1707

<210> SEQ ID NO 41
<211> LENGTH: 1485
<212> TYPE: DNA
<213> ORGANISM: Arabidopsis thaliana

<400> SEQUENCE: 41
atggtactcg caaccaactc tgactccgac gagcatttgc attccacttt tgcttctaga 60
tatgtccgtg ctgttgttcc caggttcaag atgcctgacc attgcatgcc caaagatgct 120
gcttatcaag tgatcaatga tgagttgatg cttgatggta atcccaggct taacctagcc 180
tcctttgtca ccacttggat ggaacctgag tgtgacaaac tcatcatgga ttctgtcaat 240
aagaactatg ttgatatgga tgaatatcct gtcaccactg agctccagaa ccggtgtgta 300
aatatgatag caaacttgtt ccatgctccc gttggagaag acgaggctgc tattgggtgt 360
ggaactgttg gttcatctga ggctataatg cttgctggtt tggctttcaa aaggaaatgg 420
caacatagga gaaaagctca gggtctacct attgataagc ctaacattgt cactggagcc 480
aatgttcagg tgtgctggga gaagtttgca aggtactttg aggtagagct caaagaggtg 540
aaactaagtg aagactacta tgttatggat ccagctaaag ctgtagagat ggtggatgag 600
aataccatct gtgttgcagc aattctagga tccacactta ctggagagtt tgaggacgtt 660
aagcaattga acgatctctt agctgagaaa aacgcagaga caggatggga aactcctatt 720
catgttgatg cagccagtgg aggattcatt gctccttttcc tctaccctga tcttgaatgg 780
gactttaggc ttccatgggt gaagagtatt aacgtcagtg gtcacaagta tggacttgtg 840
tatgcaggag ttggttgggt tgtctggaga acaaaagatg atttgccaga ggaacttgtc 900
ttccacatca actacttggg agctgatcaa cccactttca ctctcaactt ctcaaaaggg 960
tcgagccaaa tcattgctca gtactatcag tttatccgac taggctttga gggatacaag 1020
aacataatgg aaaactgcat ggataacgca aggaggctaa gagaaggaat agagatgaca 1080
gggaagttca acattgtgtc caaagatatt ggcgtgccac tagtggcatt ctctctcaaa 1140
gacagtagca agcacacggt gtttgagatc gcagagtctt tgagaaaatt cgggtggatc 1200
ataccggctt acactatgcc tgcagatgca cagcacattg ctgtgctcag agttgtgata 1260
agagaagact ttagccgagg ccttgcagat agactcatca cacatatcat tcaggtgctg 1320
aaagagattg aagggcttcc tagcaggatt gcacatcttg ctgcggctgc agcggttagt 1380
ggtgatgatg aagaagttaa agtgaagact gccaagatgt ccttggagga tatcactaag 1440
tattggaaac gccttgtgga acacaagaga aatattgtct gctaa 1485

<210> SEQ ID NO 42
<211> LENGTH: 1482
<212> TYPE: DNA
<213> ORGANISM: Arabidopsis thaliana

<400> SEQUENCE: 42
atggttttgt ctaagacagt ttccgaatct gatgtctcaa tccattcaac ttttgcttct 60

```
cgttacgtcc gcaactctct tccacgattc gaaatgcctg agaactcaat cccaaaagaa    120

gcagcttacc aaatcatcaa cgacgagcta atgctcgatg gtaacccaag gctgaaccta    180

gcttccttcg tgaccacatg gatggagcca gaatgtgaca agctcatgat ggagtccatc    240

aacaagaact acgtcgacat ggacgagtac cctgtcacca ctgagcttca gaaccgatgt    300

gttaacatga tagcacgtct cttcaacgcg ccgcttggtg acggtgaagc tgccgttggt    360

gttggcaccg tcggatcgtc ggaggcgatt atgttggccg gtttggcttt taagagacaa    420

tggcagaata agcgtaaggc ccaagggctt ccttatgata agcccaatat cgtaaccggt    480

gctaatgtcc aggtttgctg ggagaaattc gcaaggtatt tcgaagtgga gcttaaggaa    540

gtgaacctaa gagaagacta ttacgtgatg gaccctgtaa aggcggtcga aatggtagac    600

gaaaacacaa tttgtgtcgc tgccatcctc ggttcaacgt taaccggtga attcgaagac    660

gttaagctcc tcaacgacct ccttgtcgag aaaaacaagc aaaccggatg ggacacgcca    720

atacacgtgg acgcagcgag tggtgggttt attgctccgt tcttgtatcc ggagctggag    780

tgggatttcc ggctaccgtt ggttaagagt attaatgtga gtggtcacaa atacggtttg    840

gtttacgccg gtattggttg ggttgtatgg agaaccaaaa ccgatttgcc tgatgaactt    900

atcttccata tcaattatct tggcgctgat caaccaacct ttacactcaa cttctccaaa    960

ggttcaagtc aagtgattgc tcagtactac cagctgattc gtcttggatt cgagggttat   1020

cgcaatgtga tggataattg tcgggaaaac atgatggtac taagacaagg attagagaaa   1080

acgggacgtt ttaaaatcgt ctccaaagaa aacggtgttc cgttagtggc gttttctctc   1140

aaagatagta gccgccacaa cgagttcgag gtggcccata cactccgtcg cttcggctgg   1200

atcgttccgg cctacacgat gcctgcggat gcgcagcatg tcactgtcct tcgagttgtt   1260

atccgagaag atttctctcg aaccttagcc gagagattgg tagctgattt cgagaaggtt   1320

ctacacgagc tcgatacgct tccggcgagg gttcacgcca agatggctaa tggaaaagtt   1380

aacggtgtta agaagacgcc agaggagacg cagagagaag tcacggccta ctggaagaag   1440

ttgttggaga ctaagaagac caacaagaac acaatttgct aa                       1482
```

<210> SEQ ID NO 43
<211> LENGTH: 1712
<212> TYPE: DNA
<213> ORGANISM: Arabidopsis thaliana

<400> SEQUENCE: 43

```
acatattatt caactacaaa acaaaaacat tgcacatttt tccctttact tttctttagc     60

tcatttcaag aagatggttt tatctaagac agcttccaaa tccgatgatt caatccattc    120

aacttttgct tcccgttatg tccgcaactc tatctcacga ttcgaaatac ctaagaactc    180

gatccctaag gaagcagcat accaaatcat caacgacgag ctcaagtttg acggtaaccc    240

gaggctaaac ctggcctcct ttgtgaccac ttggatggag ccagaatgtg acaagctcat    300

gatggaatcc atcaacaaga acaacgttga gatggaccaa taccctgtta ccaccgacct    360

tcagaatcga tgcgttaaca tgattgcgcg tctcttcaac gcgcctttag gtgacggtga    420

agccgccatt ggtgttggca cggtggggtc atcggaggca gtgatgttgg ccggactggc    480

ctttaagaga cagtggcaga acaagcgtaa ggccctaggg ctgccttatg atagacctaa    540

tattgtaacc ggagccaata ttcaggtttg cttggagaaa tttgcaaggt attttgaagt    600

ggagcttaag gaagtgaagc tgagagaagg atattacgtg atggaccctg acaaagcggt    660
```

tgaaatggta gacgaaaaca ctatatgcgt cgtggccatc ctcggttcga cactaaccgg 720
agaattcgaa gacgttaagc tcctcaacga ccttttagtc gagaaaaaca agaaaaccgg 780
atgggatacg ccgattcacg tggacgcagc gagtggtggg tttattgctc ccttcttgta 840
tccggacttg gagtgggatt tccggttacc gttggttaag agcataaatg tgagtggtca 900
caaatacggt ttggtttacg ccggtatcgg ttgggtcgta tggagaacca aaaccgattt 960
gcctgatgaa cttatcttcc atatcaatta tcttggagct gatcaaccca catttaccct 1020
caacttctct aaagggtcaa gtcaagtgat tgctcagtac taccagttga ttcgtcttgg 1080
attcgaggga tatcgcaacg tgatggataa ttgccgcgag aacatgatgg tactaagaca 1140
aggattagag aaaacgggac gttttaacat cgtctccaaa gaaaacggtg ttccgttagt 1200
ggcgttttct ctcaaagata gtagccgcca caacgagttc gaggtggccg aaatgcttcg 1260
tcgcttcggc tggatcgttc cggcctacac gatgcctgcg gatgcgcaac atgtcacggt 1320
ccttcgagtt gttatccgag aagatttctc tcgaacctta gctgagagat tggtagccga 1380
tttcgagaag gttctacacg agctcgatac gcttcccgcg agggttcacg ccaagatggc 1440
tagtggaaaa gttaacggtg ttaagaagac gccagaggag acgcaaagag aagtcacggc 1500
ctactggaag aagtttgtgg acactaagac tgacaagaac ggcgttccgt tagtagcaag 1560
tattaccaat caatgatggg ccaaatgtat attcaaatta ttgggtgcag acaaattttt 1620
ttttagctaa aggcccaact acaccatagc aaatcagcac cattcgatct cagaccattc 1680
aaacactgta ataaaaacat ttttagtttt ac 1712

<210> SEQ ID NO 44
<211> LENGTH: 1776
<212> TYPE: DNA
<213> ORGANISM: Nicotiana tabacum
<220> FEATURE:
<221> NAME/KEY: misc_feature
<222> LOCATION: (1616)..(1616)
<223> OTHER INFORMATION: n is a, c, g, or t
<220> FEATURE:
<221> NAME/KEY: misc_feature
<222> LOCATION: (1652)..(1652)
<223> OTHER INFORMATION: n is a, c, g, or t
<220> FEATURE:
<221> NAME/KEY: misc_feature
<222> LOCATION: (1719)..(1719)
<223> OTHER INFORMATION: n is a, c, g, or t
<220> FEATURE:
<221> NAME/KEY: misc_feature
<222> LOCATION: (1729)..(1729)
<223> OTHER INFORMATION: n is a, c, g, or t

<400> SEQUENCE: 44
aaaattaatt ctcctccttt ttctctgatc ttttgtacca aggtttaacc tcattctttc 60
tagttttcct tgttcatttt ttcccaaaat ggttctctcg aaaacctcct ctgagtcgga 120
cgtttcggta cactccactt ttgcctctcg ctatgttcga acttcccttc caaggtttga 180
gatggcggag aattcgatac caaaagaggc ggcatttcaa ataattaacg acgagttgat 240
gcttgacggg aatccaaggc tgaacttggc ttcatttgtg acaacatgga tggagccaga 300
gtgtgataag cttatgatgg actccattaa caagaactat gttgacatgg atgaataccc 360
tgttaccact gagcttcaga atcgctgcgt gaacatgata gcacgtttat tcaacgcgcc 420
actagaagag aaggagacag cagttggagt gggtacagtt ggttcatcgg aggccataat 480
gctagcgggg cttgcattca agagaaattg gcaaaacaaa cgcaaagctg agggcaaacc 540
ttacaataag cccaacattg tcactggcgc caatgttcag gtgtgctggg agaaatttgc 600

-continued caactatttt gaagtggaat tgaaagaagt aaagctaagg gaagggtact atgtgatgga 660
cccagtccag gctgtggaga tggttgatga gaacaccatt tgtgttgctg caatcttggg 720
ttcaaccctt aatggagaat ttgaagatgt caagctcttg aatgatcttt tgattgaaaa 780
gaacaagcaa actggatgga acacaccaat tcatgtggat gcagcaagtg gtggattcat 840
tgcaccattc ctgtacccag agctggagtg ggactttagg cttcccttag tgaagagcat 900
aaatgtgagt gggcacaaat atgggcttgt ctatgctggt attggttggg ttatttggag 960
gaccaaacaa gatttgcctg aagaactcat tttccacatc aactatcttg gagctgatca 1020
gcccaccttt actctcaatt tctccaaagg ttcaagtcaa gtcattgctc aatattatca 1080
gctaatccgt ttgggctatg aggggtaccg aaatgtaatg gagaactgtc gcgaaaatgc 1140
cattgtgcta agagaaggac tcgaaaaaac aggacgtttt aacatagtct ccaaagatga 1200
aggtgtccct ttggtggcct tttccctcaa ggacaatagc cgtcacaatg agttcgaggt 1260
gtccgagacg ctccgtaggt tcgggtggat cgtcccggcc tacacgatgc ccgctgacgc 1320
ccaacacgtc acggtgcttc gtgtggtgat ccgggaggac ttctcgcgaa ccctagcaga 1380
gcgtctcgtc ctcgacattg tcaaggtcct ccacgagctg gacacacttc cagctaggct 1440
gagcgccaaa ttagaggagg tgaagctggt caagaatgga aagaaatttg aacttgaagt 1500
tcaaagggaa gttaccaatt attggaagaa gtttgtttta gctaggaaag cacctgtttg 1560
ctagagaagg atttttgaag gaattagtaa caaaactagg attttccttt tctttnattt 1620
tttgggggtt atctttcctc ctaaattttg tngaaaaaca aacgaaattt tcataagaat 1680
gatgacggta tcaaaatttg aatgtaatgg aactttttnt tggaagttng tctttttgta 1740
aaaaaaaaaa aaaaaaaaaa aaaaaaaaaa aaaaaa 1776

<210> SEQ ID NO 45
<211> LENGTH: 1672
<212> TYPE: DNA
<213> ORGANISM: Nicotiana tabacum
<220> FEATURE:
<221> NAME/KEY: misc_feature
<222> LOCATION: (1550)..(1550)
<223> OTHER INFORMATION: n is a, c, g, or t
<220> FEATURE:
<221> NAME/KEY: misc_feature
<222> LOCATION: (1578)..(1578)
<223> OTHER INFORMATION: n is a, c, g, or t
<220> FEATURE:
<221> NAME/KEY: misc_feature
<222> LOCATION: (1588)..(1588)
<223> OTHER INFORMATION: n is a, c, g, or t
<220> FEATURE:
<221> NAME/KEY: misc_feature
<222> LOCATION: (1602)..(1602)
<223> OTHER INFORMATION: n is a, c, g, or t
<220> FEATURE:
<221> NAME/KEY: misc_feature
<222> LOCATION: (1650)..(1650)
<223> OTHER INFORMATION: n is a, c, g, or t
<220> FEATURE:
<221> NAME/KEY: misc_feature
<222> LOCATION: (1652)..(1652)
<223> OTHER INFORMATION: n is a, c, g, or t

<400> SEQUENCE: 45
gccatggttc tgtccaagac agcgtcggaa agtgacgtct ccatccactc cactttcgct 60
tcccgatatg ttcgaacttc tcttcccagg tttaagatgc cagagaattc tataccaaaa 120
gaagcagcat atcaaatcat aaatgatgag cttatgttag atggaaatcc aaggctaaat 180

```
ttagcatctt ttgtgacaac atggatggaa ccagagtgta ataagttaat gatggattcc    240
attaacaaga actacgttga catgggtgaa taccctgtaa ccactgagct tcagaatcga    300
tgtgtaaata tgatagctca tttgtttaac gcaccacttg gagatggaga gactgcagtt    360
ggagttggaa ctgttggatc ctctgaggct attatgcttg ctggattagc cttcaagaga    420
aaatggcaaa ataaaatgaa agcccaaggg aagccctgcg acaagcccaa tattgtcact    480
ggtgccaatg tccaggtgtg ttgggagaaa tttgcaaggt attttgaagt ggagttgaaa    540
gaagtaaaat tgagtgatgg atactatgtg atggaccctg agaaagctgt ggaaatggtg    600
gatgagaata caatttgtgt agctgctatc ttgggttcca ctctcaatgg tgaatttgaa    660
gatgttaagc gcttgaatga cctcttgatt gagaagaaca aagaaaccgg gtgggacact    720
ccaattcatg tggatgcagc aagtggtgga ttcattgcac cattccttta tcctgagctt    780
gaatgggatt ttagattacc attggtgaag agtattaatg tgagtggtca caaatatggt    840
cttgtctatg ctggtattgg ttgggccatt tggaggaata aggaagactt gcctgatgaa    900
cttattttcc acattaatta tcttggtgct gatcaaccta ctttcactct caacttctct    960
aaaggttcta gccaagtaat tgctcaatat taccaactta ttcgcttggg ttttgagggt   1020
tacaagaatg ttatggagaa ttgtcaagaa aatgcaaggg tactaagaga aggacttgaa   1080
aaaagtggaa gattcaatat aatctccaaa gaaattggag ttccattagt agctttctct   1140
cttaaagaca acagtcaaca caatgagttc gaaatttctg aaactcttag aagatttgga   1200
tggattattc ctgcatatac tatgccacca aatgctcaac atgtcacagt tctcagagtt   1260
gttattagag aagatttctc ccgtacactc gcggagcgac tggtgataga cattgaaaaa   1320
gtcctccacg agctagacac acttccggcg agggtcaacg ctaagctcgc cgtggccgag   1380
gcgaatggca gcggcgtgca taagaaaaca gatagagaag tgcagctgga gattactgct   1440
gcatggaaga aatttgttgc tgataagaag aagaagacta atggagtttg ttaatttaat   1500
ttacaaaata tgttataata tgatgattta tgactactag caatattggn attgctgttt   1560
aaatttgaat tgttgggnct ttgggtanac ttgaggagct anctatttat tgcaaggcaa   1620
aactgggtga ttttgggcaa aataatgggn tnataaaccc aattttcttg tg           1672
```

<210> SEQ ID NO 46
<211> LENGTH: 1597
<212> TYPE: DNA
<213> ORGANISM: Glycine max

<400> SEQUENCE: 46

```
tgggaaccca aggttgaatt tggcatcatt tgtgacgact tggatggagc cagagtgtga     60
taaactcatc atggctgcca ttaataagaa ctatgttgac atggacgagt accctgtcac    120
cactgagcta cagaatcgat gtgttaacat gatagctcat cttttcaatg caccactaga    180
agagactgag gcagcagttg gtgttggcac ggttggctca tcagaggcca ttatgttggc    240
tggattggca ttcaaaagaa agtggcaaaa cagaaggaaa caagagggaa agccttatga    300
caaacccaac attgtcactg gagccaacgt tcaggtttgc tgggagaaat ttgcaaggta    360
ctttgaggtg gagttaaagg aggtgaagct ccgtgatgat tattatgtaa tggaccctga    420
aaaggccgtg gaattggtgg atgagaacac tatttgtgtt gctgctatcc ttggttccac    480
actaaatgga gagtttgaag atgtcaaacg cttaaatgat ctcctaattg aaaagaacaa    540
aataactggg tgggacactc ctattcatgt tgatgcagcc agcggtgggt tcatagcccc    600
atttatttac ccagagcttg agtgggactt ccggttacaa ctagtgaaga gcatcaatgt    660
```

-continued

```
tagtgggcac aagtatggtt tggtctatgc tggaatcggt tgggttatct ggagaagcaa    720

gcaggacttg cctgaggaac tcatctttca catcaactat cttggggctg atcaacccac    780

cttcaccctt aacttctcca aaggttctag ccaagtcatt gctcaatact accaactgat    840

tcgccttggt tttgagggat atagaaacgt gatggaaaac tgcagggaca acatgctggt    900

gctgaaagag ggactcgaga aaacagggcg attttcaatt gtgtccaaag acaatggtgt    960

gcctttggtg gctttcacac tgaaagacca cacccacttt gacgaattcc aaatctcaga   1020

ctttttaagg cgctttgggt ggatagtgcc agcatacacc atgcccccag atgctcaaca   1080

tgtcacagtg cttcgtgttg tcatcaggga ggacttctca aggaccctcg cggagcgtct   1140

cgtgtccgat gtggagaagg tgctgcatga gcttgattca cttcctgcaa gggtcatcag   1200

cagcaccact gtgacactca gtgcagaaga aaatggcaag gtagtggttg ctaagaagaa   1260

tcctatggag actcagaggg aaatcactgc catttggaag aagtttgtgt tggagaggaa   1320

gaagaacaat gacaagatga atggtgtttg ttagtgttag cttcaagggg gtgttgtgcc   1380

tatgcctctg ccttattgta cttctttatt atatatataa tttgggcagt aagtactttt   1440

gattgagtca agctatttat ctgtttcagt tgtttattga tgagaggcaa atattaaatt   1500

gtgttttcgt ttgtacaagt agtgattcac tgtattttga ctattttctc tgaatcatga   1560

attatattta tctcccctaa aaaaaaaaaa aaaaaaa                             1597
```

<210> SEQ ID NO 47
<211> LENGTH: 1745
<212> TYPE: DNA
<213> ORGANISM: Nicotiana tabacum

<400> SEQUENCE: 47

```
tctagatcgt actaccacca ctacgccgcc atggttctgt ccaagacagc gtcggaaagt     60

gacgtctcca tccactccac tttcgcttcc cgatatgttc gaacttctct tcccaggttt    120

aagatgccag agaattcaat accaaaggaa gcagcatatc agattataaa tgatgagctt    180

atgttagatg gaaatccaag gctaaattta gcatctttcg ttacaacatg gatggagcca    240

gaatgtaata cgttaatgat ggattccatt aacaagaact acgttgacat ggatgaatac    300

cctgtaacca ctgagcttca gaatcgatgt gtaaatatga tagctcattt gtttaatgca    360

ccacttggag atggagagac tgcagttgga gttggaactg ttggatcctc tgaagctatt    420

atgcttgctg gattagcctt taaaagaaaa tggcaaaata aaatgaaagc ccaaggcaag    480

ccctttgata agcccaatat cgtcaccggt gctaatgtcc aggtgtgttg ggagaaattt    540

gcaaggtatt ttgaagtgga gttgaaagaa gtaaaattga gtgatggata ctatgtgatg    600

gaccctgaga aagctgtgga aatggtggat gagaatacca tttgtgttgc tgctatctta    660

ggttcaacac tcaatggtga atttgaagat gttaagcgtt tgaatgacct tttgattgag    720

aagaacaaag aaaccgggtg ggacactcca attcatgtgg atgcagcaag tggtggattt    780

attgcaccat tcctttatcc agagcttgaa tgggacttta gattgccatt ggtgaagagt    840

attaatgtga gtggtcacaa atatggtctt gtctatgctg gtattggttg ggccatttgg    900

aggaataagg aagacttgcc tgatgaactt attttccaca tcaattacct tggtgctgat    960

caacctactt tcactctcaa cttctctaaa ggttctagcc aagtaattgc tcaatattac   1020

caacttattc gcttgggttt tgagggttac aagaatgtta tggagaattg tcaagaaaat   1080

gcaagggtat taagagaagg aattgaaaaa agtggaagat tcaacataat ctccaaagaa   1140
```

```
attggagttc ccttagtagc attttctctt aaagacaaca gtcaacacaa tgagttcgaa   1200
atttctgaaa ctcttagaag atttggatgg attgttcctg catatactat gccaccaaat   1260
gctcaacatg ttacagttct cagagttgtc attagagaag atttctcccg cacactagcg   1320
gagcgactgg taatagacat tgaaaaagtc ctccacgagc tagacacact tccggcgagg   1380
gtcaacgcta agctagccgt ggccgaggcg aatggcagcg gcgtgcataa gaaaacagat   1440
agagaagtgc agctagagat tactactgca tggaagaaat ttgttgctga taagaagaag   1500
aagactaatg gagtttgtta atttaattta acaaaaaaaa agtttataat atggtgattt   1560
atgtaactac tagcagtcgt actgcttgtt ttttatattt gagttgatgt gttttttgag   1620
cacttgagga gctagctagt tattgctagt gaaaaattgg atgatatatt ttggactact   1680
ttgtaagttt gtattattaa tccaaattaa acgatattta tcatgcaaaa aaaaaaaaaa   1740
aaaaa                                                               1745
```

```
<210> SEQ ID NO 48
<211> LENGTH: 1605
<212> TYPE: DNA
<213> ORGANISM: Arabidopsis thaliana

<400> SEQUENCE: 48

atatttttat gttcaacaat tcagcataac tcaaacacaa tggtactcgc aaccaactct     60
gactccgacg agcatttgca ttccactttt gcttctagat atgtccgtgc tgttgttccc    120
aggttcaaga tgcctgacca ttgcatgccc aaagatgctg cttatcaagt gatcaatgat    180
gagttgatgc ttgatggtaa tcccaggctt aacctagcct cctttgtcac cacttggatg    240
gaacctgagt gtgacaaact catcatggat tctgtcaata agaactatgt tgatatggat    300
gaatatcctg tcaccactga gctccagaac cggtgtgtaa atatgatagc aaactttttc    360
catgctcccg ttggagaaga cgaggctgct attgggtgtg gaactgttgg ttcatctgag    420
gctataatgc ttgctggttt ggctttcaaa aggaaatggc aacataggag aaaagctcag    480
ggtctaccta ttgataagcc taacattgtc actggagcca atgttcaggt gtgctgggag    540
aagtttgcaa ggtactttga ggtagagctc aaagaggtga aactaagtga agactactat    600
gttatggatc cagctaaagc tgtagagatg gtggatgaga ataccatctg tgttgcagca    660
attctaggat ctacacttac tggagagttt gaggacgtta agcaattgaa cgatctctta    720
gctgagaaaa acgcagagac aggatgggaa actcctattc atgttgatgc agccagtgga    780
ggattcattg ctcctttcct ctaccctgat cttgaatggg actttaggct tccatgggtg    840
aagagtatta acgtcagtgg tcacaagtat ggacttgtgt atgcaggagt tggttgggtt    900
gtctggagaa caaaagatga tttgccagag gaacttgtct tccacatcaa ctacttggga    960
gctgatcaac ccactttcac tctcaacttc tcaaaagggt cgagccaaat cattgctcag   1020
tactatcagt ttatccgact aggctttgag ggatacaaga acataatgga aaactgcatg   1080
gataacgcaa ggaggctaag agaaggaata gagatgacag ggaagttcaa cattgtgtcc   1140
aaagatattg gcgtgccact agtggcattc tctctcaaag acagtagcaa gcacacggtg   1200
tttgagatcg cagagtcttt gagaaaattc gggtggatca taccggctta cactatgcct   1260
gcagatgcac agcacattgc tgtgctcaga gttgtgataa gagaagactt tagccgaggc   1320
cttgcagata gactcatcac acatatcatt caggtgctga aagagattga agggcttcct   1380
agcaggattg cacatcttgc tgcggctgca gcggttagtg gtgatgatga agaagttaaa   1440
gtgaagactg ccaagatgtc cttggaggat atcactaagt attggaaacg ccttgtggaa   1500
```

```
cacaagagaa atattgtctg ctaagcgcaa gtcttattct ttgcacttat atggtaataa   1560

ggttttgatt tagaccattt ggcggtaata aggttttaat ttttt                   1605


<210> SEQ ID NO 49
<211> LENGTH: 2441
<212> TYPE: DNA
<213> ORGANISM: Oryza sativa

<400> SEQUENCE: 49

tgatagctcg gcaggcaaga tggtgctctc caaggccgtc tccgagagtg acatgtccgt     60

gcactccacc ttcgcctccc gctacgtccg cgcctccctc ccaaggtacg tgctctcgat    120

ctgctctctc tctgttcttg ctgttcttgg cccaatgcag agcttcttcc aatatttcat    180

ggctgactcg atgggattga tcgattggtg ttattaggta ccggatgccg gagaactcga    240

tcccgaagga ggcggcgtac cagatcatca acgacgagct gatgctggac ggcaacccgc    300

ggctgaacct ggcgtcgttc gtcaccacgt ggatggagcc cgagtgcgac aagctcatca    360

tggccgccat caacaagaac tacgtcgaca tggacgagta ccccgtcacc accgagctcc    420

aggtacagca ccctgcaggc atctctgctt cgttgaattt tctcctatca cctcgcgttt    480

tctcgccgcc gcgcgcggct cgaatgcaca ctggaaatcc ccggattttt ggtcgataaa    540

accggcttgg ccagttggcc tggcctggca gattggtgat aagaatctca ggctagaaac    600

tttatttccg agtttatcat ttgcgtcatt cacgggaggc agaatggggg aagaacatgg    660

cacagtttcc gagatgatca ccaattcgca ttagaaaaaa tatataggaa gtccaataaa    720

taaagtaagg ggatgggaag aatgatcacc atatctcttc atttttcgca ttaaaatatg    780

gaaggtgcat gaatgaaggg aaatgggaaa gaataatgcc tggtttggtc aaaacagggc    840

aagagaccaa agttccatct actgaaacgg cgtggacaac agtcaaaacc tggaacacag    900

aagacaccac tgcaactttc ccctttttgc gaatgagaca cattattagt cctttttca    960

gccagacatg ctttgggcca gatgatgtcc tagcatgaac tgtacaacat tttttttggg   1020

ccgggccgtt ctacagctaa ttaacgaacg ctttggatgt gtgacgctgt gcagaaccgg   1080

tgcgtgaaca tgatcgcgca cctgttccac gcgccgctcg gggaggacga gacggcggtg   1140

ggcgtgggca cggtgggttc gtcggaggcc atcatgctgg ccgggctggc cttcaagcgg   1200

cggtggcaga acaagcgcaa ggccgagggg aagccgttcg acaagcccaa catcatcacc   1260

ggcgccaacg tgcaggtgtg ctgggagaag ttcgcccgct acttcgaggt ggagctcaag   1320

gaggtgaagc tccgcgacgg ctactacgtc atggaccccg agaaggccgt cgacatggtc   1380

aacgagaaca ccatctgcgt cgccgccatc ctcggctcca ccctcaacgg cgagttcgag   1440

gacgtcaagc tactcaacga cctcctcgac aagaagaaca aggagactgg gtaactaaaa   1500

ttactatttc tactacacta aattatctat ctatgaaagt gagattaatc gatgtcattg   1560

cggccgtggt gtgcaggtgg gagacgccga tccacgtgga cgcggcgagc ggcgggttca   1620

tcgcgccgtt cctgtacccg gagctggagt gggacttccg gctgccgtgg gtgaagagca   1680

tcaacgtgag cggtcacaag tacgggctcg tctacgccgg catcggctgg tgcatctggc   1740

gcaacaagga ggacctgccc gaggagctca tcttccacat caactacctc ggcaccgacc   1800

agccaacctt caccctcaac ttctccaagg gctccagcca ggtcatcgcc cagtactacc   1860

agctcatccg ccacggcttc gaggtataat caatggaaca caattaactc tcttgatcag   1920

atgaattttt tttagctgat ctgacacacc catcgatccg atgttatttg caggggtaca   1980
```

-continued

```
ggaacatcat ggagaactgc cacgagaacg cgatggtgct gaaggaaggg ctggtgaaga   2040
cggggaggtt cgacatcgtg tccaaggacg aaggggtgcc gctggtggcg ttctcgctca   2100
aggaccggag ccggcacgac gagttcgaga tctccgacat gctgcgccgc ttcggctgga   2160
tcgtgccggc gtacaccatg ccgcccgacg cccagcacgt cacggtgctc cgcgtggtca   2220
tccgggagga gttcagccgc accctcgccg agcgcctcgt cctcgacatc gagaaggtga   2280
tgtaccagct cgacgcgctc ccctccaggc tcatgccccc cgtgccgccg gcgccgctgc   2340
tggtggtcgc caagaagtcg gagctcgaga cgcagcggtc ggtgacggag gcgtggaaga   2400
agttcgtgct cgccaagagg accaacggcg tctgctagtc t                        2441
```

<210> SEQ ID NO 50
<211> LENGTH: 1650
<212> TYPE: DNA
<213> ORGANISM: Arabidopsis thaliana

<400> SEQUENCE: 50

```
ctcagattct ctttcactaa acagaaacaa agatggtttt gacaaaaacc gcaacgaatg     60
atgaatctgt ctgcaccatg ttcggatctc gctatgttcg cactacactt cccaagtatg    120
agattggtga gaattcgata ccgaaagacg ctgcgtatca gatcataaaa gatgagctga    180
tgcttgatgg taacccaagg cttaacctag cttcttttgt gactacatgg atggaaccta    240
gtgtgacaaa ctcatcatgg actctatcaa taagaactac gttgatatgg atgagtaccc    300
tgtcacaact gagctccaga accgatgtgt aaacattata gctcgactgt tcaatgcgcc    360
actcgaggaa tctgagacgg cggtgggagt agggacagtt ggttcttcag aagccatcat    420
gttagccgga ttggccttca aaagaaaatg gcagaacaaa cgcaaggctg agggtaaacc    480
ctatgacaaa cccaacattg tcaccggagc caatgttcaa gtttgctggg agaaattcgc    540
tcggtacttc gaggtggagc taaaggaagt aaacctaagt gaaggttact acgtgatgga    600
tccagacaaa gcagcagaaa tggtagacga gaacacaatc tgtgtcgcag ccatattggg    660
atccacactc aacggtgagt tcgaagacgt gaaacgtctc aatgacttgc tagtcaagaa    720
aaacgaggag actggttgga acacaccgat ccacgtggat gcagcaagtg gagggttcat    780
agctccgttt atctatcctg aattagaatg ggactttagg cttcctttgg ttaagagcat    840
caacgtgagt ggtcacaagt atggactagt ctatgctggt attggttggg tcgtgtggag    900
ggcagcagag gatttacctg aagagcttat ctttcatatt aattatcttg gtgctgatca    960
acccactttc actctcaatt tctccaaggg atcgagccaa attattgctc aatactacca   1020
gctcattcgt cttggattcg aggggtacaa aaatgtgatg gagaattgca tagagaacat   1080
ggtggttctc aaagaaggta tagagaaaac agagcgtttc aacatagtct caaaggacca   1140
aggagtgcca gtcgtcgcct tctctctcaa ggaccatagt ttccacaacg agttcgagat   1200
ctctgagatg ctacgtcgtt ttggctggat cgtcccagct tacactatgc ctgccgatgc   1260
acagcacatc acggttctgc gtgttgtcat cagggaagat ttctcaagaa cactcgcgga   1320
gagacttgtt gctgatattt cgaaggtgct tcatgagcta gataccttgc cttccaagat   1380
atctaagaag atgggaatag aagggatcgc gaaaaatgta aaggagaaga agatggagaa   1440
ggagattctg atggaagtta ttgttggatg gaggaagttt gtgaaggaga ggaagaagat   1500
gaatggtgtg tgctaagcaa gtgtgttgcc tttgtgtgga aatgaagagg tacttgcgag   1560
gactttgcgt ttatcagttt atgtgtttgt atatctattt gatccagtta ttatggatta   1620
tatacgcttg aaactcattt taagccattg                                    1650
```

<210> SEQ ID NO 51
<211> LENGTH: 1506
<212> TYPE: DNA
<213> ORGANISM: Oryza sativa

<400> SEQUENCE: 51
atggtggtga gcgtggccgc gaccgactcg gacacggccc agccggtgca gtactccacc 60
ttcttcgcct cccgctacgt ccgcgacccg ctcccgcggt tcaggatgcc ggagcagtcg 120
atcccgaggg aggcggcgta ccagatcatc aacgacgagc tgatgctgga cgggaacccg 180
cggctgaacc tggcgtcctt cgtcaccacg tggatggagc ccgagtgcga caagctcatc 240
atggactccg ttaacaagaa ctacgtcgac atggacgagt accctgtcac cacggagctc 300
cagaaccgtt gtgtgaatat gatagctcac ctgttcaatg caccaatcaa ggaggatgaa 360
acagctattg gagttgggac ggtgggatcc tcagaagcaa ttatgcttgc aggactggca 420
ttcaagagga agtggcaaaa caaacggaag gaacagggga agccatgtga caaacccaac 480
attgttactg gtgctaatgt tcaggtttgc tgggagaaat ttgccagata ttttgaagta 540
gaactgaagg aggttaagct cagtgaagga tactatgtca tggatcctgt aaaggctgtt 600
gaaatggtgg atgagaacac tatatgcgtt gcggccatct tgggctctac tctcactgga 660
gagtttgagg atgttaagtt attgaataat ctcctaacag aaaagaataa ggaaactggg 720
tgggatgtgc caattcatgt tgatgcagca agtggaggat ttatagcacc ttttctatac 780
cctgagcttg aatgggactt caggctacca ctggtgaaga gcatcaatgt cagtgggcac 840
aagtatggcc ttgtgtatcc aggtgttggt tgggtcattt ggcgaagcaa agaggatttg 900
cctgaagaac tcattttcca tataaactat ctggggacag accagccgac gttcactctg 960
aacttctcca aaggttccag ccagataatc gcacagtact atcaactaat acgcctggga 1020
ttcgagggat acaagaacat catgcagaat tgcatggaga acacagcaat actaagggaa 1080
ggcatagagg cgactggtcg attcgaaatc ctctccaagg aggccggtgt gcccttggtg 1140
gcgttctcgc tcaaggacag cggcaggtac accgtgttcg acatctccga gcacctgagg 1200
aggttcggct ggatcgtgcc ggcgtacacc atgccggcca acgccgagca cgtcgccgtc 1260
ctccgcgtcg tcatcaggga ggacttcagc cggagcctcg ccgagcggct cgtctcggac 1320
atcgtcaaga tcctgcacga gctggacgcc cattcggccc aggtgctgaa gatctccagc 1380
gccatcgcga agcagcaatc gggcgacgat ggcgtggtca ccaagaagag cgtcctggag 1440
accgagaggg agatcttcgc gtactggagg gaccaggtga agaagaagca gaccggaatc 1500
tgctag 1506

<210> SEQ ID NO 52
<211> LENGTH: 1685
<212> TYPE: DNA
<213> ORGANISM: Arabidopsis thaliana

<400> SEQUENCE: 52
agattctctt tcactaaaca gaaacaaaga tggttttgac aaaaaccgca acgaatgatg 60
aatctgtctg caccatgttc ggatctcgct atgttcgcac tacacttccc aagtatgaga 120
ttggtgagaa ttcgataccg aaagacgctg cgtatcagat cataaaagat gagctgatgc 180
ttgatggtaa cccaaggctt aacctagctt cttttgtgac tacatggatg gaaccagagt 240
gtgacaaact catcatggac tctatcaata agaactacgt tgatatggat gagtaccctg 300
tcacaactga gctccagaac cgatgtgtaa acattatagc tcgactgttc aatgcgccac 360
tcgaggaatc tgagacggcg gtgggagtag ggacagttgg ttcttcagaa gccatcatgt 420
tagccggatt ggccttcaaa agaaaatggc agaacaaacg caaggctgag ggtaaaccct 480
atgacaaacc caacattgtc accggagcca atgttcaagt ttgctgggag aaattcgctc 540
ggtacttcga ggtggagcta aaggaagtaa acctaagtga aggttactac gtgatggatc 600
cagacaaagc agcagaaatg gtagacgaga acacaatctg tgtcgcagcc atattgggat 660
ccacactcaa cggtgagttc gaagacgtga aacgtctcaa tgacttgcta gtcaagaaaa 720
acgaggagac tggttggaac acaccgatcc acgtggatgc agcaagtgga gggttcatag 780
ctccgtttat ctatcctgaa ttagaatggg actttaggct tcctttggtt aagagcatca 840
acgtgagtgg tcacaagtat ggactagtct atgctggtat tggttgggtc gtgtggaggg 900
cagcagagga tttacctgaa gagcttatct ttcatattaa ttatcttggt gctgatcaac 960
ccactttcac tctcaatttc tccaagggat cgagccaaat tattgctcaa tactaccagc 1020
tcattcgtct tggattcgag ggtacaaaaa atgtgatgga gaattgcata gagaacatgg 1080
tggttctcaa agaaggtata gagaaaacag agcgtttcaa catagtctca aaggaccaag 1140
gagtgccagt cgtcgccttc tctctcaagg accatagttt ccacaacgag ttcgagatct 1200
ctgagatgct acgtcgtttt ggctggatcg tcccagctta cactatgcct gccgatgtac 1260
agcacatcac ggttctgcgt gttgtcatca gggaagattt ctcaagaaca ctcgcggaga 1320
gacttgttgc tgatatttcg aaggtgcttc atgagctaga taccttgcct tccaagatat 1380
ctaagaagat gggaatagaa gggatcgcgg aaaatgtaaa ggagaagaag atggagaagg 1440
agattctgat ggaagttatt gttggatgga ggaagtttgt gaaggagagg aagaagatga 1500
atggtgtgtg ctaagcaagt gtgttgcctt tgtgtggaaa tgaagaggta cttgcgagga 1560
ctttgcgttt atcagtttat gtgtttgtat atctatttga tccagttatt atggattata 1620
tacgcttgaa actcatttta agccattgtt attgaacgtt tatcaaatac tttattatgc 1680
caaat 1685

<210> SEQ ID NO 53
<211> LENGTH: 1771
<212> TYPE: DNA
<213> ORGANISM: Nicotiana tabacum

<400> SEQUENCE: 53
tattttcatt ttctctcctg ttttaatttc tgatcttctc cgtcgtacta ccaccactac 60
gccgccatgg ttctgtccaa gacagcgtcg gaaagtgacg tctccgttca ctccactttc 120
gcctcccgat atgttcgaac ttctcttccc aggtttaaaa tgccagagaa ttcaatacca 180
aaggaagcag catatcagat tataaatgat gagcttatgt tagatggaaa tccaaggcta 240
aatttagcat ctttcgttac aacatggatg gagccagaat gtaatacgtt aatgatggat 300
tccattaaca agaactacgt tgacatggat gaataccctg taaccactga gcttcagaat 360
cgatgtgtaa atatgatagc tcatttgttt aatgcaccac ttggagatgg agagactgca 420
gttggagttg gaactgttgg atcctctgaa gctattatgc ttgctggatt agcctttaag 480
agaaaatggc aaaataaaat gaaagcccaa ggcaagccct ttgataagcc caatattgtc 540
accggtgcta atgtccaggt gtgttgggag aaatttgcaa ggtattttga agtggagttg 600
aaagaagtaa aattgagtga tggatactat gtgatggacc ctgagaaagc tgtggaaatg 660
gtggatgaga ataccatttg tgttgctgct atcttaggtt caacactcaa tggtgaattt 720

-continued gaagatgtta agcgtttgaa tgaccttttg attgagaaga acaaagaaac cgggtgggac 780
actccaattc atgtggatgc agcaagtggt ggatttattg caccattcct ttatccagag 840
cttgaatggg actttagatt gccattggag aagagtatta atgtgagtgg tcacaaatat 900
ggtcttgtct atgctggtat tggttgggcc atttggagga ataaggaaga cttgcctgat 960
gaacttattt tccacatcaa ttaccttggt gctgatcaac ctactttcac tctcaacttc 1020
tctaaaggtt ctagccaagt aattgctcaa tattaccaac ttattcgctt gggttttgag 1080
ggttacaaga atgttatgga gaattgtcaa gaaaatgcaa gggtattaag agaaggaatt 1140
gaaaaaagtg gaagattcaa cataatctcc aaagaaattg gagttccctt agtagcattt 1200
tctcttaaag acaacagtca acacaatgag ttcgaaattt ctgaaactct tagaagattt 1260
ggatggattg ttctggcata tactatgcca ccaaatgctc aacatgtcac agttctcaga 1320
gttgtcatta gagaagattt ctcccgcaca ctagcggagc gactggtaat agacattgaa 1380
aaagtcttcc acggagtaga cacacttccg gcgagggtca acgctaagct agccgtggcc 1440
gaggcgaatg gcagcggcgt gcataagaaa acagatagag aagtgcagct agagattact 1500
actgcatggt tgaaatttgt tgctgataag aagaagaaga ctaatggagt ttgttaattt 1560
aatttaacaa aaaaaaagtt tataatatgg tgatttatgt aactactagc agtcgtactg 1620
cttgtttttt atatttgagt tgatgtgttt tttgagcact tgaggagcta gctagttatt 1680
gctagtgaaa aattggatga tatattttgg actactttgt aagtttgtat tattaatcca 1740
aattaaacga tatttatcat aaaaaaaaaa a 1771

<210> SEQ ID NO 54
<211> LENGTH: 1485
<212> TYPE: DNA
<213> ORGANISM: Arabidopsis thaliana

<400> SEQUENCE: 54
atggttttga caaaaaccgc aacgaatgat gaatctgtct gcaccatgtt cggatctcgc 60
tatgttcgca ctacacttcc caagtatgag attggtgaga attcgatacc gaaagacgct 120
gcgtatcaga tcataaaaga tgagctgatg cttgatggta acccaaggct taacctagct 180
tcttttgtga ctacatggat ggaaccagag tgtgacaaac tcatcatgga ctctatcaat 240
aagaactacg ttgatatgga tgagtaccct gtcacaactg agctccagaa ccgatgtgta 300
aacattatag ctcgactgtt caatgcgcca ctcgaggaat ctgagacggc ggtgggagta 360
gggacagttg gttcttcaga agccatcatg ttagccggat tggccttcaa aagaaaatgg 420
cagaacaaac gcaaggctga gggtaaaccc tatgacaaac ccaacattgt caccggagcc 480
aatgttcaag tttgctggga gaaattcgct cggtacttcg aggtggagct aaaggaagta 540
aacctaagtg aaggttacta cgtgatggat ccagacaaag cagcagaaat ggtagacgag 600
aacacaatct gtgtcgcagc catattggga tccacactca acggtgagtt cgaagacgtg 660
aaacgtctca atgacttgct agtcaagaaa aacgaggaga ctggttggaa cacaccgatc 720
cacgtggatg cagcaagtgg agggttcata gctccgttta tctatcctga attagaatgg 780
gactttaggc ttcctttggt taagagcatc aacgtgagtg gtcacaagta tggactagtc 840
tatgctggta ttggttgggt cgtgtggagg gcagcagagg atttacctga agagcttatc 900
tttcatatta attatcttgg tgctgatcaa cccactttca ctctcaattt ctccaaggga 960
tcgagccaaa ttattgctca atactaccag ctcattcgtc ttggattcga ggggtacaaa 1020

-continued

```
aatgtgatgg agaattgcat agagaacatg gtggttctca aagaaggtat agagaaaaca   1080

gagcgtttca acatagtctc aaaggaccaa ggagtgccag tcgtcgcctt ctctctcaag   1140

gaccatagtt tccacaacga gttcgagatc tctgagatgc tacgtcgttt tggctggatc   1200

gtcccagctt acactatgcc tgccgatgca cagcacatca cggttctgcg tgttgtcatc   1260

agggaagatt tctcaagaac actcgcggag agacttgttg ctgatatttc gaaggtgctt   1320

catgagctag ataccttgcc ttccaagata tctaagaaga tgggaataga agggatcgcg   1380

gaaaatgtaa aggagaagaa gatggagaag gagattctga tggaagttat tgttggatgg   1440

aggaagtttg tgaaggagag gaagaagatg aatggtgtgt gctaa                   1485
```

```
<210> SEQ ID NO 55
<211> LENGTH: 1705
<212> TYPE: DNA
<213> ORGANISM: Nicotiana tabacum

<400> SEQUENCE: 55

aaaatatctc catttctcc cttgttttag tctctgatct tctccgtcgt actaccacca      60

ctacgccgcc atggttctgt ccaagacagc gtcggaaagt gacgtctcca tccactccac    120

tttcgcttcc cgatatgttc gtacttctct tccgaggttt aagatgccag agaattcgat    180

accaaaggaa gcagcatatc aaatcataaa tgatgagctt atgttagatg gaaatccaag    240

actaaattta gcatcttttg tgacaacatg gatggaacca gagtgtaaca aactgatgat    300

ggattccatt aacaagaatt acgttgacat ggatgaatac cctgtaacca ctgaacttca    360

gaatcgatgt gtaaacatga tagctcattt gtttaacgca ccacttggag atggagagac    420

tgcagttgga gttggaactg ttggatcctc tgaggctatt atgcttgctg gattagcttt    480

caagagaaaa tggcaaaata aaatgaaagc ccaaggcaag ccctgtgaca agcccaatat    540

tgtcactggt gccaatgtcc aggtgtgttg ggagaaattt gcaaggtatt ttgaagtgga    600

gctaaaggaa gtaaagttga gtgatggata ctatgtgatg gaccctgaga aagctgtgga    660

aatggtggat gagaacacaa tttgtgtagc tgctatcttg ggttccacac tcaatggtga    720

atttgaagat gttaagcgct tgaatgacct cttgattgag aagaacaaag aaaccgggtg    780

ggacactcca attcatgtgg atgcagcaag tggtggattt attgcaccat tcctttatcc    840

agagcttgaa tgggacttta gattgccatt ggtgaagagt ataaacgtga gtggtcacaa    900

atatggtctt gtttatgctg gtattggttg ggccatttgg aggaataagg aagacttacc    960

tgacgaactt atcttccaca ttaattatct tggtgctgat caacctactt tcactctcaa   1020

cttctctaaa ggttctagcc aagtaattgc tcaatattac caacttattc gcttgggttt   1080

tgagggttac aagaatgtta tggagaattg tcaagaaaat gcaagggtac taagagaagg   1140

acttgaaaaa agtggaagat tcaacataat atccaaagaa attggagttc cattagtagc   1200

tttctctctt aaagacaaca gtcaacacaa tgagttcgaa atttctgaaa ctcttagaag   1260

atttggatgg attattcctg catatactat gccaccaaat gctcaacatg tcacagttct   1320

cagagttgtc attagagaag atttctcccg tacactcgcc gagcgactgg taatagacat   1380

tgaaaaagtc ctccacgagc tagacacact tccggcgagg gtcaacgcta agctagccgt   1440

ggccgaggcg aatggcagcg gcgtgcataa gaaaacagat agagaagtgc agcttgagat   1500

tactactgca tggaagaaat ttgttgctga taagaagaag aagactaacg gagtttgtta   1560

atttaattta acaaaatatg tttataatta atatgatgat ttataactac tagcagtggt   1620

actgcttgtt tttatatttg aattgttggg ttttttgagt atgaggagct agctatttat   1680
```

-continued

```
tgctagtgaa atattggttg aaaaa                                          1705


<210> SEQ ID NO 56
<211> LENGTH: 1929
<212> TYPE: DNA
<213> ORGANISM: Nicotiana tabacum

<400> SEQUENCE: 56

atctccattt tctcccttgt tttagtctct gatcttctcc gtcgtactac caccactacg      60

ccgccatggt tctgtccaag acagcgtcgg aaagtgacgt ctccatccac tccactttcg     120

cttcccgata tgttcgtact tctcttccga ggtttaagat gccagagaat tcgataccaa     180

aggaagcagc atatcaaatc ataaatgatg agcttatgtt agatggaaat ccaagactaa     240

atttagcatc ttttgtgaca acatggatgg aaccagagtg taacaaactg atgatggatt     300

ccattaacaa gaattacgtt gacatggatg aataccctgt aaccactgaa cttcagaatc     360

gatgtgtaaa catgatagct catttgttta acgcaccact tggagatgga gagactgcag     420

ttggagttgg aactgttgga tcctctgagg ctattatgct tgctggatta gctttcaaga     480

gaaaatggca aaataaaatg aaagcccaag gcaagccctg tgacaagccc aatattgtca     540

ctggtgccaa tgtccaggtg tgttgggaga aatttgcaag gtattttgaa gtggagctaa     600

aggaagtaaa gttgagtgat ggatactatg tgatggaccc tgagaaagct gtggaaatgg     660

tggatgagaa cacaatttgt gtagctgcta tcttgggttc cacactcaat ggtgaatttg     720

aagatgttaa gcgcttgaat gacctcttga ttgagaagaa caaagaaacc gggtgggaca     780

ctccaattca tgtggatgca gcaagtggtg aatttattgc accattcctt tatccagagc     840

ttgaatggga ctttagattg ccattggtga agagtattaa cgtgagtggt cacaaatatg     900

gtcttgttta tgctggtatt ggttgggcca tttggaggaa taaggaagac ttacctgacg     960

aacttatctt ccacattaat tatcttggtg ctgatcaacc tactttcact ctcaacttct    1020

ctaaaggttc tagccaagta attgctcaat attaccaact tattcgcttg ggttttgagg    1080

gttacaagaa tgttatggag aattgtcaag aaaatgcaag ggtactaaga gaaggacttg    1140

aaaaaagtgg aagattcaac ataaatatcca aagaaattgg agttccatta gtagctttct    1200

ctcttaaaga caacagtcaa cacaatgagt tcgaaatttc tgaaactctt agaagatttg    1260

gatggattat tcctgcatat actatgccac caaatgctca acatgtcaca gttctcagag    1320

ttgtcattag agaagatttc tcccgtacac tcgccgagcg actggtaata gacattgaaa    1380

aagtcctcca cgagctagac acacttccgg cgagggtcaa cgctaagcta gccgtggccg    1440

aggcgaatgg cagcggcgtg cataagaaaa cagatagaga agtgcagctt gagattacta    1500

ctgcatggaa gaaatttgtt gctgataaga agaagaagac taacggagtt tgttaattta    1560

atttaacaaa atatgtttat aattaatatg atgatttata actactagca gtggtactgc    1620

ttgtttttat atttgaattg ttgggttttt tgagtatgag gagctagcta tttattgcta    1680

gtgaaatatt ggttgatttt ggactacttt gtattattaa tgttaatttt cttaagtact    1740

taatatgagg atatttatca tgcatgtgat atagaaaaaa gttgtgagtg cctgaggtct    1800

agtttaatcc tttatattcc aatataaaaa acatatacat gggcggaggt agaaaaacca    1860

atatatttgt attaagaata ttattatatt aaattttaaa ttcaattatt agatcccaaa    1920

aaaaaaaaa                                                            1929


<210> SEQ ID NO 57
```

<211> LENGTH: 1509
<212> TYPE: DNA
<213> ORGANISM: Arabidopsis thaliana

<400> SEQUENCE: 57

```
atggtgctct cccacgccgt atcggagtcg gacgtctccg tccactccac attcgcatca     60
cgttacgtcc gtacttcact tcctaggttc aagatgccgg aaaactcgat tcctaaggaa    120
gcggcgtatc agatcatcaa cgacgagctg atgcttgacg ggaatccacg gttgaactta    180
gcctcctttg tgacgacatg gatggagcct gagtgtgata aactcatcat gtcctccatc    240
aacaagaact atgttgacat ggacgagtac cccgtcacca ccgaacttca gaaccgatgt    300
gtgaacatga ttgcacatct attcaatgca ccgttagaag aggcggagac cgccgtcgga    360
gtaggaaccg ttggatcatc ggaggccata atgttggccg gtttggcctt caagcgtaaa    420
tggcagaaca agcgcaaagc tgaaggcaaa cccgtcgata aacccaacat tgtcaccgga    480
gccaatgttc aagtgtgttg ggagaaattc gctaggtact ttgaggttga acttaaggaa    540
gtgaaattga gtgaaggata ctatgtgatg gaccctcaac aagctgttga tatggttgat    600
gagaacacca tttgtgttgc ggacattctt ggttccactc ttaatggaga attcgaagat    660
gttaaactct tgaacgatct cttggtcgaa aagaacaaag aaaccggatg ggatacacca    720
atccacgtgg atgcggcaag tggaggattc attgcaccgt ttttgtatcc ggaattggaa    780
tgggacttta gacttccctt ggtgaagagt atcaatgtga gtggtcacaa gtatggactt    840
gtgtacgcag ggattggttg ggtgatctgg agaaacaaag aggatttgcc tgaggaactc    900
atcttccata tcaattatct tggtgctgac caacccacct ttactctcaa tttctccaaa    960
ggttcaagtc aagtcattgc tcaatactac caacttatcc gattgggcca cgagggttac   1020
agaaatgtga tggagaattg cagagagaat atgatcgtcc taagggaagg acttgagaag   1080
acagaaaggt tcaacatcgt ctcaaaggac gagggagtgc cacttgtcgc tttctccttg   1140
aaagatagca gctgtcacac tgagttcgaa atctccgaca tgcttcgcag gtatggatgg   1200
atagtgccgg cctacacaat gcctccaaat gcacaacaca tcactgttct tcgtgtggtt   1260
atcagagaag atttctcgag aacactcgct gagagacttg tgatcgatat agagaaagtg   1320
atgcgtgagc tcgatgagct tccttcgaga gtgattcaca aaatatcact tggacaagag   1380
aagagtgaat ctaacagcga taacttgatg gtcacggtga agaagagcga tatcgacaag   1440
cagagagata tcatcactgg ctggaagaag tttgtcgccg acaggaagaa gacgagtggt   1500
atctgctaa                                                           1509
```

<210> SEQ ID NO 58
<211> LENGTH: 1785
<212> TYPE: DNA
<213> ORGANISM: Petunia hybrida

<400> SEQUENCE: 58

```
aaagagtaca aactaatatc cacttaaatt gtatttctcc attttctctc tttatttagt     60
ctgtcataac aatggttcta tcaaagacag tgtcgcagag cgatgtgtcc attcactcca    120
cgtttgcttc tcgatatgtt cgaacttctc ttcccaggtt taaaatgcca gataattcga    180
taccaaaaga agcagcatat cagatcataa atgatgaact gatgttagat ggaaacccaa    240
ggctgaactt ggcttctttt gttacaacat ggatggaacc agagtgtgat aagttgatga    300
tggactctat taacaagaac tatgttgata tggatgaata tcctgttacc actgagcttc    360
agaatcgatg tgtaaacatg atagctcatt tgtttaatgc accacttgaa gatggagaaa    420
```

```
ctgcagttgg agttggaact gttggatcct ctgaagccat tatgcttgct ggattagctt    480
tcaagagaaa atggcagaac aaaatgaaag cccaaggcaa accctgtgac aagcccaaca    540
ttgttactgg tgcaaatgtc caggtgtgct gggagaaatt tgcaaggtat tttgaagtgg    600
agctaaagga agtaaagctt agtgaaggat actatgtgat ggaccctgag aaagctgtgg    660
agatggtgga tgaaaacacc atttgtgtag ctgctatctt aggttccacc ctcaatggag    720
aatttgaaga cgttaagcgc ttgaatgatc tcttggtcga gaagaacaaa gaaaccgggt    780
gggacactcc aattcatgtg gatgcagcaa gtggtggatt tattgcaccg ttcatttacc    840
cagagcttga gtgggacttt agattgccat tagtgaagag cattaatgta agtggtcaca    900
aatatggtct tgtctatgct ggtattggtt gggtcgtttg gaggaacaag gatgatttgc    960
ctgatgaact tatcttccac attaattatc ttggtgctga tcaacctact ttcactctca   1020
acttttctaa aggttctagc caagtaattg ctcaatatta ccaacttatt cgcttgggtt   1080
atgagggtta caagaatgtg atggagaatt gtcaagaaaa tgcatcggta ctaagagaag   1140
ggctagaaaa gacaggaaga ttcaacataa tctccaaaga aattggagta cctttagtag   1200
cattctctct taaagacaac aggcaacaca acgagttcga gatttctgaa actttaagga   1260
gatttggttg gattgttcct gcatatacta tgccaccaaa cgcacaacac attacagttc   1320
tcagagttgt gatcagagaa gatttctccc gtacgcttgc agaacgactg gtaagagaca   1380
tcgaaaaagt ccttcatgaa cttgacacac tccctgcacg tgtcaatgct aagctcgctg   1440
tggccgagga gcaggcggct gcgaatggca gcgaggtgca taagaaaaca gatagcgaag   1500
tgcagttgga gatgataact gcatggaaga agtttgttga agaaaagaag aagaagacta   1560
atcgagtttg ttaattaatt atattagtgt ttataatatg atgaatatgg ctattatcat   1620
tggtgactgc ttgttagtat attagctgtg attatcacca atatgagttt ggttttcttg   1680
atttggttct tttcagtact tgaaaagttg ttattgatat tgtaaaattg tactttttaa   1740
ctatttggat tattaatgcc aattttctag tgtacttaat aaaaa                   1785
```

<210> SEQ ID NO 59
<211> LENGTH: 906
<212> TYPE: DNA
<213> ORGANISM: Oryza sativa

<400> SEQUENCE: 59

```
ggagagtttg aggatgttaa gttattgaat aatctcctaa cagaaaagaa taaggaaact     60
gggtgggatg tgccaattca tgttgatgca gcaagtggag gatttatagc accttttcta    120
taccctgagc ttgaatggga cttcaggcta ccactggtga agagcatcaa tgtcagtggg    180
cacaagtatg gccttgtgta tccaggtgtt ggttgggtca tttggcgaag caaagaggat    240
ttgcctgaag aactcatttt ccatataaac tatctgggga cagaccagcc gacgttcact    300
ctgaacttct ccaaaggttc cagccagata atcgcacagt actatcaact aatacgcctg    360
ggattcgagg gatacaagaa catcatgcag aattgcatgg agaccccagc aatattaagg    420
gaaggcatag aggcgactgg tcgattcgaa atcctctcca aggaggccgg tgtgcccttg    480
gtggcgttct cgctcaaggc cagcggcagg tacaccgtgt tcgacatctc cgagcacctg    540
aggaggttcg gctggatcgt gccggcgtac accatgccgg ccaacgccga gcacgtcgcc    600
atcctccgcg tcgtcatcag ggaggacttc agccggagcc tcgccgagcg gctcgtctcg    660
gacatcgtca agatcctgca cgagctggac gcccattcgg cccaggtgct gaagatctcc    720
```

-continued agcgccatcg cgaagcagca atcgggcgac gatggcgcgg tcaccaagaa gagcgtcctg 780
gagaccgaga gggagatctt cgcgtactgg agggaccagg tgaagaagaa gcagaccgga 840
atctgctagt gtggctctgt gagaaatgct tgaataacgt ggcatgctcg atttgtgcat 900
gggatg 906

<210> SEQ ID NO 60
<211> LENGTH: 1783
<212> TYPE: DNA
<213> ORGANISM: Lycopersicon esculentum

<400> SEQUENCE: 60
aaaaaatggt gttaacaacg acgtcgataa gagattcaga agagagcttg cactgtacat 60
ttgcatcaag atatgtacag gaacctttac ctaagttcaa aatgcctaaa aaatccatgc 120
cgaaagaagc agcttatcag attgtaaacg acgagcttat gttggatggt aaccccaggt 180
tgaatttagc ttcctttgtt agcacatgga tggagcccga gtgcgataag ctcatcatgt 240
catccattaa taaaaactat gtcgacatgg atgagtatcc tgtcaccact gaacttcaaa 300
atagatgtgt taacatgtta gcacatcttt tccatgcccc ggttggtgat gatgagactg 360
cagttggagt tggtacagtg ggttcatcag aggcaataat gcttgctggc cttgctttca 420
aacgcaaatg gcaatcgaaa agaaaagcag aaggcaaacc tttcgataag cctaatatag 480
tcactggagc taatgtgcag gtctgctggg aaaaatttgc aaggtatttt gaggttgagt 540
tgaaggaggt gaaactaaaa gaaggatact atgtaatgga ccctgccaaa gcagtagaga 600
tagtggatga gaatacaata tgtgttgctg caatccttgg ttctactctg actggggagt 660
ttgaggatgt gaagctccta aacgagctcc ttacaaaaaa gaacaaggaa accggatggg 720
agacaccgat tcatgtcgat gctgcgagtg gaggatttat tgctcctttc ctctggccag 780
atcttgaatg ggatttccgt ttgcctcttg tgaaaagtat aaatgtcagc ggtcacaagt 840
atggccttgt atatgctggt gtcggttggg tgatatggcg gagcaaggaa gacttgcccg 900
atgaactcgt ctttcatata aactaccttg ggtctgatca gcctactttt actctcaact 960
tctctaaagg ttcctatcaa ataattgcac agtattatca gttaataaga cttggctttg 1020
agggttataa gaacgtcatg aagaattgct tatcaaacgc aaaagtacta acagagggaa 1080
tcacaaaaat ggggcggttc gatattgtct ctaaggatgt gggtgttcct gttgtagcat 1140
tttctctcag ggacagcagc aaatatacgg tatttgaagt atctgagcat ctcagaagat 1200
ttggatggat cgtccctgca tacacaatgc caccggatgc tgaacacatt gctgtactgc 1260
gggttgtcat tagagaggat ttcagccaca gcctagctga gagacttgtt tctgacattg 1320
agaaaattct gtcagagttg gacacacagc ctcctcgttt gcccaccaaa gctgtccgtg 1380
tcactgctga ggaagtgcgt gatgacaagg gtgatgggct tcatcatttt cacatggata 1440
ctgtagagac tcagaaagac attatcaaac attggaggaa aatcgcaggg aagaagacca 1500
gcggagtctg ctaggtctgg ccacacttgt tatctgggct ccgcttccat cgccatcctg 1560
tagtatgtat tacgtgtgtt gtttccatct tatgtagtag ttggtactgt aatctgtgta 1620
aatgctttca tgatcttggc tctgtatatg ctaaataagc actgcatttc aagttcctgg 1680
aagtatttat gtatgaatca atccgggcat aattggtaga atgccctctc tgcgtcatct 1740
ttgaatttca cgtgcaataa tatttgaaat ctacacctat tat 1783

<210> SEQ ID NO 61
<211> LENGTH: 1503

<212> TYPE: DNA
<213> ORGANISM: Oryza sativa

<400> SEQUENCE: 61
atggttctga cgcacgtcga ggcggtggag gagggcagcg aggcggcggc cgccgtgttc 60
gcgtcgaggt acgtgcagga cccggtgccg aggtacgagc tcggcgagag gtcgatatcc 120
aaggacgccg cgtaccagat cgtccacgac gagctcctcc tggacagcag cccgcgcctg 180
aacctggcgt ccttcgtcac cacctggatg gagcccgagt gcgacaggct catcctcgag 240
gccatcaaca agaactacgc cgacatggac gagtaccccg tcaccaccga gctccagaac 300
cggtgcgtga acatcatagc gaggctgttc aatgcgccgg tgggcgacgg cgagaaggcg 360
gtcggggtgg gcacggtggg gtcgtcggag gccataatgc tggccgggct ggcgttcaag 420
cggcggtggc agaaccggcg gaaggcggcg gggaagcccc acgacaagcc caacatcgtg 480
acgggggcca acgtgcaggt gtgctgggag aagttcgcgc gctacttcga ggtggagctc 540
aaggaggtga agctgaccga aggctgctac gtgatggacc ccgtcaaggc cgtggacatg 600
gtcgacgaga acaccatctg cgtcgccgcc atcctcggct ccaccctcac cggcgagttc 660
gaggacgtca ggcgcctcaa cgacctcctc gccgccaaga acaagcggac gggttgggac 720
acgccgatcc acgtcgacgc ggcgagcggc gggttcatcg cgccgttcat ctacccggag 780
ctggagtggg acttccggct gccgctggtg aagagcatca acgtcagcgg ccacaagtac 840
gggctcgtct acgccggcgt cgggtgggtc atctggcgca acaaggagga cctccccgag 900
gagctcatct tccacatcaa ctacctcggc gccgaccagc caaccttcac gctcaacttc 960
tccaaagggt ccagtcagat tattgcgcaa tattaccagt ttcttcgact cggatttgag 1020
gggtacaaga gcgtgatgaa gaactgcatg gagagcgcga ggacgctccg ggagggcctg 1080
gagaagacgg ggcggttcac catcatctcc aaggaggagg gcgtgccgct ggtggccttc 1140
acgttcaagg acggcgccgg cgcgcaggcc ttcaggctgt cgtcgggcct gcgccggtac 1200
gggtggatcg tgccggcgta cacgatgccg gcggcgctgg agcacatgac ggtgctccgc 1260
gtcgtcgtcc gggaagactt cggccggccg ctcgccgagc ggttcctgtc ccacgtcagg 1320
atggccctgg acgagatgga cctcgccgcc agggcccccg tgcccagggt gcagctcacc 1380
atcgagctcg gccccgcccg gaccgccggc gaggaggcct cgatcagggt ggtcaagagc 1440
gaggccgtgc ccgtgcgcaa gagcgtcccg ctcgtcgccg gcaaaaccaa gggcgtttgc 1500
tag 1503

<210> SEQ ID NO 62
<211> LENGTH: 1542
<212> TYPE: DNA
<213> ORGANISM: Oryza sativa

<400> SEQUENCE: 62
atggtgctct cccacggcgt gtcgggctcc gatgagtccg tccactccac gttcgcctcc 60
cgctacgtcc gcacctccct ccccaggcac gcacgctcgc ctctgtctcg agcgccattg 120
gcgccgatcg attcggtgat tgattgggag ttccggatgc cggagcagtc gatccccaag 180
gaggcggcgt accagatcat caacgacgag ctgatgctgg acggcaaccc gcggctgaac 240
ctcgcgtcgt tcgtcaccac gtggatggag cccgagtgcg acaagctcat ccaggcctcc 300
gtcaacaaga actacgtcga catggacgag taccccgtca ccaccgaact ccagaaccga 360
tgtgtgaaca tgattgcaca cctcttcaat gctcctctag ggactctgga aacggccgtc 420
ggagtcggca ctgtcggctc gtctgaggcc atcatgctcg ccggtttggc cttcaagagg 480
aggtggcaga acaagatgaa ggcagccggc aagccatgcg acaagcctaa cattgtcacc 540
ggcgccaatg tccaagtttg ctgggagaag ttcgcgcgat acttcgaggt tgagctcaag 600
gaagtgaagc tgagtgacgg ctactacgtc atggacccag ctaaggccgt ggatatggtc 660
gacgagaaca ccatctgcgt cgcggcgatc ctcgggtcga cgctgaacgg ggagttcgag 720
gacgtgaagc tgctcaacga tctgctcacc aagaagaacg ctgaaacagg ctgggacacg 780
ccgatccacg tggacgcggc gagcggcggg ttcatcgcgc cgttcctgta cccggagctg 840
gagtgggact tccggctgcc gctggtgaag agcatcaacg tgagcgggca caagtacggc 900
ctcgtctacg ccgggatcgg gtggtgcatc tggaggagca aggaggatct gcctgaggag 960
ctcatcttcc acatcaacta cctcggcgcc gaccagccca ccttcaccct caacttctcc 1020
aagggttcca gccaggtcat tgcacagtat taccaactaa tccgcctagg ctttgagggg 1080
tacaagaaca tcatggagaa ctgccaggag aacgcgatgg tgctgaagca ggggctggag 1140
aagacggggc ggttcaacat cgtgtccaag gacaacggcg tgccgctggt ggccttctcc 1200
ctcaaggaca gcgcccggca caacgagttc gagatctccg acttcctccg ccgcttcggc 1260
tggatcgtgc cggcctacac catgcccccc gacgcgcagc acgtcaccgt gctccgcgtc 1320
gtcatccgcg aggacttcag ccgcacgctc gccgagcgcc tcgtgctcga cgtcgagaag 1380
gtgctgcacg agctcgacgc gctccccgcc cgcgtcgtcg ccaacggcgg cgacgccgcc 1440
gccgcgtcgg cgagcgagag ggagatggag aagcagcgcg aggtgatctc cctctggaag 1500
agggccgtgc tggccaagaa gaagaccaac ggcgtctgct aa 1542

<210> SEQ ID NO 63
<211> LENGTH: 3983
<212> TYPE: DNA
<213> ORGANISM: Oryza sativa

<400> SEQUENCE: 63
ctcgatcatt aactgtgagt taagtgagtt atttgtacac ttattaacta gttccgcgag 60
catatcttaa atacatgaca tgtcatgtag aattgaaaag ttacatataa aattaaaaaa 120
aacatgtatt tttttccttt cccatggtac tacaattggc aatgcaaaaa attagtaaaa 180
ccaaatcatt ttagtttcat gttttgaaga gtgtagttct cggcttgcca tcaaacatga 240
gcacctttta ttttcgatct ccatgttctt ttccacccaa ttacatctgc acatttttag 300
aagtattttt tttcaatcct agatgacatg ccacgtgtac aaggtatgct cacttggata 360
tgtagtttga tggacgtaca tatgacttac ttaactcaga ctagtgatcc aattgtgtat 420
tttgaaagta gagtgcacat atatgataca tataaacaag ttgaatggca cttcatgcat 480
tttactctta cgtctatcat aaaaaaacaa aaagaagcaa tcctcaactc atatacccag 540
gtaaaaacac acctttgcaa acttaaacgg tgtgagccaa tatccatact atcaagattt 600
gaaatgtatc caattaggcc aacctacacc aaaacttttt ttttaataat ggaacagaat 660
cccaccaaaa actaaatatg ctcaatgttt ctatttgtga agttatctgg gggagagcag 720
tttataattt gagtgcatat gctttaatat tttatatgtc attcaaatgg ttgttttttt 780
aaaagaaaat atagtgccac gttatatatc agtccatcaa cacacaaatc taaataaact 840
tgtactaagt tgtaaaaatc caactagagt actatccaac ctacatgggg atgtgatacg 900
tatcatctag cgcaacaaat ctaaagaggg aattatctaa atttattgca tgtccatatt 960
cactgtccta aatggtgtta ctcccatcta gatcgggttt gtttggaatg gaaggagtat 1020

-continued

```
gtccagatac atacaaaatg aatgtaccaa aaaagtcaaa gtgatttata atgtagaacg   1080
gagggagtat catactacaa tccttttgaa aacgatatca tttctttatt atccttttgg   1140
aaactatatc ggtaccgtcg aggatttttc ataattttga aatttagcca cttcgatagg   1200
atgcaaatat aaattgaaaa aaactaaatt ccataataaa aaacaatata attttctatt   1260
atttaacggt atcggtactg tcgaaaattt ttcatactgt tttcatccct attcaggatg   1320
aatgagacgc aacaacacga gacgtcgaga cccctcacgg aggcacgaaa aatccatttc   1380
ttgatgcggg ggaaggagtg ttagctcaac cggggggggct aatcactatc gaataattta   1440
acaagccacg caacgaagca gcaggaggaa gcaaccaaag gctagcaagc aaagcagcac   1500
ctcagcatta cgcaataatt caggccgaag cagagtcacc cagcagcaag aacatgggac   1560
aagcaaagca caagccacat tctaaggtag tgtacaagct agctgacctg ggagtccagt   1620
atataagtgc gtgtagccgc atgtacacag ggtggccaaa acgagacgtg cagagagaga   1680
caccaatctc gtacgtagca tatctacatc gcaggaacac ccaaatcact cgtgcgtagg   1740
tatggttctg acgcacgtcg aggcggtgga ggagggcagc gaggcggcgg ccgccgtgtt   1800
cgcgtcgagg tacgtgcagg acccggtgcc gaggtacgag ctcggcgaga ggtcgatatc   1860
caaggacgcc gcgtaccaga tcgtccacga cgagctcctc ctggacagca gcccgcgcct   1920
gaacctggcg tccttcgtca ccacctggat ggagcccgag tgcgacaggc tcatcctcga   1980
ggccatcaac aagaactacg ccgacatgga cgagtacccc gtcaccaccg agctccaggc   2040
aagcaatcaa acaaaccaaa ccatataccc tcgtctcctc catatccttt cgttgcattg   2100
cgttgtggtt gacgtacgac gacgatggcc ctggcgttgc agaaccggtg cgtgaacatc   2160
atagcgaggc tgttcaatgc gccggtgggc gacggcgaga aggcggtcgg ggtgggcacg   2220
gtggggtcgt cggaggccat aatgctggcc gggctggcgt tcaagcggcg gtggcagaac   2280
cggcggaagg cggcggggaa gccccacgac aagcccaaca tcgtgacggg ggccaacgtg   2340
caggtgtgct gggagaagtt cgcgcgctac ttcgaggtgg agctcaagga ggtgaagctg   2400
accgaaggct gctacgtgat ggaccccgtc aaggccgtgg acatggtcga cgagaacacc   2460
atctgcgtcg ccgccatcct cggctccacc ctcaccggcg agttcgagga cgtcaggcgc   2520
ctcaacgacc tcctcgccgc caagaacaag cggacgggtt gggacacgcc gatccacgtc   2580
gacgcggcga gcggcgggtt catcgcgccg ttcatctacc cggagctgga gtgggacttc   2640
cggctgccgc tggtgaagag catcaacgtc agcggccaca agtacgggct cgtctacgcc   2700
ggcgtcgggt gggtcatctg gcgcaacaag gaggacctcc ccgaggagct catcttccac   2760
atcaactacc tcggcgccga ccagccaacc ttcacgctca acttctccaa aggcacgaaa   2820
ttatttttcc agaattaaat gatccgtaca tatatagagt ggagtagtac attttgtgac   2880
ttggcaagtt catttttgtg cagggtccag tcagattatt gcgcaatatt accagtttct   2940
tcgactcgga tttgaggtat actgagacta attgccccaa aatttcgaat ttaaaatttt   3000
gaaaatttta tgtcaaactc ctataatttc gatttttttt ttggccggat gcacatccta   3060
ccggaacaca ccggcataac tgaaatttcg caaaattctt tctgaaattg tgcacattta   3120
tttcagtttg attgaaccgt tgggttgttt gattgttgca ggggtacaag agcgtgatga   3180
agaactgcat ggagagcgcg aggacgctcc gggagggcct ggagaagacg gggcggttca   3240
ccatcatctc caaggaggag ggcgtgccgc tggtggcctt cacgttcaag gacggcgccg   3300
gcgcgcaggc cttcaggctg tcgtcgggcc tgcgccggta cgggtggatc gtgccggcgt   3360
```

```
acacgatgcc ggcggcgctg gagcacatga cggtcgtccg cgtcgtcgtc cgggaagact   3420

tcggccggcc gctcgccgag cggttcctgt cccacgtcag gatggccctg gacgagatgg   3480

acctcgccgc cagggccccc gtgcccaggg tgcagctcac catcgagctc ggccccgccc   3540

ggaccgccgg cgaggaggcc tcgatcaggg tggtcaagag cgaggccgtg cccgtgcgca   3600

agagcgtccc gctcgtcgcc ggcaaaacca agggcgtttg ctagaccggg ttaaattttt   3660

ttttaaaata ctggtgggaa cacgaccaaa ataaaatttc aaaatgggag cgtactaaac   3720

cttctttatg ctacagtaac tatgtagtac aagcatgccg aaagttaatc atcgtgtgta   3780

atcgtattag agtttgcaac agcatattat aatgtggaga agaacacgca agcgacatca   3840

accaggactc tgcacttctg atgaagttct gaaacccata aggattcaga taaacatgag   3900

cagacactga aatatgtatg tacataaaaa atttgtgcga ggcatgcaca tcatgcttga   3960

gcacgttatt gttgcagaaa aca                                            3983
```

<210> SEQ ID NO 64
<211> LENGTH: 2064
<212> TYPE: DNA
<213> ORGANISM: Oryza sativa

<400> SEQUENCE: 64

```
aaggagagag ccttcccgtc tcctttttt ccttccatcc aaaaaattcc aaatggagta      60

gtagttcaca tttttacacc gtcgtcttcg caaatttaat actactatac gaaggaggag    120

gaagctctcg cgccgcggtc gctttccttc ccctaaatta aatcccgtgc gacgcgtaga    180

gacctcctcc tccgctttct cctccaaagc ccaagctaat ccccctcctc ttcctcgtcg    240

ccggcgagag ctcttcgtct tctccaactc gaccggaagc aagcgcgctt ccgatccgcc    300

atggtgctct cccacggcgt gtcgggctcc gatgagtccg tccactccac gttcgcctcc    360

cgctacgtcc gcacctccct ccccaggttc cggatgccgg agcagtcgat ccccaaggag    420

gcggcgtacc agatcatcaa cgacgagctg atgctggacg gcaacccgcg gctgaacctc    480

gcgtcgttcg tcaccacgtg gatggagccc gagtgcgaca agctcatcca ggcctccgtc    540

aacaagaact acgtcgacat ggacgagtac cccgtcacca ccgaactcca gaaccgatgt    600

gtgaacatga ttgcacacct cttcaatgct cctctagggg actctgaaac ggccgtcgga    660

gtcggcactg tcggctcgtc tgaggccatc atgctcgccg gtttggcctt caagaggagg    720

tggcagaaca agatgaaggc agccggcaag ccatgcgaca agcctaacat tgtcaccggc    780

gccaatgtcc aagtttgctg ggagaagttc gcgcgatact tcgaggttga gctcaaggaa    840

gtgaagctga gtgacggcta ctacgtcatg gacccagcta aggccgtgga tatggtcgac    900

gagaacacca tctgcgtcgc ggcgatcctc gggtcgacgc tgaacgggga gttcgaggac    960

gtgaagctgc tcaacgatct gctcaccaag aagaacgctg aaacaggctg ggacacgccg   1020

atccacgtgg acgcggcgag cggcgggttc atcgcgccgt tcctgtaccc ggagctggag   1080

tgggacttcc ggctgccgct ggtgaagagc atcaacgtga gcgggcacaa gtacggcctc   1140

gtctacgccg ggatcgggtg gtgcatctgg aggagcaagg aggatctgcc tgaggagctc   1200

atcttccaca tcaactacct cggcgccgac cagcccacct tcaccctcaa cttctccaag   1260

ggttccagcc aggtcattgc acagtattac caactaatcc gcctaggctt tgaggggtac   1320

aagaacatca tggagaactg ccaggagaac gcgatggtgc tgaagcaggg gctggagaag   1380

acggggcggt tcaacatcgt gtccaaggac aacggcgtgc cgctggtggc cttctccctc   1440

aaggacagcg cccggcacaa cgagttcgag atctccgact tcctccgccg cttcggctgg   1500
```

atcgtgccgg cctacaccat gccccccgac gcgcagcacg tcaccgtgct ccgcgtcgtc 1560
atccgcgagg acttcagccg cacgctcgcc gagcgcctcg tgctcgacgt cgagaaggtg 1620
ctgcacgagc tcgacgcgct ccccgcccgc gtcgtcgcca acggcggcga cgccgccgcc 1680
gcgtcggcga gcgagaggga gatggagaag cagcgcgagg tgatctccct ctggaagagg 1740
gccgtgctgg ccaagaagaa gaccaacggc gtctgctaaa gcaagtcagc tgcgcagcgg 1800
ggatcgtata ctattattat ggtccacttc gtaattgcga cttcttaatt tttaccgtgt 1860
cgatcggttt accgtctcaa gtctgctctc atccgatttt cggattgatg ctgcttaatt 1920
atgtaccaag ttaattaatt cttagaggac ggaatagttc cgactcaata cgaagcattg 1980
cctgtataag tcgaacacgg gatcatgcat tttacgttgg gtgtgtagca gtgaattgat 2040
cagtgatgct ccatctctac tctg 2064

<210> SEQ ID NO 65
<211> LENGTH: 1473
<212> TYPE: DNA
<213> ORGANISM: Hordeum vulgare

<400> SEQUENCE: 65
atggtggtga ccgtggcagc gacggggccg gacacggccg agacgctgca ctccaccacc 60
ttcgcctccc gctacgtccg cgaccagctc ccccggtacc ggatgccgga gaactcgatc 120
cccaaggagg cggcgtacca gatcatcagc gacgagctga tgctggacgg caacccgcgg 180
ctgaacctgg cgtccttcgt caccacctgg atggagcccg agtgcggcaa gctcatcatg 240
gactccgtca acaagaacta cgtcgacatg gacgagtacc ccgtcaccac cgagctccag 300
gaccgttgcg taaacatgat agctcacttg ttcaatgcac cgatcggcga ggacgagaca 360
gctatcggag tctcgacggt ggggtcttcg gaagcaatca tgcttgcagg cctggcgttc 420
aagaggaagt gggcgaacaa aatgaaggag caggggaagc catgcgacaa acctaacatt 480
gttactggtg caaatgttca ggtttgctgg gagaaatttg ctaggtattt tgaagtggaa 540
ttgaaggagg tcaagttgac tgaagggtac tatgtcatgg atcctaagaa ggctgttgaa 600
atggtggatg agaacactat atgtgtcgcc gccatcctgg gatctactct cactggagag 660
tacgaagatg tcaaactgtt gaatgacctt cttgtggaga agaacaagga aacagggtgg 720
aacgtgccga tccatgttga tgctgccagc ggaggattta tcgctccgtt tcttcagcct 780
gagcttgaat gggacttcag gctaccattg gtgaagagca tcaacgttag tgggcacaag 840
tatggccttg tgtaccctgg tgttggatgg gtcatctggc ggagcaagga cgatttgccc 900
gaagaactca ttttccacat aaactatcta ggagcagatc agcccacatt cacgctcaac 960
ttctccaagg gtcagcagat catcgcgcaa tactatcagc tcatccgcct cggcttcgag 1020
gggtacaagc acatcatgga gaactgcaag ctgaacgcgg cggtgctgaa ggagggcatc 1080
gacgcgacgg ggcggttcga cgtgctgtcc aaggcggacg gcgtgccgct ggtggccatc 1140
cggctcaagg acagcaccaa cttcagcgtg ttcgacatct cggagaacct gaggcggttc 1200
gggtggatcg tgccggcgta caccatgccc gccgacgcgg agcatgtggc cgtgctccgc 1260
atagtcatcc gggaggactt caaccggagc ctcgcgcagc ggctcctcgc cgacatcaac 1320
aagatcatcg gcgagctgga cgcgcacgcc gtccacgcca tcaagctctc caccgccgcc 1380
gctggtgggg acggcgcgag taagagcgcg gtcgacgccg ccaccgaggc cttcaaggac 1440
ctggcgggga agaagaaggc cggagtatgc tga 1473

<210> SEQ ID NO 66
<211> LENGTH: 11688
<212> TYPE: DNA
<213> ORGANISM: Artificial
<220> FEATURE:
<223> OTHER INFORMATION: vector

<400> SEQUENCE: 66
ggaattcgat atcaagcttg gcactggccg tcgttttaca acgtcgtgac tgggaaaacc 60
ctggcgttac ccaacttaat cgccttgcag cacatccccc tttcgccagc tggcgtaata 120
gcgaagaggc ccgcaccgat cgcccttccc aacagttgcg cagcctgaat ggcgaatgct 180
agagcagctt gagcttggat cagattgtcg tttcccgcct tcagtttaaa ctatcagtgt 240
ttgacaggat atattggcgg gtaaacctaa gagaaaagag cgtttattag aataacggat 300
atttaaaagg gcgtgaaaag gtttatccgt tcgtccattt gtatgtgcat gccaaccaca 360
gggttcccct cgggatcaaa gtactttgat ccaacccctc cgctgctata gtgcagtcgg 420
cttctgacgt tcagtgcagc cgtcttctga aaacgacatg tcgcacaagt cctaagttac 480
gcgacaggct gccgccctgc ccttttcctg gcgttttctt gtcgcgtgtt ttagtcgcat 540
aaagtagaat acttgcgact agaaccggag acattacgcc atgaacaaga gcgccgccgc 600
tggcctgctg ggctatgccc gcgtcagcac cgacgaccag gacttgacca accaacgggc 660
cgaactgcac gcggccggct gcaccaagct gttttccgag aagatcaccg gcaccaggcg 720
cgaccgcccg gagctggcca ggatgcttga ccacctacgc cctggcgacg ttgtgacagt 780
gaccaggcta gaccgcctgg cccgcagcac ccgcgaccta ctggacattg ccgagcgcat 840
ccaggaggcc ggcgcgggcc tgcgtagcct ggcagagccg tgggccgaca ccaccacgcc 900
ggccggccgc atggtgttga ccgtgttcgc cggcattgcc gagttcgagc gttccctaat 960
catcgaccgc acccggagcg ggcgcgaggc cgccaaggcc cgaggcgtga agtttggccc 1020
ccgccctacc ctcaccccgg cacagatcgc gcacgcccgc gagctgatcg accaggaagg 1080
ccgcaccgtg aaagaggcgg ctgcactgct tggcgtgcat cgctcgaccc tgtaccgcgc 1140
acttgagcgc agcgaggaag tgacgcccac cgaggccagg cggcgcggtg ccttccgtga 1200
ggacgcattg accgaggccg acgccctggc ggccgccgag aatgaacgcc aagaggaaca 1260
agcatgaaac cgcaccagga cggccaggac gaaccgtttt tcattaccga agagatcgag 1320
gcggagatga tcgcggccgg gtacgtgttc gagccgcccg cgcacgtctc aaccgtgcgg 1380
ctgcatgaaa tcctggccgg tttgtctgat gccaagctgg cggcctggcc ggccagcttg 1440
gccgctgaag aaaccgagcg ccgccgtcta aaaaggtgat gtgtatttga gtaaaacagc 1500
ttgcgtcatg cggtcgctgc gtatatgatg cgatgagtaa ataaacaaat acgcaagggg 1560
aacgcatgaa ggttatcgct gtacttaacc agaaaggcgg gtcaggcaag acgaccatcg 1620
caacccatct agcccgcgcc ctgcaactcg ccggggccga tgttctgtta gtcgattccg 1680
atccccaggg cagtgcccgc gattgggcgg ccgtgcggga agatcaaccg ctaaccgttg 1740
tcggcatcga ccgcccgacg attgaccgcg acgtgaaggc catcggccgg cgcgacttcg 1800
tagtgatcga cggagcgccc caggcggcgg acttggctgt gtccgcgatc aaggcagccg 1860
acttcgtgct gattccggtg cagccaagcc cttacgacat atgggccacc gccgacctgg 1920
tggagctggt taagcagcgc attgaggtca cggatggaag gctacaagcg gcctttgtcg 1980
tgtcgcgggc gatcaaaggc acgcgcatcg gcggtgaggt tgccgaggcg ctggccgggt 2040
acgagctgcc cattcttgag tcccgtatca cgcagcgcgt gagctaccca ggcactgccg 2100

-continued

```
ccgccggcac aaccgttctt gaatcagaac ccgagggcga cgctgcccgc gaggtccagg   2160
cgctggccgc tgaaattaaa tcaaaactca tttgagttaa tgaggtaaag agaaaatgag   2220
caaaagcaca aacacgctaa gtgccggccg tccgagcgca cgcagcagca aggctgcaac   2280
gttggccagc ctggcagaca cgccagccat gaagcgggtc aactttcagt tgccggcgga   2340
ggatcacacc aagctgaaga tgtacgcggt acgccaaggc aagaccatta ccgagctgct   2400
atctgaatac atcgcgcagc taccagagta aatgagcaaa tgaataaatg agtagatgaa   2460
ttttagcggc taaaggaggc ggcatggaaa atcaagaaca accaggcacc gacgccgtgg   2520
aatgccccat gtgtggagga acgggcggtt ggccaggcgt aagcggctgg gttgtctgcc   2580
ggccctgcaa tggcactgga acccccaagc ccgaggaatc ggcgtgacgg tcgcaaacca   2640
tccggcccgg tacaaatcgg cgcggcgctg ggtgatgacc tggtggagaa gttgaaggcc   2700
gcgcaggccg cccagcggca acgcatcgag gcagaagcac gccccggtga atcgtggcaa   2760
gcggccgctg atcgaatccg caaagaatcc cggcaaccgc cggcagccgg tgcgccgtcg   2820
attaggaagc cgcccaaggg cgacgagcaa ccagattttt tcgttccgat gctctatgac   2880
gtgggcaccc gcgatagtcg cagcatcatg gacgtggccg ttttccgtct gtcgaagcgt   2940
gaccgacgag ctggcgaggt gatccgctac gagcttccag acgggcacgt agaggtttcc   3000
gcagggccgg ccggcatggc cagtgtgtgg gattacgacc tggtactgat ggcggtttcc   3060
catctaaccg aatccatgaa ccgataccgg gaagggaagg gagacaagcc cggccgcgtg   3120
ttccgtccac acgttgcgga cgtactcaag ttctgccggc gagccgatgg cggaaagcag   3180
aaagacgacc tggtagaaac ctgcattcgg ttaaacacca cgcacgttgc catgcagcgt   3240
acgaagaagg ccaagaacgg ccgcctggtg acggtatccg agggtgaagc cttgattagc   3300
cgctacaaga tcgtaaagag cgaaaccggg cggccggagt acatcgagat cgagctagct   3360
gattggatgt accgcgagat cacagaaggc aagaacccgg acgtgctgac ggttcacccc   3420
gattactttt tgatcgatcc cggcatcggc cgttttctct accgcctggc acgccgcgcc   3480
gcaggcaagg cagaagccag atggttgttc aagacgatct acgaacgcag tggcagcgcc   3540
ggagagttca agaagttctg tttcaccgtg cgcaagctga tcgggtcaaa tgacctgccg   3600
gagtacgatt tgaaggagga ggcggggcag gctggcccga tcctagtcat gcgctaccgc   3660
aacctgatcg agggcgaagc atccgccggt tcctaatgta cggagcagat gctagggcaa   3720
attgccctag caggggaaaa aggtcgaaaa ggtctctttc ctgtggatag cacgtacatt   3780
gggaacccaa agccgtacat tgggaaccgg aacccgtaca ttgggaaccc aaagccgtac   3840
attgggaacc ggtcacacat gtaagtgact gatataaaag agaaaaaagg cgatttttcc   3900
gcctaaaact ctttaaaact tattaaaact cttaaaaccc gcctggcctg tgcataactg   3960
tctggccagc gcacagccga agagctgcaa aaagcgccta cccttcggtc gctgcgctcc   4020
ctacgccccg ccgcttcgcg tcggcctatc gcggccgctg gccgctcaaa aatggctggc   4080
ctacggccag gcaatctacc agggcgcgga caagccgcgc cgtcgccact cgaccgccgg   4140
cgcccacatc aaggcaccct gcctcgcgcg tttcggtgat gacggtgaaa acctctgaca   4200
catgcagctc ccggagacgg tcacagcttg tctgtaagcg gatgccggga gcagacaagc   4260
ccgtcagggc gcgtcagcgg gtgttggcgg gtgtcggggc gcagccatga cccagtcacg   4320
tagcgatagc ggagtgtata ctggcttaac tatgcggcat cagagcagat tgtactgaga   4380
gtgcaccata tgcggtgtga aataccgcac agatgcgtaa ggagaaaata ccgcatcagg   4440
```

-continued

```
cgctcttccg cttcctcgct cactgactcg ctgcgctcgg tcgttcggct gcggcgagcg   4500
gtatcagctc actcaaaggc ggtaatacgg ttatccacag aatcagggga taacgcagga   4560
aagaacatgt gagcaaaagg ccagcaaaag gccaggaacc gtaaaaaggc cgcgttgctg   4620
gcgtttttcc ataggctccg cccccctgac gagcatcaca aaaatcgacg ctcaagtcag   4680
aggtggcgaa acccgacagg actataaaga taccaggcgt ttccccctgg aagctccctc   4740
gtgcgctctc ctgttccgac cctgccgctt accggatacc tgtccgcctt tctcccttcg   4800
ggaagcgtgg cgctttctca tagctcacgc tgtaggtatc tcagttcggt gtaggtcgtt   4860
cgctccaagc tgggctgtgt gcacgaaccc cccgttcagc ccgaccgctg cgccttatcc   4920
ggtaactatc gtcttgagtc caacccggta agacacgact tatcgccact ggcagcagcc   4980
actggtaaca ggattagcag agcgaggtat gtaggcggtg ctacagagtt cttgaagtgg   5040
tggcctaact acggctacac tagaaggaca gtatttggta tctgcgctct gctgaagcca   5100
gttaccttcg gaaaaagagt tggtagctct tgatccggca aacaaaccac cgctggtagc   5160
ggtggttttt ttgtttgcaa gcagcagatt acgcgcagaa aaaaaggatc tcaagaagat   5220
cctttgatct tttctacggg gtctgacgct cagtggaacg aaaactcacg ttaagggatt   5280
ttggtcatgc attctaggta ctaaaacaat tcatccagta aaatataata ttttattttc   5340
tcccaatcag gcttgatccc cagtaagtca aaaaatagct cgacatactg ttcttccccg   5400
atatcctccc tgatcgaccg gacgcagaag gcaatgtcat accacttgtc cgccctgccg   5460
cttctcccaa gatcaataaa gccacttact ttgccatctt tcacaaagat gttgctgtct   5520
cccaggtcgc cgtgggaaaa gacaagttcc tcttcgggct tttccgtctt taaaaaatca   5580
tacagctcgc gcggatcttt aaatggagtg tcttcttccc agttttcgca atccacatcg   5640
gccagatcgt tattcagtaa gtaatccaat tcggctaagc ggctgtctaa gctattcgta   5700
tagggacaat ccgatatgtc gatggagtga aagagcctga tgcactccgc atacagctcg   5760
ataatctttt cagggctttg ttcatcttca tactcttccg agcaaaggac gccatcggcc   5820
tcactcatga gcagattgct ccagccatca tgccgttcaa agtgcaggac ctttggaaca   5880
ggcagctttc cttccagcca tagcatcatg tccttttccc gttccacatc ataggtggtc   5940
cctttatacc ggctgtccgt catttttaaa tataggtttt cattttctcc caccagctta   6000
tataccttag caggagacat tccttccgta tcttttacgc agcggtattt ttcgatcagt   6060
tttttcaatt ccggtgatat tctcatttta gccatttatt atttccttcc tcttttctac   6120
agtatttaaa gataccccaa gaagctaatt ataacaagac gaactccaat tcactgttcc   6180
ttgcattcta aaaccttaaa taccagaaaa cagctttttc aaagttgttt tcaaagttgg   6240
cgtataacat agtatcgacg gagccgattt tgaaaccgcg gtgatcacag gcagcaacgc   6300
tctgtcatcg ttacaatcaa catgctaccc tccgcgagat catccgtgtt tcaaacccgg   6360
cagcttagtt gccgttcttc cgaatagcat cggtaacatg agcaaagtct gccgccttac   6420
aacggctctc ccgctgacgc cgtcccggac tgatgggctg cctgtatcga gtggtgattt   6480
tgtgccgagc tgccggtcgg ggagctgttg gctggctggt ggcaggatat attgtggtgt   6540
aaacaaattg acgcttagac aacttaataa cacattgcgg acgtttttaa tgtactgaat   6600
taacgccgaa ttaattcggg ggatctggat tttagtactg gattttggtt ttaggaatta   6660
gaaattttat tgatagaagt attttacaaa tacaaataca tactaagggt ttcttatatg   6720
ctcaacacat gagcgaaacc ctataggaac cctaattccc ttatctggga actactcaca   6780
cattattatg gagaaactcg agcttgtcga tcgacagatc cggtcggcat ctactctatt   6840
```

```
tctttgccct cggacgagtg ctggggcgtc ggtttccact atcggcgagt acttctacac   6900
agccatcggt ccagacggcc gcgcttctgc gggcgatttg tgtacgcccg acagtcccgg   6960
ctccggatcg gacgattgcg tcgcatcgac cctgcgccca agctgcatca tcgaaattgc   7020
cgtcaaccaa gctctgatag agttggtcaa gaccaatgcg gagcatatac gcccggagtc   7080
gtggcgatcc tgcaagctcc ggatgcctcc gctcgaagta gcgcgtctgc tgctccatac   7140
aagccaacca cggcctccag aagaagatgt tggcgacctc gtattgggaa tccccgaaca   7200
tcgcctcgct ccagtcaatg accgctgtta tgcggccatt gtccgtcagg acattgttgg   7260
agccgaaatc cgcgtgcacg aggtgccgga cttcggggca gtcctcggcc caaagcatca   7320
gctcatcgag agcctgcgcg acggacgcac tgacggtgtc gtccatcaca gtttgccagt   7380
gatacacatg gggatcagca atcgcgcata tgaaatcacg ccatgtagtg tattgaccga   7440
ttccttgcgg tccgaatggg ccgaacccgc tcgtctggct aagatcggcc gcagcgatcg   7500
catccatagc ctccgcgacc ggttgtagaa cagcgggcag ttcggtttca ggcaggtctt   7560
gcaacgtgac accctgtgca cggcgggaga tgcaataggt caggctctcg ctaaactccc   7620
caatgtcaag cacttccgga atcgggagcg cggccgatgc aaagtgccga taaacataac   7680
gatctttgta gaaaccatcg gcgcagctat ttacccgcag gacatatcca cgccctccta   7740
catcgaagct gaaagcacga gattcttcgc cctccgagag ctgcatcagg tcggagacgc   7800
tgtcgaactt ttcgatcaga aacttctcga cagacgtcgc ggtgagttca ggcttttcca   7860
tatctcattg ccccccccgga tctgcgaaag ctcgagagag atagatttgt agagagagac   7920
tggtgatttc agcgtgtcct ctccaaatga aatgaacttc cttatataga ggaaggtctt   7980
gcgaaggata gtgggattgt gcgtcatccc ttacgtcagt ggagatatca catcaatcca   8040
cttgctttga agacgtggtt ggaacgtctt ctttttccac gatgctcctc gtgggtgggg   8100
gtccatcttt gggaccactg tcggcagagg catcttgaac gatagccttt cctttatcgc   8160
aatgatggca tttgtaggtg ccaccttcct tttctactgt ccttttgatg aagtgacaga   8220
tagctgggca atggaatccg aggaggtttc ccgatattac cctttgttga aaagtctcaa   8280
tagccctttg gtcttctgag actgtatctt tgatattctt ggagtagacg agagtgtcgt   8340
gctccaccat gttatcacat caatccactt gctttgaaga cgtggttgga acgtcttctt   8400
tttccacgat gctcctcgtg ggtgggggtc catctttggg accactgtcg gcagaggcat   8460
cttgaacgat agcctttcct ttatcgcaat gatggcattt gtaggtgcca ccttcctttt   8520
ctactgtcct tttgatgaag tgacagatag ctgggcaatg gaatccgagg aggtttcccg   8580
atattaccct ttgttgaaaa gtctcaatag ccctttggtc ttctgagact gtatctttga   8640
tattcttgga gtagacgaga gtgtcgtgct ccaccatgtt ggcaagctgc tctagccaat   8700
acgcaaaccg cctctccccg cgcgttggcc gattcattaa tgcagctggc acgacaggtt   8760
tcccgactgg aaagcgggca gtgagcgcaa cgcaattaat gtgagttagc tcactcatta   8820
ggcaccccag gctttacact ttatgcttcc ggctcgtatg ttgtgtggaa ttgtgagcgg   8880
ataacaattt cacacaggaa acagctatga ccatgattac gaattccctt aattaaggcg   8940
cgccgatact gaattaacgc cgaattaatt cgggggatct ggattttagt actggatttt   9000
ggttttagga attagaaatt ttattgatag aagtatttta caaatacaaa tacatactaa   9060
gggtttctta tatgctcaac acatgagcga aaccctatag gaaccctaat tcccttatct   9120
gggaactact cacacattat tatggagaaa ccaggccgga gccaggtatt cacggttcag   9180
```

-continued

```
atatactcca ggaaaaatag atacatatag tacgtacgtg cgtactgtgc cggcatgccc   9240
ttcagcaggg tccagtcttc ttgttcttta ccaggtcctt gcaggccgcg gcgaactcct   9300
tctcgatgtc cagaacgccc ttcttggtca ccacgccatc ctcagcaccc tcgccggttt   9360
gtgtcgcgat agcagtggtc atcttaatgg catggaccgc gtgggcatct agctcctgca   9420
cgaccctgtt gatgtcggcg aggagccgct gggagaggct gcggttgaag tcctccctga   9480
tgacgacgcg gaggacagcc acgtgctctg cgtccgcagg catggtgtag gcaggcacaa   9540
tccagccaaa cctcctcagg ttctcggaga tgtcgaacac gctgaatttg gagctgtcct   9600
tgagccggat ggccactagg ggcacaccgt cctctttgga caggatgtcg aatcgcccgg   9660
ttgcctctaa gccctccctc agcgcggttg cattggcctg gcaattctcc atgatgtgct   9720
tatatccctc gaagcctagg cgtatcagtt gatagtattg cgcaatgatc tggctagcac   9780
ctttggagaa gttcaatgtg aatgtgggct gatctgttcc caggtagttt atatggaaaa   9840
tgagttctcc aggcaaatcg tctttgctcc gccagatgac ccatccaaca ccagggtaga   9900
cgaggccata cttgtgccca ctaacattga tgctcttcac caatggtagc ctgaagtccc   9960
actcaagctc agggtgaaga aaaggggcta taaatcctcc acttgcagca tcaacatgga  10020
tcggcacatt aaaccctgtt ttcttgttct tttccacaag caggtcattc aatagtttaa  10080
catcttcata ctctccagtg agagtagatc ccaagatggc tgcaacacat atagtgttct  10140
catccaccat ttcaacagct ttcaaaggat ccatgacata gtatccttca gttaacttga  10200
cctccttcaa ttctacttca aaatatctag caaatttttc ccagcaaacc tgaacatttg  10260
caccagtaac aatgttaggt ttgtcatatg gcttcccctc ctcctttctt ttatttgccc  10320
acttcctctt gaaggccagg cctgcaagca ttattgcttc tgaggatccc actgtcgcaa  10380
ctccaattgc tgtctcctcc tccttgatcg gtgcattgaa caggtgggct atcatattta  10440
cacaacggtt ctggagctcg gtggtgacgg ggtactcgtc catgtcgacg tagttcttgt  10500
tgacggagtc catgatgagc ttgccgacct cgggctccat ccgggtggtg acgaaggatg  10560
cgaggttgag gcgcgggttg ccgtcgagca tgagctcgtc gctgatgatc tggtacgccg  10620
cctccttggg gatcgagttc tccggcatcc ggtaccgggg gagctggtcg cggacgtagc  10680
gggtggcgaa gaaggtggag ttgagcggct cggccgtgtc cgcggcggtc gctgccacag  10740
tgagaaccat ggttgctggc ggtcgcggtc gcggcttgca cggagacagt gacggcaggt  10800
cggccgcgcg cagcgaaggg aatcggccgc gagctcgagg aaaggtggtg ccgtggagat  10860
gctaatggag agagatagat ttgtagagag agactggtga tttcagcgtg tcctctccaa  10920
atgaaatgaa cttccttata tagaggaagg gtcttgcgaa ggatagtggg attgtgcgtc  10980
atcccttacg tcagtggaga tatcacatca atccacttgc tttgaagacg tggttggaac  11040
gtcttctttt tccacgatgc tcctcgtggg tgggggtcca tctttgggac cactgtcggc  11100
agagcatctt gaacgatagc ctttccttta tcgcaatgat ggcatttgta ggtgccacct  11160
tccttttcta ctgtcctttt gatgaagtga cagatagctg ggcaatggaa tccgaggagg  11220
tttcccgata ttaccctttg ttgaaaagtc tcaatagccc tttggccttc tgagactgta  11280
tctttgatat tcttggagta gacgagagtg tcgtgctcca ccatgttcac atcaatccac  11340
ttgctttgaa gacgtggttg gaacgtcttc tttttccacg atgctcctcg tgggtggggg  11400
tccatctttg ggaccactgt cggcagaggc atcttgaacg atagcctttc ctttatcgca  11460
atgatggcat ttgtaggtgc caccttcctt ttctactgtc cttttgatga agtgacagat  11520
agctgggcaa tggaatccga ggaggtttcc cgatattacc ctttgttgaa aagtctcaat  11580
```

-continued

```
agccctttgg tcttctgaga ctgtatcttt gatattcttg gagtagacga gagtgtcgtg  11640

ctccaccatg ttggcaagct gctcttatta attaaggcgc gccctgca              11688
```

<210> SEQ ID NO 67
<211> LENGTH: 1509
<212> TYPE: DNA
<213> ORGANISM: Arabidopsis thaliana

<400> SEQUENCE: 67

```
atggtgctct cccacgccgt atcggagtcg gacgtctccg tccactccac attcgcatca     60

cgttacgtcc gtacttcact tcctaggttc aagatgccgg aaaactcgat tcctaaggaa    120

gcggcgtatc agatcatcaa cgacgagctg atgcttgacg ggaatccacg gttgaactta    180

gcctcctttg tgacgacatg gatggagcct gagtgtgata aactcatcat gtcctccatc    240

aacaagaact atgttgacat ggacgagtac cccgtcacca ccgaacttca gaaccgatgt    300

gtgaacatga ttgcacatct attcaatgca ccgttagaag aggcggagac cgccgtcgga    360

gtaggaaccg ttggatcatc ggaggccata atgttggccg gtttggcctt caagcgtaaa    420

tggcagaaca agcgcaaagc tgaaggcaaa cccgtcgata aacccaacat tgtcaccgga    480

gccaatgttc aagtgtgttg ggagaaattc gctaggtact ttgaggttga acttaaggaa    540

gtgaaattga gtgaaggata ctatgtgatg gaccctcaac aagctgttga tatggttgat    600

gagaacacca tttgtgttgc ggacattctt ggttccactc ttaatggaga attcgaagat    660

gttaaactct tgaacgatct cttggtcgaa aagaacaaag aaaccggatg ggatacacca    720

atccacgtgg atgcggcaag tggaggattc attgcaccgt ttttgtatcc ggaattggaa    780

tgggacttta gacttccctt ggtgaagagt atcaatgtga gtggtcacaa gtatggactt    840

gtgtacgcag ggattggttg ggtgatctgg agaaacaaag aggatttgcc tgaggaactc    900

atcttccata tcaattatct tggtgctgac caacccacct ttactctcaa tttctccaaa    960

ggttcaagtc aagtcattgc tcaatactac caacttatcc gattgggcca cgagggttac   1020

agaaatgtga tggagaattg cagagagaat atgatcgtcc taagggaagg acttgagaag   1080

acagaaaggt tcaacatcgt ctcaaaggac gagggagtgc cacttgtcgc tttctccttg   1140

aaagatagca gctgtcacac tgagttcgaa atctccgaca tgcttcgcag gtatggatgg   1200

atagtgccgg cctacacaat gcctccaaat gcacaacaca tcactgttct tcgtgtggtt   1260

atcagagaag atttctcgag aacactcgct gagagacttg tgatcgatat agagaaagtg   1320

atgcgtgagc tcgatgagct tccttcgaga gtgattcaca aaatatcact tggacaagag   1380

aagagtgaat ctaacagcga taacttgatg gtcacggtga agaagagcga tatcgacaag   1440

cagagagata tcatcactgg ctggaagaag tttgtcgccg acaggaagaa gacgagtggt   1500

atctgctaa                                                            1509
```

<210> SEQ ID NO 68
<211> LENGTH: 1485
<212> TYPE: DNA
<213> ORGANISM: Arabidopsis thaliana

<400> SEQUENCE: 68

```
atggttttga caaaaaccgc aacgaatgat gaatctgtct gcaccatgtt cggatctcgc     60

tatgttcgca ctacacttcc caagtatgag attggtgaga attcgatacc gaaagacgct    120

gcatatcaga tcataaaaga tgagctgatg cttgatggta acccgaggct taacctagct    180
```

```
tcgtttgtga ctacatggat ggaaccagag tgtgacaaac tcatcatgga ctctatcaac    240
aagaactacg ttgatatgga tgagtaccct gtcacaactg agctccagaa ccgatgtgta    300
aacattatag ctcgactgtt caatgcgcca ctcgaggaat ctgagacggc ggtgggagta    360
gggacagttg gttcttcaga agccatcatg ttagccggat tggccttcaa aagaaaatgg    420
cagaacaaac gcaaggctga gggtaaaccc tatgacaaac ccaacattgt cactggagcc    480
aatgttcaag tttgctggga gaaattcgct cggtacttcg aggtggagct aaaggaagta    540
aacctaagtg aaggttacta cgtgatggat ccagacaaag cagcagaaat ggtagacgag    600
aacacaatct gtgtcgcagc catattggga tccacactca acggtgagtt cgaagacgtg    660
aaacgtctca atgacttgct agtcaagaaa aacgaggaga ctggttggaa cacaccgatc    720
cacgtggatg cagcaagtgg agggttcata gctccgttta tctatcctga attagaatgg    780
gactttagac ttcctttggt taagagtatc aacgtgagtg gtcacaagta tggactggtc    840
tatgctggta ttggttgggt cgtgtggagg gcagcagagg atttgcctga agagcttatc    900
tttcatatta attatcttgg tgctgatcaa cccactttca ctctcaattt ctccaaggga    960
tcgagccaaa ttattgctca atactaccag ctcattcgtc ttggattcga ggggtacaaa   1020
aatgtgatgg agaattgcat agagaacatg gtggttctca aagaagggat agagaaaaca   1080
gagcgtttca acatagtctc aaaggaccaa ggagtgccag tcgtagcctt ctctctcaag   1140
gaccatagtt tccacaacga gttcgagatc tctgagatgc tacgtcgttt tggctggatc   1200
gtcccagctt acactatgcc tgccgatgca cagcacatca cggttctgcg tgttgtcatc   1260
agggaagatt tctcaagaac actcgcggag agacttgttg ctgatatttc gaaggtgctt   1320
catgagctag ataccttgcc ttccaagata tctaagaaga tggaatagaa agggatcgcg   1380
gaaaatgtaa aggagaagaa gatggagaag gagattctga tggaagttat tgttggatgg   1440
aggaagtttg tgaaggagag gaagaagatg aatggtgtgt gctaa                   1485


<210> SEQ ID NO 69
<211> LENGTH: 1503
<212> TYPE: DNA
<213> ORGANISM: Petunia x hybrid

<400> SEQUENCE: 69

atggttctat caaagacagt gtcgcagagc gatgtgtcca ttcactccac gtttgcttct     60
cgatatgttc gaacttctct tcccaggttt aaaatgccag ataattcgat accaaaagaa    120
gcagcatatc agatcataaa tgatgaactg atgttagatg gaaacccaag gctgaacttg    180
gcttcttttg ttacaacatg gatggaacca gagtgtgata agttgatgat ggactctatt    240
aacaagaact atgttgatat ggatgaatat cctgttacca ctgagcttca gaatcgatgt    300
gtaaacatga tagctcattt gtttaatgca ccacttgaag atggagaaac tgcagttgga    360
gttggaactg ttggatcctc tgaagccatt atgcttgctg gattagcttt caagagaaaa    420
tggcagaaca aaatgaaagc ccaaggcaaa ccctgtgaca agcccaacat tgttactggt    480
gcaaatgtcc aggtgtgctg ggagaaattt gcaaggtatt ttgaagtgga gctaaaggaa    540
gtaaagctta gtgaaggata ctatgtgatg gaccctgaga aagctgtgga gatggtggat    600
gaaaacacca tttgtgtagc tgctatctta ggttccaccc tcaatggaga atttgaagac    660
gttaagcgct tgaatgatct cttggtcgag aagaacaaag aaaccgggtg ggacactcca    720
attcatgtgg atgcagcaag tggtggattt attgcaccgt tcatttaccc agagcttgag    780
tgggacttta gattgccatt agtgaagagc attaatgtaa gtggtcacaa atatggtctt    840
```

```
gtctatgctg gtattggttg ggtcgtttgg aggaacaagg atgatttgcc tgatgaactt    900
atcttccaca ttaattatct tggtgctgat caacctactt tcactctcaa cttttctaaa    960
ggttctagcc aagtaattgc tcaatattac caacttattc gcttgggtta tgagggttac   1020
aagaatgtga tggagaattg tcaagaaaat gcatcggtac taagagaagg gctagaaaag   1080
acaggaagat tcaacataat ctccaaagaa attggagtac ctttagtagc attctctctt   1140
aaagacaaca ggcaacacaa cgagttcgag atttctgaaa ctttaaggag atttggttgg   1200
attgttcctg catatactat gccaccaaac gcacaacaca ttacagttct cagagttgtg   1260
atcagagaag atttctcccg tacgcttgca gaacgactgg taagagacat cgaaaaagtc   1320
cttcatgaac ttgacacact ccctgcacgt gtcaatgcta agctcgctgt ggccgaggag   1380
caggcggctg cgaatggcag cgaggtgcat aagaaaacag atagcgaagt gcagttggag   1440
atgataactg catggaagaa gtttgttgaa gaaaagaaga agaagactaa tcgagtttgt   1500
taa                                                                 1503
```

<210> SEQ ID NO 70
<211> LENGTH: 1509
<212> TYPE: DNA
<213> ORGANISM: Solanum lyopersicum

<400> SEQUENCE: 70

```
atggtgttaa caacgacgtc gataagagat tcagaagaga gcttgcactg tacatttgca     60
tcaagatatg tacaggaacc tttacctaag ttcaaaatgc ctaaaaaatc catgccgaaa    120
gaagcagctt atcagattgt aaacgacgag cttatgttgg atggtaaccc caggttgaat    180
ttagcttcct ttgttagcac atggatggag cccgagtgcg ataagctcat catgtcatcc    240
attaataaaa actatgtcga catggatgag tatcctgtca ccactgaact tcaaaataga    300
tgtgttaaca tgttagcaca tcttttccat gccccggttg gtgatgatga gactgcagtt    360
ggagttggta cagtgggttc atcagaggca ataatgcttg ctggccttgc tttcaaacgc    420
aaatggcaat cgaaaagaaa agcagaaggc aaacctttcg ataagcctaa tatagtcact    480
ggagctaatg tgcaggtctg ctgggaaaaa tttgcaaggt attttgaggt tgagttgaag    540
gaggtgaaac taaaagaagg atactatgta atggaccctg ccaaagcagt agagatagtg    600
gatgagaata caatatgtgt tgctgcaatc cttggttcta ctctgactgg ggagtttgag    660
gatgtgaagc tcctaaacga gctccttaca aaaaagaaca aggaaaccgg atgggagaca    720
ccgattcatg tcgatgctgc gagtggagga tttattgctc ctttcctctg gccagatctt    780
gaatgggatt tccgtttgcc tcttgtgaaa agtataaatg tcagcggtca caagtatggc    840
cttgtatatg ctggtgtcgg ttgggtgata tggcggagca aggaagactt gcccgatgaa    900
ctcgtctttc atataaacta ccttgggtct gatcagccta cttttactct caacttctct    960
aaaggttcct atcaaataat tgcacagtat tatcagttaa taagacttgg ctttgagggt   1020
tataagaacg tcatgaagaa ttgcttatca aacgcaaaag tactaacaga gggaatcaca   1080
aaaatggggc ggttcgatat tgtctctaag gatgtgggtg ttcctgttgt agcattttct   1140
ctcagggaca gcagcaaata tacggtattt gaagtatctg agcatctcag aagatttgga   1200
tggatcgtcc ctgcatacac aatgccaccg gatgctgaac acattgctgt actgcgggtt   1260
gtcattagag aggatttcag ccacagccta gctgagagac ttgtttctga cattgagaaa   1320
attctgtcag agttggacac acagcctcct cgtttgccca ccaaagctgt ccgtgtcact   1380
```

gctgaggaag tgcgtgatga caagggtgat gggcttcatc attttcacat ggatactgta 1440
gagactcaga aagacattat caaacattgg aggaaaatcg cagggaagaa gaccagcgga 1500
gtctgctag 1509

<210> SEQ ID NO 71
<211> LENGTH: 1500
<212> TYPE: DNA
<213> ORGANISM: Populus tremula x Populus alba

<400> SEQUENCE: 71
atggttctct ccaagacagc ttcagaatct gatgtctccg ttcactcgac ttttgcctcc 60
agatatgttc gagcttcact tcccaggttc aagatgccgg agaactcgat cccgaaggag 120
gcggcctttc agatcataaa cgatgagctc atgctggatg gaaaccctag gctgaacctc 180
gcatcgtttg tgacgacatg gatggagcct gaatgtgaca agcttatcat cgcttctatc 240
aacaaaaact acgtcgacat ggatgaatac ccggtcacca ccgagcttca gaatcgatgc 300
gttaacatga tagcccatct cttcaatgct ccacttggag actcggagac agcggttgga 360
gtaggaactg ttggatcttc tgaggctata atgttggctg gtctggcctt caagaggaag 420
tggcaaaaca agagaaaagc tgagggaaag ccttacgata aacctaacat tgtcactgga 480
gccaatgttc aggtatgctg ggagaaattt gcaaggtact ttgaggtgga gttgaaggag 540
gtgaagctta gtgatggcta ttatgtgatg gatcctgaga aagcagtgca aatggtggat 600
gagaacacaa tctgtgttgc agctattctt ggttccactc ttaatggaga atttgaagat 660
gtcaagctct tgaatgatct cctggtggag aagaacaaat caacaggttg ggatactccg 720
atccatgtcg atgcggccag cggcggcttc attgcacctt ttatataccc ggagctcgag 780
tgggatttcc ggttgccatt ggtgaagagt atcaatgtca gtgggcacaa atatggactc 840
gtctatgctg gtattggatg ggtcatttgg aggaacaagg aggacttgcc tgaagaactc 900
atcttccata tcaattatct tggagctgat caaccaacct tcacccttaa cttctccaaa 960
ggatctagtc aagttattgc tcaatattac caactcattc ggttgggtta cgagggatac 1020
aaaaatgtta tggaaaattg tagagacaac atgctggtgc tgaaacaagg tctagagaag 1080
acaggcaagt tcaacattgt ttcgaaagac aagggggtgc cactggtggc cttttctttg 1140
aaggacaata gcctccacaa cgaatttgag gtgtccgaca tgttaaggcg ttttggttgg 1200
attgtgcctg cctacaccat gcctcccgat gctcaacatg ttactgtgct gcgcgtcgta 1260
atccgagaag atttttctcg gacactcgct gagcgtcttg tcattgacat tggcaaggtt 1320
cttcatgagc ttgagacgtt gccgtccagg atcagtgcca agattgtgtt ggctaatgaa 1380
gagaaggatg ccgtggccgc cggtaaagag aagaaggacg tccagaacga aacaagagag 1440
attattacag cttggaggaa gcttgtcgtg caaaggaaga agttgaatgg tgtttgctag 1500

<210> SEQ ID NO 72
<211> LENGTH: 1479
<212> TYPE: DNA
<213> ORGANISM: Oryza sativa Indica

<400> SEQUENCE: 72
atggtgctct ccaaggccgt ctccgagagt gacatgtccg tgcactccac cttcgcctcc 60
cgctacgtcc gcgcctccct cccaaggtac cggatgccgg agaactcgat cccgaaggag 120
gcggcgtacc agatcatcaa cgacgagctg atgctggacg gcaacccgcg gctgaacctg 180
gcgtcgttcg tcaccacgtg gatggagccc gagtgcgaca agctcatcat ggccgccatc 240

-continued aacaagaact acgtcgacat ggacgagtac cccgtcacca ccgagctcca gaaccggtgc 300
gtgaacatga tcgcgcacct gttccacgcg ccgctcgggg aggacgagac ggcggtgggc 360
gtgggcacgg tgggttcgtc ggaggccatc atgctggccg ggctggcctt caagcggcgg 420
tggcagaaca agcgcaaggc cgaggggaag ccgttcgaca agcccaacat catcaccggc 480
gccaacgtgc aggtgtgctg ggagaagttc gcccgctact tcgaggtgga gctcaaggag 540
gtgaagctcc gcgacggcta ctacgtcatg gaccccgaga aggccgtcga catggtcgac 600
gagaacacca tctgcgtcgc cgccatcctc ggctccaccc tcaacggcga gttcgaggac 660
gtcaagctac tcaacgacct cctcgacaag aagaacaagg agactgggtg ggagacgccg 720
atccacgtgg acgcggcgag cggcgggttc atcgcgccgt tcctgtaccc ggagctggag 780
tgggacttcc ggctgccgtg ggtgaagagc atcaacgtga gcggtcacaa gtacgggctc 840
gtctacgccg gcatcggctg gtgcatctgg cgcaacaagg aggacctgcc cgaggagctc 900
atcttccaca tcaactacct cggcgccgac cagccaacct tcaccctcaa cttctccaag 960
ggctccagcc aggtcatcgc ccagtactac cagctcatcc gccacggctt cgaggggtac 1020
aggaacatca tggagaactg ccacgagaac gcgatggtgc tgaaggaagg gctggtgaag 1080
acggggaggt tcgacatcgt gtccaaggac gaaggcgtgc cgctggtggc gttctcgctc 1140
aaggaccgga gccggcacga cgagttcgag atctccgaca tgctgcgccg cttcggctgg 1200
atcgtgccgg cgtacaccat gccgcccgac gcccagcacg tcacggtgct ccgcgtggtc 1260
atccgggagg agttcagccg caccctcgcc gagcgcctcg tcctcgacat cgagaaggtg 1320
atgtaccagc tcgacgcgct cccctccagg ctcatgcccc ccgtgccgcc ggcgccgctg 1380
cttgtggtcg ccaagaagtc ggagctcgag acgcagcggt cggtgacgga ggcgtggaag 1440
aagttcgtgc tcgccaagag gaccaacggc gtctgctag 1479

<210> SEQ ID NO 73
<211> LENGTH: 1386
<212> TYPE: DNA
<213> ORGANISM: Oryza sativa Japonica

<400> SEQUENCE: 73
atgccggagc agtcgatccc caaggaggcg gcgtaccaga tcatcaacga cgagctgatg 60
ctggacggca acccgcggct gaacctcgcg tcgttcgtca ccacgtggat ggagcccgag 120
tgcgacaagc tcatccaggc ctccgtcaac aagaactacg tcgacatgga cgagtacccc 180
gtcaccaccg aactccagaa ccgatgtgtg aacatgattg cacacctctt caatgctcct 240
ctaggggact ctgaaacggc cgtcggagtc ggcactgtcg gctcgtctga ggccatcatg 300
ctcgccggtt tggccttcaa gaggaggtgg cagaacaaga tgaaggcagc cggcaagcca 360
tgcgacaagc ctaacattgt caccggcgcc aatgtccaag tttgctggga gaagttcgcg 420
cgatacttcg aggttgagct caaggaagtg aagctgagtg acggctacta cgtcatggac 480
ccagctaagg ccgtggatat ggtcgacgag aacaccatct gcgtcgcggc gatcctcggg 540
tcgacgctga acggggagtt cgaggacgtg aagctgctca acgatctgct caccaagaag 600
aacgctgaaa caggctggga cacgccgatc cacgtggacg cggcgagcgg cgggttcatc 660
gcgccgttcc tgtacccgga gctggagtgg gacttccggc tgccgctggt gaagagcatc 720
aacgtgagcg ggcacaagta cggcctcgtc tacgccggga tcgggtggtg catctggagg 780
agcaaggagg atctgcctga ggagctcatc ttccacatca actacctcgg cgccgaccag 840

```
cccaccttca ccctcaactt ctccaagggt tccagccagg tcattgcaca gtattaccaa    900

ctaatccgcc taggctttga ggggtacaag aacatcatgg agaactgcca ggagaacgcg    960

atggtgctga agcaggggct ggagaagacg gggcggttca acatcgtgtc caaggacaac   1020

ggcgtgccgc tggtggcctt ctccctcaag gacagcgccc ggcacaacga gttcgagatc   1080

tccgacttcc tccgccgctt cggctggatc gtgccggcct acaccatgcc ccccgacgcg   1140

cagcacgtca ccgtgctccg cgtcgtcatc cgcgaggact tcagccgcac gctcgccgag   1200

cgcctcgtgc tcgacgtcga gaaggtgctg cacgagctcg acgcgctccc cgcccgcgtc   1260

gtcgccaacg gcgacaaccc ggccgccgcg tcggcgagcg agagggagat ggagaagcag   1320

cgcgaggtga tctccctctg gaagagggcc gtgctggcca agaagaagac caacggcgtc   1380

tgctaa                                                              1386
```

<210> SEQ ID NO 74
<211> LENGTH: 1470
<212> TYPE: DNA
<213> ORGANISM: Vitis vinifera

<400> SEQUENCE: 74

```
atggttctct caaaaactgc ttctgagtcg gatgtctccg tgcactccac ctttgcctct     60

cgctacgtga aagcttcgct tccgaggttc aagttgccgg agaactcgat cccgaaggag    120

gcggcgtacc agatcataaa cgacgagctg atgcttgatg gcaatcctag gctaaacctg    180

gcttcgtttg tgactacttg gatggagcct gaatgtgata agcttatgat ggctgccata    240

aacaagaact atgtggacat ggatgaatac ccgaaccgat gcgtgaacat catagcccat    300

ctattcaatg ctccattgga agactcagag gctgccgtgg gagtggggac ggtggggtcc    360

tccgaggcga taatgctagc agggcttgct ttcaagagga agtggcagaa caagagaaag    420

gctgagggga agccttatga caagcccaac atcgtcactg gtgctaatgt tcaggtgtgc    480

tgggagaagt tcgcaaggta ctttgaggta gaactgaagg aagtgaaatt gagggacggc    540

tactatgtaa tggacccaga gaaagctgtg gaaatggtgg atgaaaacac catctgtgtt    600

gcggcaatct tgggctcaac tctcaatgga gaatttgaag atgttaagct cttgaacgat    660

ctcttggtcg aaaagaacaa gcaaayagga tgggataccc caattcatgt tgatgcagct    720

agtggtggat tcattgcacc attcctttat ccggaactgg agtgggactt ccgccttcca    780

ttggtaaaga gcattaatgt tagtggccac aagtatggcc tcgtatatgc tggaattggg    840

tgggttgttt ggaggagcaa agaggacttg cccgaagaac ttatcttcca cataaactac    900

cttggagccg atcaaccaac cttcactctc aatttctcca aaggttctag tcaagtcatc    960

gcccagtatt atcaactaat tcgcttgggt ttcgagggat accgaaatgt gatggagaat   1020

tgccaggaaa atgctatggc gctgaaagaa ggactggaga agactgggcg ctttaacatc   1080

atctccaagg acaatggggt ccctctggtg gccttctctc tcaaggacaa ttcatgccat   1140

gatgagtttg aggttgcaga catgcttcgc cgctttggct ggattgtgcc tgcctacacc   1200

atgccaccag atgctcagca tgttacagtg ctccgagttg tggttaggga agacttttca   1260

cgcacccttg ctgagcgcct tgtatttgac atcaccaagg tgctccatga acttgatatg   1320

ctcccagcaa agctcagtgc caagatttct gtcgaagaga aaaagcaaaa tggcacaatt   1380

ctgaagaaat ccgtgatcga gacacagagg gaaatcaccg atgcttggaa gaaatttgtc   1440

atggccaaga aaacgaacgg cgtttgttag                                    1470
```

<210> SEQ ID NO 75
<211> LENGTH: 1488
<212> TYPE: DNA
<213> ORGANISM: Vitis vinifera

<400> SEQUENCE: 75
atggttctct caaaaactgc ttctgagtcg gatgtctccg tgcactccac ctttgcctct 60
cgctacgtga aagcttcgct tccgaggttc aagttgccgg agaactcgat cccgaaggag 120
gcggcgtacc agatcataaa cgacgaactg atgcttgatg gcaatcctag gctaaacctg 180
gcttcgtttg tgactacttg gatggagcct gaatgtgata agcttatgat ggctgccata 240
aacaagaact atgtggacat ggatgaatac ccggttacca ctgagcttca gaaccgatgc 300
gtgaacatca tagcccatct attcaatgct ccattggaag actcagaggc tgccgtggga 360
gtggggacgg tggggtcctc cgaggcgata atgctagcag ggcttgcttt caagaggaag 420
tggcagaaca agagaaaggc tgaggggaag ccttatgaca agcccaacat cgtcactggt 480
gctaatgttc aggtgtgctg ggagaagttc gcaaggtact ttgaggtaga actgaaggaa 540
gtgaaattga gggacggcta ctatgtaatg gacccagaga aagctgtgga aatggtggat 600
gaaaacacca tctgtgttgc ggcaatcttg ggctcaactc tcaatggaga atttgaagat 660
gttaagctct tgaacgatct cttggtcgaa aagaacaagc aaacaggatg ggatacccca 720
attcatgttg atgcagctag tggtggattc attgcaccat tcctttatcc ggaactggag 780
tgggacttcc gccttccatt ggtgaagagc attaatgtta gtggccacaa gtatggcctc 840
gtatatgctg gaattgggtg ggttgtttgg aggagcaaag aggacttgcc cgaagaactt 900
atctttcaca taaactacct tggagccgat caaccaacct tcactctcaa tttctccaaa 960
ggttctagtc aagtcatcgc ccagtattat caactaattc gcttgggttt cgagggatac 1020
cgaaatgtga tggagaattg ccaggaaaat gctatggcgc tgaaagaagg actggagaag 1080
actgggcgct ttaacatcat ctccaaggac aatggggtcc ctctggtggc cttctctctc 1140
aaggacaatt catgccatga tgagtttgag gttgcagaca tgcttcgccg cttcggctgg 1200
attgtgcctg cctacaccat gccaccagat gctcagcatg ttacagtgct ccgagttgtg 1260
gttagggaag acttttcacg cacccttgct gagcgccttg tatttgacat caccaaggtg 1320
ctccatgaac ttgatatgct cccagcaaag ctcagtgcca agatttctgt cgaagagaaa 1380
aagcaaaatg gcacaattct gaagaaatcc gtgatcgaga cacagaggga aatcaccgat 1440
gcttggaaga aatttgtcat ggccaagaaa acgaacggcg tttgttag 1488

<210> SEQ ID NO 76
<211> LENGTH: 1431
<212> TYPE: DNA
<213> ORGANISM: Vitis vinifera

<400> SEQUENCE: 76
atgccggaga aatcgattcc aaaagaagca gcataccaga tagtacacga tgaattacta 60
ttagatggtc ttcccaggct taacttggct acattcgtca ccacatggat ggaacctgag 120
tgtgataagc tgatggcaga agccatcaac aagaattatg tagacatgga tgaataccca 180
gtcacaactg agcttcagaa tcggtgcgtg aacatgattg caaaactttt caacgctcca 240
tcagctgatc agacaaaaca agcagttgga gttgggacag tgggatcctc agaggcaatg 300
atgttggccg gattggcatt caagaagaag tggcaaaaca agagaaaggc gcaaaagaaa 360
ccttttgaca agcctaatat tgttactggt gccaatgttc aggtttgttg ggagaaattt 420

-continued

```
gcaagatact ttgaagtgga gttgaaggaa gtgaaactaa gagaagggta ctatgtgatg    480

gacccggtga aagcggtgga gatggtggat gagaacacca tctgtgttgc agctatcctg    540

ggttctacct tcaatggtga atttgaagat gtcaagctct tgaacactct ccttactcaa    600

aagaacaaga gaactgggtg ggacacccca attcatgtgg atgcagccag tggaggattt    660

gtggctcctt ttttataccc agaactggaa tgggatttcc ggctaccttt ggtgaagagc    720

atcaatgtca gcggccacaa atacggcctt gtctacgctg gagttgggtg ggccatttgg    780

aggagcaaag aggaattgcc tgaagaactc atcttccaca taaactacct tggtggtgat    840

gaacccacct tcaccctcaa cttctccaag ggcaatcagg ttattgcaca atactaccag    900

ttcttgcgca tgggctttga gggatacaag aaagtgatga gcaactgcat ggaaagtgcg    960

aggatacttc gagagggatt ggagaaaaca gggcgtttcc aaataatttc aaaggagaaa   1020

ggagtacccg tcgtggcctt tgcattcaag ggtaacgatc gtaaaaactt ggcattcgga   1080

ttatcaaaag ccttgaggaa ctacgggtgg attgttccag cttacacgat gccagccaat   1140

gcggagaatg tcacggtcct tcgggtggtt gttcgtgagg actttgggcg gcagctggtt   1200

gagaagttgc ttttccacat tggagttgcg ttgaaggagg tcacggatgc agcaagtagt   1260

gttccaatga taagacttac agtggaaatg aaggcagatg agagtgaaat gaatgcaggt   1320

gagggaactc tacacatacc ggcggcttca gtgcactgga agcatgataa acccgaaact   1380

gttgacactc aagtgcccat aatggatggt aaaactaaag ggtttgctg a             1431
```

<210> SEQ ID NO 77
<211> LENGTH: 1491
<212> TYPE: DNA
<213> ORGANISM: Nicotiana tabacum

<400> SEQUENCE: 77

```
atggttctgt ccaagacagc gtcggaaagt gacgtctccg ttcactccac tttcgcctcc     60

cgatatgttc gaacttctct tcccaggttt aaaatgccag agaattcaat accaaaggaa    120

gcagcatatc agattataaa tgatgagctt atgttagatg gaaatccaag gctaaattta    180

gcatctttcg ttacaacatg gatggagcca gaatgtaata cgttaatgat ggattccatt    240

aacaagaact acgttgacat ggatgaatac cctgtaacca ctgagcttca gaatcgatgt    300

gtaaatatga tagctcattt gtttaatgca ccacttggag atggagagac tgcagttgga    360

gttggaactg ttggatcctc tgaagctatt atgcttgctg gattagcctt taagagaaaa    420

tggcaaaata aaatgaaagc ccaaggcaag ccctttgata agcccaatat tgtcaccggt    480

gctaatgtcc aggtgtgttg ggagaaattt gcaaggtatt ttgaagtgga gttgaaagaa    540

gtaaaattga gtgatggata ctatgtgatg gaccctgaga aagctgtgga aatggtggat    600

gagaatacca tttgtgttgc tgctatctta ggttcaacac tcaatggtga atttgaagat    660

gttaagcgtt tgaatgacct tttgattgag aagaacaaag aaaccgggtg ggacactcca    720

attcatgtgg atgcagcaag tggtggattt attgcaccat tcctttatcc agagcttgaa    780

tgggacttta gattgccatt ggagaagagt attaatgtga gtggtcacaa atatggtctt    840

gtctatgctg gtattggttg ggccatttgg aggaataagg aagacttgcc tgatgaactt    900

attttccaca tcaattacct tggtgctgat caacctactt tcactctcaa cttctctaaa    960

ggttctagcc aagtaattgc tcaatattac caacttattc gcttgggttt tgagggttac   1020

aagaatgtta tggagaattg tcaagaaaat gcaagggtat taagagaagg aattgaaaaa   1080

agtggaagat tcaacataat ctccaaagaa attggagttc ccttagtagc attttctctt   1140
```

aaagacaaca gtcaacacaa tgagttcgaa atttctgaaa ctcttagaag atttggatgg 1200
attgttctgg catatactat gccaccaaat gctcaacatg tcacagttct cagagttgtc 1260
attagagaag atttctcccg cacactagcg gagcgactgg taatagacat tgaaaaagtc 1320
ttccacggag tagacacact tccggcgagg gtcaacgcta agctagccgt ggccgaggcg 1380
aatggcagcg gcgtgcataa gaaaacagat agagaagtgc agctagagat tactactgca 1440
tggttgaaat ttgttgctga taagaagaag aagactaatg gagtttgtta a 1491

<210> SEQ ID NO 78
<211> LENGTH: 1491
<212> TYPE: DNA
<213> ORGANISM: Nicotiana tabacum

<400> SEQUENCE: 78
atggttctgt ccaagacagc gtcggaaagt gacgtctcca tccactccac tttcgcttcc 60
cgatatgttc gtacttctct tccgaggttt aagatgccag agaattcgat accaaaggaa 120
gcagcatatc aaatcataaa tgatgagctt atgttagatg gaaatccaag actaaattta 180
gcatcttttg tgacaacatg gatggaacca gagtgtaaca aactgatgat ggattccatt 240
aacaagaatt acgttgacat ggatgaatac cctgtaacca ctgaacttca gaatcgatgt 300
gtaaacatga tagctcattt gtttaacgca ccacttggag atggagagac tgcagttgga 360
gttggaactg ttggatcctc tgaggctatt atgcttgctg gattagcttt caagagaaaa 420
tggcaaaata aaatgaaagc ccaaggcaag ccctgtgaca agcccaatat tgtcactggt 480
gccaatgtcc aggtgtgttg ggagaaattt gcaaggtatt ttgaagtgga gctaaaggaa 540
gtaaagttga gtgatggata ctatgtgatg gaccctgaga aagctgtgga aatggtggat 600
gagaacacaa tttgtgtagc tgctatcttg ggttccacac tcaatggtga atttgaagat 660
gttaagcgct tgaatgacct cttgattgag aagaacaaag aaaccgggtg ggacactcca 720
attcatgtgg atgcagcaag tggtggattt attgcaccat tcctttatcc agagcttgaa 780
tgggacttta gattgccatt ggtgaagagt ataaacgtga gtggtcacaa atatggtctt 840
gtttatgctg gtattggttg ggccatttgg aggaataagg aagacttacc tgacgaactt 900
atcttccaca ttaattatct tggtgctgat caacctactt tcactctcaa cttctctaaa 960
ggttctagcc aagtaattgc tcaatattac caacttattc gcttgggttt tgagggttac 1020
aagaatgtta tggagaattg tcaagaaaat gcaagggtac taagagaagg acttgaaaaa 1080
agtggaagat tcaacataat atccaaagaa attggagttc cattagtagc tttctctctt 1140
aaagacaaca gtcaacacaa tgagttcgaa atttctgaaa ctcttagaag atttggatgg 1200
attattcctg catatactat gccaccaaat gctcaacatg tcacagttct cagagttgtc 1260
attagagaag atttctcccg tacactcgcc gagcgactgg taatagacat tgaaaaagtc 1320
ctccacgagc tagacacact tccggcgagg gtcaacgcta agctagccgt ggccgaggcg 1380
aatggcagcg gcgtgcataa gaaaacagat agagaagtgc agcttgagat tactactgca 1440
tggaagaaat ttgttgctga taagaagaag aagactaacg gagtttgtta a 1491

<210> SEQ ID NO 79
<211> LENGTH: 1491
<212> TYPE: DNA
<213> ORGANISM: Nicotiana tabacum

<400> SEQUENCE: 79

```
atggttctgt ccaagacagc gtcggaaagt gacgtctcca tccactccac tttcgcttcc     60
cgatatgttc gtacttctct tccgaggttt aagatgccag agaattcgat accaaaggaa    120
gcagcatatc aaatcataaa tgatgagctt atgttagatg gaaatccaag actaaattta    180
gcatcttttg tgacaacatg gatggaacca gagtgtaaca aactgatgat ggattccatt    240
aacaagaatt acgttgacat ggatgaatac cctgtaacca ctgaacttca gaatcgatgt    300
gtaaacatga tagctcattt gtttaacgca ccacttggag atggagagac tgcagttgga    360
gttggaactg ttggatcctc tgaggctatt atgcttgctg gattagcttt caagagaaaa    420
tggcaaaata aaatgaaagc ccaaggcaag ccctgtgaca agcccaatat tgtcactggt    480
gccaatgtcc aggtgtgttg ggagaaattt gcaaggtatt ttgaagtgga gctaaaggaa    540
gtaaagttga gtgatggata ctatgtgatg gaccctgaga aagctgtgga aatggtggat    600
gagaacacaa tttgtgtagc tgctatcttg ggttccacac tcaatggtga atttgaagat    660
gttaagcgct tgaatgacct cttgattgag aagaacaaag aaaccgggtg ggacactcca    720
attcatgtgg atgcagcaag tggtgaattt attgcaccat tcctttatcc agagcttgaa    780
tgggacttta gattgccatt ggtgaagagt attaacgtga gtggtcacaa atatggtctt    840
gtttatgctg gtattggttg ggccatttgg aggaataagg aagacttacc tgacgaactt    900
atcttccaca ttaattatct tggtgctgat caacctactt tcactctcaa cttctctaaa    960
ggttctagcc aagtaattgc tcaatattac caacttattc gcttgggttt tgagggttac   1020
aagaatgtta tggagaattg tcaagaaaat gcaagggtac taagagaagg acttgaaaaa   1080
agtggaagat tcaacataat atccaaagaa attggagttc cattagtagc tttctctctt   1140
aaagacaaca gtcaacacaa tgagttcgaa atttctgaaa ctcttagaag atttggatgg   1200
attattcctg catatactat gccaccaaat gctcaacatg tcacagttct cagagttgtc   1260
attagagaag atttctcccg tacactcgcc gagcgactgg taatagacat tgaaaaagtc   1320
ctccacgagc tagacacact tccggcgagg gtcaacgcta agctagccgt ggccgaggcg   1380
aatggcagcg gcgtgcataa gaaaacagat agagaagtgc agcttgagat tactactgca   1440
tggaagaaat ttgttgctga taagaagaag aagactaacg gagtttgtta a            1491
```

<210> SEQ ID NO 80
<211> LENGTH: 1503
<212> TYPE: DNA
<213> ORGANISM: Oryza sativa

<400> SEQUENCE: 80

```
atggttctga cgcacgtcga ggcggtggag gagggcagcg aggcggcggc cgccgtgttc     60
gcgtcgaggt acgtgcagga cccggtgccg aggtacgagc tcggcgagag gtcgatatcc    120
aaggacgccg cgtaccagat cgtccacgac gagctcctcc tggacagcag cccgcgcctg    180
aacctggcgt ccttcgtcac cacctggatg gagcccgagt gcgacaggct catcctcgag    240
gccatcaaca agaactacgc cgacatggac gagtaccccg tcaccaccga gctccagaac    300
cggtgcgtga acatcatagc gaggctgttc aatgcgccgg tgggcgacgg cgagaaggcg    360
gtcggggtgg gcacggtggg gtcgtcggag gccataatgc tggccgggct ggcgttcaag    420
cggcggtggc agaaccggcg gaaggcggcg gggaagcccc acgacaagcc caacatcgtg    480
acgggggcca acgtgcaggt gtgctgggag aagttcgcgc gctacttcga ggtggagctc    540
aaggaggtga agctgaccga aggctgctac gtgatggacc ccgtcaaggc cgtggacatg    600
gtcgacgaga acaccatctg cgtcgccgcc atcctcggct ccaccctcac cggcgagttc    660
```

```
gaggacgtca ggcgcctcaa cgacctcctc gccgccaaga acaagcggac gggttgggac    720
acgccgatcc acgtcgacgc ggcgagcggc gggttcatcg cgccgttcat ctacccggag    780
ctggagtggg acttccggct gccgctggtg aagagcatca acgtcagcgg ccacaagtac    840
gggctcgtct acgccggcgt cgggtgggtc atctggcgca acaaggagga cctccccgag    900
gagctcatct tccacatcaa ctacctcggc gccgaccagc caaccttcac gctcaacttc    960
tccaaagggt ccagtcagat tattgcgcaa tattaccagt ttcttcgact cggatttgag   1020
gggtacaaga gcgtgatgaa gaactgcatg gagagcgcga ggacgctccg ggagggcctg   1080
gagaagacgg ggcggttcac catcatctcc aaggaggagg gcgtgccgct ggtggccttc   1140
acgttcaagg acggcgccgg cgcgcaggcc ttcaggctgt cgtcgggcct gcgccggtac   1200
gggtggatcg tgccggcgta cacgatgccg gcggcgctgg agcacatgac ggtgctccgc   1260
gtcgtcgtcc gggaagactt cggccggccg ctcgccgagc ggttcctgtc ccacgtcagg   1320
atggccctgg acgagatgga cctcgccgcc agggcccccg tgcccagggt gcagctcacc   1380
atcgagctcg gccccgcccg gaccgccggc gaggaggcct cgatcagggt ggtcaagagc   1440
gaggccgtgc ccgtgcgcaa gagcgtcccg ctcgtcgccg gcaaaaccaa gggcgtttgc   1500
tag                                                                 1503
```

<210> SEQ ID NO 81
<211> LENGTH: 1485
<212> TYPE: DNA
<213> ORGANISM: Citrus sinensis

<400> SEQUENCE: 81

```
atggttcttt caaagacatt ttccgaatcc gatgagtcaa ttcactccac ctttgcctct     60
cgctacgtcc gaaactctct tcctcggttc acgatgccgg agaactcgat accgaaggag    120
gcggcgtacc agatcataaa cgacgagctg atgctcgacg ggaatccaag attgaacttg    180
gcttccttcg tcacaacgtg gatggagcct gaatgtgaca agcttatgat ggctgccatt    240
aacaagaact acgttgacat ggatgagtat cctgtcacca ccgagcttca gaatcgatgt    300
gtgaacatta tagcccgact gttcaatgct ccactggagg actccgagac ggctgtcgga    360
gttggaaccg taggatcatc ggaagccata atgttggccg gccttgcatt caaaagaaag    420
tggcagaaca agcgcaaggc tgaaggaaag ccctttgaca aacccaacat tgtcactgga    480
gcgaacgttc aggtctgctg ggagaaattt gcaaggtatt ttgaggtgga gttgaaggaa    540
gtgaagctgt cggaaggcta ctacgtgatg gacccagcca aagctgtaga aatggtggat    600
gaaaacacta tctgtgttgc tgctattctg ggttctactc tcaatggaga atttgaagat    660
gtcaagctct tgaacgacct tttgacagag aagaacaagg aaacaggatg ggatactcca    720
attcatgttg atgctgctag tggtggcttc attgcaccat tttgtaccc agagcttgaa    780
tgggacttcc gcttgccgct ggtgaagagt attaatgtta gtggccacaa gtacgggctt    840
gtgtatgctg gtattggttg ggttgtttgg agaaacaaag aagacttgcc tgaagaactc    900
atcttccaca tcaattacct aggagctgat caacccacct tcaccctcaa tttttctaaa    960
ggttctagcc aagtaattgc tcagtactac caactaatcc gcttaggttt tgagggatac   1020
cgcaatgtga tggagaattg tcacgaaaat gcaatggtgc tgaaagaagg actagagaaa   1080
accggccgct tcaacattgt gtcaaaggac gaaggggttc cgttggtggc attttctctc   1140
aaggacaaca aacgccacga tgaattcgaa gtggccgaat tgctgcgccg ttttggttgg   1200
```

```
attgtgccag cgtacaccat gcccgctgac gctcagcaca tcaccgtgtt acgtgtcgtc   1260

atcagggaag acttctctcg cacacttgcc gagcgccttg tgctcgacat cacaaaagtg   1320

cttcatgagc ttgattcgct tccttcaaaa gtgcttgtac ctgcttctga acagaatgga   1380

aggaatggaa agaagactga aattgagact cagagggaag tcactactta ctggaggaaa   1440

ttcgtctccg aaaggaaagc taataacaag aataaaattt gttaa                   1485
```

<210> SEQ ID NO 82
<211> LENGTH: 1479
<212> TYPE: DNA
<213> ORGANISM: Oryza sativa Japonica

<400> SEQUENCE: 82

```
atggtgctct cccacggcgt gtcgggctcc gatgagtccg tccactccac gttcgcctcc     60

cgctacgtcc gcacctccct ccccaggttc cggatgccgg agcagtcgat ccccaaggag    120

gcggcgtacc agatcatcaa cgacgagctg atgctggacg gcaacccgcg gctgaacctc    180

gcgtcgttcg tcaccacgtg gatggagccc gagtgcgaca agctcatcca ggcctccgtc    240

aacaagaact acgtcgacat ggacgagtac cccgtcacca ccgaactcca gaaccgatgt    300

gtgaacatga ttgcacacct cttcaatgct cctctagggg actctgaaac ggccgtcgga    360

gtcggcactg tcggctcgtc tgaggccatc atgctcgccg gtttggcctt caagaggagg    420

tggcagaaca agatgaaggc agccggcaag ccatgcgaca agcctaacat tgtcaccggc    480

gccaatgtcc aagtttgctg ggagaagttc gcgcgatact tcgaggttga gctcaaggaa    540

gtgaagctga gtgacggcta ctacgtcatg gacccagcta aggccgtgga tatggtcgac    600

gagaacacca tctgcgtcgc ggcgatcctc gggtcgacgc tgaacgggga gttcgaggac    660

gtgaagctgc tcaacgatct gctcaccaag aagaacgctg aaacaggctg ggacacgccg    720

atccacgtgg acgcggcgag cggcgggttc atcgcgccgt tcctgtaccc ggagctggag    780

tgggacttcc ggctgccgct ggtgaagagc atcaacgtga gcgggcacaa gtacggcctc    840

gtctacgccg ggatcgggtg gtgcatctgg aggagcaagg aggatctgcc tgaggagctc    900

atcttccaca tcaactacct cggcgccgac cagcccacct tcaccctcaa cttctccaag    960

ggttccagcc aggtcattgc acagtattac caactaatcc gcctaggctt tgaggggtac   1020

aagaacatca tggagaactg ccaggagaac gcgatggtgc tgaagcaggg gctggagaag   1080

acggggcggt tcaacatcgt gtccaaggac aacggcgtgc cgctggtggc cttctccctc   1140

aaggacagcg cccggcacaa cgagttcgag atctccgact tcctccgccg cttcggctgg   1200

atcgtgccgg cctacaccat gcccccgac gcgcagcacg tcaccgtgct ccgcgtcgtc    1260

atccgcgagg acttcagccg cacgctcgcc gagcgcctcg tgctcgacgt cgagaaggtg   1320

ctgcacgagc tcgacgcgct ccccgcccgc gtcgtcgcca acggcggcga cgccgccgcc   1380

gcgtcggcga gcgagaggga gatggagaag cagcgcgagg tgatctccct ctggaagagg   1440

gccgtgctgg ccaagaagaa gaccaacggc gtctgctaa                          1479
```

<210> SEQ ID NO 83
<211> LENGTH: 1482
<212> TYPE: DNA
<213> ORGANISM: Brassica juncea

<400> SEQUENCE: 83

```
atggttttgt ctaagacagc ttctggaact gatgtttccg tccattcaac ttttgcttct     60

cgttatgtcc gcaactcgct ccctcgattc gagatgcctg agaactccat cccgaaggaa    120
```

-continued gcagcgtacc agatcatcaa cgatgagcta atgctcgacg gtaaccctag gctaaatcta 180
gcctccttcg tgactacgtg gatggagcca gagtgtgaca agctcatgat ggaatctatc 240
aacaagaact acgttgacat ggacgagtac cctgtcacca ccgagcttca gaaccgatgt 300
gtcaacatga ttgcgcgtct ctttaacgcg ccgctaggtg acggtgaggc tgcggttggt 360
gtcggcaccg tgggatcgtc tgaggcgatt atgttggccg ggttggcttt taagagacag 420
tggcagaaca agcgtaaggc ccaagggctt ccttatgata agcctaatat cgtaaccgga 480
gctaatgttc aggtttgctg ggagaaattc gcaaggtatt tcgaggtgga acttaaggaa 540
gtgaagctga gagaaggata ctacgtgatg gaccctgaaa aggcagtcga aatggtagac 600
gagaacacca tttgtgtcgc agccatcctc ggttcgacgc taaccggaga attcgaagac 660
gttaagctcc tcaatgacct cctagtcgag aaaaacaagc aaaccggatg ggatactggg 720
aatcacgtgg acgcagcaag tggtgggttt attgcaccgt tcttgtatcc ggagctggag 780
tgggatttcc ggttaccatt ggttaagagc ataaatgtta gtggccacaa atacggtctg 840
gtttatgctg gaatcggttg ggttgtgtgg agaaccaaat ctgatttgcc tgatgaactt 900
atcttccaca tcaattatct tggcgctgat caacccacct tcactctcaa cttctccaag 960
ggttcgagtc aagtgattgc tcagtactac caactgattc gtcttggatt cgagggatat 1020
cgtaacgtga tggataattg tcgtgaaaac atgatggtcc taagagaagg actagagaaa 1080
acgggacgtt tcaacattgt ctccaaagaa aacggtgttc cgttagtggc gttttctcta 1140
aaagacagta gccgccacaa tgagttcgaa gtggcggaaa ctctccgccg ctttggatgg 1200
atcgttccgg cctacacggt gccagcggat gcagaacatg tcaccgtcct ccgagtggtg 1260
attcgagaag atttctctcg aaccttagct gagagattgg ttgcagactt tgagaaggtt 1320
cttcacgagc tcgatacact tccggccagg gttcgcgcca agatggctaa tggaaaagct 1380
aaagttgtta aacagacgga ggaggagacg acgagggaag ttacggcata ttggaagaag 1440
tttgtggaga caaagaagac taaccagaac aagatttgct aa 1482

<210> SEQ ID NO 84
<211> LENGTH: 1482
<212> TYPE: DNA
<213> ORGANISM: Brassica juncea

<400> SEQUENCE: 84
atggttttgt ctaagacagc ttcggaatct gatgtttcaa tccattcaac ttttgcttct 60
cgttacgtcc gcacctctct cccacgattt gagatgcctg agaactcgat cccaaaggaa 120
gcagcgtacc aaatcatcaa cgacgagcta atgctcgacg gtaacccaag gctaaatcta 180
gcctccttcg tgaccacgtg gatggagcca gagtgcgaca agctcatgat ggaatccatc 240
aacaagaact acgtcgacat ggacgagtac cctgtcacca ccgagcttca gaaccgatgc 300
gtcaacatga tcgcgcgtct cttcaacgcg ccgctaggtg acggcgaggc tgcggttggc 360
gtcggcaccg tgggatcgtc ggaggcgatt atgttggctg gattggcctt taagagacag 420
tggcagaata agcgtaaggc tcaagggctt ccttatgata agcccaatat cgttaccgga 480
gccaatgttc aggtttgctg ggagaagttt gcaaggtatt tcgaggtgga gcttaaagaa 540
gttaagctaa gagaaggata ctacgtgatg gacccagaga aggcggtcga aatggtagac 600
gagaacacaa tctgtgttgc agccatcctc ggttccactc taacaggaga attcgaagac 660
gttaagctcc ttaacgacct cctagtcgag aaaaacaagc aaaccggatg ggatacgggg 720
atccatgtgg acgcagcgag tggtgggttt attgctcctt tcttgtatcc agagctggag 780
tgggatttcc ggttaccatt ggttaagagc ataaatgtga gtggtcacaa atacggtttg 840
gtttacgctg gaatcggttg ggttgtatgg agaaccaaat ccgatttgcc tgatgaactt 900
atcttccata tcaactatct tggcgctgac caaccgacct tcactctcaa cttctccaaa 960
ggttcaagtc aagtgattgc tcagtactac cagctgattc gtcttggatt cgagggatat 1020
cgcaacgtga tggataattg ccgtgaaaat atgatggtcc taagagaagg attagagaag 1080
acaggacgtt tcaacatagt ctcaaaagaa aacggtgttc cgttagtggc attttcttta 1140
aaagacagta gtcgccacga cgagttcgaa gtggccgaga ctctccgtcg ctttgggtgg 1200
attgttccgg cctacacgat gcccgcggat gctcaacatg tcaccgtcct ccgagtggtg 1260
attcgagaag atttctctcg aactttggct gagagattgg tcgcagactt cgagaaggtt 1320
ctccacgagc tcgatacgct tccggcgagg gttcaggcca agatggctaa cggaaacgct 1380
aacggtgtta agaagacgga agaggaaacg acgagggaag ttactgcgta ttggaagaag 1440
tttgtggaag caaagaagag taacaagaac aggatttgct aa 1482

<210> SEQ ID NO 85
<211> LENGTH: 1485
<212> TYPE: DNA
<213> ORGANISM: Brassica juncea

<400> SEQUENCE: 85
atggttctaa gtcgagcggc caccgaaagt ggcgaaaatg tttgctcgac gttcggatct 60
cgctatgtcc gcaccgcact gcccaagcat aagattggtg agagctcgat cccgaaggag 120
gctgcgtatc agatcataaa agatgagctg atgcttgatg gtaacccgag gctgaacctg 180
gcttcgtttg tgacgacatg gatggagcca gagtgtgaca aactcatcat ggaatctatc 240
aacaagaact acgtcgacat ggacgagtac cctgtcacta ccgaactcca gaaccgatgt 300
gtaaacatga tagctcggct gttcaatgcg ccgcttgagg aaactgagac cgccatggga 360
gtaggcactg ttgggtcttc ggaagccatc atgttagccg gattggcctt caaaaggaat 420
tggcagaaca aacgcaaagc tgagggtaaa ccctatgaca aacccaacat tgtcaccgga 480
gccaatgttc aagtgtgctg ggagaaattc gctaggtact tcgaggtgga gctaaaagaa 540
gtgaagctta gtgaaggtta ctacgtgatg gatccggata aagcagctga aatggtagac 600
gagaatacaa tctgtgttgc tgccatactt ggttctacac tcaacggtga gttcgaagac 660
gtcaagcgcc ttaatgactt gctggtcaag aaaaacgaag agactggctg gaacactcca 720
atccacgttg acgcagcaag tggaggcttc atagctccgt ttatctaccc tgagttggaa 780
tgggacttta ggcttccttt ggtgaagagt atcaatgtga gtggtcataa gtatgggctg 840
gtctatgctg gtattggctg ggtcgtgtgg aggacacaac aggatttgcc tgatgagctc 900
atctttcata ttaactatct tggtgctgat caacccacat ttactctcaa tttctccaag 960
ggatcgagcc aaattattgc tcaatattat cagctcattc gtcttggctt cgagggctac 1020
aagaacgtga tggagaactg cagagagaac atggtggttc tgagagaagg gatcgagaaa 1080
acagagcgtt tcaacatagt ctcaaaggag gtaggagttc cactcgtagc cttctccctc 1140
aaggaccaca gtttccacaa cgagttcgaa atctcagaga tgctacgccg tttcggctgg 1200
attgtcccgg cttacacaat gcctgcggat gcgcaacaca tcacagttct gcgtgttgtc 1260
atcagggaag atttctcaag aacacttgcg gagagacttg tggctgatat tgtgaaggtg 1320
cttcacgagc tcgacacctt gccttccaag atatctaaga agatgggagc agaggatttc 1380
ggaaacgtga aagggaagaa ggtggatagg gatgttctga tggaagtcat tgttggatgg 1440
aggaagtttg tgaaggacag gaagaagatg aatggtgtgt gttga 1485

<210> SEQ ID NO 86
<211> LENGTH: 1494
<212> TYPE: DNA
<213> ORGANISM: Oryza sativa Japonica

<400> SEQUENCE: 86
atggtgctct cgcacgcgag ctccggccgg gacgacgccg tgcgctgcac cttcgcgacg 60
cgctacgcct gcgagacgct gccgcggttc aggatgccgg agcagtcgat cccgagggag 120
gcggcgtacc agatcatcaa cgacgagctg atgctggacg ggaacccgcg gctgaacctg 180
gcgtccttcg tcaccacgtg gatggagccc gagtgcgaca agctcatcat ggactccgtt 240
aacaagaact acgtcgacat ggacgagtac cctgtcacca cggagctcca gaaccgttgt 300
gtgaatatga tagctcacct gttcaatgca ccaatcaagg aggatgaaac agctattgga 360
gttgggacgg tgggatcctc agaagcaatt atgcttgcag gactggcatt caagaggaag 420
tggcaaaaca aacggaagga acaggggaag ccatgtgaca aacccaacat tgttactggt 480
gctaatgttc aggtttgctg ggagaaattt gccagatatt ttgaagtaga actgaaggag 540
gttaagctca gtgaaggata ctatgtcatg gatcctgtaa aggctgttga aatggtggat 600
gagaacacta tatgcgttgc ggccatcttg ggctctactc tcactggaga gtttgaggat 660
gttaagttat tgaataatct cctaacagaa aagaataagg aaactgggtg ggatgtgcca 720
attcatgttg atgcagcaag tggaggattt atagcacctt ttctataccc tgagcttgaa 780
tgggacttca ggctaccact ggtgaagagc atcaatgtca gtgggcacaa gtatggcctt 840
gtgtatccag gtgttggttg ggtcatttgg cgaagcaaag aggatttgcc tgaagaactc 900
attttccata taaactatct ggggacagac cagccgacgt tcactctgaa cttctccaaa 960
ggttccagcc agataatcgc acagtactat caactaatac gcctgggatt cgagggatac 1020
aagaacatca tgcagaattg catggagaac acagcaatac taagggaagg catagaggcg 1080
actggtcgat tcgaaatcct ctccaaggag gccggtgtgc ccttggtggc gttctcgctc 1140
aaggacagcg gcaggtacac cgtgttcgac atctccgagc acctgaggag gttcggctgg 1200
atcgtgccgg cgtacaccat gccggccaac gccgagcacg tcgccgtcct ccgcgtcgtc 1260
atcagggagg acttcagccg gagcctcgcc gagcggctcg tctcggacat cgtcaagatc 1320
ctgcacgagc tggacgccca ttcggcccag gtgctgaaga tctccagcgc catcgcgaag 1380
cagcaatcgg gcgacgatgg cgtggtcacc aagaagagcg tcctggagac cgagagggag 1440
atcttcgcgt actggaggga ccaggtgaag aagaagcaga ccggaatctg ctag 1494

<210> SEQ ID NO 87
<211> LENGTH: 1473
<212> TYPE: DNA
<213> ORGANISM: Hordeum vulgare

<400> SEQUENCE: 87
atggtggtga ccgtggcagc gacggggccg gacacggccg agacgctgca ctccaccacc 60
ttcgcctccc gctacgtccg cgaccagctc ccccggtacc ggatgccgga gaactcgatc 120
cccaaggagg cggcgtacca gatcatcagc gacgagctga tgctggacgg caacccgcgg 180
ctgaacctgg cgtccttcgt caccacctgg atggagcccg agtgcggcaa gctcatcatg 240

```
gactccgtca acaagaacta cgtcgacatg gacgagtacc ccgtcaccac cgagctccag    300

gaccgttgcg taaacatgat agctcacttg ttcaatgcac cgatcggcga ggacgagaca    360

gctatcggag tctcgacggt ggggtcttcg gaagcaatca tgcttgcagg cctggcgttc    420

aagaggaagt gggcgaacaa aatgaaggag caggggaagc catgcgacaa acctaacatt    480

gttactggtg caaatgttca ggtttgctgg gagaaatttg ctaggtattt tgaagtggaa    540

ttgaaggagg tcaagttgac tgaagggtac tatgtcatgg atcctaagaa ggctgttgaa    600

atggtggatg agaacactat atgtgtcgcc gccatcctgg gatctactct cactggagag    660

tacgaagatg tcaaactgtt gaatgacctt cttgtggaga agaacaagga aacagggtgg    720

aacgtgccga tccatgttga tgctgccagc ggaggattta tcgctccgtt tcttcagcct    780

gagcttgaat gggacttcag gctaccattg gtgaagagca tcaacgttag tgggcacaag    840

tatggccttg tgtaccctgg tgttggatgg gtcatctggc ggagcaagga cgatttgccc    900

gaagaactca ttttccacat aaactatcta ggagcagatc agcccacatt cacgctcaac    960

ttctccaagg gtcagcagat catcgcgcaa tactatcagc tcatccgcct cggcttcgag   1020

gggtacaagc acatcatgga gaactgcaag ctgaacgcgg cggtgctgaa ggagggcatc   1080

gacgcgacgg ggcggttcga cgtgctgtcc aaggcggacg gcgtgccgct ggtggccatc   1140

cggctcaagg acagcaccaa cttcagcgtg ttcgacatct cggagaacct gaggcggttc   1200

gggtggatcg tgccggcgta caccatgccc gccgacgcgg agcatgtggc cgtgctccgc   1260

atagtcatcc gggaggactt caaccggagc ctcgcgcagc ggctcctcgc cgacatcaac   1320

aagatcatcg gcgagctgga cgcgcacgcc gtccacgcca tcaagctctc caccgccgcc   1380

gctggtgggg acggcgcgag taagagcgcg gtcgacgccg ccaccgaggc cttcaaggac   1440

ctggcgggga agaagaaggc cggagtatgc tga                                1473
```

<210> SEQ ID NO 88
<211> LENGTH: 1479
<212> TYPE: DNA
<213> ORGANISM: Oryza sativa Japonica

<400> SEQUENCE: 88

```
atggtgctct ccaaggccgt ctccgagagt gacatgtccg tgcactccac cttcgcctcc     60

cgctacgtcc gcgcctccct cccaaggtac cggatgccgg agaactcgat cccgaaggag    120

gcggcgtacc agatcatcaa cgacgagctg atgctggacg gcaacccgcg gctgaacctg    180

gcgtcgttcg tcaccacgtg gatggagccc gagtgcgaca agctcatcat ggccgccatc    240

aacaagaact acgtcgacat ggacgagtac cccgtcacca ccgagctcca gaaccggtgc    300

gtgaacatga tcgcgcacct gttccacgcg ccgctcgggg aggacgagac ggcggtgggc    360

gtgggcacgg tgggttcgtc ggaggccatc atgctggccg ggctggcctt caagcggcgg    420

tggcagaaca agcgcaaggc cgaggggaag ccgttcgaca agcccaacat catcaccggc    480

gccaacgtgc aggtgtgctg ggagaagttc gcccgctact tcgaggtgga gctcaaggag    540

gtgaagctcc gcgacggcta ctacgtcatg gaccccgaga aggccgtcga catggtcaac    600

gagaacacca tctgcgtcgc cgccatcctc ggctccaccc tcaacggcga gttcgaggac    660

gtcaagctac tcaacgacct cctcgacaag aagaacaagg agactgggtg ggagacgccg    720

atccacgtgg acgcggcgag cggcgggttc atcgcgccgt tcctgtaccc ggagctggag    780

tgggacttcc ggctgccgtg ggtgaagagc atcaacgtga gcggtcacaa gtacgggctc    840

gtctacgccg gcatcggctg gtgcatctgg cgcaacaagg aggacctgcc cgaggagctc    900
```

atcttccaca tcaactacct cggcaccgac cagccaacct tcaccctcaa cttctccaag 960
ggctccagcc aggtcatcgc ccagtactac cagctcatcc gccacggctt cgaggggtac 1020
aggaacatca tggagaactg ccacgagaac gcgatggtgc tgaaggaagg gctggtgaag 1080
acggggaggt tcgacatcgt gtccaaggac gaaggggtgc cgctggtggc gttctcgctc 1140
aaggaccgga gccggcacga cgagttcgag atctccgaca tgctgcgccg cttcggctgg 1200
atcgtgccgg cgtacaccat gccgcccgac gcccagcacg tcacggtgct ccgcgtggtc 1260
atccgggagg agttcagccg caccctcgcc gagcgcctcg tcctcgacat cgagaaggtg 1320
atgtaccagc tcgacgcgct cccctccagg ctcatgcccc ccgtgccgcc ggcgccgctg 1380
ctggtggtcg ccaagaagtc ggagctcgag acgcagcggt cggtgacgga ggcgtggaag 1440
aagttcgtgc tcgccaagag gaccaacggc gtctgctag 1479

<210> SEQ ID NO 89
<211> LENGTH: 1485
<212> TYPE: DNA
<213> ORGANISM: Arabidopsis thaliana

<400> SEQUENCE: 89
atggtactcg caaccaactc tgactccgac gagcatttgc attccacttt tgcttctaga 60
tatgtccgtg ctgttgttcc caggttcaag atgcctgacc attgcatgcc caaagatgct 120
gcttatcaag tgatcaatga tgagttgatg cttgatggta atcccaggct taacctagcc 180
tcctttgtca ccacttggat ggaacctgag tgtgacaaac tcatcatgga ttctgtcaat 240
aagaactatg ttgatatgga tgaatatcct gtcaccactg agctccagaa ccggtgtgta 300
aatatgatag caaacttttt ccatgctccc gttggagaag acgaggctgc tattgggtgt 360
ggaactgttg gttcatctga ggctataatg cttgctggtt tggctttcaa aaggaaatgg 420
caacatagga gaaaagctca gggtctacct attgataagc ctaacattgt cactggagcc 480
aatgttcagg tgtgctggga gaagtttgca aggtactttg aggtagagct caaagaggtg 540
aaactaagtg aagactacta tgttatggat ccagctaaag ctgtagagat ggtggatgag 600
aataccatct gtgttgcagc aattctagga tctacactta ctggagagtt tgaggacgtt 660
aagcaattga acgatctctt agctgagaaa aacgcagaga caggatggga aactcctatt 720
catgttgatg cagccagtgg aggattcatt gctcctttcc tctaccctga tcttgaatgg 780
gactttaggc ttccatgggt gaagagtatt aacgtcagtg gtcacaagta tggacttgtg 840
tatgcaggag ttggttgggt tgtctggaga acaaaagatg atttgccaga ggaacttgtc 900
ttccacatca actacttggg agctgatcaa cccactttca ctctcaactt ctcaaaaggg 960
tcgagccaaa tcattgctca gtactatcag tttatccgac taggctttga gggatacaag 1020
aacataatgg aaaactgcat ggataacgca aggaggctaa gagaaggaat agagatgaca 1080
gggaagttca acattgtgtc caaagatatt ggcgtgccac tagtggcatt ctctctcaaa 1140
gacagtagca agcacacggt gtttgagatc gcagagtctt tgagaaaatt cgggtggatc 1200
ataccggctt acactatgcc tgcagatgca cagcacattg ctgtgctcag agttgtgata 1260
agagaagact ttagccgagg ccttgcagat agactcatca cacatatcat tcaggtgctg 1320
aaagagattg aagggcttcc tagcaggatt gcacatcttg ctgcggctgc agcggttagt 1380
ggtgatgatg aagaagttaa agtgaagact gccaagatgt ccttggagga tatcactaag 1440
tattggaaac gccttgtgga acacaagaga aatattgtct gctaa 1485

<210> SEQ ID NO 90
<211> LENGTH: 1491
<212> TYPE: DNA
<213> ORGANISM: Nicotiana tabacum

<400> SEQUENCE: 90
atggttctgt ccaagacagc gtcggaaagt gacgtctcca tccactccac tttcgcttcc 60
cgatatgttc gaacttctct tcccaggttt aagatgccag agaattcaat accaaaggaa 120
gcagcatatc agattataaa tgatgagctt atgttagatg gaaatccaag gctaaattta 180
gcatctttcg ttacaacatg gatggagcca gaatgtaata cgttaatgat ggattccatt 240
aacaagaact acgttgacat ggatgaatac cctgtaacca ctgagcttca gaatcgatgt 300
gtaaatatga tagctcattt gtttaatgca ccacttggag atggagagac tgcagttgga 360
gttggaactg ttggatcctc tgaagctatt atgcttgctg gattagcctt taaaagaaaa 420
tggcaaaata aaatgaaagc ccaaggcaag ccctttgata agcccaatat cgtcaccggt 480
gctaatgtcc aggtgtgttg ggagaaattt gcaaggtatt ttgaagtgga gttgaaagaa 540
gtaaaattga gtgatggata ctatgtgatg gaccctgaga aagctgtgga aatggtggat 600
gagaatacca tttgtgttgc tgctatctta ggttcaacac tcaatggtga atttgaagat 660
gttaagcgtt tgaatgacct tttgattgag aagaacaaag aaaccgggtg ggacactcca 720
attcatgtgg atgcagcaag tggtggattt attgcaccat tcctttatcc agagcttgaa 780
tgggacttta gattgccatt ggtgaagagt attaatgtga gtggtcacaa atatggtctt 840
gtctatgctg gtattggttg ggccatttgg aggaataagg aagacttgcc tgatgaactt 900
attttccaca tcaattacct tggtgctgat caacctactt tcactctcaa cttctctaaa 960
ggttctagcc aagtaattgc tcaatattac caacttattc gcttgggttt tgagggttac 1020
aagaatgtta tggagaattg tcaagaaaat gcaagggtat taagagaagg aattgaaaaa 1080
agtggaagat tcaacataat ctccaaagaa attggagttc ccttagtagc attttctctt 1140
aaagacaaca gtcaacacaa tgagttcgaa atttctgaaa ctcttagaag atttggatgg 1200
attgttcctg catatactat gccaccaaat gctcaacatg ttacagttct cagagttgtc 1260
attagagaag atttctcccg cacactagcg gagcgactgg taatagacat tgaaaaagtc 1320
ctccacgagc tagacacact tccggcgagg gtcaacgcta agctagccgt ggccgaggcg 1380
aatggcagcg gcgtgcataa gaaaacagat agagaagtgc agctagagat tactactgca 1440
tggaagaaat ttgttgctga taagaagaag aagactaatg gagtttgtta a 1491

<210> SEQ ID NO 91
<211> LENGTH: 1485
<212> TYPE: DNA
<213> ORGANISM: Arabidopsis thaliana

<400> SEQUENCE: 91
atggttttga caaaaaccgc aacgaatgat gaatctgtct gcaccatgtt cggatctcgc 60
tatgttcgca ctacacttcc caagtatgag attggtgaga attcgatacc gaaagacgct 120
gcgtatcaga tcataaaaga tgagctgatg cttgatggta acccaaggct taacctagct 180
tcttttgtga ctacatggat ggaaccagag tgtgacaaac tcatcatgga ctctatcaat 240
aagaactacg ttgatatgga tgagtaccct gtcacaactg agctccagaa ccgatgtgta 300
aacattatag ctcgactgtt caatgcgcca ctcgaggaat ctgagacggc ggtgggagta 360
gggacagttg gttcttcaga agccatcatg ttagccggat tggccttcaa aagaaaatgg 420

```
cagaacaaac gcaaggctga gggtaaaccc tatgacaaac ccaacattgt caccggagcc    480

aatgttcaag tttgctggga gaaattcgct cggtacttcg aggtggagct aaaggaagta    540

aacctaagtg aaggttacta cgtgatggat ccagacaaag cagcagaaat ggtagacgag    600

aacacaatct gtgtcgcagc catattggga tccacactca acggtgagtt cgaagacgtg    660

aaacgtctca atgacttgct agtcaagaaa aacgaggaga ctggttggaa cacaccgatc    720

cacgtggatg cagcaagtgg agggttcata gctccgttta tctatcctga attagaatgg    780

gactttaggc ttcctttggt taagagcatc aacgtgagtg gtcacaagta tggactagtc    840

tatgctggta ttggttgggt cgtgtggagg gcagcagagg atttacctga agagcttatc    900

tttcatatta attatcttgg tgctgatcaa cccactttca ctctcaattt ctccaaggga    960

tcgagccaaa ttattgctca atactaccag ctcattcgtc ttggattcga ggggtacaaa   1020

aatgtgatgg agaattgcat agagaacatg gtggttctca aagaaggtat agagaaaaca   1080

gagcgtttca acatagtctc aaaggaccaa ggagtgccag tcgtcgcctt ctctctcaag   1140

gaccatagtt tccacaacga gttcgagatc tctgagatgc tacgtcgttt tggctggatc   1200

gtcccagctt acactatgcc tgccgatgta cagcacatca cggttctgcg tgttgtcatc   1260

agggaagatt tctcaagaac actcgcggag agacttgttg ctgatatttc gaaggtgctt   1320

catgagctag ataccttgcc ttccaagata tctaagaaga tgggaataga agggatcgcg   1380

gaaaatgtaa aggagaagaa gatggagaag gagattctga tggaagttat tgttggatgg   1440

aggaagtttg tgaaggagag gaagaagatg aatggtgtgt gctaa                   1485
```

<210> SEQ ID NO 92
<211> LENGTH: 1476
<212> TYPE: DNA
<213> ORGANISM: Nicotiana tabacum

<400> SEQUENCE: 92

```
atggttctct cgaaaacctc ctctgagtcg gacgtttcgg tacactccac ttttgcctct     60

cgctatgttc gaacttccct tccaaggttt gagatggcgg agaattcgat accaaaagag    120

gcggcatttc aaataattaa cgacgagttg atgcttgacg ggaatccaag gctgaacttg    180

gcttcatttg tgacaacatg gatggagcca gagtgtgata agcttatgat ggactccatt    240

aacaagaact atgttgacat ggatgaatac cctgttacca ctgagcttca gaatcgctgc    300

gtgaacatga tagcacgttt attcaacgcg ccactagaag agaaggagac agcagttgga    360

gtgggtacag ttggttcatc ggaggccata atgctagcgg ggcttgcatt caagagaaat    420

tggcaaaaca aacgcaaagc tgagggcaaa ccttacaata agcccaacat tgtcactggc    480

gccaatgttc aggtgtgctg ggagaaattt gccaactatt ttgaagtgga attgaaagaa    540

gtaaagctaa gggaagggta ctatgtgatg gacccagtcc aggctgtgga gatggttgat    600

gagaacacca tttgtgttgc tgcaatcttg ggttcaaccc ttaatggaga atttgaagat    660

gtcaagctct tgaatgatct tttgattgaa aagaacaagc aaactggatg gaacacacca    720

attcatgtgg atgcagcaag tggtggattc attgcaccat tcctgtaccc agagctggag    780

tgggacttta ggcttccctt agtgaagagc ataaatgtga gtgggcacaa atatgggctt    840

gtctatgctg gtattggttg ggttatttgg aggaccaaac aagatttgcc tgaagaactc    900

attttccaca tcaactatct tggagctgat cagcccacct ttactctcaa tttctccaaa    960

ggttcaagtc aagtcattgc tcaatattat cagctaatcc gtttgggcta tgaggggtac   1020
```

```
cgaaatgtaa tggagaactg tcgcgaaaat gccattgtgc taagagaagg actcgaaaaa   1080

acaggacgtt ttaacatagt ctccaaagat gaaggtgtcc ctttggtggc cttttccctc   1140

aaggacaata gccgtcacaa tgagttcgag gtgtccgaga cgctccgtag gttcgggtgg   1200

atcgtcccgg cctacacgat gcccgctgac gcccaacacg tcacggtgct tcgtgtggtg   1260

atccgggagg acttctcgcg aaccctagca gagcgtctcg tcctcgacat tgtcaaggtc   1320

ctccacgagc tggacacact tccagctagg ctgagcgcca aattagagga ggtgaagctg   1380

gtcaagaatg gaaagaaatt tgaacttgaa gttcaaaggg aagttaccaa ttattggaag   1440

aagtttgttt tagctaggaa agcacctgtt tgctag                             1476
```

<210> SEQ ID NO 93
<211> LENGTH: 1503
<212> TYPE: DNA
<213> ORGANISM: Oryza sativa Japonica

<400> SEQUENCE: 93

```
atggttctga cgcacgtcga ggcggtggag gagggcagcg aggcggcggc cgccgtgttc     60

gcgtcgaggt acgtgcagga cccggtgccg aggtacgagc tcggcgagag gtcgatatcc    120

aaggacgccg cgtaccagat cgtccacgac gagctcctcc tggacagcag cccgcgcctg    180

aacctggcgt ccttcgtcac cacctggatg gagcccgagt gcgacaggct catcctcgag    240

gccatcaaca agaactacgc cgacatggac gagtaccccg tcaccaccga gctccagaac    300

cggtgcgtga acatcatagc gaggctgttc aatgcgccgg tgggcgacgg cgagaaggcg    360

gtcggggtgg gcacggtggg gtcgtcggag gccataatgc tggccgggct ggcgttcaag    420

cggcggtggc agaaccggcg gaaggcggcg gggaagcccc acgacaagcc caacatcgtg    480

acgggggcca acgtgcaggt gtgctgggag aagttcgcgc gctacttcga ggtggagctc    540

aaggaggtga agctgaccga aggctgctac gtgatggacc ccgtcaaggc cgtggacatg    600

gtcgacgaga acaccatctg cgtcgccgcc atcctcggct ccaccctcac cggcgagttc    660

gaggacgtca ggcgcctcaa cgacctcctc gccgccaaga acaagcggac gggttgggac    720

acgccgatcc acgtcgacgc ggcgagcggc gggttcatcg cgccgttcat ctacccggag    780

ctggagtggg acttccggct gccgctggtg aagagcatca acgtcagcgg ccacaagtac    840

gggctcgtct acgccggcgt cgggtgggtc atctggcgca acaaggagga cctccccgag    900

gagctcatct tccacatcaa ctacctcggc gccgaccagc caaccttcac gctcaacttc    960

tccaaagggt ccagtcagat tattgcgcaa tattaccagt ttcttcgact cggatttgag   1020

gggtacaaga gcgtgatgaa gaactgcatg gagagcgcga ggacgctccg ggagggcctg   1080

gagaagacgg ggcggttcac catcatctcc aaggaggagg gcgtgccgct ggtggccttc   1140

acgttcaagg acggcgccgg cgcgcaggcc ttcaggctgt cgtcgggcct gcgccggtac   1200

gggtggatcg tgccggcgta cacgatgccg gcggcgctgg agcacatgac ggtcgtccgc   1260

gtcgtcgtcc gggaagactt cggccggccg ctcgccgagc ggttcctgtc ccacgtcagg   1320

atggccctgg acgagatgga cctcgccgcc agggccccccg tgcccagggt gcagctcacc   1380

atcgagctcg gccccgcccg gaccgccggc gaggaggcct cgatcagggt ggtcaagagc   1440

gaggccgtgc ccgtgcgcaa gagcgtcccg ctcgtcgccg gcaaaaccaa gggcgtttgc   1500

tag                                                                 1503
```

<210> SEQ ID NO 94
<211> LENGTH: 1503

<212> TYPE: DNA
<213> ORGANISM: Oryza sativa Japonica

<400> SEQUENCE: 94
atggttctga cgcacgtcga ggcggtggag gagggcagcg aggcggcggc cgccgtgttc 60
gcgtcgaggt acgtgcagga cccggtgccg aggtacgagc tcggcgagag gtcgatatcc 120
aaggacgccg cgtaccagat cgtccacgac gagctcctcc tggacagcag cccgcgcctg 180
aacctggcgt ccttcgtcac cacctggatg gagcccgagt gcgacaggct catcctcgag 240
gccatcaaca agaactacgc cgacatggac gagtaccccg tcaccaccga gctccagaac 300
cggtgcgtga acatcatagc gaggctgttc aatgcgccgg tgggcgacgg cgagaaggcg 360
gtcggggtgg gcacggtggg gtcgtcggag gccataatgc tggccgggct ggcgttcaag 420
cggcggtggc agaaccggcg gaaggcggcg gggaagcccc acgacaagcc caacatcgtg 480
acgggggcca acgtgcaggt gtgctgggag aagttcgcgc gctacttcga ggtggagctc 540
aaggaggtga agctgaccga aggctgctac gtgatggacc ccgtcaaggc cgtggacatg 600
gtcgacgaga acaccatctg cgtcgccgcc atcctcggct ccaccctcac cggcgagttc 660
gaggacgtca ggcgcctcaa cgacctcctc gccgccaaga acaagcggac gggttgggac 720
acgccgatcc acgtcgacgc ggcgagcggc gggttcatcg cgccgttcat ctacccggag 780
ctggagtggg acttccggct gccgctggtg aagagcatca acgtcagcgg ccacaagtac 840
gggctcgtct acgccggcgt cgggtgggtc atctggcgca acaaggagga cctccccgag 900
gagctcatct tccacatcaa ctacctcggc gccgaccagc caaccttcac gctcaacttc 960
tccaaagggt ccagtcagat tattgcgcaa tattaccagt ttcttcgact cggatttgag 1020
gggtacaaga gcgtgatgaa gaactgcatg gagagcgcga ggacgctccg ggagggcctg 1080
gagaagacgg ggcggttcac catcatctcc aaggaggagg gcgtgccgct ggtggccttc 1140
acgttcaagg acggcgccgg cgcgcaggcc ttcaggctgt cgtcgggcct gcgccggtac 1200
gggtggatcg tgccggcgta cacgatgccg gcggcgctgg agcacatgac ggtcgtccgc 1260
gtcgtcgtcc gggaagactt cggccggccg ctcgccgagc ggttcctgtc ccacgtcagg 1320
atggccctgg acgagatgga cctcgccgcc agggcccccg tgcccagggt gcagctcacc 1380
atcgagctcg gccccgcccg gaccgccggc gaggaggcct cgatcagggt ggtcaagagc 1440
gaggccgtgc ccgtgcgcaa gagcgtcccg ctcgtcgccg gcaaaaccaa gggcgtttgc 1500
tag 1503

<210> SEQ ID NO 95
<211> LENGTH: 1491
<212> TYPE: DNA
<213> ORGANISM: Nicotiana tabacum

<400> SEQUENCE: 95
atggttctgt ccaagacagc gtcggaaagt gacgtctcca tccactccac tttcgcttcc 60
cgatatgttc gaacttctct tcccaggttt aagatgccag agaattctat accaaaagaa 120
gcagcatatc aaatcataaa tgatgagctt atgttagatg gaaatccaag gctaaattta 180
gcatcttttg tgacaacatg gatggaacca gagtgtaata agttaatgat ggattccatt 240
aacaagaact acgttgacat gggtgaatac cctgtaacca ctgagcttca gaatcgatgt 300
gtaaatatga tagctcattt gtttaacgca ccacttggag atggagagac tgcagttgga 360
gttggaactg ttggatcctc tgaggctatt atgcttgctg gattagcctt caagagaaaa 420

-continued

```
tggcaaaata aaatgaaagc ccaagggaag ccctgcgaca agcccaatat tgtcactggt    480

gccaatgtcc aggtgtgttg ggagaaattt gcaaggtatt ttgaagtgga gttgaaagaa    540

gtaaaattga gtgatggata ctatgtgatg gaccctgaga aagctgtgga aatggtggat    600

gagaatacaa tttgtgtagc tgctatcttg ggttccactc tcaatggtga atttgaagat    660

gttaagcgct tgaatgacct cttgattgag aagaacaaag aaaccgggtg ggacactcca    720

attcatgtgg atgcagcaag tggtggattc attgcaccat tcctttatcc tgagcttgaa    780

tgggatttta gattaccatt ggtgaagagt attaatgtga gtggtcacaa atatggtctt    840

gtctatgctg gtattggttg ggccatttgg aggaataagg aagacttgcc tgatgaactt    900

attttccaca ttaattatct tggtgctgat caacctactt tcactctcaa cttctctaaa    960

ggttctagcc aagtaattgc tcaatattac caacttattc gcttgggttt tgagggttac   1020

aagaatgtta tggagaattg tcaagaaaat gcaagggtac taagagaagg acttgaaaaa   1080

agtggaagat tcaatataat ctccaaagaa attggagttc cattagtagc tttctctctt   1140

aaagacaaca gtcaacacaa tgagttcgaa atttctgaaa ctcttagaag atttggatgg   1200

attattcctg catatactat gccaccaaat gctcaacatg tcacagttct cagagttgtt   1260

attagagaag atttctcccg tacactcgcg gagcgactgg tgatagacat tgaaaaagtc   1320

ctccacgagc tagacacact tccggcgagg gtcaacgcta agctcgccgt ggccgaggcg   1380

aatggcagcg gcgtgcataa gaaaacagat agagaagtgc agctggagat tactgctgca   1440

tggaagaaat ttgttgctga taagaagaag aagactaatg gagtttgtta a            1491


<210> SEQ ID NO 96
<211> LENGTH: 1485
<212> TYPE: DNA
<213> ORGANISM: Arabidopsis thaliana

<400> SEQUENCE: 96

atggtactcg caaccaactc tgactccgac gagcatttgc attccacttt tgcttctaga     60

tatgtccgtg ctgttgttcc caggttcaag atgcctgacc attgcatgcc caaagatgct    120

gcttatcaag tgatcaatga tgagttgatg cttgatggta atcccaggct taacctagcc    180

tcctttgtca ccacttggat ggaacctgag tgtgacaaac tcatcatgga ttctgtcaat    240

aagaactatg ttgatatgga tgaatatcct gtcaccactg agctccagaa ccggtgtgta    300

aatatgatag caaacttgtt ccatgctccc gttggagaag acgaggctgc tattgggtgt    360

ggaactgttg gttcatctga ggctataatg cttgctggtt tggctttcaa aaggaaatgg    420

caacatagga gaaaagctca gggtctacct attgataagc ctaacattgt cactggagcc    480

aatgttcagg tgtgctggga gaagtttgca aggtactttg aggtagagct caaagaggtg    540

aaactaagtg aagactacta tgttatggat ccagctaaag ctgtagagat ggtggatgag    600

aataccatct gtgttgcagc aattctagga tccacactta ctggagagtt tgaggacgtt    660

aagcaattga acgatctctt agctgagaaa aacgcagaga caggatggga aactcctatt    720

catgttgatg cagccagtgg aggattcatt gctcctttcc tctaccctga tcttgaatgg    780

gactttaggc ttccatgggt gaagagtatt aacgtcagtg gtcacaagta tggacttgtg    840

tatgcaggag ttggttgggt tgtctggaga acaaaagatg atttgccaga ggaacttgtc    900

ttccacatca actacttggg agctgatcaa cccactttca ctctcaactt ctcaaaaggg    960

tcgagccaaa tcattgctca gtactatcag tttatccgac taggctttga gggatacaag   1020

aacataatgg aaaactgcat ggataacgca aggaggctaa gagaaggaat agagatgaca   1080
```

```
gggaagttca acattgtgtc caaagatatt ggcgtgccac tagtggcatt ctctctcaaa   1140

gacagtagca agcacacggt gtttgagatc gcagagtctt tgagaaaatt cgggtggatc   1200

ataccggctt acactatgcc tgcagatgca cagcacattg ctgtgctcag agttgtgata   1260

agagaagact ttagccgagg ccttgcagat agactcatca cacatatcat tcaggtgctg   1320

aaagagattg aagggcttcc tagcaggatt gcacatcttg ctgcggctgc agcggttagt   1380

ggtgatgatg aagaagttaa agtgaagact gccaagatgt ccttggagga tatcactaag   1440

tattggaaac gccttgtgga acacaagaga aatattgtct gctaa                   1485


<210> SEQ ID NO 97
<211> LENGTH: 484
<212> TYPE: PRT
<213> ORGANISM: Oryza sativa

<400> SEQUENCE: 97

Met Ala Leu Ser Thr Ala Gln Thr Gly Glu Ser Met His Ser Ser Thr
1               5                   10                  15

Phe Ala Ser Arg Tyr Val Arg Thr Ala Leu Pro Arg Phe Arg Met Pro
            20                  25                  30

Glu Lys Ser Ile Pro Lys Asp Ala Ala Tyr Gln Ile Ile Asn Asp Glu
        35                  40                  45

Leu Met Leu Asp Gly Asn Pro Arg Leu Asn Leu Ala Ser Phe Val Thr
    50                  55                  60

Thr Trp Met Glu Pro Glu Cys Asp Lys Leu Met Met Ala Ala Ile Asn
65                  70                  75                  80

Lys Asn Tyr Val Asp Met Asp Glu Tyr Pro Val Thr Thr Glu Leu Gln
                85                  90                  95

Asn Arg Cys Val Asn Met Ile Ala His Leu Phe Asn Ala Pro Ile Gly
            100                 105                 110

Asp Asp Glu Thr Ala Val Gly Val Gly Thr Val Gly Ser Ser Glu Ala
        115                 120                 125

Ile Met Leu Ala Gly Leu Ala Phe Lys Arg Lys Trp Gln Asn Arg Met
    130                 135                 140

Lys Ala Glu Gly Lys Pro His Asp Lys Pro Asn Ile Val Thr Gly Ala
145                 150                 155                 160

Asn Val Gln Val Cys Trp Glu Lys Phe Ala Arg Tyr Phe Glu Val Glu
                165                 170                 175

Leu Lys Glu Val Lys Leu Thr Gln Gly Tyr Tyr Val Met Asn Pro Glu
            180                 185                 190

Lys Ala Val Glu Met Val Asp Glu Asn Thr Ile Cys Val Ala Ala Ile
        195                 200                 205

Leu Gly Ser Thr Leu Asn Gly Glu Phe Glu Asp Val Lys Met Leu Asn
    210                 215                 220

Asp Leu Leu Thr Ala Lys Asn Ala Glu Thr Gly Trp Asn Thr Pro Ile
225                 230                 235                 240

His Val Asp Ala Ala Ser Gly Gly Phe Ile Ala Pro Phe Ile Tyr Pro
                245                 250                 255

Glu Leu Glu Trp Asp Phe Arg Leu Pro Leu Val Lys Ser Ile Asn Val
            260                 265                 270

Ser Gly His Lys Tyr Gly Leu Val Tyr Ala Gly Val Gly Trp Val Ile
        275                 280                 285

Trp Arg Asn Lys Glu Asp Leu Pro Asp Glu Leu Ile Phe His Ile Asn
    290                 295                 300
```

```
Tyr Leu Gly Ala Asp Gln Pro Thr Phe Thr Leu Asn Phe Ser Lys Gly
305                 310                 315                 320

Ser Asn Gln Ile Ile Ala Gln Tyr Tyr Gln Leu Ile Arg Leu Gly Phe
                325                 330                 335

Glu Gly Tyr Lys Asp Ile Met Gln Asn Cys Arg Asp Asn Ala Thr Val
            340                 345                 350

Leu Arg Glu Gly Ile Glu Lys Thr Gly His Phe Asp Val Val Ser Lys
        355                 360                 365

Asp Ser Gly Val Pro Leu Val Ala Phe Ser Leu Lys Asp Ser Ser Arg
    370                 375                 380

Tyr Thr Val Phe Glu Val Ala Glu Ser Leu Arg Arg Phe Gly Trp Ile
385                 390                 395                 400

Val Pro Ala Tyr Thr Met Pro Ala Asp Ala Glu His Val Ala Val Met
                405                 410                 415

Arg Val Val Ile Arg Glu Asp Phe Ser Arg Gly Leu Ala Glu Arg Leu
            420                 425                 430

Ile Thr Asp Leu Thr Lys Thr Val Ala Asp Met Asp Ala His Ala Val
        435                 440                 445

Lys Lys Ala Ala Ala Glu Pro Ala Lys Lys Thr Val Arg Glu Ile Glu
    450                 455                 460

Lys Glu Val Thr Thr Tyr Trp Arg Ser Phe Val Ala Arg Lys Lys Ser
465                 470                 475                 480

Ser Leu Val Cys


<210> SEQ ID NO 98
<211> LENGTH: 502
<212> TYPE: PRT
<213> ORGANISM: Arabidopsis thaliana

<400> SEQUENCE: 98

Met Val Leu Ser His Ala Val Ser Glu Ser Asp Val Ser Val His Ser
1               5                   10                  15

Thr Phe Ala Ser Arg Tyr Val Arg Thr Ser Leu Pro Arg Phe Lys Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Ile Met Ser Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Leu
            100                 105                 110

Glu Glu Ala Glu Thr Ala Val Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140

Arg Lys Ala Glu Gly Lys Pro Val Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Glu Gly Tyr Tyr Val Met Asp Pro
            180                 185                 190
```

```
Gln Gln Ala Val Asp Met Val Asp Glu Asn Thr Ile Cys Val Ala Ala
        195                 200                 205

Ile Leu Gly Ser Thr Leu Asn Gly Glu Phe Glu Asp Val Lys Leu Leu
    210                 215                 220

Asn Asp Leu Leu Val Glu Lys Asn Lys Glu Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Ile Trp Arg Asn Lys Glu Asp Leu Pro Glu Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

His Glu Gly Tyr Arg Asn Val Met Glu Asn Cys Arg Glu Asn Met Ile
            340                 345                 350

Val Leu Arg Glu Gly Leu Glu Lys Thr Glu Arg Phe Asn Ile Val Ser
        355                 360                 365

Lys Asp Glu Gly Val Pro Leu Val Ala Phe Ser Leu Lys Asp Ser Ser
    370                 375                 380

Cys His Thr Glu Phe Glu Ile Ser Asp Met Leu Arg Arg Tyr Gly Trp
385                 390                 395                 400

Ile Val Pro Ala Tyr Thr Met Pro Pro Asn Ala Gln His Ile Thr Val
                405                 410                 415

Leu Arg Val Val Ile Arg Glu Asp Phe Ser Arg Thr Leu Ala Glu Arg
            420                 425                 430

Leu Val Ile Asp Ile Glu Lys Val Met Arg Glu Leu Asp Glu Leu Pro
        435                 440                 445

Ser Arg Val Ile His Lys Ile Ser Leu Gly Gln Glu Lys Ser Glu Ser
    450                 455                 460

Asn Ser Asp Asn Leu Met Val Thr Val Lys Lys Ser Asp Ile Asp Lys
465                 470                 475                 480

Gln Arg Asp Ile Ile Thr Gly Trp Lys Lys Phe Val Ala Asp Arg Lys
                485                 490                 495

Lys Thr Ser Gly Ile Cys
            500


<210> SEQ ID NO 99
<211> LENGTH: 497
<212> TYPE: PRT
<213> ORGANISM: Oryza sativa

<400> SEQUENCE: 99

Met Val Leu Ser His Ala Ser Ser Gly Arg Asp Asp Ala Val Arg Cys
1               5                   10                  15

Thr Phe Ala Thr Arg Tyr Ala Cys Glu Thr Leu Pro Arg Phe Arg Met
            20                  25                  30

Pro Glu Gln Ser Ile Pro Arg Glu Ala Ala Tyr Gln Ile Ile Asn Asp
        35                  40                  45

Glu Leu Met Leu Asp Gly Asn Pro Arg Leu Asn Leu Ala Ser Phe Val
```

-continued

```
    50                  55                  60

Thr Thr Trp Met Glu Pro Glu Cys Asp Lys Leu Ile Met Asp Ser Val
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Ile
            100                 105                 110

Lys Glu Asp Glu Thr Ala Ile Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140

Arg Lys Glu Gln Gly Lys Pro Cys Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Glu Gly Tyr Tyr Val Met Asp Pro
            180                 185                 190

Val Lys Ala Val Glu Met Val Asp Glu Asn Thr Ile Cys Val Ala Ala
        195                 200                 205

Ile Leu Gly Ser Thr Leu Thr Gly Glu Phe Glu Asp Val Lys Leu Leu
    210                 215                 220

Asn Asn Leu Leu Thr Glu Lys Asn Lys Glu Thr Gly Trp Asp Val Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Pro Gly Val Gly Trp Val
        275                 280                 285

Ile Trp Arg Ser Lys Glu Asp Leu Pro Glu Glu Leu Ile Phe His Ile
    290                 295                 300

Asn Tyr Leu Gly Thr Asp Gln Pro Thr Phe Thr Leu Asn Phe Ser Lys
305                 310                 315                 320

Gly Ser Ser Gln Ile Ile Ala Gln Tyr Tyr Gln Leu Ile Arg Leu Gly
                325                 330                 335

Phe Glu Gly Tyr Lys Asn Ile Met Gln Asn Cys Met Glu Asn Thr Ala
            340                 345                 350

Ile Leu Arg Glu Gly Ile Glu Ala Thr Gly Arg Phe Glu Ile Leu Ser
        355                 360                 365

Lys Glu Ala Gly Val Pro Leu Val Ala Phe Ser Leu Lys Asp Ser Gly
    370                 375                 380

Arg Tyr Thr Val Phe Asp Ile Ser Glu His Leu Arg Arg Phe Gly Trp
385                 390                 395                 400

Ile Val Pro Ala Tyr Thr Met Pro Ala Asn Ala Glu His Val Ala Val
                405                 410                 415

Leu Arg Val Val Ile Arg Glu Asp Phe Ser Arg Ser Leu Ala Glu Arg
            420                 425                 430

Leu Val Ser Asp Ile Val Lys Ile Leu His Glu Leu Asp Ala His Ser
        435                 440                 445

Ala Gln Val Leu Lys Ile Ser Ser Ala Ile Ala Lys Gln Gln Ser Gly
    450                 455                 460

Asp Asp Gly Val Val Thr Lys Lys Ser Val Leu Glu Thr Glu Arg Glu
465                 470                 475                 480
```

```
Ile Phe Ala Tyr Trp Arg Asp Gln Val Lys Lys Lys Gln Thr Gly Ile
                485                 490                 495

Cys


<210> SEQ ID NO 100
<211> LENGTH: 493
<212> TYPE: PRT
<213> ORGANISM: Brassica juncea

<400> SEQUENCE: 100

Met Val Leu Ser Lys Thr Ala Ser Gly Thr Asp Val Ser Val His Ser
1               5                   10                  15

Thr Phe Ala Ser Arg Tyr Val Arg Asn Ser Leu Pro Arg Phe Glu Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Glu Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala Arg Leu Phe Asn Ala Pro Leu
            100                 105                 110

Gly Asp Gly Glu Ala Ala Val Gly Val Gly Thr Val Gly Ser Ser Glu
        115                 120                 125

Ala Ile Met Leu Ala Gly Leu Ala Phe Lys Arg Gln Trp Gln Asn Lys
    130                 135                 140

Arg Lys Ala Gln Gly Leu Pro Tyr Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Arg Glu Gly Tyr Tyr Val Met Asp Pro
            180                 185                 190

Glu Lys Ala Val Glu Met Val Asp Glu Asn Thr Ile Cys Val Ala Ala
        195                 200                 205

Ile Leu Gly Ser Thr Leu Thr Gly Glu Phe Glu Asp Val Lys Leu Leu
    210                 215                 220

Asn Asp Leu Leu Val Glu Lys Asn Lys Gln Thr Gly Trp Asp Thr Gly
225                 230                 235                 240

Asn His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Thr Lys Ser Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Arg Asn Val Met Asp Asn Cys Arg Glu Asn Met Met
            340                 345                 350
```

```
Val Leu Arg Glu Gly Leu Glu Lys Thr Gly Arg Phe Asn Ile Val Ser
        355                 360                 365

Lys Glu Asn Gly Val Pro Leu Val Ala Phe Ser Leu Lys Asp Ser Ser
    370                 375                 380

Arg His Asn Glu Phe Glu Val Ala Glu Thr Leu Arg Arg Phe Gly Trp
385                 390                 395                 400

Ile Val Pro Ala Tyr Thr Val Pro Ala Asp Ala Glu His Val Thr Val
                405                 410                 415

Leu Arg Val Val Ile Arg Glu Asp Phe Ser Arg Thr Leu Ala Glu Arg
            420                 425                 430

Leu Val Ala Asp Phe Glu Lys Val Leu His Glu Leu Asp Thr Leu Pro
        435                 440                 445

Ala Arg Val Arg Ala Lys Met Ala Asn Gly Lys Ala Lys Val Val Lys
    450                 455                 460

Gln Thr Glu Glu Glu Thr Thr Arg Glu Val Thr Ala Tyr Trp Lys Lys
465                 470                 475                 480

Phe Val Glu Thr Lys Lys Thr Asn Gln Asn Lys Ile Cys
                485                 490


<210> SEQ ID NO 101
<211> LENGTH: 493
<212> TYPE: PRT
<213> ORGANISM: Brassica juncea

<400> SEQUENCE: 101

Met Val Leu Ser Lys Thr Ala Ser Glu Ser Asp Val Ser Ile His Ser
1               5                   10                  15

Thr Phe Ala Ser Arg Tyr Val Arg Thr Ser Leu Pro Arg Phe Glu Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Glu Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala Arg Leu Phe Asn Ala Pro Leu
            100                 105                 110

Gly Asp Gly Glu Ala Ala Val Gly Val Gly Thr Val Gly Ser Ser Glu
        115                 120                 125

Ala Ile Met Leu Ala Gly Leu Ala Phe Lys Arg Gln Trp Gln Asn Lys
    130                 135                 140

Arg Lys Ala Gln Gly Leu Pro Tyr Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Arg Glu Gly Tyr Tyr Val Met Asp Pro
            180                 185                 190

Glu Lys Ala Val Glu Met Val Asp Glu Asn Thr Ile Cys Val Ala Ala
        195                 200                 205

Ile Leu Gly Ser Thr Leu Thr Gly Glu Phe Glu Asp Val Lys Leu Leu
    210                 215                 220

Asn Asp Leu Leu Val Glu Lys Asn Lys Gln Thr Gly Trp Asp Thr Gly
```

```
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Thr Lys Ser Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Arg Asn Val Met Asp Asn Cys Arg Glu Asn Met Met
            340                 345                 350

Val Leu Arg Glu Gly Leu Glu Lys Thr Gly Arg Phe Asn Ile Val Ser
        355                 360                 365

Lys Glu Asn Gly Val Pro Leu Val Ala Phe Ser Leu Lys Asp Ser Ser
    370                 375                 380

Arg His Asp Glu Phe Glu Val Ala Glu Thr Leu Arg Arg Phe Gly Trp
385                 390                 395                 400

Ile Val Pro Ala Tyr Thr Met Pro Ala Asp Ala Gln His Val Thr Val
                405                 410                 415

Leu Arg Val Val Ile Arg Glu Asp Phe Ser Arg Thr Leu Ala Glu Arg
            420                 425                 430

Leu Val Ala Asp Phe Glu Lys Val Leu His Glu Leu Asp Thr Leu Pro
        435                 440                 445

Ala Arg Val Gln Ala Lys Met Ala Asn Gly Asn Ala Asn Gly Val Lys
    450                 455                 460

Lys Thr Glu Glu Glu Thr Thr Arg Glu Val Thr Ala Tyr Trp Lys Lys
465                 470                 475                 480

Phe Val Glu Ala Lys Lys Ser Asn Lys Asn Arg Ile Cys
                485                 490


<210> SEQ ID NO 102
<211> LENGTH: 494
<212> TYPE: PRT
<213> ORGANISM: Brassica juncea

<400> SEQUENCE: 102

Met Val Leu Ser Arg Ala Ala Thr Glu Ser Gly Glu Asn Val Cys Ser
1               5                   10                  15

Thr Phe Gly Ser Arg Tyr Val Arg Thr Ala Leu Pro Lys His Lys Ile
            20                  25                  30

Gly Glu Ser Ser Ile Pro Lys Glu Ala Ala Tyr Gln Ile Ile Lys Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Ile Met Glu Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala Arg Leu Phe Asn Ala Pro Leu
            100                 105                 110
```

-continued

```
Glu Glu Thr Glu Thr Ala Met Gly Val Gly Thr Val Gly Ser Ser Glu
        115                 120                 125

Ala Ile Met Leu Ala Gly Leu Ala Phe Lys Arg Asn Trp Gln Asn Lys
    130                 135                 140

Arg Lys Ala Glu Gly Lys Pro Tyr Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Glu Gly Tyr Tyr Val Met Asp Pro
            180                 185                 190

Asp Lys Ala Ala Glu Met Val Asp Glu Asn Thr Ile Cys Val Ala Ala
        195                 200                 205

Ile Leu Gly Ser Thr Leu Asn Gly Glu Phe Glu Asp Val Lys Arg Leu
    210                 215                 220

Asn Asp Leu Leu Val Lys Lys Asn Glu Glu Thr Gly Trp Asn Thr Pro
225                 230                 235                 240

Ile His Val Asp Ala Ala Ser Gly Gly Phe Ile Ala Pro Phe Ile Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Thr Gln Gln Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Ile Ile Ala Gln Tyr Tyr Gln Leu Ile Arg Leu Gly
                325                 330                 335

Phe Glu Gly Tyr Lys Asn Val Met Glu Asn Cys Arg Glu Asn Met Val
            340                 345                 350

Val Leu Arg Glu Gly Ile Glu Lys Thr Glu Arg Phe Asn Ile Val Ser
        355                 360                 365

Lys Glu Val Gly Val Pro Leu Val Ala Phe Ser Leu Lys Asp His Ser
    370                 375                 380

Phe His Asn Glu Phe Glu Ile Ser Glu Met Leu Arg Arg Phe Gly Trp
385                 390                 395                 400

Ile Val Pro Ala Tyr Thr Met Pro Ala Asp Ala Gln His Ile Thr Val
                405                 410                 415

Leu Arg Val Val Ile Arg Glu Asp Phe Ser Arg Thr Leu Ala Glu Arg
            420                 425                 430

Leu Val Ala Asp Ile Val Lys Val Leu His Glu Leu Asp Thr Leu Pro
        435                 440                 445

Ser Lys Ile Ser Lys Lys Met Gly Ala Glu Asp Phe Gly Asn Val Lys
    450                 455                 460

Gly Lys Lys Val Asp Arg Asp Val Leu Met Glu Val Ile Val Gly Trp
465                 470                 475                 480

Arg Lys Phe Val Lys Asp Arg Lys Lys Met Asn Gly Val Cys
                485                 490
```

<210> SEQ ID NO 103
<211> LENGTH: 494
<212> TYPE: PRT
<213> ORGANISM: Arabidopsis thaliana

<400> SEQUENCE: 103

```
Met Val Leu Ala Thr Asn Ser Asp Ser Asp Glu His Leu His Ser Thr
1               5                   10                  15

Phe Ala Ser Arg Tyr Val Arg Ala Val Val Pro Arg Phe Lys Met Pro
            20                  25                  30

Asp His Cys Met Pro Lys Asp Ala Ala Tyr Gln Val Ile Asn Asp Glu
        35                  40                  45

Leu Met Leu Asp Gly Asn Pro Arg Leu Asn Leu Ala Ser Phe Val Thr
    50                  55                  60

Thr Trp Met Glu Pro Glu Cys Asp Lys Leu Ile Met Asp Ser Val Asn
65                  70                  75                  80

Lys Asn Tyr Val Asp Met Asp Glu Tyr Pro Val Thr Thr Glu Leu Gln
                85                  90                  95

Asn Arg Cys Val Asn Met Ile Ala Asn Leu Phe His Ala Pro Val Gly
            100                 105                 110

Glu Asp Glu Ala Ala Ile Gly Cys Gly Thr Val Gly Ser Ser Glu Ala
        115                 120                 125

Ile Met Leu Ala Gly Leu Ala Phe Lys Arg Lys Trp Gln His Arg Arg
    130                 135                 140

Lys Ala Gln Gly Leu Pro Ile Asp Lys Pro Asn Ile Val Thr Gly Ala
145                 150                 155                 160

Asn Val Gln Val Cys Trp Glu Lys Phe Ala Arg Tyr Phe Glu Val Glu
                165                 170                 175

Leu Lys Glu Val Lys Leu Ser Glu Asp Tyr Tyr Val Met Asp Pro Ala
            180                 185                 190

Lys Ala Val Glu Met Val Asp Glu Asn Thr Ile Cys Val Ala Ala Ile
        195                 200                 205

Leu Gly Ser Thr Leu Thr Gly Glu Phe Glu Asp Val Lys Gln Leu Asn
    210                 215                 220

Asp Leu Leu Ala Glu Lys Asn Ala Glu Thr Gly Trp Glu Thr Pro Ile
225                 230                 235                 240

His Val Asp Ala Ala Ser Gly Gly Phe Ile Ala Pro Phe Leu Tyr Pro
                245                 250                 255

Asp Leu Glu Trp Asp Phe Arg Leu Pro Trp Val Lys Ser Ile Asn Val
            260                 265                 270

Ser Gly His Lys Tyr Gly Leu Val Tyr Ala Gly Val Gly Trp Val Val
        275                 280                 285

Trp Arg Thr Lys Asp Asp Leu Pro Glu Glu Leu Val Phe His Ile Asn
    290                 295                 300

Tyr Leu Gly Ala Asp Gln Pro Thr Phe Thr Leu Asn Phe Ser Lys Gly
305                 310                 315                 320

Ser Ser Gln Ile Ile Ala Gln Tyr Tyr Gln Phe Ile Arg Leu Gly Phe
                325                 330                 335

Glu Gly Tyr Lys Asn Ile Met Glu Asn Cys Met Asp Asn Ala Arg Arg
            340                 345                 350

Leu Arg Glu Gly Ile Glu Met Thr Gly Lys Phe Asn Ile Val Ser Lys
        355                 360                 365

Asp Ile Gly Val Pro Leu Val Ala Phe Ser Leu Lys Asp Ser Ser Lys
    370                 375                 380

His Thr Val Phe Glu Ile Ala Glu Ser Leu Arg Lys Phe Gly Trp Ile
385                 390                 395                 400

Ile Pro Ala Tyr Thr Met Pro Ala Asp Ala Gln His Ile Ala Val Leu
                405                 410                 415
```

```
Arg Val Val Ile Arg Glu Asp Phe Ser Arg Gly Leu Ala Asp Arg Leu
            420                 425                 430

Ile Thr His Ile Ile Gln Val Leu Lys Glu Ile Glu Gly Leu Pro Ser
        435                 440                 445

Arg Ile Ala His Leu Ala Ala Ala Ala Ala Val Ser Gly Asp Asp Glu
    450                 455                 460

Glu Val Lys Val Lys Thr Ala Lys Met Ser Leu Glu Asp Ile Thr Lys
465                 470                 475                 480

Tyr Trp Lys Arg Leu Val Glu His Lys Arg Asn Ile Val Cys
                485                 490


<210> SEQ ID NO 104
<211> LENGTH: 493
<212> TYPE: PRT
<213> ORGANISM: Arabidopsis thaliana

<400> SEQUENCE: 104

Met Val Leu Ser Lys Thr Val Ser Glu Ser Asp Val Ser Ile His Ser
1               5                   10                  15

Thr Phe Ala Ser Arg Tyr Val Arg Asn Ser Leu Pro Arg Phe Glu Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Glu Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala Arg Leu Phe Asn Ala Pro Leu
            100                 105                 110

Gly Asp Gly Glu Ala Ala Val Gly Val Gly Thr Val Gly Ser Ser Glu
        115                 120                 125

Ala Ile Met Leu Ala Gly Leu Ala Phe Lys Arg Gln Trp Gln Asn Lys
    130                 135                 140

Arg Lys Ala Gln Gly Leu Pro Tyr Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Asn Leu Arg Glu Asp Tyr Tyr Val Met Asp Pro
            180                 185                 190

Val Lys Ala Val Glu Met Val Asp Glu Asn Thr Ile Cys Val Ala Ala
        195                 200                 205

Ile Leu Gly Ser Thr Leu Thr Gly Glu Phe Glu Asp Val Lys Leu Leu
    210                 215                 220

Asn Asp Leu Leu Val Glu Lys Asn Lys Gln Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Thr Lys Thr Asp Leu Pro Asp Glu Leu Ile Phe His Ile
    290                 295                 300
```

```
Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Arg Asn Val Met Asp Asn Cys Arg Glu Asn Met Met
            340                 345                 350

Val Leu Arg Gln Gly Leu Glu Lys Thr Gly Arg Phe Lys Ile Val Ser
        355                 360                 365

Lys Glu Asn Gly Val Pro Leu Val Ala Phe Ser Leu Lys Asp Ser Ser
    370                 375                 380

Arg His Asn Glu Phe Glu Val Ala His Thr Leu Arg Arg Phe Gly Trp
385                 390                 395                 400

Ile Val Pro Ala Tyr Thr Met Pro Ala Asp Ala Gln His Val Thr Val
                405                 410                 415

Leu Arg Val Val Ile Arg Glu Asp Phe Ser Arg Thr Leu Ala Glu Arg
            420                 425                 430

Leu Val Ala Asp Phe Glu Lys Val Leu His Glu Leu Asp Thr Leu Pro
        435                 440                 445

Ala Arg Val His Ala Lys Met Ala Asn Gly Lys Val Asn Gly Val Lys
    450                 455                 460

Lys Thr Pro Glu Glu Thr Gln Arg Glu Val Thr Ala Tyr Trp Lys Lys
465                 470                 475                 480

Leu Leu Glu Thr Lys Lys Thr Asn Lys Asn Thr Ile Cys
                485                 490
```

<210> SEQ ID NO 105
<211> LENGTH: 500
<212> TYPE: PRT
<213> ORGANISM: Arabidopsis thaliana

<400> SEQUENCE: 105

```
Met Val Leu Ser Lys Thr Ala Ser Lys Ser Asp Asp Ser Ile His Ser
1               5                   10                  15

Thr Phe Ala Ser Arg Tyr Val Arg Asn Ser Ile Ser Arg Phe Glu Ile
            20                  25                  30

Pro Lys Asn Ser Ile Pro Lys Glu Ala Ala Tyr Gln Ile Ile Asn Asp
        35                  40                  45

Glu Leu Lys Phe Asp Gly Asn Pro Arg Leu Asn Leu Ala Ser Phe Val
    50                  55                  60

Thr Thr Trp Met Glu Pro Glu Cys Asp Lys Leu Met Met Glu Ser Ile
65                  70                  75                  80

Asn Lys Asn Asn Val Glu Met Asp Gln Tyr Pro Val Thr Thr Asp Leu
                85                  90                  95

Gln Asn Arg Cys Val Asn Met Ile Ala Arg Leu Phe Asn Ala Pro Leu
            100                 105                 110

Gly Asp Gly Glu Ala Ala Ile Gly Val Gly Thr Val Gly Ser Ser Glu
        115                 120                 125

Ala Val Met Leu Ala Gly Leu Ala Phe Lys Arg Gln Trp Gln Asn Lys
    130                 135                 140

Arg Lys Ala Leu Gly Leu Pro Tyr Asp Arg Pro Asn Ile Val Thr Gly
145                 150                 155                 160

Ala Asn Ile Gln Val Cys Leu Glu Lys Phe Ala Arg Tyr Phe Glu Val
                165                 170                 175

Glu Leu Lys Glu Val Lys Leu Arg Glu Gly Tyr Tyr Val Met Asp Pro
```

```
            180                 185                 190

Asp Lys Ala Val Glu Met Val Asp Glu Asn Thr Ile Cys Val Val Ala
        195                 200                 205

Ile Leu Gly Ser Thr Leu Thr Gly Glu Phe Glu Asp Val Lys Leu Leu
    210                 215                 220

Asn Asp Leu Leu Val Glu Lys Asn Lys Lys Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Asp Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Thr Lys Thr Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Arg Asn Val Met Asp Asn Cys Arg Glu Asn Met Met
            340                 345                 350

Val Leu Arg Gln Gly Leu Glu Lys Thr Gly Arg Phe Asn Ile Val Ser
        355                 360                 365

Lys Glu Asn Gly Val Pro Leu Val Ala Phe Ser Leu Lys Asp Ser Ser
    370                 375                 380

Arg His Asn Glu Phe Glu Val Ala Glu Met Leu Arg Arg Phe Gly Trp
385                 390                 395                 400

Ile Val Pro Ala Tyr Thr Met Pro Ala Asp Ala Gln His Val Thr Val
                405                 410                 415

Leu Arg Val Val Ile Arg Glu Asp Phe Ser Arg Thr Leu Ala Glu Arg
            420                 425                 430

Leu Val Ala Asp Phe Glu Lys Val Leu His Glu Leu Asp Thr Leu Pro
        435                 440                 445

Ala Arg Val His Ala Lys Met Ala Ser Gly Lys Val Asn Gly Val Lys
    450                 455                 460

Lys Thr Pro Glu Glu Thr Gln Arg Glu Val Thr Ala Tyr Trp Lys Lys
465                 470                 475                 480

Phe Val Asp Thr Lys Thr Asp Lys Asn Gly Val Pro Leu Val Ala Ser
                485                 490                 495

Ile Thr Asn Gln
            500


<210> SEQ ID NO 106
<211> LENGTH: 491
<212> TYPE: PRT
<213> ORGANISM: Nicotiana tabacum

<400> SEQUENCE: 106

Met Val Leu Ser Lys Thr Ser Ser Glu Ser Asp Val Ser Val His Ser
1               5                   10                  15

Thr Phe Ala Ser Arg Tyr Val Arg Thr Ser Leu Pro Arg Phe Glu Met
            20                  25                  30

Ala Glu Asn Ser Ile Pro Lys Glu Ala Ala Phe Gln Ile Ile Asn Asp
        35                  40                  45
```

```
Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Asp Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala Arg Leu Phe Asn Ala Pro Leu
            100                 105                 110

Glu Glu Lys Glu Thr Ala Val Gly Val Gly Thr Val Gly Ser Ser Glu
        115                 120                 125

Ala Ile Met Leu Ala Gly Leu Ala Phe Lys Arg Asn Trp Gln Asn Lys
    130                 135                 140

Arg Lys Ala Glu Gly Lys Pro Tyr Asn Lys Pro Asn Ile Val Thr Gly
145                 150                 155                 160

Ala Asn Val Gln Val Cys Trp Glu Lys Phe Ala Asn Tyr Phe Glu Val
                165                 170                 175

Glu Leu Lys Glu Val Lys Leu Arg Glu Gly Tyr Tyr Val Met Asp Pro
            180                 185                 190

Val Gln Ala Val Glu Met Val Asp Glu Asn Thr Ile Cys Val Ala Ala
        195                 200                 205

Ile Leu Gly Ser Thr Leu Asn Gly Glu Phe Glu Asp Val Lys Leu Leu
    210                 215                 220

Asn Asp Leu Leu Ile Glu Lys Asn Lys Gln Thr Gly Trp Asn Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Ile Trp Arg Thr Lys Gln Asp Leu Pro Glu Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Tyr Glu Gly Tyr Arg Asn Val Met Glu Asn Cys Arg Glu Asn Ala Ile
            340                 345                 350

Val Leu Arg Glu Gly Leu Glu Lys Thr Gly Arg Phe Asn Ile Val Ser
        355                 360                 365

Lys Asp Glu Gly Val Pro Leu Val Ala Phe Ser Leu Lys Asp Asn Ser
    370                 375                 380

Arg His Asn Glu Phe Glu Val Ser Glu Thr Leu Arg Arg Phe Gly Trp
385                 390                 395                 400

Ile Val Pro Ala Tyr Thr Met Pro Ala Asp Ala Gln His Val Thr Val
                405                 410                 415

Leu Arg Val Val Ile Arg Glu Asp Phe Ser Arg Thr Leu Ala Glu Arg
            420                 425                 430

Leu Val Leu Asp Ile Val Lys Val Leu His Glu Leu Asp Thr Leu Pro
        435                 440                 445

Ala Arg Leu Ser Ala Lys Leu Glu Glu Val Lys Leu Val Lys Asn Gly
    450                 455                 460

Lys Lys Phe Glu Leu Glu Val Gln Arg Glu Val Thr Asn Tyr Trp Lys
```

465 470 475 480

Lys Phe Val Leu Ala Arg Lys Ala Pro Val Cys
485 490

<210> SEQ ID NO 107
<211> LENGTH: 496
<212> TYPE: PRT
<213> ORGANISM: Nicotiana tabacum

<400> SEQUENCE: 107

Met Val Leu Ser Lys Thr Ala Ser Glu Ser Asp Val Ser Ile His Ser
1 5 10 15

Thr Phe Ala Ser Arg Tyr Val Arg Thr Ser Leu Pro Arg Phe Lys Met
20 25 30

Pro Glu Asn Ser Ile Pro Lys Glu Ala Ala Tyr Gln Ile Ile Asn Asp
35 40 45

Glu Leu Met Leu Asp Gly Asn Pro Arg Leu Asn Leu Ala Ser Phe Val
50 55 60

Thr Thr Trp Met Glu Pro Glu Cys Asn Lys Leu Met Met Asp Ser Ile
65 70 75 80

Asn Lys Asn Tyr Val Asp Met Gly Glu Tyr Pro Val Thr Thr Glu Leu
85 90 95

Gln Asn Arg Cys Val Asn Met Ile Ala His Leu Phe Asn Ala Pro Leu
100 105 110

Gly Asp Gly Glu Thr Ala Val Gly Val Gly Thr Val Gly Ser Ser Glu
115 120 125

Ala Ile Met Leu Ala Gly Leu Ala Phe Lys Arg Lys Trp Gln Asn Lys
130 135 140

Met Lys Ala Gln Gly Lys Pro Cys Asp Lys Pro Asn Ile Val Thr Gly
145 150 155 160

Ala Asn Val Gln Val Cys Trp Glu Lys Phe Ala Arg Tyr Phe Glu Val
165 170 175

Glu Leu Lys Glu Val Lys Leu Ser Asp Gly Tyr Tyr Val Met Asp Pro
180 185 190

Glu Lys Ala Val Glu Met Val Asp Glu Asn Thr Ile Cys Val Ala Ala
195 200 205

Ile Leu Gly Ser Thr Leu Asn Gly Glu Phe Glu Asp Val Lys Arg Leu
210 215 220

Asn Asp Leu Leu Ile Glu Lys Asn Lys Glu Thr Gly Trp Asp Thr Pro
225 230 235 240

Ile His Val Asp Ala Ala Ser Gly Gly Phe Ile Ala Pro Phe Leu Tyr
245 250 255

Pro Glu Leu Glu Trp Asp Phe Arg Leu Pro Leu Val Lys Ser Ile Asn
260 265 270

Val Ser Gly His Lys Tyr Gly Leu Val Tyr Ala Gly Ile Gly Trp Ala
275 280 285

Ile Trp Arg Asn Lys Glu Asp Leu Pro Asp Glu Leu Ile Phe His Ile
290 295 300

Asn Tyr Leu Gly Ala Asp Gln Pro Thr Phe Thr Leu Asn Phe Ser Lys
305 310 315 320

Gly Ser Ser Gln Val Ile Ala Gln Tyr Tyr Gln Leu Ile Arg Leu Gly
325 330 335

Phe Glu Gly Tyr Lys Asn Val Met Glu Asn Cys Gln Glu Asn Ala Arg
340 345 350

```
Val Leu Arg Glu Gly Leu Glu Lys Ser Gly Arg Phe Asn Ile Ile Ser
        355                 360                 365

Lys Glu Ile Gly Val Pro Leu Val Ala Phe Ser Leu Lys Asp Asn Ser
    370                 375                 380

Gln His Asn Glu Phe Glu Ile Ser Glu Thr Leu Arg Arg Phe Gly Trp
385                 390                 395                 400

Ile Ile Pro Ala Tyr Thr Met Pro Pro Asn Ala Gln His Val Thr Val
                405                 410                 415

Leu Arg Val Val Ile Arg Glu Asp Phe Ser Arg Thr Leu Ala Glu Arg
            420                 425                 430

Leu Val Ile Asp Ile Glu Lys Val Leu His Glu Leu Asp Thr Leu Pro
        435                 440                 445

Ala Arg Val Asn Ala Lys Leu Ala Val Ala Glu Ala Asn Gly Ser Gly
    450                 455                 460

Val His Lys Lys Thr Asp Arg Glu Val Gln Leu Glu Ile Thr Ala Ala
465                 470                 475                 480

Trp Lys Lys Phe Val Ala Asp Lys Lys Lys Lys Thr Asn Gly Val Cys
                485                 490                 495


<210> SEQ ID NO 108
<211> LENGTH: 450
<212> TYPE: PRT
<213> ORGANISM: Glycine max

<400> SEQUENCE: 108

Gly Asn Pro Arg Leu Asn Leu Ala Ser Phe Val Thr Thr Trp Met Glu
1               5                   10                  15

Pro Glu Cys Asp Lys Leu Ile Met Ala Ala Ile Asn Lys Asn Tyr Val
            20                  25                  30

Asp Met Asp Glu Tyr Pro Val Thr Thr Glu Leu Gln Asn Arg Cys Val
        35                  40                  45

Asn Met Ile Ala His Leu Phe Asn Ala Pro Leu Glu Glu Thr Glu Ala
    50                  55                  60

Ala Val Gly Val Gly Thr Val Gly Ser Ser Glu Ala Ile Met Leu Ala
65                  70                  75                  80

Gly Leu Ala Phe Lys Arg Lys Trp Gln Asn Arg Arg Lys Gln Glu Gly
                85                  90                  95

Lys Pro Tyr Asp Lys Pro Asn Ile Val Thr Gly Ala Asn Val Gln Val
            100                 105                 110

Cys Trp Glu Lys Phe Ala Arg Tyr Phe Glu Val Glu Leu Lys Glu Val
        115                 120                 125

Lys Leu Arg Asp Asp Tyr Tyr Val Met Asp Pro Glu Lys Ala Val Glu
    130                 135                 140

Leu Val Asp Glu Asn Thr Ile Cys Val Ala Ala Ile Leu Gly Ser Thr
145                 150                 155                 160

Leu Asn Gly Glu Phe Glu Asp Val Lys Arg Leu Asn Asp Leu Leu Ile
                165                 170                 175

Glu Lys Asn Lys Ile Thr Gly Trp Asp Thr Pro Ile His Val Asp Ala
            180                 185                 190

Ala Ser Gly Gly Phe Ile Ala Pro Phe Ile Tyr Pro Glu Leu Glu Trp
        195                 200                 205

Asp Phe Arg Leu Gln Leu Val Lys Ser Ile Asn Val Ser Gly His Lys
    210                 215                 220

Tyr Gly Leu Val Tyr Ala Gly Ile Gly Trp Val Ile Trp Arg Ser Lys
225                 230                 235                 240
```

Gln Asp Leu Pro Glu Glu Leu Ile Phe His Ile Asn Tyr Leu Gly Ala
245 250 255

Asp Gln Pro Thr Phe Thr Leu Asn Phe Ser Lys Gly Ser Ser Gln Val
260 265 270

Ile Ala Gln Tyr Tyr Gln Leu Ile Arg Leu Gly Phe Glu Gly Tyr Arg
275 280 285

Asn Val Met Glu Asn Cys Arg Asp Asn Met Leu Val Leu Lys Glu Gly
290 295 300

Leu Glu Lys Thr Gly Arg Phe Ser Ile Val Ser Lys Asp Asn Gly Val
305 310 315 320

Pro Leu Val Ala Phe Thr Leu Lys Asp His Thr His Phe Asp Glu Phe
325 330 335

Gln Ile Ser Asp Phe Leu Arg Arg Phe Gly Trp Ile Val Pro Ala Tyr
340 345 350

Thr Met Pro Pro Asp Ala Gln His Val Thr Val Leu Arg Val Val Ile
355 360 365

Arg Glu Asp Phe Ser Arg Thr Leu Ala Glu Arg Leu Val Ser Asp Val
370 375 380

Glu Lys Val Leu His Glu Leu Asp Ser Leu Pro Ala Arg Val Ile Ser
385 390 395 400

Ser Thr Thr Val Thr Leu Ser Ala Glu Glu Asn Gly Lys Val Val Val
405 410 415

Ala Lys Lys Asn Pro Met Glu Thr Gln Arg Glu Ile Thr Ala Ile Trp
420 425 430

Lys Lys Phe Val Leu Glu Arg Lys Lys Asn Asn Asp Lys Met Asn Gly
435 440 445

Val Cys
450

<210> SEQ ID NO 109
<211> LENGTH: 496
<212> TYPE: PRT
<213> ORGANISM: Nicotiana tabacum

<400> SEQUENCE: 109

Met Val Leu Ser Lys Thr Ala Ser Glu Ser Asp Val Ser Ile His Ser
1 5 10 15

Thr Phe Ala Ser Arg Tyr Val Arg Thr Ser Leu Pro Arg Phe Lys Met
20 25 30

Pro Glu Asn Ser Ile Pro Lys Glu Ala Ala Tyr Gln Ile Ile Asn Asp
35 40 45

Glu Leu Met Leu Asp Gly Asn Pro Arg Leu Asn Leu Ala Ser Phe Val
50 55 60

Thr Thr Trp Met Glu Pro Glu Cys Asn Thr Leu Met Met Asp Ser Ile
65 70 75 80

Asn Lys Asn Tyr Val Asp Met Asp Glu Tyr Pro Val Thr Thr Glu Leu
85 90 95

Gln Asn Arg Cys Val Asn Met Ile Ala His Leu Phe Asn Ala Pro Leu
100 105 110

Gly Asp Gly Glu Thr Ala Val Gly Val Gly Thr Val Gly Ser Ser Glu
115 120 125

Ala Ile Met Leu Ala Gly Leu Ala Phe Lys Arg Lys Trp Gln Asn Lys
130 135 140

Met Lys Ala Gln Gly Lys Pro Phe Asp Lys Pro Asn Ile Val Thr Gly

-continued 145 150 155 160

Ala Asn Val Gln Val Cys Trp Glu Lys Phe Ala Arg Tyr Phe Glu Val
165 170 175

Glu Leu Lys Glu Val Lys Leu Ser Asp Gly Tyr Tyr Val Met Asp Pro
180 185 190

Glu Lys Ala Val Glu Met Val Asp Glu Asn Thr Ile Cys Val Ala Ala
195 200 205

Ile Leu Gly Ser Thr Leu Asn Gly Glu Phe Glu Asp Val Lys Arg Leu
210 215 220

Asn Asp Leu Leu Ile Glu Lys Asn Lys Glu Thr Gly Trp Asp Thr Pro
225 230 235 240

Ile His Val Asp Ala Ala Ser Gly Gly Phe Ile Ala Pro Phe Leu Tyr
245 250 255

Pro Glu Leu Glu Trp Asp Phe Arg Leu Pro Leu Val Lys Ser Ile Asn
260 265 270

Val Ser Gly His Lys Tyr Gly Leu Val Tyr Ala Gly Ile Gly Trp Ala
275 280 285

Ile Trp Arg Asn Lys Glu Asp Leu Pro Asp Glu Leu Ile Phe His Ile
290 295 300

Asn Tyr Leu Gly Ala Asp Gln Pro Thr Phe Thr Leu Asn Phe Ser Lys
305 310 315 320

Gly Ser Ser Gln Val Ile Ala Gln Tyr Tyr Gln Leu Ile Arg Leu Gly
325 330 335

Phe Glu Gly Tyr Lys Asn Val Met Glu Asn Cys Gln Glu Asn Ala Arg
340 345 350

Val Leu Arg Glu Gly Ile Glu Lys Ser Gly Arg Phe Asn Ile Ile Ser
355 360 365

Lys Glu Ile Gly Val Pro Leu Val Ala Phe Ser Leu Lys Asp Asn Ser
370 375 380

Gln His Asn Glu Phe Glu Ile Ser Glu Thr Leu Arg Arg Phe Gly Trp
385 390 395 400

Ile Val Pro Ala Tyr Thr Met Pro Pro Asn Ala Gln His Val Thr Val
405 410 415

Leu Arg Val Val Ile Arg Glu Asp Phe Ser Arg Thr Leu Ala Glu Arg
420 425 430

Leu Val Ile Asp Ile Glu Lys Val Leu His Glu Leu Asp Thr Leu Pro
435 440 445

Ala Arg Val Asn Ala Lys Leu Ala Val Ala Glu Ala Asn Gly Ser Gly
450 455 460

Val His Lys Lys Thr Asp Arg Glu Val Gln Leu Glu Ile Thr Thr Ala
465 470 475 480

Trp Lys Lys Phe Val Ala Asp Lys Lys Lys Lys Thr Asn Gly Val Cys
485 490 495

<210> SEQ ID NO 110
<211> LENGTH: 494
<212> TYPE: PRT
<213> ORGANISM: Arabidopsis thaliana

<400> SEQUENCE: 110

Met Val Leu Ala Thr Asn Ser Asp Ser Asp Glu His Leu His Ser Thr
1 5 10 15

Phe Ala Ser Arg Tyr Val Arg Ala Val Val Pro Arg Phe Lys Met Pro
20 25 30

```
Asp His Cys Met Pro Lys Asp Ala Ala Tyr Gln Val Ile Asn Asp Glu
        35                  40                  45

Leu Met Leu Asp Gly Asn Pro Arg Leu Asn Leu Ala Ser Phe Val Thr
    50                  55                  60

Thr Trp Met Glu Pro Glu Cys Asp Lys Leu Ile Met Asp Ser Val Asn
65                  70                  75                  80

Lys Asn Tyr Val Asp Met Asp Glu Tyr Pro Val Thr Thr Glu Leu Gln
                85                  90                  95

Asn Arg Cys Val Asn Met Ile Ala Asn Phe Phe His Ala Pro Val Gly
            100                 105                 110

Glu Asp Glu Ala Ala Ile Gly Cys Gly Thr Val Gly Ser Ser Glu Ala
        115                 120                 125

Ile Met Leu Ala Gly Leu Ala Phe Lys Arg Lys Trp Gln His Arg Arg
    130                 135                 140

Lys Ala Gln Gly Leu Pro Ile Asp Lys Pro Asn Ile Val Thr Gly Ala
145                 150                 155                 160

Asn Val Gln Val Cys Trp Glu Lys Phe Ala Arg Tyr Phe Glu Val Glu
                165                 170                 175

Leu Lys Glu Val Lys Leu Ser Glu Asp Tyr Tyr Val Met Asp Pro Ala
            180                 185                 190

Lys Ala Val Glu Met Val Asp Glu Asn Thr Ile Cys Val Ala Ala Ile
        195                 200                 205

Leu Gly Ser Thr Leu Thr Gly Glu Phe Glu Asp Val Lys Gln Leu Asn
    210                 215                 220

Asp Leu Leu Ala Glu Lys Asn Ala Glu Thr Gly Trp Glu Thr Pro Ile
225                 230                 235                 240

His Val Asp Ala Ala Ser Gly Gly Phe Ile Ala Pro Phe Leu Tyr Pro
                245                 250                 255

Asp Leu Glu Trp Asp Phe Arg Leu Pro Trp Val Lys Ser Ile Asn Val
            260                 265                 270

Ser Gly His Lys Tyr Gly Leu Val Tyr Ala Gly Val Gly Trp Val Val
        275                 280                 285

Trp Arg Thr Lys Asp Asp Leu Pro Glu Glu Leu Val Phe His Ile Asn
    290                 295                 300

Tyr Leu Gly Ala Asp Gln Pro Thr Phe Thr Leu Asn Phe Ser Lys Gly
305                 310                 315                 320

Ser Ser Gln Ile Ile Ala Gln Tyr Tyr Gln Phe Ile Arg Leu Gly Phe
                325                 330                 335

Glu Gly Tyr Lys Asn Ile Met Glu Asn Cys Met Asp Asn Ala Arg Arg
            340                 345                 350

Leu Arg Glu Gly Ile Glu Met Thr Gly Lys Phe Asn Ile Val Ser Lys
        355                 360                 365

Asp Ile Gly Val Pro Leu Val Ala Phe Ser Leu Lys Asp Ser Ser Lys
    370                 375                 380

His Thr Val Phe Glu Ile Ala Glu Ser Leu Arg Lys Phe Gly Trp Ile
385                 390                 395                 400

Ile Pro Ala Tyr Thr Met Pro Ala Asp Ala Gln His Ile Ala Val Leu
                405                 410                 415

Arg Val Val Ile Arg Glu Asp Phe Ser Arg Gly Leu Ala Asp Arg Leu
            420                 425                 430

Ile Thr His Ile Ile Gln Val Leu Lys Glu Ile Glu Gly Leu Pro Ser
        435                 440                 445

Arg Ile Ala His Leu Ala Ala Ala Ala Ala Val Ser Gly Asp Asp Glu
```

450 455 460

Glu Val Lys Val Lys Thr Ala Lys Met Ser Leu Glu Asp Ile Thr Lys
465 470 475 480

Tyr Trp Lys Arg Leu Val Glu His Lys Arg Asn Ile Val Cys
485 490

<210> SEQ ID NO 111
<211> LENGTH: 492
<212> TYPE: PRT
<213> ORGANISM: Oryza sativa

<400> SEQUENCE: 111

Met Val Leu Ser Lys Ala Val Ser Glu Ser Asp Met Ser Val His Ser
1 5 10 15

Thr Phe Ala Ser Arg Tyr Val Arg Ala Ser Leu Pro Arg Tyr Arg Met
20 25 30

Pro Glu Asn Ser Ile Pro Lys Glu Ala Ala Tyr Gln Ile Ile Asn Asp
35 40 45

Glu Leu Met Leu Asp Gly Asn Pro Arg Leu Asn Leu Ala Ser Phe Val
50 55 60

Thr Thr Trp Met Glu Pro Glu Cys Asp Lys Leu Ile Met Ala Ala Ile
65 70 75 80

Asn Lys Asn Tyr Val Asp Met Asp Glu Tyr Pro Val Thr Thr Glu Leu
85 90 95

Gln Asn Arg Cys Val Asn Met Ile Ala His Leu Phe His Ala Pro Leu
100 105 110

Gly Glu Asp Glu Thr Ala Val Gly Val Gly Thr Val Gly Ser Ser Glu
115 120 125

Ala Ile Met Leu Ala Gly Leu Ala Phe Lys Arg Arg Trp Gln Asn Lys
130 135 140

Arg Lys Ala Glu Gly Lys Pro Phe Asp Lys Pro Asn Ile Ile Thr Gly
145 150 155 160

Ala Asn Val Gln Val Cys Trp Glu Lys Phe Ala Arg Tyr Phe Glu Val
165 170 175

Glu Leu Lys Glu Val Lys Leu Arg Asp Gly Tyr Tyr Val Met Asp Pro
180 185 190

Glu Lys Ala Val Asp Met Val Asn Glu Asn Thr Ile Cys Val Ala Ala
195 200 205

Ile Leu Gly Ser Thr Leu Asn Gly Glu Phe Glu Asp Val Lys Leu Leu
210 215 220

Asn Asp Leu Leu Asp Lys Lys Asn Lys Glu Thr Gly Trp Glu Thr Pro
225 230 235 240

Ile His Val Asp Ala Ala Ser Gly Gly Phe Ile Ala Pro Phe Leu Tyr
245 250 255

Pro Glu Leu Glu Trp Asp Phe Arg Leu Pro Trp Val Lys Ser Ile Asn
260 265 270

Val Ser Gly His Lys Tyr Gly Leu Val Tyr Ala Gly Ile Gly Trp Cys
275 280 285

Ile Trp Arg Asn Lys Glu Asp Leu Pro Glu Glu Leu Ile Phe His Ile
290 295 300

Asn Tyr Leu Gly Thr Asp Gln Pro Thr Phe Thr Leu Asn Phe Ser Lys
305 310 315 320

Gly Ser Ser Gln Val Ile Ala Gln Tyr Tyr Gln Leu Ile Arg His Gly
325 330 335

-continued

```
Phe Glu Gly Tyr Arg Asn Ile Met Glu Asn Cys His Glu Asn Ala Met
            340                 345                 350

Val Leu Lys Glu Gly Leu Val Lys Thr Gly Arg Phe Asp Ile Val Ser
        355                 360                 365

Lys Asp Glu Gly Val Pro Leu Val Ala Phe Ser Leu Lys Asp Arg Ser
    370                 375                 380

Arg His Asp Glu Phe Glu Ile Ser Asp Met Leu Arg Arg Phe Gly Trp
385                 390                 395                 400

Ile Val Pro Ala Tyr Thr Met Pro Pro Asp Ala Gln His Val Thr Val
                405                 410                 415

Leu Arg Val Val Ile Arg Glu Glu Phe Ser Arg Thr Leu Ala Glu Arg
            420                 425                 430

Leu Val Leu Asp Ile Glu Lys Val Met Tyr Gln Leu Asp Ala Leu Pro
        435                 440                 445

Ser Arg Leu Met Pro Pro Val Pro Pro Ala Pro Leu Leu Val Val Ala
    450                 455                 460

Lys Lys Ser Glu Leu Glu Thr Gln Arg Ser Val Thr Glu Ala Trp Lys
465                 470                 475                 480

Lys Phe Val Leu Ala Lys Arg Thr Asn Gly Val Cys
                485                 490
```

<210> SEQ ID NO 112
<211> LENGTH: 419
<212> TYPE: PRT
<213> ORGANISM: Arabidopsis thaliana

<400> SEQUENCE: 112

```
Met Asp Ser Ile Asn Lys Asn Tyr Val Asp Met Asp Glu Tyr Pro Val
1               5                   10                  15

Thr Thr Glu Leu Gln Asn Arg Cys Val Asn Ile Ile Ala Arg Leu Phe
            20                  25                  30

Asn Ala Pro Leu Glu Glu Ser Glu Thr Ala Val Gly Val Gly Thr Val
        35                  40                  45

Gly Ser Ser Glu Ala Ile Met Leu Ala Gly Leu Ala Phe Lys Arg Lys
    50                  55                  60

Trp Gln Asn Lys Arg Lys Ala Glu Gly Lys Pro Tyr Asp Lys Pro Asn
65                  70                  75                  80

Ile Val Thr Gly Ala Asn Val Gln Val Cys Trp Glu Lys Phe Ala Arg
                85                  90                  95

Tyr Phe Glu Val Glu Leu Lys Glu Val Asn Leu Ser Glu Gly Tyr Tyr
            100                 105                 110

Val Met Asp Pro Asp Lys Ala Ala Glu Met Val Asp Glu Asn Thr Ile
        115                 120                 125

Cys Val Ala Ala Ile Leu Gly Ser Thr Leu Asn Gly Glu Phe Glu Asp
    130                 135                 140

Val Lys Arg Leu Asn Asp Leu Leu Val Lys Lys Asn Glu Glu Thr Gly
145                 150                 155                 160

Trp Asn Thr Pro Ile His Val Asp Ala Ala Ser Gly Gly Phe Ile Ala
                165                 170                 175

Pro Phe Ile Tyr Pro Glu Leu Glu Trp Asp Phe Arg Leu Pro Leu Val
            180                 185                 190

Lys Ser Ile Asn Val Ser Gly His Lys Tyr Gly Leu Val Tyr Ala Gly
        195                 200                 205

Ile Gly Trp Val Val Trp Arg Ala Ala Glu Asp Leu Pro Glu Glu Leu
    210                 215                 220
```

Ile Phe His Ile Asn Tyr Leu Gly Ala Asp Gln Pro Thr Phe Thr Leu
225 230 235 240

Asn Phe Ser Lys Gly Ser Ser Gln Ile Ile Ala Gln Tyr Tyr Gln Leu
245 250 255

Ile Arg Leu Gly Phe Glu Gly Tyr Lys Asn Val Met Glu Asn Cys Ile
260 265 270

Glu Asn Met Val Val Leu Lys Glu Gly Ile Glu Lys Thr Glu Arg Phe
275 280 285

Asn Ile Val Ser Lys Asp Gln Gly Val Pro Val Val Ala Phe Ser Leu
290 295 300

Lys Asp His Ser Phe His Asn Glu Phe Glu Ile Ser Glu Met Leu Arg
305 310 315 320

Arg Phe Gly Trp Ile Val Pro Ala Tyr Thr Met Pro Ala Asp Ala Gln
325 330 335

His Ile Thr Val Leu Arg Val Val Ile Arg Glu Asp Phe Ser Arg Thr
340 345 350

Leu Ala Glu Arg Leu Val Ala Asp Ile Ser Lys Val Leu His Glu Leu
355 360 365

Asp Thr Leu Pro Ser Lys Ile Ser Lys Lys Met Gly Ile Glu Gly Ile
370 375 380

Ala Lys Asn Val Lys Glu Lys Lys Met Glu Lys Glu Ile Leu Met Glu
385 390 395 400

Val Ile Val Gly Trp Arg Lys Phe Val Lys Glu Arg Lys Lys Met Asn
405 410 415

Gly Val Cys

<210> SEQ ID NO 113
<211> LENGTH: 501
<212> TYPE: PRT
<213> ORGANISM: Oryza sativa

<400> SEQUENCE: 113

Met Val Val Ser Val Ala Ala Thr Asp Ser Asp Thr Ala Gln Pro Val
1 5 10 15

Gln Tyr Ser Thr Phe Phe Ala Ser Arg Tyr Val Arg Asp Pro Leu Pro
20 25 30

Arg Phe Arg Met Pro Glu Gln Ser Ile Pro Arg Glu Ala Ala Tyr Gln
35 40 45

Ile Ile Asn Asp Glu Leu Met Leu Asp Gly Asn Pro Arg Leu Asn Leu
50 55 60

Ala Ser Phe Val Thr Thr Trp Met Glu Pro Glu Cys Asp Lys Leu Ile
65 70 75 80

Met Asp Ser Val Asn Lys Asn Tyr Val Asp Met Asp Glu Tyr Pro Val
85 90 95

Thr Thr Glu Leu Gln Asn Arg Cys Val Asn Met Ile Ala His Leu Phe
100 105 110

Asn Ala Pro Ile Lys Glu Asp Glu Thr Ala Ile Gly Val Gly Thr Val
115 120 125

Gly Ser Ser Glu Ala Ile Met Leu Ala Gly Leu Ala Phe Lys Arg Lys
130 135 140

Trp Gln Asn Lys Arg Lys Glu Gln Gly Lys Pro Cys Asp Lys Pro Asn
145 150 155 160

Ile Val Thr Gly Ala Asn Val Gln Val Cys Trp Glu Lys Phe Ala Arg
165 170 175

```
Tyr Phe Glu Val Glu Leu Lys Glu Val Lys Leu Ser Glu Gly Tyr Tyr
            180                 185                 190

Val Met Asp Pro Val Lys Ala Val Glu Met Val Asp Glu Asn Thr Ile
        195                 200                 205

Cys Val Ala Ala Ile Leu Gly Ser Thr Leu Thr Gly Glu Phe Glu Asp
    210                 215                 220

Val Lys Leu Leu Asn Asn Leu Leu Thr Glu Lys Asn Lys Glu Thr Gly
225                 230                 235                 240

Trp Asp Val Pro Ile His Val Asp Ala Ala Ser Gly Gly Phe Ile Ala
                245                 250                 255

Pro Phe Leu Tyr Pro Glu Leu Glu Trp Asp Phe Arg Leu Pro Leu Val
            260                 265                 270

Lys Ser Ile Asn Val Ser Gly His Lys Tyr Gly Leu Val Tyr Pro Gly
        275                 280                 285

Val Gly Trp Val Ile Trp Arg Ser Lys Glu Asp Leu Pro Glu Glu Leu
    290                 295                 300

Ile Phe His Ile Asn Tyr Leu Gly Thr Asp Gln Pro Thr Phe Thr Leu
305                 310                 315                 320

Asn Phe Ser Lys Gly Ser Ser Gln Ile Ile Ala Gln Tyr Tyr Gln Leu
                325                 330                 335

Ile Arg Leu Gly Phe Glu Gly Tyr Lys Asn Ile Met Gln Asn Cys Met
            340                 345                 350

Glu Asn Thr Ala Ile Leu Arg Glu Gly Ile Glu Ala Thr Gly Arg Phe
        355                 360                 365

Glu Ile Leu Ser Lys Glu Ala Gly Val Pro Leu Val Ala Phe Ser Leu
    370                 375                 380

Lys Asp Ser Gly Arg Tyr Thr Val Phe Asp Ile Ser Glu His Leu Arg
385                 390                 395                 400

Arg Phe Gly Trp Ile Val Pro Ala Tyr Thr Met Pro Ala Asn Ala Glu
                405                 410                 415

His Val Ala Val Leu Arg Val Val Ile Arg Glu Asp Phe Ser Arg Ser
            420                 425                 430

Leu Ala Glu Arg Leu Val Ser Asp Ile Val Lys Ile Leu His Glu Leu
        435                 440                 445

Asp Ala His Ser Ala Gln Val Leu Lys Ile Ser Ser Ala Ile Ala Lys
    450                 455                 460

Gln Gln Ser Gly Asp Asp Gly Val Val Thr Lys Lys Ser Val Leu Glu
465                 470                 475                 480

Thr Glu Arg Glu Ile Phe Ala Tyr Trp Arg Asp Gln Val Lys Lys Lys
                485                 490                 495

Gln Thr Gly Ile Cys
            500
```

<210> SEQ ID NO 114
<211> LENGTH: 494
<212> TYPE: PRT
<213> ORGANISM: Arabidopsis thaliana

<400> SEQUENCE: 114

```
Met Val Leu Thr Lys Thr Ala Thr Asn Asp Glu Ser Val Cys Thr Met
1               5                   10                  15

Phe Gly Ser Arg Tyr Val Arg Thr Thr Leu Pro Lys Tyr Glu Ile Gly
            20                  25                  30

Glu Asn Ser Ile Pro Lys Asp Ala Ala Tyr Gln Ile Ile Lys Asp Glu
```

```
        35                  40                  45

Leu Met Leu Asp Gly Asn Pro Arg Leu Asn Leu Ala Ser Phe Val Thr
    50                  55                  60

Thr Trp Met Glu Pro Glu Cys Asp Lys Leu Ile Met Asp Ser Ile Asn
65                  70                  75                  80

Lys Asn Tyr Val Asp Met Asp Glu Tyr Pro Val Thr Thr Glu Leu Gln
                85                  90                  95

Asn Arg Cys Val Asn Ile Ile Ala Arg Leu Phe Asn Ala Pro Leu Glu
            100                 105                 110

Glu Ser Glu Thr Ala Val Gly Val Gly Thr Val Gly Ser Ser Glu Ala
        115                 120                 125

Ile Met Leu Ala Gly Leu Ala Phe Lys Arg Lys Trp Gln Asn Lys Arg
    130                 135                 140

Lys Ala Glu Gly Lys Pro Tyr Asp Lys Pro Asn Ile Val Thr Gly Ala
145                 150                 155                 160

Asn Val Gln Val Cys Trp Glu Lys Phe Ala Arg Tyr Phe Glu Val Glu
                165                 170                 175

Leu Lys Glu Val Asn Leu Ser Glu Gly Tyr Tyr Val Met Asp Pro Asp
            180                 185                 190

Lys Ala Ala Glu Met Val Asp Glu Asn Thr Ile Cys Val Ala Ala Ile
        195                 200                 205

Leu Gly Ser Thr Leu Asn Gly Glu Phe Glu Asp Val Lys Arg Leu Asn
    210                 215                 220

Asp Leu Leu Val Lys Lys Asn Glu Glu Thr Gly Trp Asn Thr Pro Ile
225                 230                 235                 240

His Val Asp Ala Ala Ser Gly Gly Phe Ile Ala Pro Phe Ile Tyr Pro
                245                 250                 255

Glu Leu Glu Trp Asp Phe Arg Leu Pro Leu Val Lys Ser Ile Asn Val
            260                 265                 270

Ser Gly His Lys Tyr Gly Leu Val Tyr Ala Gly Ile Gly Trp Val Val
        275                 280                 285

Trp Arg Ala Ala Glu Asp Leu Pro Glu Glu Leu Ile Phe His Ile Asn
    290                 295                 300

Tyr Leu Gly Ala Asp Gln Pro Thr Phe Thr Leu Asn Phe Ser Lys Gly
305                 310                 315                 320

Ser Ser Gln Ile Ile Ala Gln Tyr Tyr Gln Leu Ile Arg Leu Gly Phe
                325                 330                 335

Glu Gly Tyr Lys Asn Val Met Glu Asn Cys Ile Glu Asn Met Val Val
            340                 345                 350

Leu Lys Glu Gly Ile Glu Lys Thr Glu Arg Phe Asn Ile Val Ser Lys
        355                 360                 365

Asp Gln Gly Val Pro Val Val Ala Phe Ser Leu Lys Asp His Ser Phe
    370                 375                 380

His Asn Glu Phe Glu Ile Ser Glu Met Leu Arg Arg Phe Gly Trp Ile
385                 390                 395                 400

Val Pro Ala Tyr Thr Met Pro Ala Asp Val Gln His Ile Thr Val Leu
                405                 410                 415

Arg Val Val Ile Arg Glu Asp Phe Ser Arg Thr Leu Ala Glu Arg Leu
            420                 425                 430

Val Ala Asp Ile Ser Lys Val Leu His Glu Leu Asp Thr Leu Pro Ser
        435                 440                 445

Lys Ile Ser Lys Lys Met Gly Ile Glu Gly Ile Ala Glu Asn Val Lys
    450                 455                 460
```

Glu Lys Lys Met Glu Lys Glu Ile Leu Met Glu Val Ile Val Gly Trp
465 470 475 480

Arg Lys Phe Val Lys Glu Arg Lys Lys Met Asn Gly Val Cys
485 490

<210> SEQ ID NO 115
<211> LENGTH: 496
<212> TYPE: PRT
<213> ORGANISM: Nicotiana tabacum

<400> SEQUENCE: 115

Met Val Leu Ser Lys Thr Ala Ser Glu Ser Asp Val Ser Val His Ser
1 5 10 15

Thr Phe Ala Ser Arg Tyr Val Arg Thr Ser Leu Pro Arg Phe Lys Met
20 25 30

Pro Glu Asn Ser Ile Pro Lys Glu Ala Ala Tyr Gln Ile Ile Asn Asp
35 40 45

Glu Leu Met Leu Asp Gly Asn Pro Arg Leu Asn Leu Ala Ser Phe Val
50 55 60

Thr Thr Trp Met Glu Pro Glu Cys Asn Thr Leu Met Met Asp Ser Ile
65 70 75 80

Asn Lys Asn Tyr Val Asp Met Asp Glu Tyr Pro Val Thr Thr Glu Leu
85 90 95

Gln Asn Arg Cys Val Asn Met Ile Ala His Leu Phe Asn Ala Pro Leu
100 105 110

Gly Asp Gly Glu Thr Ala Val Gly Val Gly Thr Val Gly Ser Ser Glu
115 120 125

Ala Ile Met Leu Ala Gly Leu Ala Phe Lys Arg Lys Trp Gln Asn Lys
130 135 140

Met Lys Ala Gln Gly Lys Pro Phe Asp Lys Pro Asn Ile Val Thr Gly
145 150 155 160

Ala Asn Val Gln Val Cys Trp Glu Lys Phe Ala Arg Tyr Phe Glu Val
165 170 175

Glu Leu Lys Glu Val Lys Leu Ser Asp Gly Tyr Tyr Val Met Asp Pro
180 185 190

Glu Lys Ala Val Glu Met Val Asp Glu Asn Thr Ile Cys Val Ala Ala
195 200 205

Ile Leu Gly Ser Thr Leu Asn Gly Glu Phe Glu Asp Val Lys Arg Leu
210 215 220

Asn Asp Leu Leu Ile Glu Lys Asn Lys Glu Thr Gly Trp Asp Thr Pro
225 230 235 240

Ile His Val Asp Ala Ala Ser Gly Gly Phe Ile Ala Pro Phe Leu Tyr
245 250 255

Pro Glu Leu Glu Trp Asp Phe Arg Leu Pro Leu Glu Lys Ser Ile Asn
260 265 270

Val Ser Gly His Lys Tyr Gly Leu Val Tyr Ala Gly Ile Gly Trp Ala
275 280 285

Ile Trp Arg Asn Lys Glu Asp Leu Pro Asp Glu Leu Ile Phe His Ile
290 295 300

Asn Tyr Leu Gly Ala Asp Gln Pro Thr Phe Thr Leu Asn Phe Ser Lys
305 310 315 320

Gly Ser Ser Gln Val Ile Ala Gln Tyr Tyr Gln Leu Ile Arg Leu Gly
325 330 335

Phe Glu Gly Tyr Lys Asn Val Met Glu Asn Cys Gln Glu Asn Ala Arg

```
            340                 345                 350

Val Leu Arg Glu Gly Ile Glu Lys Ser Gly Arg Phe Asn Ile Ile Ser
        355                 360                 365

Lys Glu Ile Gly Val Pro Leu Val Ala Phe Ser Leu Lys Asp Asn Ser
    370                 375                 380

Gln His Asn Glu Phe Glu Ile Ser Glu Thr Leu Arg Arg Phe Gly Trp
385                 390                 395                 400

Ile Val Leu Ala Tyr Thr Met Pro Pro Asn Ala Gln His Val Thr Val
                405                 410                 415

Leu Arg Val Val Ile Arg Glu Asp Phe Ser Arg Thr Leu Ala Glu Arg
            420                 425                 430

Leu Val Ile Asp Ile Glu Lys Val Phe His Gly Val Asp Thr Leu Pro
        435                 440                 445

Ala Arg Val Asn Ala Lys Leu Ala Val Ala Glu Ala Asn Gly Ser Gly
    450                 455                 460

Val His Lys Lys Thr Asp Arg Glu Val Gln Leu Glu Ile Thr Thr Ala
465                 470                 475                 480

Trp Leu Lys Phe Val Ala Asp Lys Lys Lys Lys Thr Asn Gly Val Cys
                485                 490                 495


<210> SEQ ID NO 116
<211> LENGTH: 494
<212> TYPE: PRT
<213> ORGANISM: Arabidopsis thaliana

<400> SEQUENCE: 116

Met Val Leu Thr Lys Thr Ala Thr Asn Asp Glu Ser Val Cys Thr Met
1               5                   10                  15

Phe Gly Ser Arg Tyr Val Arg Thr Thr Leu Pro Lys Tyr Glu Ile Gly
            20                  25                  30

Glu Asn Ser Ile Pro Lys Asp Ala Ala Tyr Gln Ile Ile Lys Asp Glu
        35                  40                  45

Leu Met Leu Asp Gly Asn Pro Arg Leu Asn Leu Ala Ser Phe Val Thr
    50                  55                  60

Thr Trp Met Glu Pro Glu Cys Asp Lys Leu Ile Met Asp Ser Ile Asn
65                  70                  75                  80

Lys Asn Tyr Val Asp Met Asp Glu Tyr Pro Val Thr Thr Glu Leu Gln
                85                  90                  95

Asn Arg Cys Val Asn Ile Ile Ala Arg Leu Phe Asn Ala Pro Leu Glu
            100                 105                 110

Glu Ser Glu Thr Ala Val Gly Val Gly Thr Val Gly Ser Ser Glu Ala
        115                 120                 125

Ile Met Leu Ala Gly Leu Ala Phe Lys Arg Lys Trp Gln Asn Lys Arg
    130                 135                 140

Lys Ala Glu Gly Lys Pro Tyr Asp Lys Pro Asn Ile Val Thr Gly Ala
145                 150                 155                 160

Asn Val Gln Val Cys Trp Glu Lys Phe Ala Arg Tyr Phe Glu Val Glu
                165                 170                 175

Leu Lys Glu Val Asn Leu Ser Glu Gly Tyr Tyr Val Met Asp Pro Asp
            180                 185                 190

Lys Ala Ala Glu Met Val Asp Glu Asn Thr Ile Cys Val Ala Ala Ile
        195                 200                 205

Leu Gly Ser Thr Leu Asn Gly Glu Phe Glu Asp Val Lys Arg Leu Asn
    210                 215                 220
```

-continued

Asp Leu Leu Val Lys Lys Asn Glu Glu Thr Gly Trp Asn Thr Pro Ile
225 230 235 240

His Val Asp Ala Ala Ser Gly Gly Phe Ile Ala Pro Phe Ile Tyr Pro
245 250 255

Glu Leu Glu Trp Asp Phe Arg Leu Pro Leu Val Lys Ser Ile Asn Val
260 265 270

Ser Gly His Lys Tyr Gly Leu Val Tyr Ala Gly Ile Gly Trp Val Val
275 280 285

Trp Arg Ala Ala Glu Asp Leu Pro Glu Glu Leu Ile Phe His Ile Asn
290 295 300

Tyr Leu Gly Ala Asp Gln Pro Thr Phe Thr Leu Asn Phe Ser Lys Gly
305 310 315 320

Ser Ser Gln Ile Ile Ala Gln Tyr Tyr Gln Leu Ile Arg Leu Gly Phe
325 330 335

Glu Gly Tyr Lys Asn Val Met Glu Asn Cys Ile Glu Asn Met Val Val
340 345 350

Leu Lys Glu Gly Ile Glu Lys Thr Glu Arg Phe Asn Ile Val Ser Lys
355 360 365

Asp Gln Gly Val Pro Val Val Ala Phe Ser Leu Lys Asp His Ser Phe
370 375 380

His Asn Glu Phe Glu Ile Ser Glu Met Leu Arg Arg Phe Gly Trp Ile
385 390 395 400

Val Pro Ala Tyr Thr Met Pro Ala Asp Ala Gln His Ile Thr Val Leu
405 410 415

Arg Val Val Ile Arg Glu Asp Phe Ser Arg Thr Leu Ala Glu Arg Leu
420 425 430

Val Ala Asp Ile Ser Lys Val Leu His Glu Leu Asp Thr Leu Pro Ser
435 440 445

Lys Ile Ser Lys Lys Met Gly Ile Glu Gly Ile Ala Glu Asn Val Lys
450 455 460

Glu Lys Lys Met Glu Lys Glu Ile Leu Met Glu Val Ile Val Gly Trp
465 470 475 480

Arg Lys Phe Val Lys Glu Arg Lys Lys Met Asn Gly Val Cys
485 490

<210> SEQ ID NO 117
<211> LENGTH: 496
<212> TYPE: PRT
<213> ORGANISM: Nicotiana tabacum

<400> SEQUENCE: 117

Met Val Leu Ser Lys Thr Ala Ser Glu Ser Asp Val Ser Ile His Ser
1 5 10 15

Thr Phe Ala Ser Arg Tyr Val Arg Thr Ser Leu Pro Arg Phe Lys Met
20 25 30

Pro Glu Asn Ser Ile Pro Lys Glu Ala Ala Tyr Gln Ile Ile Asn Asp
35 40 45

Glu Leu Met Leu Asp Gly Asn Pro Arg Leu Asn Leu Ala Ser Phe Val
50 55 60

Thr Thr Trp Met Glu Pro Glu Cys Asn Lys Leu Met Met Asp Ser Ile
65 70 75 80

Asn Lys Asn Tyr Val Asp Met Asp Glu Tyr Pro Val Thr Thr Glu Leu
85 90 95

Gln Asn Arg Cys Val Asn Met Ile Ala His Leu Phe Asn Ala Pro Leu
100 105 110

```
Gly Asp Gly Glu Thr Ala Val Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140

Met Lys Ala Gln Gly Lys Pro Cys Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Asp Gly Tyr Tyr Val Met Asp Pro
            180                 185                 190

Glu Lys Ala Val Glu Met Val Asp Glu Asn Thr Ile Cys Val Ala Ala
        195                 200                 205

Ile Leu Gly Ser Thr Leu Asn Gly Glu Phe Glu Asp Val Lys Arg Leu
    210                 215                 220

Asn Asp Leu Leu Ile Glu Lys Asn Lys Glu Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Ala
        275                 280                 285

Ile Trp Arg Asn Lys Glu Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Lys Asn Val Met Glu Asn Cys Gln Glu Asn Ala Arg
            340                 345                 350

Val Leu Arg Glu Gly Leu Glu Lys Ser Gly Arg Phe Asn Ile Ile Ser
        355                 360                 365

Lys Glu Ile Gly Val Pro Leu Val Ala Phe Ser Leu Lys Asp Asn Ser
    370                 375                 380

Gln His Asn Glu Phe Glu Ile Ser Glu Thr Leu Arg Arg Phe Gly Trp
385                 390                 395                 400

Ile Ile Pro Ala Tyr Thr Met Pro Pro Asn Ala Gln His Val Thr Val
                405                 410                 415

Leu Arg Val Val Ile Arg Glu Asp Phe Ser Arg Thr Leu Ala Glu Arg
            420                 425                 430

Leu Val Ile Asp Ile Glu Lys Val Leu His Glu Leu Asp Thr Leu Pro
        435                 440                 445

Ala Arg Val Asn Ala Lys Leu Ala Val Ala Glu Ala Asn Gly Ser Gly
    450                 455                 460

Val His Lys Lys Thr Asp Arg Glu Val Gln Leu Glu Ile Thr Thr Ala
465                 470                 475                 480

Trp Lys Lys Phe Val Ala Asp Lys Lys Lys Lys Thr Asn Gly Val Cys
                485                 490                 495
```

<210> SEQ ID NO 118
<211> LENGTH: 496
<212> TYPE: PRT
<213> ORGANISM: Nicotiana tabacum

<400> SEQUENCE: 118

Met Val Leu Ser Lys Thr Ala Ser Glu Ser Asp Val Ser Ile His Ser
1               5                   10                  15

Thr Phe Ala Ser Arg Tyr Val Arg Thr Ser Leu Pro Arg Phe Lys Met
            20                  25                  30

Pro Glu Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asn Lys Leu Met Met Asp Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Leu
            100                 105                 110

Gly Asp Gly Glu Thr Ala Val Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140

Met Lys Ala Gln Gly Lys Pro Cys Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Asp Gly Tyr Tyr Val Met Asp Pro
            180                 185                 190

Glu Lys Ala Val Glu Met Val Asp Glu Asn Thr Ile Cys Val Ala Ala
        195                 200                 205

Ile Leu Gly Ser Thr Leu Asn Gly Glu Phe Glu Asp Val Lys Arg Leu
    210                 215                 220

Asn Asp Leu Leu Ile Glu Lys Asn Lys Glu Thr Gly Trp Asp Thr Pro
225                 230                 235                 240

Ile His Val Asp Ala Ala Ser Gly Glu Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Ala
        275                 280                 285

Ile Trp Arg Asn Lys Glu Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Lys Asn Val Met Glu Asn Cys Gln Glu Asn Ala Arg
            340                 345                 350

Val Leu Arg Glu Gly Leu Glu Lys Ser Gly Arg Phe Asn Ile Ile Ser
        355                 360                 365

Lys Glu Ile Gly Val Pro Leu Val Ala Phe Ser Leu Lys Asp Asn Ser
    370                 375                 380

Gln His Asn Glu Phe Glu Ile Ser Glu Thr Leu Arg Arg Phe Gly Trp
385                 390                 395                 400

Ile Ile Pro Ala Tyr Thr Met Pro Pro Asn Ala Gln His Val Thr Val
                405                 410                 415

Leu Arg Val Val Ile Arg Glu Asp Phe Ser Arg Thr Leu Ala Glu Arg
420 425 430

Leu Val Ile Asp Ile Glu Lys Val Leu His Glu Leu Asp Thr Leu Pro
435 440 445

Ala Arg Val Asn Ala Lys Leu Ala Val Ala Glu Ala Asn Gly Ser Gly
450 455 460

Val His Lys Lys Thr Asp Arg Glu Val Gln Leu Glu Ile Thr Thr Ala
465 470 475 480

Trp Lys Lys Phe Val Ala Asp Lys Lys Lys Lys Thr Asn Gly Val Cys
485 490 495

<210> SEQ ID NO 119
<211> LENGTH: 502
<212> TYPE: PRT
<213> ORGANISM: Arabidopsis thaliana

<400> SEQUENCE: 119

Met Val Leu Ser His Ala Val Ser Glu Ser Asp Val Ser Val His Ser
1 5 10 15

Thr Phe Ala Ser Arg Tyr Val Arg Thr Ser Leu Pro Arg Phe Lys Met
20 25 30

Pro Glu Asn Ser Ile Pro Lys Glu Ala Ala Tyr Gln Ile Ile Asn Asp
35 40 45

Glu Leu Met Leu Asp Gly Asn Pro Arg Leu Asn Leu Ala Ser Phe Val
50 55 60

Thr Thr Trp Met Glu Pro Glu Cys Asp Lys Leu Ile Met Ser Ser Ile
65 70 75 80

Asn Lys Asn Tyr Val Asp Met Asp Glu Tyr Pro Val Thr Thr Glu Leu
85 90 95

Gln Asn Arg Cys Val Asn Met Ile Ala His Leu Phe Asn Ala Pro Leu
100 105 110

Glu Glu Ala Glu Thr Ala Val Gly Val Gly Thr Val Gly Ser Ser Glu
115 120 125

Ala Ile Met Leu Ala Gly Leu Ala Phe Lys Arg Lys Trp Gln Asn Lys
130 135 140

Arg Lys Ala Glu Gly Lys Pro Val Asp Lys Pro Asn Ile Val Thr Gly
145 150 155 160

Ala Asn Val Gln Val Cys Trp Glu Lys Phe Ala Arg Tyr Phe Glu Val
165 170 175

Glu Leu Lys Glu Val Lys Leu Ser Glu Gly Tyr Tyr Val Met Asp Pro
180 185 190

Gln Gln Ala Val Asp Met Val Asp Glu Asn Thr Ile Cys Val Ala Asp
195 200 205

Ile Leu Gly Ser Thr Leu Asn Gly Glu Phe Glu Asp Val Lys Leu Leu
210 215 220

Asn Asp Leu Leu Val Glu Lys Asn Lys Glu Thr Gly Trp Asp Thr Pro
225 230 235 240

Ile His Val Asp Ala Ala Ser Gly Gly Phe Ile Ala Pro Phe Leu Tyr
245 250 255

Pro Glu Leu Glu Trp Asp Phe Arg Leu Pro Leu Val Lys Ser Ile Asn
260 265 270

Val Ser Gly His Lys Tyr Gly Leu Val Tyr Ala Gly Ile Gly Trp Val
275 280 285

Ile Trp Arg Asn Lys Glu Asp Leu Pro Glu Glu Leu Ile Phe His Ile

```
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

His Glu Gly Tyr Arg Asn Val Met Glu Asn Cys Arg Glu Asn Met Ile
            340                 345                 350

Val Leu Arg Glu Gly Leu Glu Lys Thr Glu Arg Phe Asn Ile Val Ser
        355                 360                 365

Lys Asp Glu Gly Val Pro Leu Val Ala Phe Ser Leu Lys Asp Ser Ser
    370                 375                 380

Cys His Thr Glu Phe Glu Ile Ser Asp Met Leu Arg Arg Tyr Gly Trp
385                 390                 395                 400

Ile Val Pro Ala Tyr Thr Met Pro Pro Asn Ala Gln His Ile Thr Val
                405                 410                 415

Leu Arg Val Val Ile Arg Glu Asp Phe Ser Arg Thr Leu Ala Glu Arg
            420                 425                 430

Leu Val Ile Asp Ile Glu Lys Val Met Arg Glu Leu Asp Glu Leu Pro
        435                 440                 445

Ser Arg Val Ile His Lys Ile Ser Leu Gly Gln Glu Lys Ser Glu Ser
    450                 455                 460

Asn Ser Asp Asn Leu Met Val Thr Val Lys Lys Ser Asp Ile Asp Lys
465                 470                 475                 480

Gln Arg Asp Ile Ile Thr Gly Trp Lys Lys Phe Val Ala Asp Arg Lys
                485                 490                 495

Lys Thr Ser Gly Ile Cys
            500


<210> SEQ ID NO 120
<211> LENGTH: 500
<212> TYPE: PRT
<213> ORGANISM: Petunia x hybrida

<400> SEQUENCE: 120

Met Val Leu Ser Lys Thr Val Ser Gln Ser Asp Val Ser Ile His Ser
1               5                   10                  15

Thr Phe Ala Ser Arg Tyr Val Arg Thr Ser Leu Pro Arg Phe Lys Met
            20                  25                  30

Pro Asp Asn Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Asp Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Leu
            100                 105                 110

Glu Asp Gly Glu Thr Ala Val Gly Val Gly Thr Val Gly Ser Ser Glu
        115                 120                 125

Ala Ile Met Leu Ala Gly Leu Ala Phe Lys Arg Lys Trp Gln Asn Lys
    130                 135                 140

Met Lys Ala Gln Gly Lys Pro Cys Asp Lys Pro Asn Ile Val Thr Gly
145                 150                 155                 160
```

-continued

```
Ala Asn Val Gln Val Cys Trp Glu Lys Phe Ala Arg Tyr Phe Glu Val
                165                 170                 175

Glu Leu Lys Glu Val Lys Leu Ser Glu Gly Tyr Tyr Val Met Asp Pro
            180                 185                 190

Glu Lys Ala Val Glu Met Val Asp Glu Asn Thr Ile Cys Val Ala Ala
        195                 200                 205

Ile Leu Gly Ser Thr Leu Asn Gly Glu Phe Glu Asp Val Lys Arg Leu
    210                 215                 220

Asn Asp Leu Leu Val Glu Lys Asn Lys Glu Thr Gly Trp Asp Thr Pro
225                 230                 235                 240

Ile His Val Asp Ala Ala Ser Gly Gly Phe Ile Ala Pro Phe Ile Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Asn Lys Asp Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Tyr Glu Gly Tyr Lys Asn Val Met Glu Asn Cys Gln Glu Asn Ala Ser
            340                 345                 350

Val Leu Arg Glu Gly Leu Glu Lys Thr Gly Arg Phe Asn Ile Ile Ser
        355                 360                 365

Lys Glu Ile Gly Val Pro Leu Val Ala Phe Ser Leu Lys Asp Asn Arg
    370                 375                 380

Gln His Asn Glu Phe Glu Ile Ser Glu Thr Leu Arg Arg Phe Gly Trp
385                 390                 395                 400

Ile Val Pro Ala Tyr Thr Met Pro Pro Asn Ala Gln His Ile Thr Val
                405                 410                 415

Leu Arg Val Val Ile Arg Glu Asp Phe Ser Arg Thr Leu Ala Glu Arg
            420                 425                 430

Leu Val Arg Asp Ile Glu Lys Val Leu His Glu Leu Asp Thr Leu Pro
        435                 440                 445

Ala Arg Val Asn Ala Lys Leu Ala Val Ala Glu Glu Gln Ala Ala Ala
    450                 455                 460

Asn Gly Ser Glu Val His Lys Lys Thr Asp Ser Glu Val Gln Leu Glu
465                 470                 475                 480

Met Ile Thr Ala Trp Lys Lys Phe Val Glu Glu Lys Lys Lys Lys Thr
                485                 490                 495

Asn Arg Val Cys
            500


<210> SEQ ID NO 121
<211> LENGTH: 282
<212> TYPE: PRT
<213> ORGANISM: Oryza sativa

<400> SEQUENCE: 121

Gly Glu Phe Glu Asp Val Lys Leu Leu Asn Asn Leu Leu Thr Glu Lys
1               5                   10                  15

Asn Lys Glu Thr Gly Trp Asp Val Pro Ile His Val Asp Ala Ala Ser
            20                  25                  30
```

```
Gly Gly Phe Ile Ala Pro Phe Leu Tyr Pro Glu Leu Glu Trp Asp Phe
        35                  40                  45

Arg Leu Pro Leu Val Lys Ser Ile Asn Val Ser Gly His Lys Tyr Gly
    50                  55                  60

Leu Val Tyr Pro Gly Val Gly Trp Val Ile Trp Arg Ser Lys Glu Asp
65                  70                  75                  80

Leu Pro Glu Glu Leu Ile Phe His Ile Asn Tyr Leu Gly Thr Asp Gln
                85                  90                  95

Pro Thr Phe Thr Leu Asn Phe Ser Lys Gly Ser Ser Gln Ile Ile Ala
            100                 105                 110

Gln Tyr Tyr Gln Leu Ile Arg Leu Gly Phe Glu Gly Tyr Lys Asn Ile
        115                 120                 125

Met Gln Asn Cys Met Glu Thr Pro Ala Ile Leu Arg Glu Gly Ile Glu
    130                 135                 140

Ala Thr Gly Arg Phe Glu Ile Leu Ser Lys Glu Ala Gly Val Pro Leu
145                 150                 155                 160

Val Ala Phe Ser Leu Lys Ala Ser Gly Arg Tyr Thr Val Phe Asp Ile
                165                 170                 175

Ser Glu His Leu Arg Arg Phe Gly Trp Ile Val Pro Ala Tyr Thr Met
            180                 185                 190

Pro Ala Asn Ala Glu His Val Ala Ile Leu Arg Val Val Ile Arg Glu
        195                 200                 205

Asp Phe Ser Arg Ser Leu Ala Glu Arg Leu Val Ser Asp Ile Val Lys
    210                 215                 220

Ile Leu His Glu Leu Asp Ala His Ser Ala Gln Val Leu Lys Ile Ser
225                 230                 235                 240

Ser Ala Ile Ala Lys Gln Gln Ser Gly Asp Asp Gly Ala Val Thr Lys
                245                 250                 255

Lys Ser Val Leu Glu Thr Glu Arg Glu Ile Phe Ala Tyr Trp Arg Asp
            260                 265                 270

Gln Val Lys Lys Lys Gln Thr Gly Ile Cys
        275                 280


<210> SEQ ID NO 122
<211> LENGTH: 502
<212> TYPE: PRT
<213> ORGANISM: Lycopersicon esculentum

<400> SEQUENCE: 122

Met Val Leu Thr Thr Thr Ser Ile Arg Asp Ser Glu Glu Ser Leu His
1               5                   10                  15

Cys Thr Phe Ala Ser Arg Tyr Val Gln Glu Pro Leu Pro Lys Phe Lys
            20                  25                  30

Met Pro Lys Lys Ser Met Pro Lys Glu Ala Ala Tyr Gln Ile Val Asn
        35                  40                  45

Asp Glu Leu Met Leu Asp Gly Asn Pro Arg Leu Asn Leu Ala Ser Phe
    50                  55                  60

Val Ser Thr Trp Met Glu Pro Glu Cys Asp Lys Leu Ile Met Ser Ser
65                  70                  75                  80

Ile Asn Lys Asn Tyr Val Asp Met Asp Glu Tyr Pro Val Thr Thr Glu
                85                  90                  95

Leu Gln Asn Arg Cys Val Asn Met Leu Ala His Leu Phe His Ala Pro
            100                 105                 110

Val Gly Asp Asp Glu Thr Ala Val Gly Val Gly Thr Val Gly Ser Ser
```

115 120 125

Glu Ala Ile Met Leu Ala Gly Leu Ala Phe Lys Arg Lys Trp Gln Ser
130 135 140

Lys Arg Lys Ala Glu Gly Lys Pro Phe Asp Lys Pro Asn Ile Val Thr
145 150 155 160

Gly Ala Asn Val Gln Val Cys Trp Glu Lys Phe Ala Arg Tyr Phe Glu
165 170 175

Val Glu Leu Lys Glu Val Lys Leu Lys Glu Gly Tyr Tyr Val Met Asp
180 185 190

Pro Ala Lys Ala Val Glu Ile Val Asp Glu Asn Thr Ile Cys Val Ala
195 200 205

Ala Ile Leu Gly Ser Thr Leu Thr Gly Glu Phe Glu Asp Val Lys Leu
210 215 220

Leu Asn Glu Leu Leu Thr Lys Lys Asn Lys Glu Thr Gly Trp Glu Thr
225 230 235 240

Pro Ile His Val Asp Ala Ala Ser Gly Gly Phe Ile Ala Pro Phe Leu
245 250 255

Trp Pro Asp Leu Glu Trp Asp Phe Arg Leu Pro Leu Val Lys Ser Ile
260 265 270

Asn Val Ser Gly His Lys Tyr Gly Leu Val Tyr Ala Gly Val Gly Trp
275 280 285

Val Ile Trp Arg Ser Lys Glu Asp Leu Pro Asp Glu Leu Val Phe His
290 295 300

Ile Asn Tyr Leu Gly Ser Asp Gln Pro Thr Phe Thr Leu Asn Phe Ser
305 310 315 320

Lys Gly Ser Tyr Gln Ile Ile Ala Gln Tyr Tyr Gln Leu Ile Arg Leu
325 330 335

Gly Phe Glu Gly Tyr Lys Asn Val Met Lys Asn Cys Leu Ser Asn Ala
340 345 350

Lys Val Leu Thr Glu Gly Ile Thr Lys Met Gly Arg Phe Asp Ile Val
355 360 365

Ser Lys Asp Val Gly Val Pro Val Val Ala Phe Ser Leu Arg Asp Ser
370 375 380

Ser Lys Tyr Thr Val Phe Glu Val Ser Glu His Leu Arg Arg Phe Gly
385 390 395 400

Trp Ile Val Pro Ala Tyr Thr Met Pro Pro Asp Ala Glu His Ile Ala
405 410 415

Val Leu Arg Val Val Ile Arg Glu Asp Phe Ser His Ser Leu Ala Glu
420 425 430

Arg Leu Val Ser Asp Ile Glu Lys Ile Leu Ser Glu Leu Asp Thr Gln
435 440 445

Pro Pro Arg Leu Pro Thr Lys Ala Val Arg Val Thr Ala Glu Glu Val
450 455 460

Arg Asp Asp Lys Gly Asp Gly Leu His His Phe His Met Asp Thr Val
465 470 475 480

Glu Thr Gln Lys Asp Ile Ile Lys His Trp Arg Lys Ile Ala Gly Lys
485 490 495

Lys Thr Ser Gly Val Cys
500

<210> SEQ ID NO 123
<211> LENGTH: 500
<212> TYPE: PRT
<213> ORGANISM: Oryza sativa

<400> SEQUENCE: 123

Met Val Leu Thr His Val Glu Ala Val Glu Glu Gly Ser Glu Ala Ala
1 5 10 15

Ala Ala Val Phe Ala Ser Arg Tyr Val Gln Asp Pro Val Pro Arg Tyr
20 25 30

Glu Leu Gly Glu Arg Ser Ile Ser Lys Asp Ala Ala Tyr Gln Ile Val
35 40 45

His Asp Glu Leu Leu Leu Asp Ser Ser Pro Arg Leu Asn Leu Ala Ser
50 55 60

Phe Val Thr Thr Trp Met Glu Pro Glu Cys Asp Arg Leu Ile Leu Glu
65 70 75 80

Ala Ile Asn Lys Asn Tyr Ala Asp Met Asp Glu Tyr Pro Val Thr Thr
85 90 95

Glu Leu Gln Asn Arg Cys Val Asn Ile Ile Ala Arg Leu Phe Asn Ala
100 105 110

Pro Val Gly Asp Gly Glu Lys Ala Val Gly Val Gly Thr Val Gly Ser
115 120 125

Ser Glu Ala Ile Met Leu Ala Gly Leu Ala Phe Lys Arg Arg Trp Gln
130 135 140

Asn Arg Arg Lys Ala Ala Gly Lys Pro His Asp Lys Pro Asn Ile Val
145 150 155 160

Thr Gly Ala Asn Val Gln Val Cys Trp Glu Lys Phe Ala Arg Tyr Phe
165 170 175

Glu Val Glu Leu Lys Glu Val Lys Leu Thr Glu Gly Cys Tyr Val Met
180 185 190

Asp Pro Val Lys Ala Val Asp Met Val Asp Glu Asn Thr Ile Cys Val
195 200 205

Ala Ala Ile Leu Gly Ser Thr Leu Thr Gly Glu Phe Glu Asp Val Arg
210 215 220

Arg Leu Asn Asp Leu Leu Ala Ala Lys Asn Lys Arg Thr Gly Trp Asp
225 230 235 240

Thr Pro Ile His Val Asp Ala Ala Ser Gly Gly Phe Ile Ala Pro Phe
245 250 255

Ile Tyr Pro Glu Leu Glu Trp Asp Phe Arg Leu Pro Leu Val Lys Ser
260 265 270

Ile Asn Val Ser Gly His Lys Tyr Gly Leu Val Tyr Ala Gly Val Gly
275 280 285

Trp Val Ile Trp Arg Asn Lys Glu Asp Leu Pro Glu Glu Leu Ile Phe
290 295 300

His Ile Asn Tyr Leu Gly Ala Asp Gln Pro Thr Phe Thr Leu Asn Phe
305 310 315 320

Ser Lys Gly Ser Ser Gln Ile Ile Ala Gln Tyr Tyr Gln Phe Leu Arg
325 330 335

Leu Gly Phe Glu Gly Tyr Lys Ser Val Met Lys Asn Cys Met Glu Ser
340 345 350

Ala Arg Thr Leu Arg Glu Gly Leu Glu Lys Thr Gly Arg Phe Thr Ile
355 360 365

Ile Ser Lys Glu Glu Gly Val Pro Leu Val Ala Phe Thr Phe Lys Asp
370 375 380

Gly Ala Gly Ala Gln Ala Phe Arg Leu Ser Ser Gly Leu Arg Arg Tyr
385 390 395 400

Gly Trp Ile Val Pro Ala Tyr Thr Met Pro Ala Ala Leu Glu His Met 405 410 415

Thr Val Leu Arg Val Val Val Arg Glu Asp Phe Gly Arg Pro Leu Ala
420 425 430

Glu Arg Phe Leu Ser His Val Arg Met Ala Leu Asp Glu Met Asp Leu
435 440 445

Ala Ala Arg Ala Pro Val Pro Arg Val Gln Leu Thr Ile Glu Leu Gly
450 455 460

Pro Ala Arg Thr Ala Gly Glu Glu Ala Ser Ile Arg Val Val Lys Ser
465 470 475 480

Glu Ala Val Pro Val Arg Lys Ser Val Pro Leu Val Ala Gly Lys Thr
485 490 495

Lys Gly Val Cys
500

<210> SEQ ID NO 124
<211> LENGTH: 513
<212> TYPE: PRT
<213> ORGANISM: Oryza sativa

<400> SEQUENCE: 124

Met Val Leu Ser His Gly Val Ser Gly Ser Asp Glu Ser Val His Ser
1 5 10 15

Thr Phe Ala Ser Arg Tyr Val Arg Thr Ser Leu Pro Arg His Ala Arg
20 25 30

Ser Pro Leu Ser Arg Ala Pro Leu Ala Pro Ile Asp Ser Val Ile Asp
35 40 45

Trp Glu Phe Arg Met Pro Glu Gln Ser Ile Pro Lys Glu Ala Ala Tyr
50 55 60

Gln Ile Ile Asn Asp Glu Leu Met Leu Asp Gly Asn Pro Arg Leu Asn
65 70 75 80

Leu Ala Ser Phe Val Thr Thr Trp Met Glu Pro Glu Cys Asp Lys Leu
85 90 95

Ile Gln Ala Ser Val Asn Lys Asn Tyr Val Asp Met Asp Glu Tyr Pro
100 105 110

Val Thr Thr Glu Leu Gln Asn Arg Cys Val Asn Met Ile Ala His Leu
115 120 125

Phe Asn Ala Pro Leu Gly Asp Ser Glu Thr Ala Val Gly Val Gly Thr
130 135 140

Val Gly Ser Ser Glu Ala Ile Met Leu Ala Gly Leu Ala Phe Lys Arg
145 150 155 160

Arg Trp Gln Asn Lys Met Lys Ala Ala Gly Lys Pro Cys Asp Lys Pro
165 170 175

Asn Ile Val Thr Gly Ala Asn Val Gln Val Cys Trp Glu Lys Phe Ala
180 185 190

Arg Tyr Phe Glu Val Glu Leu Lys Glu Val Lys Leu Ser Asp Gly Tyr
195 200 205

Tyr Val Met Asp Pro Ala Lys Ala Val Asp Met Val Asp Glu Asn Thr
210 215 220

Ile Cys Val Ala Ala Ile Leu Gly Ser Thr Leu Asn Gly Glu Phe Glu
225 230 235 240

Asp Val Lys Leu Leu Asn Asp Leu Leu Thr Lys Lys Asn Ala Glu Thr
245 250 255

Gly Trp Asp Thr Pro Ile His Val Asp Ala Ala Ser Gly Gly Phe Ile
260 265 270

```
Ala Pro Phe Leu Tyr Pro Glu Leu Glu Trp Asp Phe Arg Leu Pro Leu
        275                 280                 285

Val Lys Ser Ile Asn Val Ser Gly His Lys Tyr Gly Leu Val Tyr Ala
    290                 295                 300

Gly Ile Gly Trp Cys Ile Trp Arg Ser Lys Glu Asp Leu Pro Glu Glu
305                 310                 315                 320

Leu Ile Phe His Ile Asn Tyr Leu Gly Ala Asp Gln Pro Thr Phe Thr
                325                 330                 335

Leu Asn Phe Ser Lys Gly Ser Ser Gln Val Ile Ala Gln Tyr Tyr Gln
            340                 345                 350

Leu Ile Arg Leu Gly Phe Glu Gly Tyr Lys Asn Ile Met Glu Asn Cys
        355                 360                 365

Gln Glu Asn Ala Met Val Leu Lys Gln Gly Leu Glu Lys Thr Gly Arg
    370                 375                 380

Phe Asn Ile Val Ser Lys Asp Asn Gly Val Pro Leu Val Ala Phe Ser
385                 390                 395                 400

Leu Lys Asp Ser Ala Arg His Asn Glu Phe Glu Ile Ser Asp Phe Leu
                405                 410                 415

Arg Arg Phe Gly Trp Ile Val Pro Ala Tyr Thr Met Pro Pro Asp Ala
            420                 425                 430

Gln His Val Thr Val Leu Arg Val Val Ile Arg Glu Asp Phe Ser Arg
        435                 440                 445

Thr Leu Ala Glu Arg Leu Val Leu Asp Val Glu Lys Val Leu His Glu
    450                 455                 460

Leu Asp Ala Leu Pro Ala Arg Val Val Ala Asn Gly Gly Asp Ala Ala
465                 470                 475                 480

Ala Ala Ser Ala Ser Glu Arg Glu Met Glu Lys Gln Arg Glu Val Ile
                485                 490                 495

Ser Leu Trp Lys Arg Ala Val Leu Ala Lys Lys Lys Thr Asn Gly Val
            500                 505                 510

Cys


<210> SEQ ID NO 125
<211> LENGTH: 500
<212> TYPE: PRT
<213> ORGANISM: Oryza sativa

<400> SEQUENCE: 125

Met Val Leu Thr His Val Glu Ala Val Glu Glu Gly Ser Glu Ala Ala
1               5                   10                  15

Ala Ala Val Phe Ala Ser Arg Tyr Val Gln Asp Pro Val Pro Arg Tyr
            20                  25                  30

Glu Leu Gly Glu Arg Ser Ile Ser Lys Asp Ala Ala Tyr Gln Ile Val
        35                  40                  45

His Asp Glu Leu Leu Leu Asp Ser Ser Pro Arg Leu Asn Leu Ala Ser
    50                  55                  60

Phe Val Thr Thr Trp Met Glu Pro Glu Cys Asp Arg Leu Ile Leu Glu
65                  70                  75                  80

Ala Ile Asn Lys Asn Tyr Ala Asp Met Asp Glu Tyr Pro Val Thr Thr
                85                  90                  95

Glu Leu Gln Asn Arg Cys Val Asn Ile Ile Ala Arg Leu Phe Asn Ala
            100                 105                 110

Pro Val Gly Asp Gly Glu Lys Ala Val Gly Val Gly Thr Val Gly Ser
        115                 120                 125
```

```
Ser Glu Ala Ile Met Leu Ala Gly Leu Ala Phe Lys Arg Arg Trp Gln
    130                 135                 140

Asn Arg Arg Lys Ala Ala Gly Lys Pro His Asp Lys Pro Asn Ile Val
145                 150                 155                 160

Thr Gly Ala Asn Val Gln Val Cys Trp Glu Lys Phe Ala Arg Tyr Phe
                165                 170                 175

Glu Val Glu Leu Lys Glu Val Lys Leu Thr Glu Gly Cys Tyr Val Met
            180                 185                 190

Asp Pro Val Lys Ala Val Asp Met Val Asp Glu Asn Thr Ile Cys Val
        195                 200                 205

Ala Ala Ile Leu Gly Ser Thr Leu Thr Gly Glu Phe Glu Asp Val Arg
    210                 215                 220

Arg Leu Asn Asp Leu Leu Ala Ala Lys Asn Lys Arg Thr Gly Trp Asp
225                 230                 235                 240

Thr Pro Ile His Val Asp Ala Ala Ser Gly Gly Phe Ile Ala Pro Phe
                245                 250                 255

Ile Tyr Pro Glu Leu Glu Trp Asp Phe Arg Leu Pro Leu Val Lys Ser
            260                 265                 270

Ile Asn Val Ser Gly His Lys Tyr Gly Leu Val Tyr Ala Gly Val Gly
        275                 280                 285

Trp Val Ile Trp Arg Asn Lys Glu Asp Leu Pro Glu Glu Leu Ile Phe
    290                 295                 300

His Ile Asn Tyr Leu Gly Ala Asp Gln Pro Thr Phe Thr Leu Asn Phe
305                 310                 315                 320

Ser Lys Gly Ser Ser Gln Ile Ile Ala Gln Tyr Tyr Gln Phe Leu Arg
                325                 330                 335

Leu Gly Phe Glu Gly Tyr Lys Ser Val Met Lys Asn Cys Met Glu Ser
            340                 345                 350

Ala Arg Thr Leu Arg Glu Gly Leu Glu Lys Thr Gly Arg Phe Thr Ile
        355                 360                 365

Ile Ser Lys Glu Glu Gly Val Pro Leu Val Ala Phe Thr Phe Lys Asp
    370                 375                 380

Gly Ala Gly Ala Gln Ala Phe Arg Leu Ser Ser Gly Leu Arg Arg Tyr
385                 390                 395                 400

Gly Trp Ile Val Pro Ala Tyr Thr Met Pro Ala Ala Leu Glu His Met
                405                 410                 415

Thr Val Val Arg Val Val Val Arg Glu Asp Phe Gly Arg Pro Leu Ala
            420                 425                 430

Glu Arg Phe Leu Ser His Val Arg Met Ala Leu Asp Glu Met Asp Leu
        435                 440                 445

Ala Ala Arg Ala Pro Val Pro Arg Val Gln Leu Thr Ile Glu Leu Gly
    450                 455                 460

Pro Ala Arg Thr Ala Gly Glu Glu Ala Ser Ile Arg Val Val Lys Ser
465                 470                 475                 480

Glu Ala Val Pro Val Arg Lys Ser Val Pro Leu Val Ala Gly Lys Thr
                485                 490                 495

Lys Gly Val Cys
            500
```

<210> SEQ ID NO 126
<211> LENGTH: 492
<212> TYPE: PRT
<213> ORGANISM: Oryza sativa

<400> SEQUENCE: 126

```
Met Val Leu Ser His Gly Val Ser Gly Ser Asp Glu Ser Val His Ser
1               5                   10                  15

Thr Phe Ala Ser Arg Tyr Val Arg Thr Ser Leu Pro Arg Phe Arg Met
            20                  25                  30

Pro Glu Gln Ser Ile Pro Lys Glu Ala Ala Tyr Gln Ile Ile Asn Asp
        35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Ile Gln Ala Ser Val
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala His Leu Phe Asn Ala Pro Leu
            100                 105                 110

Gly Asp Ser Glu Thr Ala Val Gly Val Gly Thr Val Gly Ser Ser Glu
        115                 120                 125

Ala Ile Met Leu Ala Gly Leu Ala Phe Lys Arg Arg Trp Gln Asn Lys
    130                 135                 140

Met Lys Ala Ala Gly Lys Pro Cys Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Lys Leu Ser Asp Gly Tyr Tyr Val Met Asp Pro
            180                 185                 190

Ala Lys Ala Val Asp Met Val Asp Glu Asn Thr Ile Cys Val Ala Ala
        195                 200                 205

Ile Leu Gly Ser Thr Leu Asn Gly Glu Phe Glu Asp Val Lys Leu Leu
    210                 215                 220

Asn Asp Leu Leu Thr Lys Lys Asn Ala Glu Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Cys
        275                 280                 285

Ile Trp Arg Ser Lys Glu Asp Leu Pro Glu Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Lys Asn Ile Met Glu Asn Cys Gln Glu Asn Ala Met
            340                 345                 350

Val Leu Lys Gln Gly Leu Glu Lys Thr Gly Arg Phe Asn Ile Val Ser
        355                 360                 365

Lys Asp Asn Gly Val Pro Leu Val Ala Phe Ser Leu Lys Asp Ser Ala
    370                 375                 380

Arg His Asn Glu Phe Glu Ile Ser Asp Phe Leu Arg Arg Phe Gly Trp
385                 390                 395                 400

Ile Val Pro Ala Tyr Thr Met Pro Pro Asp Ala Gln His Val Thr Val
                405                 410                 415
```

```
Leu Arg Val Val Ile Arg Glu Asp Phe Ser Arg Thr Leu Ala Glu Arg
            420                 425                 430

Leu Val Leu Asp Val Glu Lys Val Leu His Glu Leu Asp Ala Leu Pro
        435                 440                 445

Ala Arg Val Val Ala Asn Gly Gly Asp Ala Ala Ala Ala Ser Ala Ser
    450                 455                 460

Glu Arg Glu Met Glu Lys Gln Arg Glu Val Ile Ser Leu Trp Lys Arg
465                 470                 475                 480

Ala Val Leu Ala Lys Lys Lys Thr Asn Gly Val Cys
                485                 490


<210> SEQ ID NO 127
<211> LENGTH: 490
<212> TYPE: PRT
<213> ORGANISM: Hordeum vulgare

<400> SEQUENCE: 127

Met Val Val Thr Val Ala Ala Thr Gly Pro Asp Thr Ala Glu Thr Leu
1               5                   10                  15

His Ser Thr Thr Phe Ala Ser Arg Tyr Val Arg Asp Gln Leu Pro Arg
            20                  25                  30

Tyr Arg Met Pro Glu Asn Ser Ile Pro Lys Glu Ala Ala Tyr Gln Ile
        35                  40                  45

Ile Ser Asp Glu Leu Met Leu Asp Gly Asn Pro Arg Leu Asn Leu Ala
    50                  55                  60

Ser Phe Val Thr Thr Trp Met Glu Pro Glu Cys Gly Lys Leu Ile Met
65                  70                  75                  80

Asp Ser Val Asn Lys Asn Tyr Val Asp Met Asp Glu Tyr Pro Val Thr
                85                  90                  95

Thr Glu Leu Gln Asp Arg Cys Val Asn Met Ile Ala His Leu Phe Asn
            100                 105                 110

Ala Pro Ile Gly Glu Asp Glu Thr Ala Ile Gly Val Ser Thr Val Gly
        115                 120                 125

Ser Ser Glu Ala Ile Met Leu Ala Gly Leu Ala Phe Lys Arg Lys Trp
    130                 135                 140

Ala Asn Lys Met Lys Glu Gln Gly Lys Pro Cys Asp Lys Pro Asn Ile
145                 150                 155                 160

Val Thr Gly Ala Asn Val Gln Val Cys Trp Glu Lys Phe Ala Arg Tyr
                165                 170                 175

Phe Glu Val Glu Leu Lys Glu Val Lys Leu Thr Glu Gly Tyr Tyr Val
            180                 185                 190

Met Asp Pro Lys Lys Ala Val Glu Met Val Asp Glu Asn Thr Ile Cys
        195                 200                 205

Val Ala Ala Ile Leu Gly Ser Thr Leu Thr Gly Glu Tyr Glu Asp Val
    210                 215                 220

Lys Leu Leu Asn Asp Leu Leu Val Glu Lys Asn Lys Glu Thr Gly Trp
225                 230                 235                 240

Asn Val Pro Ile His Val Asp Ala Ala Ser Gly Gly Phe Ile Ala Pro
                245                 250                 255

Phe Leu Gln Pro Glu Leu Glu Trp Asp Phe Arg Leu Pro Leu Val Lys
            260                 265                 270

Ser Ile Asn Val Ser Gly His Lys Tyr Gly Leu Val Tyr Pro Gly Val
        275                 280                 285

Gly Trp Val Ile Trp Arg Ser Lys Asp Asp Leu Pro Glu Glu Leu Ile
    290                 295                 300
```

Phe His Ile Asn Tyr Leu Gly Ala Asp Gln Pro Thr Phe Thr Leu Asn
305 310 315 320

Phe Ser Lys Gly Gln Gln Ile Ile Ala Gln Tyr Tyr Gln Leu Ile Arg
325 330 335

Leu Gly Phe Glu Gly Tyr Lys His Ile Met Glu Asn Cys Lys Leu Asn
340 345 350

Ala Ala Val Leu Lys Glu Gly Ile Asp Ala Thr Gly Arg Phe Asp Val
355 360 365

Leu Ser Lys Ala Asp Gly Val Pro Leu Val Ala Ile Arg Leu Lys Asp
370 375 380

Ser Thr Asn Phe Ser Val Phe Asp Ile Ser Glu Asn Leu Arg Arg Phe
385 390 395 400

Gly Trp Ile Val Pro Ala Tyr Thr Met Pro Ala Asp Ala Glu His Val
405 410 415

Ala Val Leu Arg Ile Val Ile Arg Glu Asp Phe Asn Arg Ser Leu Ala
420 425 430

Gln Arg Leu Leu Ala Asp Ile Asn Lys Ile Ile Gly Glu Leu Asp Ala
435 440 445

His Ala Val His Ala Ile Lys Leu Ser Thr Ala Ala Ala Gly Gly Asp
450 455 460

Gly Ala Ser Lys Ser Ala Val Asp Ala Ala Thr Glu Ala Phe Lys Asp
465 470 475 480

Leu Ala Gly Lys Lys Lys Ala Gly Val Cys
485 490

<210> SEQ ID NO 128
<211> LENGTH: 501
<212> TYPE: PRT
<213> ORGANISM: Oryza sativa

<400> SEQUENCE: 128

Met Val Val Ser Val Ala Ala Thr Asp Ser Asp Thr Ala Gln Pro Val
1 5 10 15

Gln Tyr Ser Thr Phe Phe Ala Ser Arg Tyr Val Arg Asp Pro Leu Pro
20 25 30

Arg Phe Arg Met Pro Glu Gln Ser Ile Pro Arg Glu Ala Ala Tyr Gln
35 40 45

Ile Ile Asn Asp Glu Leu Met Leu Asp Gly Asn Pro Arg Leu Asn Leu
50 55 60

Ala Ser Phe Val Thr Thr Trp Met Glu Pro Glu Cys Asp Lys Leu Ile
65 70 75 80

Met Asp Ser Val Asn Lys Asn Tyr Val Asp Met Asp Glu Tyr Pro Val
85 90 95

Thr Thr Glu Leu Gln Asn Arg Cys Val Asn Met Ile Ala His Leu Phe
100 105 110

Asn Ala Pro Ile Lys Glu Asp Glu Thr Ala Ile Gly Val Gly Thr Val
115 120 125

Gly Ser Ser Glu Ala Ile Met Leu Ala Gly Leu Ala Phe Lys Arg Lys
130 135 140

Trp Gln Asn Lys Arg Lys Glu Gln Gly Lys Pro Cys Asp Lys Pro Asn
145 150 155 160

Ile Val Thr Gly Ala Asn Val Gln Val Cys Trp Glu Lys Phe Ala Arg
165 170 175

Tyr Phe Glu Val Glu Leu Lys Glu Val Lys Leu Ser Glu Gly Tyr Tyr 180 185 190

Val Met Asp Pro Val Lys Ala Val Glu Met Val Asp Glu Asn Thr Ile
195 200 205

Cys Val Ala Ala Ile Leu Gly Ser Thr Leu Thr Gly Glu Phe Glu Asp
210 215 220

Val Lys Leu Leu Asn Asn Leu Leu Thr Glu Lys Asn Lys Glu Thr Gly
225 230 235 240

Trp Asp Val Pro Ile His Val Asp Ala Ala Ser Gly Gly Phe Ile Ala
245 250 255

Pro Phe Leu Tyr Pro Glu Leu Glu Trp Asp Phe Arg Leu Pro Leu Val
260 265 270

Lys Ser Ile Asn Val Ser Gly His Lys Tyr Gly Leu Val Tyr Pro Gly
275 280 285

Val Gly Trp Val Ile Trp Arg Ser Lys Glu Asp Leu Pro Glu Glu Leu
290 295 300

Ile Phe His Ile Asn Tyr Leu Gly Thr Asp Gln Pro Thr Phe Thr Leu
305 310 315 320

Asn Phe Ser Lys Gly Ser Ser Gln Ile Ile Ala Gln Tyr Tyr Gln Leu
325 330 335

Ile Arg Leu Gly Phe Glu Gly Tyr Lys Asn Ile Met Gln Asn Cys Met
340 345 350

Glu Asn Thr Ala Ile Leu Arg Glu Gly Ile Glu Ala Thr Gly Arg Phe
355 360 365

Glu Ile Leu Ser Lys Glu Ala Gly Val Pro Leu Val Ala Phe Ser Leu
370 375 380

Lys Asp Ser Gly Arg Tyr Thr Val Phe Asp Ile Ser Glu His Leu Arg
385 390 395 400

Arg Phe Gly Trp Ile Val Pro Ala Tyr Thr Met Pro Ala Asn Ala Glu
405 410 415

His Val Ala Val Leu Arg Val Val Ile Arg Glu Asp Phe Ser Arg Ser
420 425 430

Leu Ala Glu Arg Leu Val Ser Asp Ile Val Lys Ile Leu His Glu Leu
435 440 445

Asp Ala His Ser Ala Gln Val Leu Lys Ile Ser Ser Ala Ile Ala Lys
450 455 460

Gln Gln Ser Gly Asp Asp Gly Val Val Thr Lys Lys Ser Val Leu Glu
465 470 475 480

Thr Glu Arg Glu Ile Phe Ala Tyr Trp Arg Asp Gln Val Lys Lys Lys
485 490 495

Gln Thr Gly Ile Cys
500

<210> SEQ ID NO 129
<211> LENGTH: 493
<212> TYPE: PRT
<213> ORGANISM: Arabidopsis thaliana

<400> SEQUENCE: 129

Met Val Leu Ser Lys Thr Val Ser Glu Ser Asp Val Ser Ile His Ser
1 5 10 15

Thr Phe Ala Ser Arg Tyr Val Arg Asn Ser Leu Pro Arg Phe Glu Met
20 25 30

Pro Glu Asn Ser Ile Pro Lys Glu Ala Ala Tyr Gln Ile Ile Asn Asp
35 40 45

-continued

```
Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Glu Ser Ile
65                  70                  75                  80

Asn Lys Asn Tyr Val Asp Met Asp Glu Tyr Pro Val Thr Thr Glu Leu
                85                  90                  95

Gln Asn Arg Cys Val Asn Met Ile Ala Arg Leu Phe Asn Ala Pro Leu
            100                 105                 110

Gly Asp Gly Glu Ala Ala Val Gly Val Gly Thr Val Gly Ser Ser Glu
        115                 120                 125

Ala Ile Met Leu Ala Gly Leu Ala Phe Lys Arg Gln Trp Gln Asn Lys
    130                 135                 140

Arg Lys Ala Gln Gly Leu Pro Tyr Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Asn Leu Arg Glu Asp Tyr Tyr Val Met Asp Pro
            180                 185                 190

Val Lys Ala Val Glu Met Val Asp Glu Asn Thr Ile Cys Val Ala Ala
        195                 200                 205

Ile Leu Gly Ser Thr Leu Thr Gly Glu Phe Glu Asp Val Lys Leu Leu
    210                 215                 220

Asn Asp Leu Leu Val Glu Lys Asn Lys Gln Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Thr Lys Thr Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Arg Asn Val Met Asp Asn Cys Arg Glu Asn Met Met
            340                 345                 350

Val Leu Arg Gln Gly Leu Glu Lys Thr Gly Arg Phe Lys Ile Val Ser
        355                 360                 365

Lys Glu Asn Gly Val Pro Leu Val Ala Phe Ser Leu Lys Asp Ser Ser
    370                 375                 380

Arg His Asn Glu Phe Glu Val Ala His Thr Leu Arg Arg Phe Gly Trp
385                 390                 395                 400

Ile Val Pro Ala Tyr Thr Met Pro Ala Asp Ala Gln His Val Thr Val
                405                 410                 415

Leu Arg Val Val Ile Arg Glu Asp Phe Ser Arg Thr Leu Ala Glu Arg
            420                 425                 430

Leu Val Ala Asp Phe Glu Lys Val Leu His Glu Leu Asp Thr Leu Pro
        435                 440                 445

Ala Arg Val His Ala Lys Met Ala Asn Gly Lys Val Asn Gly Val Lys
    450                 455                 460

Lys Thr Pro Glu Glu Thr Gln Arg Glu Val Thr Ala Tyr Trp Lys Lys
```

```
465                 470                 475                 480

Leu Leu Glu Thr Lys Lys Thr Asn Lys Asn Thr Ile Cys
                485                 490


<210> SEQ ID NO 130
<211> LENGTH: 502
<212> TYPE: PRT
<213> ORGANISM: Solanum lycopersicum

<400> SEQUENCE: 130

Met Val Leu Thr Thr Thr Ser Ile Arg Asp Ser Glu Glu Ser Leu His
1               5                   10                  15

Cys Thr Phe Ala Ser Arg Tyr Val Gln Glu Pro Leu Pro Lys Phe Lys
            20                  25                  30

Met Pro Lys Lys Ser Met Pro Lys Glu Ala Ala Tyr Gln Ile Val Asn
        35                  40                  45

Asp Glu Leu Met Leu Asp Gly Asn Pro Arg Leu Asn Leu Ala Ser Phe
    50                  55                  60

Val Ser Thr Trp Met Glu Pro Glu Cys Asp Lys Leu Ile Met Ser Ser
65                  70                  75                  80

Ile Asn Lys Asn Tyr Val Asp Met Asp Glu Tyr Pro Val Thr Thr Glu
                85                  90                  95

Leu Gln Asn Arg Cys Val Asn Met Leu Ala His Leu Phe His Ala Pro
            100                 105                 110

Val Gly Asp Asp Glu Thr Ala Val Gly Val Gly Thr Val Gly Ser Ser
        115                 120                 125

Glu Ala Ile Met Leu Ala Gly Leu Ala Phe Lys Arg Lys Trp Gln Ser
    130                 135                 140

Lys Arg Lys Ala Glu Gly Lys Pro Phe Asp Lys Pro Asn Ile Val Thr
145                 150                 155                 160

Gly Ala Asn Val Gln Val Cys Trp Glu Lys Phe Ala Arg Tyr Phe Glu
                165                 170                 175

Val Glu Leu Lys Glu Val Lys Leu Lys Glu Gly Tyr Tyr Val Met Asp
            180                 185                 190

Pro Ala Lys Ala Val Glu Ile Val Asp Glu Asn Thr Ile Cys Val Ala
        195                 200                 205

Ala Ile Leu Gly Ser Thr Leu Thr Gly Glu Phe Glu Asp Val Lys Leu
    210                 215                 220

Leu Asn Glu Leu Leu Thr Lys Lys Asn Lys Glu Thr Gly Trp Glu Thr
225                 230                 235                 240

Pro Ile His Val Asp Ala Ala Ser Gly Gly Phe Ile Ala Pro Phe Leu
                245                 250                 255

Trp Pro Asp Leu Glu Trp Asp Phe Arg Leu Pro Leu Val Lys Ser Ile
            260                 265                 270

Asn Val Ser Gly His Lys Tyr Gly Leu Val Tyr Ala Gly Val Gly Trp
        275                 280                 285

Val Ile Trp Arg Ser Lys Glu Asp Leu Pro Asp Glu Leu Val Phe His
    290                 295                 300

Ile Asn Tyr Leu Gly Ser Asp Gln Pro Thr Phe Thr Leu Asn Phe Ser
305                 310                 315                 320

Lys Gly Ser Tyr Gln Ile Ile Ala Gln Tyr Tyr Gln Leu Ile Arg Leu
                325                 330                 335

Gly Phe Glu Gly Tyr Lys Asn Val Met Lys Asn Cys Leu Ser Asn Ala
            340                 345                 350
```

Lys Val Leu Thr Glu Gly Ile Thr Lys Met Gly Arg Phe Asp Ile Val
355 360 365

Ser Lys Asp Val Gly Val Pro Val Val Ala Phe Ser Leu Arg Asp Ser
370 375 380

Ser Lys Tyr Thr Val Phe Glu Val Ser Glu His Leu Arg Arg Phe Gly
385 390 395 400

Trp Ile Val Pro Ala Tyr Thr Met Pro Pro Asp Ala Glu His Ile Ala
405 410 415

Val Leu Arg Val Val Ile Arg Glu Asp Phe Ser His Ser Leu Ala Glu
420 425 430

Arg Leu Val Ser Asp Ile Glu Lys Ile Leu Ser Glu Leu Asp Thr Gln
435 440 445

Pro Pro Arg Leu Pro Thr Lys Ala Val Arg Val Thr Ala Glu Glu Val
450 455 460

Arg Asp Asp Lys Gly Asp Gly Leu His His Phe His Met Asp Thr Val
465 470 475 480

Glu Thr Gln Lys Asp Ile Ile Lys His Trp Arg Lys Ile Ala Gly Lys
485 490 495

Lys Thr Ser Gly Val Cys
500

<210> SEQ ID NO 131
<211> LENGTH: 500
<212> TYPE: PRT
<213> ORGANISM: Arabidopsis thaliana

<400> SEQUENCE: 131

Met Val Leu Ser Lys Thr Ala Ser Lys Ser Asp Asp Ser Ile His Ser
1 5 10 15

Thr Phe Ala Ser Arg Tyr Val Arg Asn Ser Ile Ser Arg Phe Glu Ile
20 25 30

Pro Lys Asn Ser Ile Pro Lys Glu Ala Ala Tyr Gln Ile Ile Asn Asp
35 40 45

Glu Leu Lys Phe Asp Gly Asn Pro Arg Leu Asn Leu Ala Ser Phe Val
50 55 60

Thr Thr Trp Met Glu Pro Glu Cys Asp Lys Leu Met Met Glu Ser Ile
65 70 75 80

Asn Lys Asn Asn Val Glu Met Asp Gln Tyr Pro Val Thr Thr Asp Leu
85 90 95

Gln Asn Arg Cys Val Asn Met Ile Ala Arg Leu Phe Asn Ala Pro Leu
100 105 110

Gly Asp Gly Glu Ala Ala Ile Gly Val Gly Thr Val Gly Ser Ser Glu
115 120 125

Ala Val Met Leu Ala Gly Leu Ala Phe Lys Arg Gln Trp Gln Asn Lys
130 135 140

Arg Lys Ala Leu Gly Leu Pro Tyr Asp Arg Pro Asn Ile Val Thr Gly
145 150 155 160

Ala Asn Ile Gln Val Cys Leu Glu Lys Phe Ala Arg Tyr Phe Glu Val
165 170 175

Glu Leu Lys Glu Val Lys Leu Arg Glu Gly Tyr Tyr Val Met Asp Pro
180 185 190

Asp Lys Ala Val Glu Met Val Asp Glu Asn Thr Ile Cys Val Val Ala
195 200 205

Ile Leu Gly Ser Thr Leu Thr Gly Glu Phe Glu Asp Val Lys Leu Leu
210 215 220

-continued

```
Asn Asp Leu Leu Val Glu Lys Asn Lys Lys Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Asp Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Thr Lys Thr Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Arg Asn Val Met Asp Asn Cys Arg Glu Asn Met Met
            340                 345                 350

Val Leu Arg Gln Gly Leu Glu Lys Thr Gly Arg Phe Asn Ile Val Ser
        355                 360                 365

Lys Glu Asn Gly Val Pro Leu Val Ala Phe Ser Leu Lys Asp Ser Ser
    370                 375                 380

Arg His Asn Glu Phe Glu Val Ala Glu Met Leu Arg Arg Phe Gly Trp
385                 390                 395                 400

Ile Val Pro Ala Tyr Thr Met Pro Ala Asp Ala Gln His Val Thr Val
                405                 410                 415

Leu Arg Val Val Ile Arg Glu Asp Phe Ser Arg Thr Leu Ala Glu Arg
            420                 425                 430

Leu Val Ala Asp Phe Glu Lys Val Leu His Glu Leu Asp Thr Leu Pro
        435                 440                 445

Ala Arg Val His Ala Lys Met Ala Ser Gly Lys Val Asn Gly Val Lys
    450                 455                 460

Lys Thr Pro Glu Glu Thr Gln Arg Glu Val Thr Ala Tyr Trp Lys Lys
465                 470                 475                 480

Phe Val Asp Thr Lys Thr Asp Lys Asn Gly Val Pro Leu Val Ala Ser
                485                 490                 495

Ile Thr Asn Gln
            500
```